(12) United States Patent
Fotsing et al.

(10) Patent No.: US 12,295,396 B2
(45) Date of Patent: *May 13, 2025

(54) ANTAGONISTS OF T2R54 AND COMPOSITIONS AND USES THEREOF

(71) Applicant: Firmenich Incorporated, Plainsboro, NJ (US)

(72) Inventors: Joseph R. Fotsing, San Diego, CA (US); Andrew Patron, San Diego, CA (US); Guy Servant, San Diego, CA (US); Lan Zhang, San Diego, CA (US); Mark Williams, San Diego, CA (US); Qing Chen, San Diego, CA (US); Kenneth Simone, San Diego, CA (US); Vincent Darmohusodo, San Diego, CA (US); Chad Priest, San Diego, CA (US); Melissa S. Wong, San Diego, CA (US); Thomas Brady, San Diego, CA (US)

(73) Assignee: Firmenich Incorporated, Plainsboro, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/506,526

(22) Filed: Nov. 10, 2023

(65) Prior Publication Data
US 2024/0114942 A1    Apr. 11, 2024

Related U.S. Application Data

(63) Continuation of application No. 17/265,722, filed as application No. PCT/US2019/045684 on Aug. 8, 2019, now Pat. No. 11,871,772.
(Continued)

(51) Int. Cl.
*A23L 27/00* (2016.01)
*C07D 317/66* (2006.01)
(Continued)

(52) U.S. Cl.
CPC ............ *A23L 27/86* (2016.08); *C07D 317/66* (2013.01); *C07D 401/04* (2013.01);
(Continued)

(58) Field of Classification Search
CPC .................................................... C07D 407/12
See application file for complete search history.

(56) References Cited

U.S. PATENT DOCUMENTS

| 11,871,772 B2 | 1/2024 | Fotsing et al. |
| 2008/0153845 A1 | 6/2008 | Palmer et al. |

(Continued)

FOREIGN PATENT DOCUMENTS

| EP | 0355169 A1 | * | 2/1990 | ............ C07D 317/64 |
| WO | WO-9964407 A1 | * | 12/1999 | ............ C07D 295/15 |

OTHER PUBLICATIONS

International Search Report, PCT App. No. PCT/US2019/045684, dated Nov. 22, 2019.
(Continued)

*Primary Examiner* — Changqing Li
(74) *Attorney, Agent, or Firm* — Robert S. Dailey

(57) ABSTRACT

The present disclosure generally provides compounds that antagonize certain T2R taste receptors, including related uses, methods, and compositions for the reduction of bitter taste and/or the enhancement of sweet taste. In certain aspects, the disclosure provides flavored articles or flavored compositions comprising such compounds, as well as uses of such compounds to reduce the bitter taste and/or enhance the sweet taste of such flavored articles or flavored compositions.

5 Claims, 2 Drawing Sheets

Related U.S. Application Data

(60) Provisional application No. 62/717,121, filed on Aug. 10, 2018.

(51) Int. Cl.
*C07D 401/04* (2006.01)
*C07D 405/12* (2006.01)
*C07D 405/14* (2006.01)
*C07D 407/12* (2006.01)
*C07D 409/14* (2006.01)
*C07D 413/12* (2006.01)
*C07D 413/14* (2006.01)

(52) U.S. Cl.
CPC ......... *C07D 405/12* (2013.01); *C07D 405/14* (2013.01); *C07D 407/12* (2013.01); *C07D 409/14* (2013.01); *C07D 413/12* (2013.01); *C07D 413/14* (2013.01)

(56) References Cited

U.S. PATENT DOCUMENTS

2010/0254916 A1 10/2010 Karanewski et al.
2013/0096209 A1 4/2013 Hayashi et al.
2014/0377381 A1 12/2014 Brennan et al.

OTHER PUBLICATIONS

Written Opinion of the Int'l Search Authority, PCT App. No. PCT/US2019/045684, dated Nov. 22, 2019.

* cited by examiner

ANTAGONISTS OF T2R54 AND COMPOSITIONS AND USES THEREOF

CROSS-REFERENCE TO RELATED APPLICATIONS

The present application is the United States national stage application of PCT Application No. PCT/US2019/045684, filed Aug. 8, 2019, which claims the benefit of priority of U.S. Provisional Application No. 62/717,121, filed Aug. 10, 2018, which is hereby incorporated by reference as though set forth herein in its entirety.

TECHNICAL FIELD

The present disclosure generally provides compounds that antagonize certain T2R taste receptors, including related uses, methods, and compositions for the reduction of bitter taste and/or the enhancement of sweet taste. In certain aspects, the disclosure provides flavored articles or flavored compositions comprising such compounds, as well as uses of such compounds to reduce the bitter taste and/or enhance the sweet taste of such flavored articles or flavored compositions.

DESCRIPTION OF RELATED ART

The taste system provides sensory information about the chemical composition of the external world. Taste transduction is one of the most sophisticated forms of chemical-triggered sensation in animals. Signaling of taste is found throughout the animal kingdom, from simple metazoans to the most complex of vertebrates. Mammals are believed to have five basic taste modalities: sweet, bitter, sour, salty, and umami.

Obesity, diabetes, and cardiovascular disease are major health concerns throughout the world, and are growing at an alarming rate. Sugar and calories are key components that can be limited to render a positive nutritional effect on health. Even so, because a number of foods contain components that agonize bitter taste receptors, consumers often use sugar and other sweeteners to offset the perception of bitter taste in such foods. Further, certain nutritionally useful foods, such as vegetable proteins, agonize bitter taste receptors. Thus, despite their nutritional value, consumers may avoid such foods because of their perceived poor taste. Further, many medicinal compounds, such as antibiotics, have a distinctly bitter taste. Therefore, pharmaceutical manufacturers must employ complicated formulation technologies to permit subjects to take such medicines orally without experiencing displeasure.

But the physiological basis concerning the perception of bitter taste is still not well understood. Many bitter compounds produce their bitter taste, at least in part, by modulating certain cell surface receptors, some of which belong to a family of seven transmembrane domain receptors that interact with intracellular G proteins. These include a family of G-coupled protein receptors (GCPRs), termed T2Rs, which are found in humans and rodents. Humans express at least several dozen different receptors that fall within the T2R family. One of these receptors found in humans is termed hT2R54. This receptor is believed to play a key role in the human perception of bitter taste.

Some compounds are known to antagonize hT2R54. Even so, such compounds may only antagonize the hT2R54 receptor weakly, or may interact with other taste receptors modify the taste of a flavored article in ways that humans do not perceive as offering an improvement in taste. Therefore, there is a continuing need to discover compounds that antagonize hT2R54, with the goal of discovering compounds that reduce the human perception of bitter taste without otherwise modifying the taste of an article in ways that humans tend to dislike.

SUMMARY

The present disclosure provides compounds that were discovered as antagonists, such as selective antagonists, of hT2R54. These compounds provide a broader array of compounds that can be used in food products or drug products to reduce the perception of bitter taste, and, in some cases, even have a concomitant enhancement of the perception of sweet taste in such products.

In a first aspect, the disclosure provides compounds of formula (I):

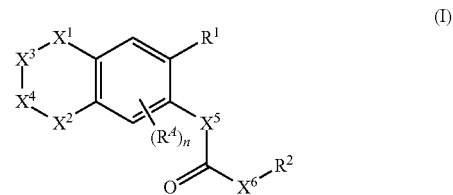

or a salt thereof, wherein:

$X^1$ and $X^2$ are each independently an oxygen atom or $>C(R^{2A})(R^{2B})$;

$X^3$ is a direct bond or $>C(R^{2C})(R^{2D})$;

$X^4$ is $>C(R^{2E})(R^{2F})$ $R^A$ is a halogen atom, —CN, nitro, —OH, —NH$_2$, —C(O)H, —O—C(O)H, —C(O)—OH, —NH—C(O) H, —C(O)—NH$_2$, —O—(C$_{1-6}$ alkyl), —NH—(C$_{1-6}$ alkyl), —N(C$_{1-6}$ alkyl)$_2$, —C(O)—(C$_{1-6}$ alkyl), —O—C(O)—(C$_{1-6}$ alkyl), —NH—C(O)—(C$_{1-6}$ alkyl), —N(C$_{1-6}$ alkyl)-C(O)—(C$_{1-6}$ alkyl), —C(O)—O—(C$_{1-6}$ alkyl), —C(O)—NH—(C$_{1-6}$ alkyl), —C(O)—N(C$_{1-6}$ alkyl)$_2$, —S(O)$_2$—(C$_{1-6}$ alkyl), —O—S(O)$_2$—(C$_{1-6}$ alkyl), —NH—S(O)$_2$—(C$_{1-6}$ alkyl), —N(C$_{1-6}$ alkyl)-S(O)$_2$—(C$_{1-6}$ alkyl), —S(O)$_2$—O—(C$_{1-6}$ alkyl), —S(O)$_2$—NH—(C$_{1-6}$ alkyl), —S(O)$_2$—N(C$_{1-6}$ alkyl)$_2$, C$_{3-10}$ cycloalkyl, C$_{2-14}$ heterocyclyl, C$_{6-14}$ aryl, or C$_{2-14}$ heteroaryl, C$_{1-6}$ alkyl, C$_{2-6}$ alkenyl, C$_{1-6}$ haloalkyl, C$_{2-6}$ haloalkenyl, C$_{1-6}$ haloalkoxy, C$_{2-6}$ haloalkenyloxy, or (C$_{1-6}$ alkoxy)-C$_{1-6}$ alkyl;

$R^1$ is a halogen atom, —C(O)—R$^{1A}$, —C(O)—O—R$^{1A}$, —O—R$^{1A}$, —O—C(O)—R$^{1A}$, or C$_{1-6}$ alkyl, where the alkyl group is optionally substituted one or more times by substituents selected independently from the group consisting of R$^{1Y}$;

$R^{1A}$ is a hydrogen atom or C$_{1-6}$ alkyl, wherein the alkyl group is optionally substituted one or more times by substituents selected independently from the group consisting of R$^{1Y}$;

$R^{1Y}$ is a halogen atom, oxo, —CN, nitro, —OH, —NH$_2$, —C(O)H, —O—C(O)H, —C(O)—OH, —NH—C(O) H, —C(O)—NH$_2$, —O—(C$_{1-6}$ alkyl), —NH—(C$_{1-6}$ alkyl), —N(C$_{1-6}$ alkyl)$_2$, —C(O)—(C$_{1-6}$ alkyl), —O—C(O)—(C$_{1-6}$ alkyl), —NH—C(O)—(C$_{1-6}$ alkyl), —C(O)—O—(C$_{1-6}$ alkyl), —C(O)—NH—(C$_{1-6}$ alkyl), —C(O)—N(C$_{1-6}$ alkyl)$_2$, —S(O)$_2$—(C$_{1-6}$ alkyl), —O—S(O)$_2$—(C$_{1-6}$ alkyl), —NH—S(O)$_2$—(C$_{1-6}$ alkyl), —S(O)$_2$—O—(C$_{1-6}$ alkyl), —S(O)$_2$—

NH—($C_{1-6}$ alkyl), —S(O)$_2$—N($C_{1-6}$ alkyl)$_2$, $C_{3-10}$ cycloalkyl, $C_{2-14}$ heterocyclyl, $C_{6-14}$ aryl, $C_{2-14}$ heteroaryl, $C_{1-6}$ alkyl, $C_{2-6}$ alkenyl, $C_{1-6}$ haloalkyl, $C_{2-6}$ haloalkenyl, $C_{1-6}$ haloalkoxy, $C_{2-6}$ haloalkenyloxy, and ($C_{1-6}$ alkoxy)-$C_{1-6}$ alkyl;

$R^{1Z}$ is a halogen atom, oxo, —CN, nitro, —OH, —NH$_2$, —C(O)H, —O—C(O)H, —C(O)—OH, —NH—C(O)H, —C(O)—NH$_2$, —O—($C_{1-6}$ alkyl), —NH—($C_{1-6}$ alkyl), —N($C_{1-6}$ alkyl)$_2$, —C(O)—($C_{1-6}$ alkyl), —O—C(O)—($C_{1-6}$ alkyl), —NH—C(O)—($C_{1-6}$ alkyl), —C(O)—O—($C_{1-6}$ alkyl), —C(O)—NH—($C_{1-6}$ alkyl), —C(O)—N($C_{1-6}$ alkyl)$_2$, —S(O)$_2$—($C_{1-6}$ alkyl), —O—S(O)$_2$—($C_{1-6}$ alkyl), —NH—S(O)$_2$—($C_{1-6}$ alkyl), —S(O)$_2$—O—($C_{1-6}$ alkyl), —S(O)$_2$—NH—($C_{1-6}$ alkyl), —S(O)$_2$—N($C_{1-6}$ alkyl)$_2$, $C_{3-10}$ cycloalkyl, $C_{2-14}$ heterocyclyl, $C_{6-14}$ aryl, $C_{2-14}$ heteroaryl, $C_{1-6}$ alkyl, $C_{2-6}$ alkenyl, $C_{1-6}$ haloalkyl, $C_{2-6}$ haloalkenyl, $C_{1-6}$ haloalkoxy, $C_{2-6}$ haloalkenyloxy, ($C_{1-6}$ alkoxy)-$C_{1-6}$ alkyl, $C_{1-6}$ alkyl, and $C_{2-6}$ alkenyl;

$R^2$ is —N($R^5$)($R^6$), wherein $R^5$ and $R^6$ optionally combine with the nitrogen atom to which they are attached to form a nitrogen-containing $C_{2-6}$ heterocyclic ring, which is optionally substituted by $C_{1-4}$ alkyl; or $R^2$ is

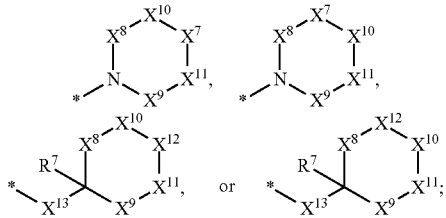

or $R^2$ is a hydrogen atom, a halogen atom, $C_{3-10}$ cycloalkyl, $C_{2-14}$ heterocyclyl, $C_{6-14}$ aryl, or $C_{2-14}$ heteroaryl, wherein the carbocyclyl, heterocyclyl, aryl, and heteroaryl are each optionally substituted one or more times by substituents selected independently from the group consisting of $R^{1Z}$;

$X^5$ is >N$R^{2G}$;

$X^6$ is $C_{1-6}$ alkylene, which is optionally substituted one or more times by substituents selected independently from the group consisting of $R^{1Y}$; or $X^7$ is an oxygen atom, a sulfur atom, >N—$R^{2L}$, or >C($R^{2J}$)($R^{2K}$);

$X^8$, $X^9$, $X^{10}$, and $X^{11}$ are each independently a direct bond, an oxygen atom, a sulfur atom, or >C($R^{2M}$)($R^{2N}$), wherein no more than one of $X^8$, $X^9$, $X^{10}$, and $X^{11}$ is a direct bond, and wherein no more than one of $X^8$, $X^9$, $X^{10}$, and $X^{11}$ is an oxygen atom or a sulfur atom;

$X^{12}$ is an oxygen atom, a sulfur atom, or >N—$R^{2L}$;

$X^{13}$ is a direct bond or >N$R^{2P}$;

$R^{2A}$, $R^{2B}$, $R^{2C}$, $R^{2D}$, $R^{2E}$, $R^{2F}$, $R^{2K}$, $R^{2M}$, and $R^{2N}$ are each independently a hydrogen atom, a halogen atom, —CN, nitro, —OH, —NH$_2$, —C(O)H, —O—C(O)H, —C(O)—OH, —NH—C(O)H, —C(O)—NH$_2$, —O—($C_{1-6}$ alkyl), —NH—($C_{1-6}$ alkyl), —N($C_{1-6}$ alkyl)$_2$, —C(O)—($C_{1-6}$ alkyl), —O—C(O)—($C_{1-6}$ alkyl), —NH—C(O)—($C_{1-6}$ alkyl), —NH—C(O)—O—($C_{1-6}$ alkyl), —C(O)—O—($C_{1-6}$ alkyl), —C(O)—NH—($C_{1-6}$ alkyl), —C(O)—N($C_{1-6}$ alkyl)$_2$, —S(O)$_2$—($C_{1-6}$ alkyl), —O—S(O)$_2$—($C_{1-6}$ alkyl), —NH—S(O)$_2$—($C_{1-6}$ alkyl), —S(O)$_2$—O—($C_{1-6}$ alkyl), —S(O)$_2$—NH—($C_{1-6}$ alkyl), —S(O)$_2$—N($C_{1-6}$ alkyl)$_2$, $C_{3-10}$ cycloalkyl, $C_{2-14}$ heterocyclyl, $C_{6-14}$ aryl, or $C_{2-14}$ heteroaryl, $C_{1-6}$ alkyl, $C_{2-6}$ alkenyl, $C_{1-6}$ haloalkyl, $C_{2-6}$ haloalkenyl, $C_{1-6}$ haloalkoxy, $C_{2-6}$ haloalkenyloxy, ($C_{1-6}$ alkoxy)-$C_{1-6}$ alkyl; or $R^{2A}$ and $R^{2B}$, or $R^{2C}$ and $R^{2D}$, or $R^{2E}$ and $R^{2F}$, or $R^{2M}$ and $R^{2N}$ optionally combine to form an oxo group; or any two of $R^{2M}$ and $R^{2N}$ attached to adjacent carbon atoms optionally combine to form a fused ring selected from the group consisting of phenyl, $C_{2-5}$ heteroaryl, $C_{4-8}$ cycloalkyl, and $C_{2-5}$ heterocyclyl, wherein each of the fused rings is optionally substituted one or more times by substituents selected independently from $R^{1Z}$.

$R^{2G}$ and $R^{2P}$ are each independently a hydrogen atom, $C_{1-6}$ alkyl, $C_{1-6}$ haloalkyl, or ($C_{1-6}$ alkoxy)-$C_{1-6}$ alkyl;

$R^{2J}$ is —$R^4$ or —$X^{14}$—$R^4$;

$R^{2L}$ is —C(O)—$R^3$, —C(O)—$X^{14}$—$R^4$, —C(S)—$R^3$, —C(S)—$X^{14}$—$R^4$, —S(O)$_2$—$R^3$, —S(O)$_2$—$X^{14}$—$R^4$, or —$X^{14}$—$R^4$;

$X^{14}$ is $C_{1-8}$ alkylene, which is optionally substituted by one or more times by substituents selected independently from the group consisting of $R^{1Y}$;

$R^3$ is a hydrogen atom, —OH, —NH$_2$, —O—$R^{3B}$, —NH—$R^{3B}$, —N($R^{3B}$)($R^{3C}$), —O—C(O)—$R^{3B}$, —NH—C(O)—$R^{3B}$, —N($R^{3C}$)—C(O)—$R^{3B}$, $C_{3-10}$ carbocyclyl, $C_{2-14}$ heterocyclyl, $C_{6-14}$ aryl, and $C_{2-14}$ heteroaryl, wherein the carbocyclyl, heterocyclyl, aryl, and heteroaryl are each optionally substituted one or more times by substituents selected independently from $R^{3A}$, wherein any two $R^{3A}$ attached to adjacent carbon atoms optionally combine to form a fused ring selected from the group consisting of phenyl, $C_{2-5}$ heteroaryl, $C_{4-8}$ cycloalkyl, and $C_{2-5}$ heterocyclyl, wherein each of the fused rings is optionally substituted one or more times by substituents selected independently from $R^{1Z}$, and wherein, when $R^{3B}$ and $R^{3C}$ are attached to the same nitrogen atom, $R^{3B}$ and $R^{3C}$ optionally combine with the nitrogen atom to which they are attached to form a nitrogen-containing $C_{2-6}$ heterocyclic ring, which is optionally substituted by $C_{1-4}$ alkyl;

$R^{3A}$ is a halogen atom, —CN, nitro, oxo, —OH, —NH$_2$, —C(O)H, —O—C(O)H, —C(O)—OH, —NH—C(O)H, —C(O)—NH$_2$, —O—$R^{3D}$, —NH—$R^{3D}$, —N($R^{3D}$)($R^{3E}$), —C(O)—$R^{3D}$, —O—C(O)—$R^{3D}$, —NH—C(O)—$R^{3D}$, —C(O)—O—$R^{3D}$, —C(O)—NH—$R^{3D}$, —C(O)—N($R^{3D}$)($R^{3E}$), —S(O)$_2$—$R^{3D}$, —O—S(O)$_2$—$R^{3D}$, —NH—S(O)$_2$—$R^{3D}$, —S(O)$_2$—O—$R^{3D}$, —S(O)$_2$—NH—$R^{3D}$, —S(O)$_2$—N($R^{3D}$)($R^{3E}$), $C_{1-8}$ alkyl, $C_{2-8}$ alkenyl, $C_{3-10}$ carbocyclyl, $C_{2-14}$ heterocyclyl, $C_{6-14}$ aryl, and $C_{2-14}$ heteroaryl, wherein the alkyl and alkenyl are each optionally substituted one or more times by substituents selected independently from the group consisting of $R^{3Y}$, and wherein the carbocyclyl, heterocyclyl, aryl, and heteroaryl are each optionally substituted one or more times by substituents selected independently from the group consisting of $R^{3Z}$;

$R^{3B}$, $R^{3C}$, $R^{3D}$, and $R^{3E}$ are each independently $C_{1-8}$ alkyl, $C_{2-8}$ alkenyl, $C_{3-10}$ carbocyclyl, $C_{2-14}$ heterocyclyl, $C_{6-14}$ aryl, or $C_{2-14}$ heteroaryl, wherein the alkyl and alkenyl are each optionally substituted one or more times by substituents selected independently from the group consisting of $R^{3Y}$, and wherein the carbocyclyl, heterocyclyl, aryl, and heteroaryl are each optionally substituted one or more times by substituents selected independently from the group consisting of $R^{3Z}$;

$R^{31}$ is a halogen atom, —CN, nitro, oxo, —OH, —NH$_2$, —C(O)H, —O—C(O)H, —C(O)—OH, —NH—C(O)

H, —C(O)—NH$_2$, —O—(C$_{1-6}$ alkyl), —NH—(C$_{1-6}$ alkyl), —N(C$_{1-6}$ alkyl)$_2$, —C(O)—(C$_{1-6}$ alkyl), —O—C(O)—(C$_{1-6}$ alkyl), —NH—C(O)—(C$_{1-6}$ alkyl), —N(C$_{1-6}$ alkyl)-C(O)—(C$_{1-6}$ alkyl), —C(O)—O—(C$_{1-6}$ alkyl), —C(O)—NH—(C$_{1-6}$ alkyl), —C(O)—N(C$_{1-6}$ alkyl)$_2$, —S(O)$_2$—(C$_{1-6}$ alkyl), —O—S(O)$_2$—(C$_{1-6}$ alkyl), —NH—S(O)$_2$—(C$_{1-6}$ alkyl), —N(C$_{1-6}$ alkyl)-S(O)$_2$—(C$_{1-6}$ alkyl), —S(O)$_2$—O—(C$_{1-6}$ alkyl), —S(O)$_2$—NH—(C$_{1-6}$ alkyl), —S(O)$_2$—N(C$_{1-6}$ alkyl)$_2$, —O—(C$_{1-6}$ alkylene)-O—(C$_{1-6}$ alkyl), C$_{3-10}$ cycloalkyl, C$_{2-14}$ heterocyclyl, C$_{6-14}$ aryl, and C$_{2-14}$ heteroaryl, wherein the cycloalkyl, heterocyclyl, aryl, and heteroaryl groups are each optionally substituted one or more times by substituents selected independently from the group consisting of R$^{1Z}$;

R$^{3Z}$ is a halogen atom, —CN, nitro, oxo, —OH, —NH$_2$, —C(O)H, —O—C(O)H, —C(O)—OH, —NH—C(O)H, —C(O)—NH$_2$, —O—(C$_{1-6}$ alkyl), —NH—(C$_{1-6}$ alkyl), —N(C$_{1-6}$ alkyl)$_2$, —C(O)—(C$_{1-6}$ alkyl), —O—C(O)—(C$_{1-6}$ alkyl), —NH—C(O)—(C$_{1-6}$ alkyl), —N(C$_{1-6}$ alkyl)-C(O)—(C$_{1-6}$ alkyl), —C(O)—O—(C$_{1-6}$ alkyl), —C(O)—NH—(C$_{1-6}$ alkyl), —C(O)—N(C$_{1-6}$ alkyl)$_2$, —S(O)$_2$—(C$_{1-6}$ alkyl), —O—S(O)$_2$—(C$_{1-6}$ alkyl), —NH—S(O)$_2$—(C$_{1-6}$ alkyl), —N(C$_{1-6}$ alkyl)-S(O)$_2$—(C$_{1-6}$ alkyl), —S(O)$_2$—O—(C$_{1-6}$ alkyl), —S(O)$_2$—NH—(C$_{1-6}$ alkyl), —S(O)$_2$—N(C$_{1-6}$ alkyl)$_2$, C$_{1-6}$ alkyl, C$_{2-6}$ alkenyl, C$_{1-6}$ haloalkyl, C$_{2-6}$ haloalkenyl, C$_{1-6}$ haloalkoxy, C$_{2-6}$ haloalkenyloxy, (C$_{1-6}$ alkoxy)-C$_{1-6}$ alkyl, C$_{3-10}$ cycloalkyl, C$_{2-14}$ heterocyclyl, C$_{6-14}$ aryl, and C$_{2-14}$ heteroaryl, wherein the cycloalkyl, heterocyclyl, aryl, and heteroaryl groups are each optionally substituted one or more times by substituents selected independently from the group consisting of R$^{1Z}$;

R$^4$ is a hydrogen atom, a halogen atom, —CN, nitro, oxo, —OH, —NH$_2$, —O—R$^{4B}$, —NH—R$^{4B}$, —N(R$^{4B}$)(R$^{4C}$), C(O)—R$^{4B}$, —O—C(O)—R$^{4B}$, —NH—C(O)—R$^{4B}$, —N(R$^{4C}$)—C(O)—R$^{4B}$, —C(O)—O—R$^{4B}$, —C(O)—NH—R$^{4B}$, —C(O)N(R$^{4B}$)(R$^{4C}$), —S(O)$_2$—R$^{4D}$, —O—S(O)$_2$—R$^{4D}$, —NH—S(O)$_2$—R$^{4D}$, —S(O)$_2$—O—R$^{4D}$, —S(O)$_2$—NH—R$^{4D}$, —S(O)$_2$—N(R$^{4D}$)(R$^{4E}$), C$_{3-10}$ carbocyclyl, C$_{2-14}$ heterocyclyl, C$_{6-14}$ aryl, and C$_{2-14}$ heteroaryl, wherein the carbocyclyl, heterocyclyl, aryl, and heteroaryl are each optionally substituted one or more times by substituents selected independently from R$^{4A}$, wherein any two R$^{4A}$ attached to adjacent carbon atoms optionally combine to form a fused ring selected from the group consisting of phenyl, C$_{2-5}$ heteroaryl, C$_{4-8}$ cycloalkyl, and C$_{2-5}$ heterocyclyl, wherein each of the fused rings is optionally substituted one or more times by substituents selected independently from R$^{1Z}$, and wherein, when R$^{4B}$ and R$^{4C}$ are attached to the same nitrogen atom, R$^{4B}$ and R$^{4C}$ optionally combine with the nitrogen atom to which they are attached to form a nitrogen-containing C$_{2-6}$ heterocyclic ring, which is optionally substituted by C$_{1-4}$ alkyl;

R$^{4A}$ is a halogen atom, —CN, nitro, oxo, —OH, —NH$_2$, —C(O)H, —O—C(O)H, —C(O)—OH, —NH—C(O)H, —C(O)—NH$_2$, —O—R$^{4D}$, —NH—R$^{4D}$, —N(R$^{4D}$)(R$^{4E}$), —C(O)—R$^{4D}$, —O—C(O)—R$^{4D}$, —NH—C(O)—R$^{4D}$, —N(R$^{4E}$)—C(O)—R$^{4D}$, —C(O)—O—R$^{4D}$, —C(O)—NH—R$^{4D}$, —C(O)—N(R$^{4D}$)(R$^{4E}$), C$_{1-8}$ alkyl, C$_{2-8}$ alkenyl, C$_{3-10}$ carbocyclyl, C$_{2-14}$ heterocyclyl, C$_{6-14}$ aryl, and C$_{2-14}$ heteroaryl, wherein the alkyl and alkenyl are each optionally substituted one or more times by substituents selected independently from the group consisting of R$^{4Y}$, and wherein the carbocyclyl, heterocyclyl, aryl, and heteroaryl are each optionally substituted one or more times by substituents selected independently from R$^{4Z}$;

R$^{4B}$, R$^{4C}$, R$^{4D}$, and R$^{4E}$ are each independently C$_{1-8}$ alkyl, C$_{2-8}$ alkenyl, C$_{3-10}$ carbocyclyl, C$_{2-14}$ heterocyclyl, C$_{6-14}$ aryl, and C$_{2-14}$ heteroaryl, wherein the alkyl and alkenyl are each optionally substituted one or more times by substituents selected independently from R$^{4Y}$, and wherein the carbocyclyl, heterocyclyl, aryl, and heteroaryl are each optionally substituted one or more times by substituents selected independently from R$^{4Z}$;

R$^{4Y}$ is a halogen atom, —CN, nitro, oxo, —OH, —NH$_2$, —C(O)H, —O—C(O)H, —C(O)—OH, —NH—C(O)H, —C(O)—NH$_2$, —O—(C$_{1-6}$ alkyl), —NH—(C$_{1-6}$ alkyl), —N(C$_{1-6}$ alkyl)$_2$, —C(O)—(C$_{1-6}$ alkyl), —O—C(O)—(C$_{1-6}$ alkyl), —NH—C(O)—(C$_{1-6}$ alkyl), —N(C$_{1-6}$ alkyl)-C(O)—(C$_{1-6}$ alkyl), —C(O)—O—(C$_{1-6}$ alkyl), —C(O)—NH—(C$_{1-6}$ alkyl), —C(O)—N(C$_{1-6}$ alkyl)$_2$, —S(O)$_2$—(C$_{1-6}$ alkyl), —O—S(O)$_2$—(C$_{1-6}$ alkyl), —NH—S(O)$_2$—(C$_{1-6}$ alkyl), —N(C$_{1-6}$ alkyl)-S(O)$_2$—(C$_{1-6}$ alkyl), —S(O)$_2$—O—(C$_{1-6}$ alkyl), —S(O)$_2$—NH—(C$_{1-6}$ alkyl), —S(O)$_2$—N(C$_{1-6}$ alkyl)$_2$, —O—(C$_{1-6}$ alkylene)-O—(C$_{1-6}$ alkyl), C$_{3-10}$ cycloalkyl, C$_{2-14}$ heterocyclyl, C$_{6-14}$ aryl, and C$_{2-14}$ heteroaryl, wherein the cycloalkyl, heterocyclyl, aryl, and heteroaryl groups are each optionally substituted one or more times by substituents selected independently from the group consisting of R$^{1Z}$;

R$^{4Z}$ is a halogen atom, —CN, nitro, oxo, —OH, —NH$_2$, —C(O)H, —O—C(O)H, —C(O)—OH, —NH—C(O)H, —C(O)—NH$_2$, —O—(C$_{1-6}$ alkyl), —NH—(C$_{1-6}$ alkyl), —N(C$_{1-6}$ alkyl)$_2$, —C(O)—(C$_{1-6}$ alkyl), —O—C(O)—(C$_{1-6}$ alkyl), —NH—C(O)—(C$_{1-6}$ alkyl), —N(C$_{1-6}$ alkyl)-C(O)—(C$_{1-6}$ alkyl), —C(O)—O—(C$_{1-6}$ alkyl), —C(O)—NH—(C$_{1-6}$ alkyl), —C(O)—N(C$_{1-6}$ alkyl)$_2$, —S(O)$_2$—(C$_{1-6}$ alkyl), —O—S(O)$_2$—(C$_{1-6}$ alkyl), —NH—S(O)$_2$—(C$_{1-6}$ alkyl), —N(C$_{1-6}$ alkyl)-S(O)$_2$—(C$_{1-6}$ alkyl), —S(O)$_2$—O—(C$_{1-6}$ alkyl), —S(O)$_2$—NH—(C$_{1-6}$ alkyl), —S(O)$_2$—N(C$_{1-6}$ alkyl)$_2$, (C$_{1-6}$ alkoxy)-C$_{1-6}$ alkyl, C$_{3-10}$ cycloalkyl, C$_{2-14}$ heterocyclyl, C$_{6-14}$ aryl, or C$_{2-14}$ heteroaryl, C$_{1-6}$ alkyl, C$_{2-6}$ alkenyl, C$_{1-6}$ haloalkyl, C$_{2-6}$ haloalkenyl, C$_{1-6}$ haloalkoxy, and C$_{2-6}$ haloalkenyloxy, wherein the cycloalkyl, heterocyclyl, aryl, and heteroaryl groups are each optionally substituted one or more times by substituents selected independently from the group consisting of R$^{1Z}$;

R$^5$ is —C(O)—R$^3$, —C(O)—X$^{14}$—R$^4$, —C(S)—R$^3$, —C(S)—X$^{14}$—R$^4$, —S(O)$_2$—R$^3$, —S(O)$_2$—X$^{14}$—R$^4$, or —X$^{14}$—R$^4$;

R$^6$ is a hydrogen atom or C$_{1-8}$ alkyl, wherein the alkyl is optionally substituted one or more times by substituents selected independently from the group consisting of R$^{6Y}$;

R$^{6Y}$ is a halogen atom, —CN, nitro, oxo, —OH, —NH$_2$, —C(O)H, —O—C(O)H, —C(O)—OH, —NH—C(O)H, —C(O)—NH$_2$, —O—(C$_{1-6}$ alkyl), —NH—(C$_{1-6}$ alkyl), —N(C$_{1-6}$ alkyl)$_2$, —C(O)—(C$_{1-6}$ alkyl), —O—C(O)—(C$_{1-6}$ alkyl), —NH—C(O)—(C$_{1-6}$ alkyl), —N(C$_{1-6}$ alkyl)-C(O)—(C$_{1-6}$ alkyl), —C(O)—O—(C$_{1-6}$ alkyl), —C(O)—NH—(C$_{1-6}$ alkyl), —C(O)—N(C$_{1-6}$ alkyl)$_2$, —S(O)$_2$—(C$_{1-6}$ alkyl), —O—S(O)$_2$—(C$_{1-6}$ alkyl), —NH—S(O)$_2$—(C$_{1-6}$ alkyl), —N(C$_{1-6}$ alkyl)-S(O)$_2$—(C$_{1-6}$ alkyl), —S(O)$_2$—

O—($C_{1-6}$ alkyl), —S(O)$_2$—NH—($C_{1-6}$ alkyl), —S(O)$_2$—N($C_{1-6}$ alkyl)$_2$, —O—($C_{1-6}$ alkylene)-O—($C_{1-6}$ alkyl), $C_{3-10}$ cycloalkyl, $C_{2-14}$ heterocyclyl, $C_{6-14}$ aryl, and $C_{2-14}$ heteroaryl, wherein the cycloalkyl, heterocyclyl, aryl, and heteroaryl groups are each optionally substituted one or more times by substituents selected independently from the group consisting of $R^{1Z}$;

$R^7$ is a hydrogen atom, a halogen atom, $C_{1-6}$ alkyl, $C_{1-6}$ haloalkyl, $C_{1-6}$ alkoxy, $C_{1-6}$ haloalkoxy, or ($C_{1-6}$ alkyl)-O—$C_{1-6}$ alkyl; and n is 0, 1, or 2.

In a second aspect, the disclosure provides uses of compounds of the first aspect (including any embodiments thereof).

In a third aspect, the disclosure provides uses of compounds of the first aspect (including any embodiments thereof) to reduce the bitterness and/or enhance the sweetness of a comestible composition or a pharmaceutical composition. In some embodiments, the disclosure provides uses of compounds of the first aspect (including any embodiments thereof) to reduce the bitterness of a comestible composition. In some further such embodiments, the comestible composition is a flavored article, such as a flavored food product. In some other embodiments, the disclosure provides uses of compounds of the first aspect (including any embodiments thereof) to reduce the bitterness of a pharmaceutical composition, such as a pharmaceutical composition (tablet, capsule, elixir, etc.) for oral administration.

In a fourth aspect, the disclosure provides uses of compounds of the first aspect (including any embodiments thereof) in the manufacture of a product for the reduction of bitter taste and/or the enhancement of sweet taste in the product. In some embodiments, the disclosure provides uses of compounds of the first aspect (including any embodiments thereof) in the manufacture of a flavored article, such as a flavored food or beverage product, for the reduction of bitter taste in the product. In some other embodiments, the disclosure provides uses of compounds of the first aspect (including any embodiments thereof) in the manufacture of a medicament for the reduction of bitter taste in the medicament.

In a fifth aspect, the disclosure provides uses of compounds of the first aspect (including any embodiments thereof) to antagonize one or more human T2R taste receptors, such as one or more human T2R54 taste receptors.

In a sixth aspect, the disclosure provides methods of reducing a bitter taste and/or enhancing a sweet taste of a flavored composition or a pharmaceutical composition, the method comprising introducing an amount (such as an effective amount) of one or more compounds of the first aspect (including any embodiments thereof) to the flavored composition or the pharmaceutical composition. In some embodiments, the disclosure provides methods of reducing a bitter taste of a flavored composition, the method comprising introducing an amount (such as an effective amount) of one or more compounds of the first aspect (including any embodiments thereof) to the flavored composition. In some such embodiments, the flavored composition if a food or beverage product. In some other embodiments, the disclosure provides methods of reducing a bitter taste of a pharmaceutical composition, the method comprising introducing an amount (such as an effective amount) of one or more compounds of the first aspect (including any embodiments thereof) to the pharmaceutical composition.

In a seventh aspect, the disclosure provides methods of antagonizing a human T2R receptor, the methods comprising contacting a human T2R receptor with one or more compounds of the first aspect (including any embodiments thereof). In some embodiments thereof, the method comprises contacting a human T2R54 receptor with one or more compounds of the first aspect (including any embodiments thereof). In some embodiments, the contacting comprises orally ingesting a composition comprising one or more compounds of the first aspect (including any embodiments thereof). In some such embodiments, composition is a flavored composition, such as a food or beverage product. In some other such embodiments, the composition is a pharmaceutical composition.

In an eighth aspect, the disclosure provides a composition comprising an amount of one or more compounds of the first aspect (including any embodiments thereof). In some embodiments, the composition comprises one or more bitter compounds and a bitter-reducing effective amount of one or more compounds of the first aspect (including any embodiments thereof). In some further embodiments, the composition is a pharmaceutical composition and the bitter compounds are one or more pharmaceutical compounds, such as active pharmaceutical ingredients (APIs). In some other embodiments, the composition is a flavored composition, such as a food or beverage product, and the bitter compounds are artificial sweeteners, caffeine, proteins (such as plant proteins), amino acids, compounds derived from natural plant extracts, and the like.

Further aspects, and embodiments thereof, are set forth below in the Detailed Description, the Drawings, the Abstract, and the Claims.

BRIEF DESCRIPTION OF THE DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

DETAILED DESCRIPTION

Figure 1:
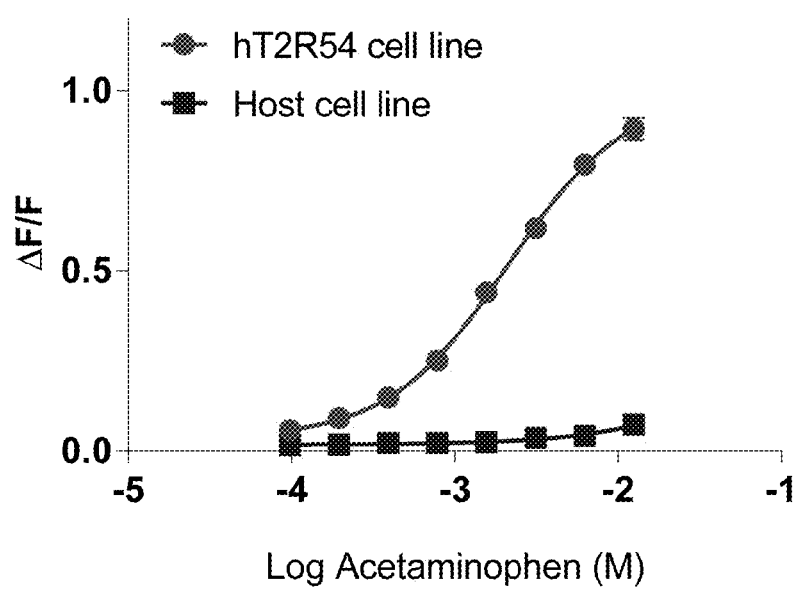
FIG. 1 shows a graph of a dose-response of acetaminophen on an hT2R54-expressing cell line and the host cell line (not expressing the bitter taste receptor).

The following Detailed Description sets forth various aspects and embodiments provided herein. The description is to be read from the perspective of the person of ordinary skill in the relevant art. Therefore, information that is well known to such ordinarily skilled artisans is not necessarily included.

Definitions

The following terms and phrases have the meanings indicated below, unless otherwise provided herein. This disclosure may employ other terms and phrases not expressly defined herein. Such other terms and phrases have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary As used herein, "solvate" means a compound formed by the interaction of one or more solvent molecules and one or more compounds described herein. In some embodiments, the solvates are physiologically acceptable solvates, such as hydrates.

As used herein, "Ca to C" or "Ca-b" in which "a" and "b" are integers, refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

As used herein, "halogen" or "halo" means any one of the radio-stable atoms of column 7 of the Periodic Table of the Elements, such as fluorine, chlorine, bromine, or iodine. In some embodiments, "halogen" or "halo" refer to fluorine or chlorine.

As used herein, "alkyl" means a straight or branched hydrocarbon chain that is fully saturated (i.e., contains no double or triple bonds). In some embodiments, an alkyl group has 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like. Unless indicated to the contrary, the term "alkyl" refers to a group that is not further substituted.

As used herein, "substituted alkyl" means an alkyl group substituted with one or more substituents independently selected from $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, aryloxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclyloxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), amino, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O).

As used herein, "alkoxy" means a moiety of the formula —OR wherein R is an alkyl, as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" means a moiety of the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" means a straight or branched hydrocarbon chain containing one or more double bonds. In some embodiments, the alkenyl group has from 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like. Unless indicated to the contrary, the term "alkenyl" refers to a group that is not further substituted.

As used herein, "alkynyl" means a straight or branched hydrocarbon chain containing one or more triple bonds. In some embodiments, the alkynyl group has from 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like. Unless indicated to the contrary, the term "alkynyl" refers to a group that is not further substituted.

As used herein, "heteroalkyl" means a straight or branched hydrocarbon chain containing one or more heteroatoms, that is, an element other than carbon, including but not limited to, nitrogen, oxygen, and sulfur, in the chain backbone. In some embodiments, the heteroalkyl group has from 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain. Unless indicated to the contrary, the term "heteroalkyl" refers to a group that is not further substituted.

As used herein, "alkylene" means a branched or straight chain fully saturated di-radical chemical group containing only carbon and hydrogen that is attached to the rest of the molecule via two points of attachment (i.e., an alkanediyl). In some embodiments, the alkylene group has from 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene. Unless indicated to the contrary, the term "alkylene" refers to a group that is not further substituted.

As used herein, "alkenylene" means a straight or branched chain di-radical chemical group containing only carbon and hydrogen and containing at least one carbon-carbon double bond that is attached to the rest of the molecule via two points of attachment. In some embodiments, the alkenylene group has from 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl. Unless indicated to the contrary, the term "alkenylene" refers to a group that is not further substituted.

As used herein, "aromatic" means a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" means an aromatic ring or ring system (i.e., two or more fused rings that share two adjacent carbon atoms) containing only carbon in the ring backbone. When the aryl is a ring system, every ring in the system is aromatic. In some embodiments, the aryl group has from 6 to 18 carbon atoms, although the present definition also covers the occurrence of the term "aryl" where no numerical range is designated. In some embodiments, the aryl group has from 6 to 10 carbon atoms. The aryl group may be designated as "$C_{6-10}$ aryl," "$C_6$-$C_{10}$ aryl," or similar designations. Examples of aryl groups include, but are not limited to, phenyl, naphthyl, azulenyl, and anthracenyl. In some embodiments, the term "aryl" refers to phenyl. Unless indicated to the contrary, the term "aryl" refers to a group that is not further substituted As used herein, "aryloxy" and "arylthio" mean moieties of the formulas RO— and RS—, respectively, in which R is an aryl as is defined above, such as "$C_{6-10}$ aryloxy" or "$C_{6-10}$ arylthio" and the like, including but not limited to phenyloxy and phenylthio.

As used herein "aralkyl" or "arylalkyl" means an aryl group connected, as a substituent, via an alkylene group, such as "$C_{7-14}$ aralkyl" and the like, including, but not limited to, benzyl, 2-phenylethyl, 3-phenylpropyl, and the like. In some embodiments, the alkylene group is a lower alkylene group (i.e., a $C_{1-4}$ alkylene group).

As used herein, "heteroaryl" means an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. In some embodiments, the heteroaryl group has from 5 to 18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has from 5 to 10 ring members or from 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinolinyl, benzimidazolyl, benzoxazolyl, benzothiazolyl, indolyl, isoindolyl, and benzothienyl. Unless indicated to the contrary, the term "heteroaryl" refers to a group that is not further substituted.

As used herein, "heteroaralkyl" or "heteroarylalkyl" means heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. In some embodiments, the carbocyclyl group has from 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl. Unless indicated to the contrary, the term "carbocyclyl" refers to a group that is not further substituted As used herein, "(carbocyclyl)alkyl" means a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system, according to any of the embodiments set forth above for carbocyclyl. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic, and according to any of the embodiments set forth above for carbocyclyl. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom (s) may be present in either a non-aromatic or aromatic ring in the ring system. In some embodiments, the heterocyclyl group has from 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidinonyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, "(heterocyclyl)alkyl" means a heterocyclyl group connected, as a substituent, via an alkylene group. Examples include, but are not limited to, imidazolinylmethyl and indolinylethyl.

An "acyl" group refers to a —C(═O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. Non-limiting examples include formyl, acetyl, propanoyl, benzoyl, and acryl.

An "O-carboxy" group refers to a "—OC(═O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "C-carboxy" group refers to a "—C(═O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. A non-limiting example includes carboxyl (i.e., —C(═O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(═O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-sulfonamido" group refers to a "—N(R$_A$)SO$_2$R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-carbamyl" group refers to an "—N(R$_A$)C(=O) OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "O-thiocarbamyl" group refers to a "—OC(=S) NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-thiocarbamyl" group refers to an "—N(R$_A$)C(=S) OR$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. A non-limiting example includes free amino (i.e., —NH$_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclyloxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), sulfhydryl (mercapto), halo($C_1$-$C_6$)alkyl (e.g., —CF$_3$), halo($C_1$-$C_6$)alkoxy (e.g., —OCF$_3$), $C_1$-$C_6$ alkylthio, arylthio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

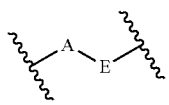

includes the substituent being oriented such that the A is attached at the leftmost attachment point of the molecule as well as the case in which A is attached at the rightmost attachment point of the molecule.

A "sweetener", "sweet flavoring agent", "sweet flavor entity", or "sweet compound" herein refers to a compound or ingestibly acceptable salt thereof that elicits a detectable sweet flavor in a subject, e.g., a compound that activates a T1R2/T1R3 receptor in vitro.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "optionally" means that the subsequently described event(s) may or may not occur. In some embodiments, the optional event does not occur. In some other embodiments, the optional event does occur one or more times.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, certain monovalent or polyvalent groups having only a single atom may be referred to by the name of the atom. For example, in some instances, the substituent "—H" may be referred to as "hydrogen" or "a hydrogen atom," or the substituent "—F" may be referred to as "fluorine" or "a fluorine atom."

Points of attachment for groups are generally indicated by a terminal dash (—) or by an asterisk (*). For example, a group such as *—CH$_2$—CH$_3$ or —CH$_2$—CH$_3$ both represent an ethyl group.

Other terms are defined in other portions of this description, even though not included in this subsection.

Antagonists of HT2R54 and SYNTHESIS

In a first aspect, the disclosure provides compounds of formula (I):

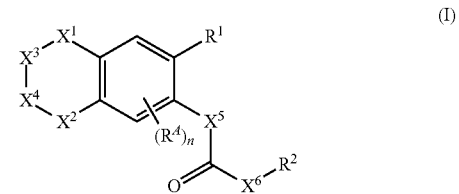

or a salt thereof, wherein:
$X^1$ and $X^2$ are each independently an oxygen atom or $>C(R^{2A})(R^{2B})$;
$X^3$ is a direct bond or $>C(R^{2C})(R^{2D})$;
$X^4$ is $>C(R^{2E})(R^{2F})$
$R^A$ is a halogen atom, —CN, nitro, —OH, —NH$_2$, —C(O)H, —O—C(O)H, —C(O)—OH, —NH—C(O)H, —C(O)—NH$_2$, —O—(C$_{1-6}$ alkyl), —NH—(C$_{1-6}$ alkyl), —N(C$_{1-6}$ alkyl)$_2$, —C(O)—(C$_{1-6}$ alkyl), —O—C(O)—(C$_{1-6}$ alkyl), —NH—C(O)—(C$_{1-6}$ alkyl), —N(C$_{1-6}$ alkyl)-C(O)—(C$_{1-6}$ alkyl), —C(O)—O—(C$_{1-6}$ alkyl), —C(O)—NH—(C$_{1-6}$ alkyl), —C(O)—N(C$_{1-6}$ alkyl)$_2$, —S(O)$_2$—(C$_{1-6}$ alkyl), —O—S(O)$_2$—(C$_{1-6}$ alkyl), —NH—S(O)$_2$—(C$_{1-6}$ alkyl), —N(C$_{1-6}$ alkyl)-S(O)$_2$—(C$_{1-6}$ alkyl), —S(O)$_2$—O—(C$_{1-6}$ alkyl), —S(O)$_2$—NH—(C$_{1-6}$ alkyl), —S(O)$_2$—N(C$_{1-6}$ alkyl)$_2$, C$_{3-10}$ cycloalkyl, C$_{2-14}$ heterocyclyl, C$_{6-14}$ aryl, or C$_{2-14}$ heteroaryl, C$_{1-6}$ alkyl, C$_{2-6}$ alkenyl, C$_{1-6}$ haloalkyl, C$_{2-6}$ haloalkenyl, C$_{1-6}$ haloalkoxy, C$_{2-6}$ haloalkenyloxy, or (C$_{1-6}$ alkoxy)-C$_{1-6}$ alkyl;
$R^1$ is a halogen atom, —C(O)—R$^{1A}$, —C(O)—O—R$^{1A}$, —O—R$^{1A}$, —O—C(O)—R$^{1A}$, or C$_{1-6}$ alkyl, where the alkyl group is optionally substituted one or more times by substituents selected independently from the group consisting of R$^{1Y}$;
$R^{1A}$ is a hydrogen atom or C$_{1-6}$ alkyl, wherein the alkyl group is optionally substituted one or more times by substituents selected independently from the group consisting of R$^{1Y}$;
$R^{1Y}$ is a halogen atom, oxo, —CN, nitro, —OH, —NH$_2$, —C(O)H, —O—C(O)H, —C(O)—OH, —NH—C(O)H, —C(O)—NH$_2$, —O—(C$_{1-6}$ alkyl), —NH—(C$_{1-6}$ alkyl), —N(C$_{1-6}$ alkyl)$_2$, —C(O)—(C$_{1-6}$ alkyl), —O—C(O)—(C$_{1-6}$ alkyl), —NH—C(O)—(C$_{1-6}$ alkyl), —C(O)—O—(C$_{1-6}$ alkyl), —C(O)—NH—(C$_{1-6}$ alkyl), —C(O)—N(C$_{1-6}$ alkyl)$_2$, —S(O)$_2$—(C$_{1-6}$ alkyl), —O—S(O)$_2$—(C$_{1-6}$ alkyl), —NH—S(O)$_2$—(C$_{1-6}$ alkyl), —S(O)$_2$—O—(C$_{1-6}$ alkyl), —S(O)$_2$—NH—(C$_{1-6}$ alkyl), —S(O)$_2$—N(C$_{1-6}$ alkyl)$_2$, C$_{3-10}$ cycloalkyl, C$_{2-14}$ heterocyclyl, C$_{6-14}$ aryl, or C$_{2-14}$ heteroaryl, C$_{1-6}$ alkyl, C$_{2-6}$ alkenyl, C$_{1-6}$ haloalkyl, C$_{2-6}$ haloalkenyl, C$_{1-6}$ haloalkoxy, C$_{2-6}$ haloalkenyloxy, and (C$_{1-6}$ alkoxy)-C$_{1-6}$ alkyl;
$R^{1Z}$ is a halogen atom, oxo, —CN, nitro, —OH, —NH$_2$, —C(O)H, —O—C(O)H, —C(O)—OH, —NH—C(O)H, —C(O)—NH$_2$, —O—(C$_{1-6}$ alkyl), —NH—(C$_{1-6}$ alkyl), —N(C$_{1-6}$ alkyl)$_2$, —C(O)—(C$_{1-6}$ alkyl), —O—C(O)—(C$_{1-6}$ alkyl), —NH—C(O)—(C$_{1-6}$ alkyl), —C(O)—O—(C$_{1-6}$ alkyl), —C(O)—NH—(C$_{1-6}$ alkyl), —C(O)—N(C$_{1-6}$ alkyl)$_2$, —S(O)$_2$—(C$_{1-6}$ alkyl), —O—S(O)$_2$—(C$_{1-6}$ alkyl), —NH—S(O)$_2$—(C$_{1-6}$ alkyl), —S(O)$_2$—O—(C$_{1-6}$ alkyl), —S(O)$_2$—NH—(C$_{1-6}$ alkyl), —S(O)$_2$—N(C$_{1-6}$ alkyl)$_2$, C$_{3-10}$ cycloalkyl, C$_{2-14}$ heterocyclyl, C$_{6-14}$ aryl, or C$_{2-14}$ heteroaryl, $C_{1-6}$ alkyl, $C_{2-6}$ alkenyl, $C_{1-6}$ haloalkyl, $C_{2-6}$ haloalkenyl, $C_{1-6}$ haloalkoxy, $C_{2-6}$ haloalkenyloxy, $(C_{1-6}$ alkoxy)-$C_{1-6}$ alkyl, $C_{1-6}$ alkyl, and $C_{2-6}$ alkenyl;

$R^2$ is $-N(R^5)(R^6)$; or $R^2$ is

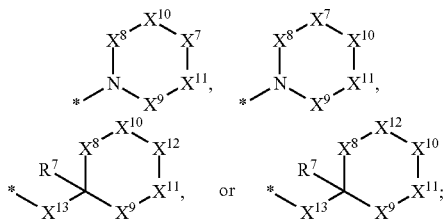

or $R^2$ is a hydrogen atom, a halogen atom, $C_{3-10}$ cycloalkyl, $C_{2-14}$ heterocyclyl, $C_{6-14}$ aryl, or $C_{2-14}$ heteroaryl, wherein the carbocyclyl, heterocyclyl, aryl, and heteroaryl are each optionally substituted one or more times by substituents selected independently from the group consisting of $R^{1Z}$;

$X^5$ is $>NR^{2G}$;

$X^6$ is $C_{1-6}$ alkylene, which is optionally substituted one or more times by substituents selected independently from the group consisting of $R^{1Y}$; or $X^7$ is an oxygen atom, a sulfur atom, $>N-R^{2L}$, or $>C(R^{2J})(R^{2K})$;

$X^8$, $X^9$, $X^{10}$, and $X^{11}$ are each independently a direct bond, an oxygen atom, a sulfur atom, or $>C(R^{2M})(R^{2N})$, wherein no more than one of $X^8$, $X^9$, $X^{10}$, and $X^{11}$ is a direct bond, and wherein no more than one of $X^8$, $X^9$, $X^{10}$, and $X^{11}$ is an oxygen atom or a sulfur atom;

$X^{12}$ is an oxygen atom, a sulfur atom, or $>N-R^{2L}$;

$X^{13}$ is a direct bond or $>NR^2$;

$R^{2A}$, $R^{2B}$, $R^{2C}$, $R^{2D}$, $R^{2E}$, $R^{2F}$, $R^{2K}$, $R^{2M}$, and $R^{2N}$ are each independently a hydrogen atom, a halogen atom, $-CN$, nitro, $-OH$, $-NH_2$, $-C(O)H$, $-O-C(O)H$, $-C(O)-OH$, $-NH-C(O)H$, $-C(O)-NH_2$, $-O-(C_{1-6}$ alkyl), $-NH-(C_{1-6}$ alkyl), $-N(C_{1-6}$ alkyl)$_2$, $-C(O)-(C_{1-6}$ alkyl), $-O-C(O)-(C_{1-6}$ alkyl), $-NH-C(O)-(C_{1-6}$ alkyl), $-NH-C(O)-O-(C_{1-6}$ alkyl), $-C(O)-O-(C_{1-6}$ alkyl), $-C(O)-NH-(C_{1-6}$ alkyl), $-C(O)-N(C_{1-6}$ alkyl)$_2$, $-S(O)_2-(C_{1-6}$ alkyl), $-O-S(O)_2-(C_{1-6}$ alkyl), $-NH-S(O)_2-(C_{1-6}$ alkyl), $-S(O)_2-O-(C_{1-6}$ alkyl), $-S(O)_2-NH-(C_{1-6}$ alkyl), $-S(O)_2-N(C_{1-6}$ alkyl)$_2$, $C_{3-10}$ cycloalkyl, $C_{2-14}$ heterocyclyl, $C_{6-14}$ aryl, or $C_{2-14}$ heteroaryl, $C_{1-6}$ alkyl, $C_{2-6}$ alkenyl, $C_{1-6}$ haloalkyl, $C_{2-6}$ haloalkenyl, $C_{1-6}$ haloalkoxy, $C_{2-6}$ haloalkenyloxy, $(C_{1-6}$ alkoxy)-$C_{1-6}$ alkyl; or $R^{2A}$ and $R^{2B}$, or $R^{2C}$ and $R^{2D}$, or $R^{2E}$ and $R^{2F}$, or $R^{2M}$ and $R^{2N}$ optionally combine to form an oxo group; or any two of $R^{2M}$ and $R^{2N}$ attached to adjacent carbon atoms optionally combine to form a fused ring selected from the group consisting of phenyl, $C_{2-5}$ heteroaryl, $C_{4-8}$ cycloalkyl, and $C_{2-5}$ heterocyclyl, wherein each of the fused rings is optionally substituted one or more times by substituents selected independently from $R^{1Z}$;

$R^{2G}$ and $R^{2P}$ are each independently a hydrogen atom, $C_{1-6}$ alkyl, $C_{1-6}$ haloalkyl, or $(C_{1-6}$ alkoxy)-$C_{1-6}$ alkyl;

$R^{2J}$ is $-R^4$ or $-X^{14}-R^4$;

$R^{2L}$ is $-C(O)-R^3$, $-C(O)-X^{14}-R^4$, $-C(S)-R^3$, $-C(S)-X^{14}-R^4$, $-S(O)_2-R^3$, $-S(O)_2-X^{14}-R^4$, or $-X^{14}-R^4$;

$X^{14}$ is $C_{1-8}$ alkylene, which is optionally substituted by one or more times by substituents selected independently from the group consisting of $R^{1Y}$;

$R^3$ is a hydrogen atom, $-OH$, $-NH_2$, $-O-R^{3B}$, $-NH-R^{3B}$, $-N(R^{3B})(R^{3C})$, $-O-C(O)-R^{3B}$, $-NH-C(O)-R^{3B}$, $-N(R^{3C})-C(O)-R^{3B}$, $C_{3-10}$ carbocyclyl, $C_{2-14}$ heterocyclyl, $C_{6-14}$ aryl, and $C_{2-14}$ heteroaryl, wherein the carbocyclyl, heterocyclyl, aryl, and heteroaryl are each optionally substituted one or more times by substituents selected independently from $R^{3A}$, wherein any two $R^{3A}$ attached to adjacent carbon atoms optionally combine to form a fused ring selected from the group consisting of phenyl, $C_{2-5}$ heteroaryl, $C_{4-8}$ cycloalkyl, and $C_{2-5}$ heterocyclyl, wherein each of the fused rings is optionally substituted one or more times by substituents selected independently from $R^{1Z}$, and wherein, when $R^{3B}$ and $R^{3C}$ are attached to the same nitrogen atom, $R^{3B}$ and $R^{3C}$ optionally combine with the nitrogen atom to which they are attached to form a nitrogen-containing $C_{2-6}$ heterocyclic ring, which is optionally substituted by $C_{1-4}$ alkyl;

$R^{3A}$ is a halogen atom, $-CN$, nitro, oxo, $-OH$, $-NH_2$, $-C(O)H$, $-O-C(O)H$, $-C(O)-OH$, $-NH-C(O)H$, $-C(O)-NH_2$, $-O-R^{3D}$, $-NH-R^{3D}$, $-N(R^{3D})(R^{3E})$, $-C(O)-R^{3D}$, $-O-C(O)-R^{3D}$, $-NH-C(O)-R^{3D}$, $-C(O)-O-R^{3D}$, $-C(O)-NH-R^{3D}$, $-C(O)-N(R^{3D})(R^{3E})$, $-S(O)_2-R^{3D}$, $-O-S(O)_2-R^{3D}$, $-NH-S(O)_2-R^{3D}$, $-S(O)_2-O-R^{3D}$, $-S(O)_2-NH-R^{3D}$, $-S(O)_2-N(R^{3D})(R^{3E})$, $C_{1-8}$ alkyl, $C_{2-8}$ alkenyl, $C_{3-10}$ carbocyclyl, $C_{2-14}$ heterocyclyl, $C_{6-14}$ aryl, and $C_{2-14}$ heteroaryl, wherein the alkyl and alkenyl are each optionally substituted one or more times by substituents selected independently from the group consisting of $R^{3Y}$, and wherein the carbocyclyl, heterocyclyl, aryl, and heteroaryl are each optionally substituted one or more times by substituents selected independently from the group consisting of $R^{3Z}$;

$R^{3B}$, $R^{3C}$, $R^{3D}$, and $R^{3E}$ are each independently $C_{1-8}$ alkyl, $C_{2-8}$ alkenyl, $C_{3-10}$ carbocyclyl, $C_{2-14}$ heterocyclyl, $C_{6-14}$ aryl, or $C_{2-14}$ heteroaryl, wherein the alkyl and alkenyl are each optionally substituted one or more times by substituents selected independently from the group consisting of $R^{3Y}$, and wherein the carbocyclyl, heterocyclyl, aryl, and heteroaryl are each optionally substituted one or more times by substituents selected independently from the group consisting of $R^{3Z}$;

$R^{3Y}$ is a halogen atom, $-CN$, nitro, oxo, $-OH$, $-NH_2$, $-C(O)H$, $-O-C(O)H$, $-C(O)-OH$, $-NH-C(O)H$, $-C(O)-NH_2$, $-O-(C_{1-6}$ alkyl), $-NH-(C_{1-6}$ alkyl), $-N(C_{1-6}$ alkyl)$_2$, $-C(O)-(C_{1-6}$ alkyl), $-O-C(O)-(C_{1-6}$ alkyl), $-NH-C(O)-(C_{1-6}$ alkyl), $-N(C_{1-6}$ alkyl)-C(O)-(C_{1-6}$ alkyl), $-C(O)-O-(C_{1-6}$ alkyl), $-C(O)-NH-(C_{1-6}$ alkyl), $-C(O)-N(C_{1-6}$ alkyl)$_2$, $-S(O)_2-(C_{1-6}$ alkyl), $-O-S(O)_2-(C_{1-6}$ alkyl), $-NH-S(O)_2-(C_{1-6}$ alkyl), $-N(C_{1-6}$ alkyl)-S(O)_2-(C_{1-6}$ alkyl), $-S(O)_2-O-(C_{1-6}$ alkyl), $-S(O)_2-NH-(C_{1-6}$ alkyl), $-S(O)_2-N(C_{1-6}$ alkyl)$_2$, $-O-(C_{1-6}$ alkylene)-O-(C_{1-6}$ alkyl), $C_{3-10}$ cycloalkyl, $C_{2-14}$ heterocyclyl, $C_{6-14}$ aryl, and $C_{2-14}$ heteroaryl, wherein the cycloalkyl, heterocyclyl, aryl, and heteroaryl groups are each optionally substituted one or more times by substituents selected independently from the group consisting of $R^{1Z}$;

$R^{3Z}$ is a halogen atom, $-CN$, nitro, oxo, $-OH$, $-NH_2$, $-C(O)H$, $-O-C(O)H$, $-C(O)-OH$, $-NH-C(O)H$, $-C(O)-NH_2$, $-O-(C_{1-6}$ alkyl), $-NH-(C_{1-6}$ alkyl), $-N(C_{1-6}$ alkyl)$_2$, $-C(O)-(C_{1-6}$ alkyl), —O—C(O)—($C_{1-6}$ alkyl), —NH—C(O)—($C_{1-6}$ alkyl), —N($C_{1-6}$ alkyl)-C(O)—($C_{1-6}$ alkyl), —C(O)—O—($C_{1-6}$ alkyl), —C(O)—NH—($C_{1-6}$ alkyl), —C(O)—N($C_{1-6}$ alkyl)$_2$, —S(O)$_2$—($C_{1-6}$ alkyl), —O—S(O)$_2$—($C_{1-6}$ alkyl), —NH—S(O)$_2$—($C_{1-6}$ alkyl), —N($C_{1-6}$ alkyl)-S(O)$_2$—($C_{1-6}$ alkyl), —S(O)$_2$—O—($C_{1-6}$ alkyl), —S(O)$_2$—NH—($C_{1-6}$ alkyl), —S(O)$_2$—N($C_{1-6}$ alkyl)$_2$, $C_{1-6}$ alkyl, $C_{2-6}$ alkenyl, $C_{1-6}$ haloalkyl, $C_{2-6}$ haloalkenyl, $C_{1-6}$ haloalkoxy, $C_{2-6}$ haloalkenyloxy, ($C_{1-6}$ alkoxy)-$C_{1-6}$ alkyl, $C_{3-10}$ cycloalkyl, $C_{2-14}$ heterocyclyl, $C_{6-14}$ aryl, and $C_{2-14}$ heteroaryl, wherein the cycloalkyl, heterocyclyl, aryl, and heteroaryl groups are each optionally substituted one or more times by substituents selected independently from the group consisting of $R^{1Z}$;

$R^4$ is a hydrogen atom, a halogen atom, —CN, nitro, oxo, —OH, —NH$_2$, —O—$R^{4B}$, —NH—$R^{4B}$, —N($R^{4B}$)($R^{4C}$), C(O)—$R^{4B}$, —O—C(O)—$R^{4B}$, —NH—C(O)—$R^{4B}$, —N($R^{4C}$)—C(O)—$R^{4B}$, —C(O)—O—$R^{4B}$, —C(O)—NH—$R^{4B}$, —C(O)N($R^{4B}$)($R^{4C}$), —S(O)$_2$—$R^{4D}$, —O—S(O)$_2$—$R^{4D}$, —NH—S(O)$_2$—$R^{4D}$, —S(O)$_2$—O—$R^{4D}$, —S(O)$_2$—NH—$R^{4D}$, —S(O)$_2$—N($R^{4D}$)($R^{4E}$), $C_{3-10}$ carbocyclyl, $C_{2-14}$ heterocyclyl, $C_{6-14}$ aryl, and $C_{2-14}$ heteroaryl, wherein the carbocyclyl, heterocyclyl, aryl, and heteroaryl are each optionally substituted one or more times by substituents selected independently from $R^{4A}$, wherein any two $R^{4A}$ attached to adjacent carbon atoms optionally combine to form a fused ring selected from the group consisting of phenyl, $C_{2-5}$ heteroaryl, $C_{4-8}$ cycloalkyl, and $C_{2-5}$ heterocyclyl, wherein each of the fused rings is optionally substituted one or more times by substituents selected independently from $R^{1Z}$, and wherein, when $R^{4B}$ and $R^{4C}$ are attached to the same nitrogen atom, $R^{4B}$ and $R^{4C}$ optionally combine with the nitrogen atom to which they are attached to form a nitrogen-containing $C_{2-6}$ heterocyclic ring, which is optionally substituted by $C_{1-4}$ alkyl;

$R^{4A}$ is a halogen atom, —CN, nitro, oxo, —OH, —NH$_2$, —C(O)H, —O—C(O)H, —C(O)—OH, —NH—C(O)H, —C(O)—NH$_2$, —O—$R^{4D}$, —NH—$R^{4D}$, —N($R^{4D}$)($R^{4E}$), —C(O)—$R^{4D}$, —O—C(O)—$R^{4D}$, —NH—C(O)—$R^{4D}$, —N($R^{4E}$)—C(O)—$R^{4D}$, —C(O)—O—$R^{4D}$, —C(O)—NH—$R^{4D}$, —C(O)—N($R^{4D}$)($R^{4E}$), $C_{1-8}$ alkyl, $C_{2-8}$ alkenyl, $C_{3-10}$ carbocyclyl, $C_{2-14}$ heterocyclyl, $C_{6-14}$ aryl, and $C_{2-14}$ heteroaryl, wherein the alkyl and alkenyl are each optionally substituted one or more times by substituents selected independently from the group consisting of $R^{4Y}$, and wherein the carbocyclyl, heterocyclyl, aryl, and heteroaryl are each optionally substituted one or more times by substituents selected independently from $R^{4Z}$;

$R^{4B}$, $R^{4C}$, $R^{4D}$, and $R^{4E}$ are each independently $C_{1-8}$ alkyl, $C_{2-8}$ alkenyl, $C_{3-10}$ carbocyclyl, $C_{2-14}$ heterocyclyl, $C_{6-14}$ aryl, and $C_{2-14}$ heteroaryl, wherein the alkyl and alkenyl are each optionally substituted one or more times by substituents selected independently from $R^{4Y}$, and wherein the carbocyclyl, heterocyclyl, aryl, and heteroaryl are each optionally substituted one or more times by substituents selected independently from $R^{4Z}$;

$R^{4Y}$ is a halogen atom, —CN, nitro, oxo, —OH, —NH$_2$, —C(O)H, —O—C(O)H, —C(O)—OH, —NH—C(O)H, —C(O)—NH$_2$, —O—($C_{1-6}$ alkyl), —NH—($C_{1-6}$ alkyl), —N($C_{1-6}$ alkyl)$_2$, —C(O)—($C_{1-6}$ alkyl), —O—C(O)—($C_{1-6}$ alkyl), —NH—C(O)—($C_{1-6}$ alkyl), —N($C_{1-6}$ alkyl)-C(O)—($C_{1-6}$ alkyl), —C(O)—O—($C_{1-6}$ alkyl), —C(O)—NH—($C_{1-6}$ alkyl), —C(O)—N($C_{1-6}$ alkyl)$_2$, —S(O)$_2$—($C_{1-6}$ alkyl), —O—S(O)$_2$—($C_{1-6}$ alkyl), —NH—S(O)$_2$—($C_{1-6}$ alkyl), —N($C_{1-6}$ alkyl)-S(O)$_2$—($C_{1-6}$ alkyl), —S(O)$_2$—O—($C_{1-6}$ alkyl), —S(O)$_2$—NH—($C_{1-6}$ alkyl), —S(O)$_2$—N($C_{1-6}$ alkyl)$_2$, —O—($C_{1-6}$ alkylene)-O—($C_{1-6}$ alkyl), $C_{3-10}$ cycloalkyl, $C_{2-14}$ heterocyclyl, $C_{6-14}$ aryl, and $C_{2-14}$ heteroaryl, wherein the cycloalkyl, heterocyclyl, aryl, and heteroaryl groups are each optionally substituted one or more times by substituents selected independently from the group consisting of $R^{1Z}$;

$R^{4Z}$ is a halogen atom, —CN, nitro, oxo, —OH, —NH$_2$, —C(O)H, —O—C(O)H, —C(O)—OH, —NH—C(O)H, —C(O)—NH$_2$, —O—($C_{1-6}$ alkyl), —NH—($C_{1-6}$ alkyl), —N($C_{1-6}$ alkyl)$_2$, —C(O)—($C_{1-6}$ alkyl), —O—C(O)—($C_{1-6}$ alkyl), —NH—C(O)—($C_{1-6}$ alkyl), —N($C_{1-6}$ alkyl)-C(O)—($C_{1-6}$ alkyl), —C(O)—O—($C_{1-6}$ alkyl), —C(O)—NH—($C_{1-6}$ alkyl), —C(O)—N($C_{1-6}$ alkyl)$_2$, —S(O)$_2$—($C_{1-6}$ alkyl), —O—S(O)$_2$—($C_{1-6}$ alkyl), —NH—S(O)$_2$—($C_{1-6}$ alkyl), —N($C_{1-6}$ alkyl)-S(O)$_2$—($C_{1-6}$ alkyl), —S(O)$_2$—O—($C_{1-6}$ alkyl), —S(O)$_2$—NH—($C_{1-6}$ alkyl), —S(O)$_2$—N($C_{1-6}$ alkyl)$_2$, ($C_{1-6}$ alkoxy)-$C_{1-6}$ alkyl, $C_{3-10}$ cycloalkyl, $C_{2-14}$ heterocyclyl, $C_{6-14}$ aryl, or $C_{2-14}$ heteroaryl, $C_{1-6}$ alkyl, $C_{2-6}$ alkenyl, $C_{1-6}$ haloalkyl, $C_{2-6}$ haloalkenyl, $C_{1-6}$ haloalkoxy, and $C_{2-6}$ haloalkenyloxy, wherein the cycloalkyl, heterocyclyl, aryl, and heteroaryl groups are each optionally substituted one or more times by substituents selected independently from the group consisting of $R^{1Z}$;

$R^5$ is —C(O)—$R^3$, —C(O)—$X^{14}$—$R^4$, —C(S)—$R^3$, —C(S)—$X^{14}$—$R^4$, —S(O)$_2$—$R^3$, —S(O)$_2$—$X^{14}$—$R^4$, or —$X^{14}$—$R^4$;

$R^6$ is a hydrogen atom or $C_{1-8}$ alkyl, wherein the alkyl is optionally substituted one or more times by substituents selected independently from the group consisting of $R^{6Y}$;

$R^{6Y}$ is a halogen atom, —CN, nitro, oxo, —OH, —NH$_2$, —C(O)H, —O—C(O)H, —C(O)—OH, —NH—C(O)H, —C(O)—NH$_2$, —O—($C_{1-6}$ alkyl), —NH—($C_{1-6}$ alkyl), —N($C_{1-6}$ alkyl)$_2$, —C(O)—($C_{1-6}$ alkyl), —O—C(O)—($C_{1-6}$ alkyl), —NH—C(O)—($C_{1-6}$ alkyl), —N($C_{1-6}$ alkyl)-C(O)—($C_{1-6}$ alkyl), —C(O)—O—($C_{1-6}$ alkyl), —C(O)—NH—($C_{1-6}$ alkyl), —C(O)—N($C_{1-6}$ alkyl)$_2$, —S(O)$_2$—($C_{1-6}$ alkyl), —O—S(O)$_2$—($C_{1-6}$ alkyl), —NH—S(O)$_2$—($C_{1-6}$ alkyl), —N($C_{1-6}$ alkyl)-S(O)$_2$—($C_{1-6}$ alkyl), —S(O)$_2$—O—($C_{1-6}$ alkyl), —S(O)$_2$—NH—($C_{1-6}$ alkyl), —S(O)$_2$—N($C_{1-6}$ alkyl)$_2$, —O—($C_{1-6}$ alkylene)-O—($C_{1-6}$ alkyl), $C_{3-10}$ cycloalkyl, $C_{2-14}$ heterocyclyl, $C_{6-14}$ aryl, and $C_{2-14}$ heteroaryl, wherein the cycloalkyl, heterocyclyl, aryl, and heteroaryl groups are each optionally substituted one or more times by substituents selected independently from the group consisting of $R^{1Z}$;

$R^7$ is a hydrogen atom, a halogen atom, $C_{1-6}$ alkyl, $C_{1-6}$ haloalkyl, $C_{1-6}$ alkoxy, $C_{1-6}$ haloalkoxy, or ($C_{1-6}$ alkyl)-O—$C_{1-6}$ alkyl; and n is 0, 1, or 2.

Various subgenuses, and combinations thereof, of the genus set forth above are also contemplated as part of the present disclosure.

For example, in some embodiments of the foregoing, $X^1$ and $X^2$ are both an oxygen atom. In some other embodiments of the foregoing, $X^1$ and $X^2$ are both >C($R^{2A}$)($R^{2B}$). In some such embodiments, one of $R^{2A}$ and $R^{2B}$ is a hydrogen atom. In some further such embodiments, one of $R^{2A}$ and $R^{2B}$ is a hydrogen atom, and the other of $R^{2A}$ and $R^{2B}$ is a hydrogen atom, a halogen atom (such as a fluorine atom), $C_{1-6}$ alkyl, $C_{1-6}$ fluoroalkyl, $C_{1-6}$ alkoxy, $C_{1-6}$ fluoroalkoxy, or —C(O)—($C_{1-6}$ alkyl). In some further such embodiments, both $R^{2A}$ and $R^{2B}$ are a hydrogen atom, such that both $X^1$ and $X^2$ are >CH$_2$.

In some embodiments of any of the foregoing embodiments, $X^3$ is a direct bond, such that $X^1$ and $X^4$ connect directly to form a five-membered fused ring. In some other embodiments of any of the foregoing embodiments, $X^3$ is >C($R^{2C}$)($R^{2D}$). In some such embodiments, one of $R^{2C}$ and $R^{2D}$ is a hydrogen atom. In some further such embodiments, one of $R^{2C}$ and $R^{2D}$ is a hydrogen atom, and the other of $R^{2C}$ and $R^{2D}$ is a hydrogen atom, a halogen atom (such as a fluorine atom), $C_{1-6}$ alkyl, $C_{1-6}$ fluoroalkyl, $C_{1-6}$ alkoxy, $C_{1-6}$ fluoroalkoxy, or —C(O)—($C_{1-6}$ alkyl). In some further such embodiments, both $R^{2C}$ and $R^{2D}$ are a hydrogen atom, such that $X^3$ is >CH$_2$.

In some other embodiments of any of the foregoing embodiments, one of $R^{2E}$ and $R^{2F}$ is a hydrogen atom. In some further such embodiments, one of $R^{2E}$ and $R^{2F}$ is a hydrogen atom, and the other of $R^{2E}$ and $R^{2F}$ is a hydrogen atom, a halogen atom (such as a fluorine atom), $C_{1-6}$ alkyl, $C_{1-6}$ fluoroalkyl, $C_{1-6}$ alkoxy, $C_{1-6}$ fluoroalkoxy, or —C(O)—($C_{1-6}$ alkyl). In some further such embodiments, both $R^{2E}$ and $R^{2F}$ are a hydrogen atom, such that $X^4$ is >CH$_2$.

As indicated above, the phenyl portion of the fused ring system in formula (I) can optionally have one or two substituents, $R^A$. Thus, in some embodiments of any of the foregoing embodiments, n is 0. In some other embodiments of any of the foregoing embodiments, n is 1. In some other embodiments of any of the foregoing embodiments, n is 2.

The substituents, $R^A$, can have any suitable value as indicated above. In some embodiments of any of the foregoing embodiments, $R^A$ is a halogen atom, —OH, —O—($C_{1-6}$ alkyl), —NH—($C_{1-6}$ alkyl), —N($C_{1-6}$ alkyl)$_2$, —C(O)—($C_{1-6}$ alkyl), —C(O)—O—($C_{1-6}$ alkyl), $C_{1-6}$ alkyl, $C_{1-6}$ haloalkyl, $C_{1-6}$ haloalkoxy, or ($C_{1-6}$ alkoxy)-$C_{1-6}$ alkyl. In some further such embodiments, $R^A$ is a fluorine atom, a chlorine atom, methyl, ethyl, isopropyl, hydroxyl, methoxy, trifluoroalkyl, or trifluoromethoxy.

The substituent $R^1$ can have any suitable value as indicated above. In some embodiments of any of the foregoing embodiments, $R^1$ is a halogen atom, such as a fluorine atom or a chlorine atom. In some such embodiments, $R^1$ is a chlorine atom. In some other embodiments, of any of the foregoing embodiments, $R^1$ is —C(O)—$R^{14}$. In some other embodiments, of any of the foregoing embodiments, $R^1$ is —C(O)—O—$R^{14}$. In some other embodiments, of any of the foregoing embodiments, $R^1$ is —O—C(O)—$R^{14}$. In some other embodiments, $R^1$ is a halogen atom, —O—$R^{14}$. In any of the foregoing embodiments, $R^{14}$ is $C_{1-6}$ alkyl, such as methyl, ethyl, propyl, isopropyl, butyl, isobutyl, sec-butyl, tert-butyl, etc. In some further such embodiments, $R^{14}$ is methyl or ethyl. In some other embodiments, of any of the foregoing embodiments, $R^1$ is —C(O)—CH$_3$. In some other embodiments, of any of the foregoing embodiments, $R^1$ is —C(O)—O—CH$_3$. In some other embodiments, of any of the foregoing embodiments, $R^1$ is —O—C(O)—CH$_3$. In some other embodiments, $R^1$ is a halogen atom, —O—CH$_3$. In some other embodiments, of any of the foregoing embodiments, $R^1$ is $C_{1-6}$ alkyl, which is optionally substituted one or more times by substituents selected independently from the group consisting of $R^1$. In some further such embodiments, $R^1$ is methyl, ethyl, propyl, isopropyl, butyl, isobutyl, sec-butyl, tert-butyl, pentyl, or hexyl. In some further such embodiments, $R^1$ is methyl, ethyl, isopropyl, or propyl. In some even further such embodiments, $R^1$ is methyl or ethyl. In some even further such embodiments, $R^1$ is ethyl.

The variable $X^5$ can have any suitable value, as indicated above. In some embodiments of any of the foregoing embodiments, $X^5$ is >NR$^{2G}$, where $R^{2G}$ is a hydrogen atom or $C_{1-6}$ alkyl. In some further such embodiments, $R^{2G}$ is a hydrogen atom. In some other such embodiments, $R^{2G}$ is methyl or ethyl.

The variable $X^6$ can have any suitable value, as indicated above. In some embodiments of any of the foregoing embodiments, $X^6$ is —CH$_2$—. In some other embodiments of any of the foregoing embodiments, $X^6$ is —CH$_2$—CH$_2$—. In some other embodiments of any of the foregoing embodiments, $X^6$ is —CH(CH$_3$)—. In some other embodiments of any of the foregoing embodiments, $X^6$ is —C(CH$_3$)$_2$—.

In some embodiments of any of the foregoing embodiments, $R^2$ is —N($R^5$)($R^6$). In some further such embodiments, $R^6$ is a hydrogen atom. In some other such embodiments, $R^6$ is $C_{1-8}$ alkyl, which is optionally substituted one or more times by substituents selected independently from the group consisting of a halogen atom, —OH, —O—($C_{1-6}$ alkyl), —NH—($C_{1-6}$ alkyl), —N($C_{1-6}$ alkyl)$_2$, —C(O)—($C_{1-6}$ alkyl), —C(O)—O—($C_{1-6}$ alkyl), $C_{1-6}$ alkyl, $C_{1-6}$ haloalkyl, $C_{1-6}$ haloalkoxy, and ($C_{1-6}$ alkoxy)-$C_{1-6}$ alkyl. In some further such embodiments, $R^6$ is unsubstituted $C_{1-8}$ alkyl, such as methyl, ethyl, propyl, isopropyl, butyl, isobutyl, sec-butyl, tert-butyl, and the like. In some further embodiments, $R^6$ is methyl.

In some further embodiments of any of the foregoing embodiments, $R^5$ is —C(O)—$R^3$, —C(O)—$X^{14}$—$R^4$, or —$X^{14}$—$R^4$. In some further such embodiments, $R^5$ is —C(O)—$R^3$. In some further such embodiments, $R^3$ is not a hydrogen atom. In some other such embodiments, $R^5$ is —C(O)—$X^{14}$—$R^4$. In some further such embodiments, $R^4$ is not a hydrogen atom. In some other such embodiments, $R^5$ is —$X^{14}$—$R^4$. In some further such embodiments, $R^4$ is not a hydrogen atom. In some further embodiments of the embodiments set forth in this paragraph, $X^{14}$ is an unsubstituted, straight-chain $C_{1-4}$ alkylene group.

In some embodiments of any of the foregoing embodiments, $R^2$ is a moiety of either of the following formulas:

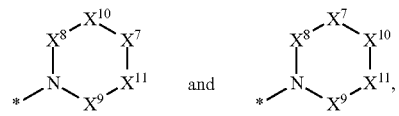

where the asterisk indicates the point of attachment of the ring to $X^6$. In some such embodiments, $R^2$ is a moiety of the first formula. In some other embodiments of the second formula.

In some further embodiments of the embodiments of the preceding paragraph, none of $X^8$, $X^9$, $X^{10}$, or $X^{11}$ is a direct bond. In some such embodiments, one of $X^8$, $X^9$, $X^{10}$, or $X^{11}$ is an oxygen atom or a sulfur atom. In some other such embodiments, none of $X^8$, $X^9$, $X^{10}$, or $X^{11}$ is an oxygen atom or a sulfur atom. In some embodiments of each of the foregoing embodiments, each $R^{2M}$ is a hydrogen atom. In some such embodiments, each $R^{2N}$ is a hydrogen atom, a halogen atom, —OH, —NH$_2$, —C(O)—OH, —C(O)—NH$_2$, —O—($C_{1-6}$ alkyl), —NH—($C_{1-6}$ alkyl), —N($C_{1-6}$ alkyl)$_2$, —C(O)—($C_{1-6}$ alkyl), —O—C(O)—($C_{1-6}$ alkyl), —NH—C(O)—($C_{1-6}$ alkyl), —NH—C(O)—O—($C_{1-6}$ alkyl), —C(O)—O—($C_{1-6}$ alkyl), —C(O)—NH—($C_{1-6}$ alkyl), —C(O)—N($C_{1-6}$ alkyl)$_2$, $C_{1-6}$ alkyl, $C_{1-6}$ haloalkyl, $C_{1-6}$ haloalkoxy, ($C_{1-6}$ alkoxy)-$C_{1-6}$ alkyl, phenyl, or $C_{2-5}$ heteroaryl, wherein the phenyl and heteroaryl groups are optionally substituted by substituents selected independently from the group consisting of $C_{1-4}$ alkyl and $C_{1-4}$ alkoxy. In some such embodiments, each $R^{2N}$ is a hydrogen atom.

In some embodiments of any of the foregoing embodiments, $X^7$ is an oxygen atom or a sulfur atom. In some such embodiments, $X^7$ is an oxygen atom. In some other such embodiments, $X^7$ is a sulfur atom.

In some embodiments of any of the foregoing embodiments, $X^7$ is >N—$R^{2L}$. In such embodiments, $R^{2L}$ can have any suitable value, according to those set forth above. In some embodiments, $R^{2L}$ is —C(O)—$R^3$. In some other embodiments, $R^{2L}$ is —C(O)—$X^{14}$—$R^4$. In some other embodiments, $R^{2L}$ is —C(S)—$R^3$. In some other embodiments, $R^{2L}$ is —C(S)—$X^{14}$—$R^4$. In some other embodiments, $R^{2L}$ is —S(O)$_2$—$R^3$. In some other embodiments, $R^{2L}$ is —S(O)$_2$—$X^{14}$—$R^4$. In some other embodiments, $R^{2L}$ is —$X^{14}$—$R^4$. In some further embodiments of any of the foregoing embodiments of this paragraph, $X^{14}$ is an unsubstituted $C_{1-8}$ alkylene group, such as a straight-chain unsubstituted $C_{1-4}$ alkylene group. In some further embodiments of any of the foregoing embodiments of this paragraph, $R^3$ is not a hydrogen atom. In some further embodiments of any of the foregoing embodiments of this paragraph, $R^4$ is not a hydrogen atom.

In some embodiments of any of the foregoing embodiments, $X^7$ is >C($R^{2J}$)($R^{2K}$). In such embodiments, $R^{2J}$ and $R^{2K}$ can have any suitable values, as set forth above. In some such embodiments, $R^{2K}$ is a hydrogen atom. In some other such embodiments, $R^{2K}$ is a $C_{1-6}$ alkyl group, such as methyl, ethyl, or isopropyl. In some further such embodiments, $R^{2K}$ is methyl. In some embodiments, $R^{2J}$ is —$R^4$. In some other embodiments, $R^{2J}$ is —$X^{14}$—$R^4$. In some further embodiments of any of the foregoing embodiments of this paragraph, $X^{14}$ is an unsubstituted $C_{1-8}$ alkylene group, such as a straight-chain unsubstituted $C_{1-4}$ alkylene group. In some further embodiments of any of the foregoing embodiments of this paragraph, $R^4$ is not a hydrogen atom.

In some embodiments of any of the foregoing embodiments, $R^2$ is a moiety of either of the following formulas:

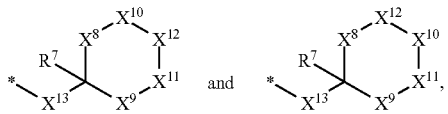

and where the asterisk indicates the point of attachment to $X^6$. In some such embodiments, $R^2$ is a moiety of the first formula. In some other embodiments of the second formula.

In some further embodiments of the embodiments of the preceding paragraph, none of $X^8$, $X^9$, $X^{10}$, or $X^{11}$ is a direct bond. In some such embodiments, one of $X^8$, $X^9$, $X^{10}$, or $X^{11}$ is an oxygen atom or a sulfur atom. In some other such embodiments, none of $X^8$, $X^9$, $X^{10}$, or $X^{11}$ is an oxygen atom or a sulfur atom. In some embodiments of each of the foregoing embodiments, each $R^{2M}$ is a hydrogen atom. In some such embodiments, each $R^{2N}$ is a hydrogen atom, a halogen atom, —OH, —NH$_2$, —C(O)—OH, —C(O)—NH$_2$, —O—($C_{1-6}$ alkyl), —NH—($C_{1-6}$ alkyl), —N($C_{1-6}$ alkyl)$_2$, —C(O)—($C_{1-6}$ alkyl), —O—C(O)—($C_{1-6}$ alkyl), —NH—C(O)—($C_{1-6}$ alkyl), —NH—C(O)—O—($C_{1-6}$ alkyl), —C(O)—O—($C_{1-6}$ alkyl), —C(O)—NH—($C_{1-6}$ alkyl), —C(O)—N($C_{1-6}$ alkyl)$_2$, $C_{1-6}$ alkyl, $C_{1-6}$ haloalkyl, $C_{1-6}$ haloalkoxy, ($C_{1-6}$ alkoxy)-$C_{1-6}$ alkyl, phenyl, or $C_{2-5}$ heteroaryl, wherein the phenyl and heteroaryl groups are optionally substituted by substituents selected independently from the group consisting of $C_{1-4}$ alkyl and $C_{1-4}$ alkoxy. In some such embodiments, each $R^{2N}$ is a hydrogen atom.

In some embodiments of any of the foregoing embodiments, $X^{12}$ is an oxygen atom or a sulfur atom. In some such embodiments, $X^{12}$ is an oxygen atom. In some other such embodiments, $X^{12}$ is a sulfur atom.

In some embodiments of any of the foregoing embodiments, $X^{12}$ is >N—$R^{2L}$. In such embodiments, $R^{2L}$ can have any suitable value, according to those set forth above. In some embodiments, $R^{2L}$ is —C(O)—$R^3$. In some other embodiments, $R^{2L}$ is —C(O)—$X^{14}$—$R^4$. In some other embodiments, $R^{2L}$ is —C(S)—$R^3$. In some other embodiments, $R^{2L}$ is —C(S)—$X^{14}$—$R^4$. In some other embodiments, $R^{2L}$ is —S(O)$_2$—$R^3$. In some other embodiments, $R^{2L}$ is —S(O)$_2$—$X^{14}$—$R^4$. In some other embodiments, $R^{2L}$ is —$X^{14}$—$R^4$. In some further embodiments of any of the foregoing embodiments of this paragraph, $X^{14}$ is an unsubstituted $C_{1-8}$ alkylene group, such as a straight-chain unsubstituted $C_{1-4}$ alkylene group. In some further embodiments of any of the foregoing embodiments of this paragraph, $R^3$ is not a hydrogen atom. In some further embodiments of any of the foregoing embodiments of this paragraph, $R^4$ is not a hydrogen atom.

The variable $X^{13}$ can have any suitable value, as indicated above. In some embodiments, $X^{13}$ is a direct bond, which means that the carbon atom of the ring bonds directly to $X^6$. In some other embodiments, $X^{13}$ is >N$R^{2P}$. The variable $R^{2P}$ can have any suitable value, as indicated above. In some embodiments, $R^{2P}$ is a hydrogen atom. In some other embodiments, $R^{2P}$ is $C_{1-6}$ alkyl, such as methyl, ethyl, or isopropyl. In some further such embodiments, $R^{2P}$ is methyl or ethyl.

The variable $R^7$ can have any suitable value, as indicated above. In some embodiments, $R^7$ is a hydrogen atom. In some other embodiments, $R^7$ is a halogen atom, $C_{1-6}$ alkyl, $C_{1-6}$ haloalkyl, $C_{1-6}$ alkoxy, $C_{1-6}$ haloalkoxy, or ($C_{1-6}$ alkyl)-O—$C_{1-6}$ alkyl. In some further embodiments, $R^7$ is methyl, trifluoromethyl, methoxy, trifluoromethoxy, 2-methoxyethyl, or methoxymethyl.

In some embodiments, the compound is any compound whose structure is set forth in any of Tables 2-9, or a salt thereof.

In some further embodiments of any of the foregoing embodiments, the salt is a comestibly acceptable salt. In some other embodiments of any of the foregoing embodiments, the salt is a pharmaceutically acceptable salt.

A number of the foregoing embodiments recite a halogen atom as a member of a particular grouping. In some embodiments of any of the foregoing embodiments, the halogen atom is a fluorine atom or a chlorine atom. In some further such embodiments, the halogen atom is a fluorine atom.

A number of the foregoing embodiments recite an aryl group as a member of a particular group. In some embodiments of any of the foregoing embodiments, the aryl group is a phenyl group, unsubstituted or substituted as indicated.

A number of the foregoing embodiments recite a carbocyclyl group as a member of a particular group. In some embodiments of any of the foregoing embodiments, the carbocyclyl group is a cycloalkyl group, unsubstituted or substituted as indicated, and having the same range of carbon numbers. In some further such embodiments, any carbocyclyl or cycloalkyl group is cyclopropyl, cyclobutyl, cyclopentyl, cyclohexyl, or cyclopentyl, unsubstituted or substituted as indicated.

A number of the foregoing embodiments recite a heteroaryl group as a member of a particular group. In some further such embodiments, any such heteroaryl group is pyrrol-1-yl, pyrrol-2-yl, pyrrol-3-yl, pyrazol-1-yl, pyrazol-3-yl, pyrazol-4-yl, imidazol-1-yl, imidazol-2-yl, imidazol-4-yl, 1,2,3-triazol-1-yl, 1,2,3-triazol-4-yl, 1,2,4-triazol-1-yl, 1,2,4-triazol-3-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, furazan-3-yl, 1,2,5-oxadiazol-3-yl, 1,2,5-oxadiazol-4-yl, 1,2,5-thiadiazol-3-yl, 1,2,5-thiadiazol-4-yl, furan-2-yl, furan-3-yl, thien-2-yl, thien-3-yl, pyridin-2-yl, pyridin-3-yl, pyridin-4-yl, pyridizin-3-yl, pyridizin-4-yl, pyrimidin-2-yl, pyrimidin-4-yl, pyrimidin-5-yl, or pyrazine-2-yl, any of which are optionally substituted as indicated. In some further embodiments, the optional substituents on any of the foregoing rings is limited to substituents selected from the group consisting of methyl, ethyl, isopropyl, hydroxyl, methoxy, a fluorine atom, a chlorine atom, trifluoromethyl, trifluoromethoxy, —$NH_2$, methylamino, dimethylamino, methylcarbonyl, ethylcarbonyl, methoxycarbonyl, and ethoxycarbonyl.

A number of the foregoing embodiments recite a heterocyclyl group as a member of a particular group. In some further such embodiments, any such heterocyclyl group is pyrrolidin-1-yl, pyrrolidin-2-yl, pyrrolidin-3-yl, pyrazolidin-1-yl, pyrazolidin-2-yl, pyrazolidin-3-yl, pyrazolidin-4-yl, imidazolidin-1-yl, imidazolidin-2-yl, imidazolidin-3-yl, imidazolidin-4-yl, imidazolidin-5-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, tetrahydrofuran-2-yl, tetrahydrofuran-3-yl, tetrahydropyran-2-yl, tetrahydropyran-3-yl, tetrahydropyran-4-yl, thian-2-yl, thian-3-yl, thian-4-yl, 1,4-dioxan-2-yl, piperidin-1-yl, piperidin-2-yl, piperidin-3-yl, piperidin-4-yl, piperazin-1-yl, piperazin-2-yl, morpholin-2-yl, morpholin-3-yl, morpholin-4-yl, thiomorpholin-2-yl, thiomorpholin-3-yl, orthiomorpholin-4-yl, any of which are optionally substituted as indicated. In some further embodiments, the optional substituents on any of the foregoing rings is limited to substituents selected from the group consisting of methyl, ethyl, isopropyl, hydroxyl, methoxy, a fluorine atom, a chlorine atom, trifluoromethyl, trifluoromethoxy, —$NH_2$, methylamino, dimethylamino, methylcarbonyl, ethylcarbonyl, methoxycarbonyl, and ethoxycarbonyl. Note that, in some instances, the heterocyclic rings are formed when two substituents on a common nitrogen atom combine to form a ring. In certain embodiments of such instances, the heterocyclic rings are pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, or orthiomorpholin-4-yl, any of which are optionally substituted as indicated. In some further embodiments, the optional substituents on any of the foregoing rings is limited to substituents selected from the group consisting of methyl, ethyl, isopropyl, hydroxyl, methoxy, a fluorine atom, a chlorine atom, trifluoromethyl, trifluoromethoxy, —$NH_2$, methylamino, dimethylamino, methylcarbonyl, ethylcarbonyl, methoxycarbonyl, and ethoxycarbonyl.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated (e.g., where the stereochemistry of a chiral center is explicitly shown), all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

In some embodiments, the compounds disclosed herein are capable of forming acid or base salts by virtue of the presence of amino or carboxyl groups or groups similar thereto. Physiologically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Physiologically acceptable salts can be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

Any of the above compounds can exist in any suitable form. For example, in some embodiments, the compounds are dissolved or suspended in a liquid carrier, such as an aqueous composition. In some other embodiments, the compounds are a crystalline, semi-crystalline, or amorphous solid, or may exist as part of a crystalline solvate, such as a crystalline hydrate, or as a co-crystal with another crystalline solid, such as a crystalline sweetener compound (e.g., erythritol, sucrose, fructose, and the like).

The above compounds can be synthesized in a manner consistent with that set forth in the Examples below.

Uses and Methods

In a second aspect, the disclosure provides uses of compounds of the first aspect, and any embodiments or combinations of embodiments set forth above.

In a related third aspect, the disclosure provides uses of compounds of the first aspect, and any embodiments or combinations of embodiments set forth above, to reduce a bitter taste or enhance a sweet taste of a composition, such as comestible composition or a pharmaceutical composition.

In some embodiments, the uses are uses to uses to reduce a bitter taste of a comestible composition. In some such embodiments, the comestible composition is a flavored article, such as a food product or a beverage product. Bitter taste can arise from a number of different sources. For example, products derived from natural sources can often contain bitter compounds. Common non-limiting examples of such bitter compounds are menthol, tannins in tea, coffee, and wine, hop extracts in beer, and the like. Bitter compounds can also be present in certain fruit and vegetable juices, such as the juice of kale, beets, and the like. Thus, one or more compounds of the first aspect can be introduced to products containing such bitter compounds for the purpose of reducing their perceived bitterness. This, in turn, leads to greater consumption of such materials or a reduction in the amount of caloric sweeteners used to offset the perception of bitterness in such products. Protein formulations, such as plant-derived protein isolates are often bitter to the taste. This, in some embodiments, one of more compounds of the first aspect are combined with such compounds to reduce the bitter taste of such proteins. Thus, one or more compounds of the first aspect can be included in products that may employ such proteins, such as protein powders, energy bars, snack foods, and various food items that use non-animal-derived products as substitutes for cheese, meat, and other products traditionally derived from animal sources. Thus, one or more compounds of the first aspect can be included in various cheese substitutes, meat substitutes, and the like. They can also be included in products in which protein is added to increase the ratio of protein to carbohydrates, where the addition of the protein may impart a bitter taste. Additionally, substitutes for salt, MSG, and other savory compounds can be replaced by healthier alternatives like potassium chloride (KCl). But these substitutes often impart a bitter taste. Thus, one or more compounds of the first aspect can be used to reduce this bitter taste when included in low-salt or MSG-free variants of traditional savory foods, such as potato chips, soup stock, meat-containing products, nuts, and the like. Thus, such compounds can be used in combination with KCl in such foods. Further, substitutes for caloric sweeteners, such as various natural or synthetic sweeteners, can impart a bitter taste when used as substitutes for caloric sweeteners, such as sucrose or fructose. This, in some embodiments, one or more compounds of the first aspect are used in combination with one or more non-caloric or low-caloric sweeteners, such as sucralose, saccharine, acesulfame K, aspartame, steviol glycosides, including rebaudiosides, mogrosides, glycyrrhizin, and flavanones, such as naringenin, hesperetin, and their glucosylated derivatives. Further, one or more compounds of the first aspect can be combined with any other taste-enhancing compounds, including: sweetness enhancers, such as sir-atose; umami enhancers, such as ericamide; other bitter taste reduction agents; and sour taste reduction agents.

In some embodiments, the uses are uses to uses to reduce a bitter taste of a pharmaceutical composition. In this case, the bitterness is caused by certain active pharmaceutical ingredients (APIs) or other excipients added to the formulation to enhance the efficacy and delivery of the drug. At present, various encapsulation strategies are employed to mask the taste of certain bitter components with drug formulations. In some instances, however, one could dispense with such sequestration technologies and merely combine the bitter compounds with one or more compounds of the first aspect to reduce the bitter taste of the pharmaceutical composition. In general, such pharmaceutical compositions are pharmaceutical composition for oral administration, such as tablets, capsules, elixirs, lozenges, and the like.

In a related fourth aspect, the disclosure provides uses of compounds of the first aspect in the manufacture of a product for the reduction of bitter taste or the enhancement of sweet taste in the product. In some embodiments, the disclosure provides uses of compounds of the first aspect in the manufacture of a flavored article, such as a flavored food or beverage product, for the reduction of bitter taste in the product. When incorporated into such products in the manufacturing process, the one or more compounds of the first aspect can be combined with other compounds in any manner described above for uses of the third aspect. In some other embodiments, the disclosure provides uses of compounds of the first aspect in the manufacture of a medicament for the reduction of bitter taste in the medicament. When incorporated into such products in the manufacturing process, the one or more compounds of the first aspect can be combined with other compounds in any manner described above for uses of the third aspect.

In a related fifth aspect, the disclosure provides uses of compounds of the first aspect to antagonize one or more human T2R taste receptors, such as one or more human T2R54 taste receptors. As noted above in the third and fourth aspects, these uses can involve incorporation into various food products and pharmaceutical products, according to any of the embodiments set forth in connection with those aspects.

In a related sixth aspect, the disclosure provides methods of reducing a bitter taste or enhancing a sweet taste of a flavored composition or a pharmaceutical composition, the method comprising introducing an amount (such as an effective amount) of one or more compounds of the first aspect to the flavored composition or the pharmaceutical composition. In some embodiments, the disclosure provides methods of reducing a bitter taste of a flavored composition, the method comprising introducing an amount (such as an effective amount) of one or more compounds of the first aspect to the flavored composition. In some such embodiments, the flavored composition if a food or beverage product. In some other embodiments, the disclosure provides methods of reducing a bitter taste of a pharmaceutical composition, the method comprising introducing an amount (such as an effective amount) of one or more compounds of the first aspect to the pharmaceutical composition. As noted above in the third and fourth aspects, these methods can involve incorporation into various food products and pharmaceutical products, according to any of the embodiments set forth in connection with those aspects. In general, the effective amount is an amount ranging from 5 to 2000 ppm, or from 5 to 1000 ppm, or from 5 to 800 ppm, or from 5 to 500 ppm, or from 5 to 400 ppm, or from 5 to 300 ppm, or from 5 to 200 ppm, based on the total weight of the composition. These amounts are also germane to the uses and methods of the preceding aspects.

In a related seventh aspect, the disclosure provides methods of antagonizing a human T2R receptor, the methods comprising contacting a human T2R receptor with one or more compounds of the first aspect. In some embodiments thereof, the method comprises contacting a human T2R54 receptor with one or more compounds of the first aspect. In some embodiments, the contacting comprises orally ingesting a composition comprising one or more compounds of the first aspect. In some such embodiments, composition is a flavored composition, such as a food or beverage product. In some other such embodiments, the composition is a pharmaceutical composition. As noted above in the third and fourth aspects, these uses can involve incorporation into various food products and pharmaceutical products, according to any of the embodiments set forth in connection with those aspects. In general, the effective amount is an amount ranging from 5 to 2000 ppm, or from 5 to 1000 ppm, or from 5 to 800 ppm, or from 5 to 500 ppm, or from 5 to 400 ppm, or from 5 to 300 ppm, or from 5 to 200 ppm, based on the total weight of the composition. These amounts are also germane to the uses and methods of the preceding aspects.

As noted in the preceding uses and methods, the compounds of the first aspect are used in various compositions, such as comestible or pharmaceutical compositions. The following details concerning compositions can be used in combination with any of the compositions described in the foregoing uses and methods.

Compositions

In certain aspects, the disclosure provides a composition comprising an amount of one or more compounds of the first aspect. In some embodiments, the composition comprises one or more bitter compounds and a bitter-reducing effective amount of one or more compounds of the first aspect. In some further embodiments, the composition is a pharmaceutical composition and the bitter compounds are one or more pharmaceutical compounds, such as active pharmaceutical ingredients (APIs). In some other embodiments, the composition is a flavored composition, such as a food or beverage product, and the bitter compounds are artificial sweeteners, caffeine, proteins (such as plant proteins), amino acids, compounds derived from natural plant extracts, and the like.

In some embodiments, compounds as disclosed and described herein, individually or in combination, can be used for one or more methods such as modifying receptor function associated with chemosensory or chemosensory related sensation or reaction. Some embodiments provide a method of modulating a chemosensory receptor that includes modulating the activity, structure, function, and/or modification of a chemosensory receptor as well as modulating, treating, or taking prophylactic measure of a condition, e.g., physiological or pathological condition, associated with a chemosensory receptor. In general, a physiological or pathological condition associated with a chemosensory receptor includes a condition, disease, or disorder associated with the chemosensory receptor and/or its ligand, e.g.; gastrointestinal disorders, metabolic disorders, functional gastrointestinal disorders, etc. In one embodiment, the method includes increasing or enhancing sweet flavor. In another embodiment, the method includes modulating a sweet receptor and/or its ligand expressed in a place of the body other than the taste buds, such as an internal organ.

In general, compounds as disclosed and described herein, individually or in combination, can be provided in a composition, such as, e.g., an ingestible (or comestible) composition. In some embodiments, compounds as disclosed and described herein, individually or in combination, reduce the perception of bitter taste associated with certain bitter compounds in a composition. In another embodiment, compounds as disclosed and described herein, individually or in combination, can increase or enhance the sweet taste of a composition by contacting the composition thereof with the compounds as disclosed and described herein to form a modified composition. In another embodiment, compounds as disclosed and described herein, individually or in combination, can be in a composition that modulates the bitterness receptors and/or their ligands expressed in the body other than in the taste buds, such as the human T2R receptors, for example, T2R54.

Some embodiments provide an ingestible composition, comprising one or more compounds of the first aspect and one or more bitter compounds. In some embodiments, the composition further comprises a vehicle. In some embodiments, the vehicle is water. In some further embodiments, the compositions can include one or more natural or artificial sweeteners. In some embodiments, the compound may be present at a concentration at or below its sweetness recognition threshold. In some embodiments, the sweetener is present in an amount from about 0.1% to about 12% by weight. In some embodiments, the sweetener is present in an amount from about 0.2% to about 10% by weight. In some embodiments, the sweetener is present in an amount from about 0.3% to about 8% by weight. In some embodiments, the sweetener is present in an amount from about 0.4% to about 6% by weight. In some embodiments, the sweetener is present in an amount from about 0.5% to about 5% by weight. In some embodiments, the sweetener is present in an amount from about 1% to about 2% by weight. In some embodiments, the sweetener is present in an amount from about 0.1% to about 5% by weight. In some embodiments, the sweetener is present in an amount from about 0.10% to about 4% by weight. In some embodiments, the sweetener is present in an amount from about 0.1% to about 3% by weight. In some embodiments, the sweetener is present in an amount from about 0.1% to about 2% by weight. In some embodiments, the sweetener is present in an amount from about 0.1% to about 1% by weight. In some embodiments, the sweetener is present in an amount from about 0.1% to about 0.5% by weight. In some embodiments, the sweetener is present in an amount from about 0.5% to about 10% by weight. In some embodiments, the sweetener is present in an amount from about 2% to about 8% by weight. In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arabinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet *Stevia*-based glycosides, carrelame and other guanidine-based sweeteners. In some embodiments, the sweetener may combinations of two or more sweeteners as disclosed herein. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener is a sugar. In some embodiments, the sugar is cane sugar. In some embodiments, the sugar is beet sugar. In some embodiments, the sugar may be sucrose, fructose, glucose or combinations thereof. In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arabinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener may be sucralose. In some embodiments, the sweetener is rebaudioside A or other sweet *Stevia*-based glycosides, such as glucosylated steviol glycosides.

In some embodiments, an ingestible composition may be a beverage. In some embodiments, the beverage may be selected from the group consisting of enhanced sparkling beverages, colas, lemon-lime flavored sparkling beverages, orange flavored sparkling beverages, grape flavored sparkling beverages, strawberry flavored sparkling beverages, pineapple flavored sparkling beverages, ginger-ales, root beers, fruit juices, fruit-flavored juices, juice drinks, nectars, vegetable juices, vegetable-flavored juices, sports drinks, energy drinks, enhanced water drinks, enhanced water with vitamins, near water drinks, coconut waters, tea type drinks, coffees, cocoa drinks, beverages containing milk components, beverages containing cereal extracts and smoothies. In some embodiments, the beverage may be a soft drink.

In some embodiments, one or more compounds as described herein and one or more sweetener as described herein may be included in a food or beverage product, wherein the food or beverage product may additionally comprise:

acids, including, for example citric acid, phosphoric acid, ascorbic acid, sodium acid sulfate, lactic acid, or tartaric acid;

bitter ingredients, including, for example caffeine, quinine, green tea, catechins, polyphenols, green *robusta* coffee extract, green coffee extract, protein isolate (such as whey protein isolate or soy protein isolate), or potassium chloride;

coloring agents, including, for example caramel color, Red #40, Yellow #5, Yellow #6, Blue #1, Red #3, purple carrot, black carrot juice, purple sweet potato, vegetable juice, fruit juice, beta carotene, turmeric curcumin, or titanium dioxide;

preservatives, including, for example sodium benzoate, potassium benzoate, potassium sorbate, sodium metabisulfate, sorbic acid, or benzoic acid;

antioxidants including, for example ascorbic acid, calcium disodium EDTA, alpha tocopherols, mixed tocopherols, rosemary extract, grape seed extract, resveratrol, or sodium hexametaphosphate;

vitamins or functional ingredients including, for example resveratrol, Co-Q10, omega 3 fatty acids, theanine, choline chloride (citocoline), fibersol, inulin (chicory root), taurine, *Panax ginseng* extract, guanana extract, ginger extract, L-phenylalanine, L-carnitine, L-tartrate, D-glucoronolactone, inositol, bioflavonoids, *Echinacea*, *Ginko biloba*, yerba mate, flax seed oil, garcinia cambogia rind extract, white tea extract, ribose, milk thistle extract, grape seed extract, pyrodixine HCl (vitamin B6), cyanoobalamin (vitamin B12), niacinamide (vitamin B3), biotin, calcium lactate, calcium pantothenate (pantothenic acid), calcium phosphate, calcium carbonate, chromium chloride, chromium polynicotinate, cupric sulfate, folic acid, ferric pyrophosphate, iron, magnesium lactate, magnesium carbonate, magnesium sulfate, monopotassium phosphate, monosodium phosphate, phosphorus, potassium iodide, potassium phosphate, riboflavin, sodium sulfate, sodium gluconate, sodium polyphosphate, sodium bicarbonate, thiamine mononitrate, vitamin D3, vitamin A palmitate, zinc gluconate, zinc lactate, or zinc sulphate;

clouding agents, including, for example ester gun, brominated vegetable oil (BVO), or sucrose acetate isobutyrate (SAIB);

buffers, including, for example sodium citrate, potassium citrate, or salt;

flavors, including, for example propylene glycol, ethyl alcohol, glycerine, gum Arabic (gum acacia), maltodextrin, modified corn starch, dextrose, natural flavor, natural flavor with other natural flavors (natural flavor WONF), natural and artificial flavors, artificial flavor, silicon dioxide, magnesium carbonate, or tricalcium phosphate; and stabilizers, including, for example pectin, xanthan gum, carboxylmethylcellulose (CMC), polysorbate 60, polysorbate 80, medium chain triglycerides, cellulose gel, cellulose gum, sodium caseinate, modified food starch, gum Arabic (gum acacia), or carrageenan.

In some further embodiments, the compositions may contain one or more flavonones, or glucosylated derivatives thereof. Non-limiting examples include blumeatin, butin, eriodictyol, hesperetin, hesperidin, homoeriodictyol, isosakuranetin, naringenin, naringin, pinocembrin, poncirin, sakuranetin, sakuranin, sterubin, pinostrobin, or glucosylated derivatives thereof.

Some embodiments provide a method of enhancing sweetness of a sweetener, comprising combining one or more compounds of the first aspect with the sweetener. In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arabinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet *Stevia*-based glycosides, carrelame and other guanidine-based sweeteners. In some embodiments, the sweetener may combinations of two or more sweeteners as disclosed herein. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener is a sugar. In some embodiments, the sugar is cane sugar. In some embodiments, the sugar is beet sugar. In some embodiments, the sugar may be sucrose, fructose, glucose or combinations thereof (for example, high fructose corn syrup). In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arabinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener may be sucralose.

In one embodiment, compounds as disclosed and described herein, individually or in combination, can be used at its ligand enhancing concentrations, e.g., very low concentrations on the order of a few parts per million, in combination with one or more known sweeteners, natural or artificial, so as to reduce the concentration of the known sweetener required to prepare an ingestible composition having the desired degree of sweetness.

In one embodiment, compounds as disclosed and described herein, individually or in combination, can enhance the sweetness of a sweetener under a broad range of pH, e.g., from lower pH to neutral pH. The lower and neutral pH includes, but is not limited to, a pH from about 2.5 to about 8.5; from about 3.0 to about 8.0; from about 3.5 to about 7.5; and from about 4.0 to about 7. In certain embodiments, compounds as disclosed and described herein, individually or in combination, can enhance the perceived sweetness of a fixed concentration of a sweetener in taste tests at a compound concentration of about 500 µM, 200 µM, 100 µM, 75 µM, 50 µM, 40 µM, 30 µM, 20 µM, or 10 µM at both low to neutral pH value. In certain embodiments, the enhancement factor of the compounds as disclosed and described herein, individually or in combination, at the lower pH is substantially similar to the enhancement factor of the compounds at neutral pH. Such consistent sweet enhancing property under a broad range of pH allow a broad use in a wide variety of foods and beverages of the compounds as disclosed and described herein, individually or in combination. In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arabinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet *Stevia*-based glycosides, carrelame and other guanidine-based sweeteners. In some embodiments, the sweetener may combinations of two or more sweeteners as disclosed herein. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener may be a sugar. In some embodiments, the sugar is cane sugar. In some embodiments, the sugar is beet sugar. In some embodiments, the sweetener may be a combination of one or more sugars and other natural and artificial sweeteners. In some embodiments, the sugar may be sucrose, fructose, glucose or combinations thereof (for example, high fructose corn syrup). In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arabinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener is sucralose.

Sweeteners have a wide range of chemically distinct structures and hence possess varying properties, such as, without limitation, odor, flavor, mouthfeel, and aftertaste.

In at least one aspect, the disclosure provides formulations comprising one or more compounds of the first aspect (of any of the embodiments set forth above, or as any individual compounds of Tables 2-9, or combinations thereof) and one or more sweeteners, such as natural or artificial sweeteners. In some such embodiments, the formulations comprise the one or more sweeteners at concentrations below the concentration of optimal sweetness, if used alone or without the hT2R54 antagonists disclosed herein.

Any suitable natural or artificial sweeteners, or any combinations thereof, may be used. Natural or artificial sweeteners for use in the formulation comprising a sweetener in combination with a bitterness reducer (i.e., the T2R54 modulators disclosed herein) include but are not limited to natural or synthetic carbohydrates or carbohydrate analogues, including monosaccharides, disaccharides, oligosaccharides, and polysaccharides, and including rare sugars, or sugars in either of the D- or L-conformations, and include, for example, sucrose, fructose, glucose, L-arabinose, L-fucose, L-glucose, L-ribose, D-arabino-hexulose, psicose, altrose, arabinose, turanose, abequose, allose, abrusoside A, aldotriose, threose, xylose, xylulose, xylo-oligosaccharide (such as xylotriose and xylobiose), lyxose, polydextrose, oligofructose, fucose, galacto-oligosaccharide, galactosamine, galactose, gentio-oligosaccharide (such as gentiobiose, gentiotriose, and gentiotetraose), dextrose, cellobiose, D-leucrose, D-psicose, D-ribose, D-tagatose, trehalose (mycose), neotrehalose, isotrehalose, raffinose, idose, tagatose, melibiose, mannan-oligosaccharide, rhamnose, ribose, ribulose, malto-oligosaccharide (such as maltotriose, maltotetraose, maltopentaose, maltohexaose, and maltoheptaose), maltose, sucrose acetate isobutyrate, dextrose, erythrose, erythrulose, deoxyribose, gulose, ketotriose, lactose, lactulose, kestose, nystose, mannose, sucralose, palatinose, polydextrose, sorbose, sugaridextrose (blended sugar), or talose, or combinations of any two or more of the aforementioned sweeteners.

The sweetener can also include, for example, sweetener compositions comprising one or more natural or synthetic carbohydrate, such as corn syrup, high fructose corn syrup, high maltose corn syrup, glucose syrup, sucralose syrup, hydrogenated glucose syrup (HGS), hydrogenated starch hydrolyzate (HSH), or other syrups or sweetener concentrates derived from natural fruit and vegetable sources, or semi-synthetic "sugar alcohol" sweeteners such as polyols. Non-limiting examples of polyols in some embodiments include erythritol, maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, isomaltulose, maltodextrin, and the like, and sugar alcohols or any other carbohydrates or combinations thereof capable of being reduced which do not adversely affect taste.

The sweetener may be a natural or synthetic sweetener that includes, but is not limited to, agave inulin, agave nectar, agave syrup, amazake, brazzein, brown rice syrup, coconut crystals, coconut sugars, coconut syrup, date sugar, fructans (also referred to as inulin fiber, fructo-oligosaccharides, or oligo-fructose), green *stevia* powder, *Stevia rebaudiana*, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside N, rebaudioside O, rebaudioside M and other sweet *stevia*-based glycosides, stevioside, stevioside extracts, honey, Jerusalem artichoke syrup, licorice root, luo han guo (fruit, powder, or extracts), lucuma (fruit, powder, or extracts), maple sap (including, for example, sap extracted from *Acer saccharum, Acer nigrum, Acer rubrum, Acer saccharinum, Acer platanoides, Acer negundo, Acer macrophyllum, Acer grandidentatum, Acer glabrum, Acer mono*), maple syrup, maple sugar, walnut sap (including, for example, sap extracted from *Juglans cinerea, Juglans nigra, Juglans ailatifolia, Juglans regia*), birch sap (including, for example, sap extracted from *Betula papyrifera, Betula alleghaniensis, Betula lenta, Betula nigra, Betula populifolia, Betula pendula*), sycamore sap (such as, for example, sap extracted from *Platanus occidentalis*), ironwood sap (such as, for example, sap extracted from *Ostrya virginiana*), mascobado, molasses (such as, for example, blackstrap molasses), molasses sugar, monatin, monellin, cane sugar (also referred to as natural sugar, unrefined cane sugar, or sucrose), palm sugar, panocha, piloncillo, rapadura, raw sugar, rice syrup, sorghum, sorghum syrup, cassava syrup (also referred to as tapioca syrup), thaumatin, yacon root, malt syrup, barley malt syrup, barley malt powder, beet sugar, cane sugar, crystalline juice crystals, caramel, carbitol, carob syrup, castor sugar, hydrogenated starch hydrolates, hydrolyzed can juice, hydrolyzed starch, invert sugar, anethole, arabinogalactan, arrope, syrup, P-4000, acesulfame potassium (also referred to as acesulfame K or ace-K), alitame (also referred to as aclame), advantame, aspartame, baiyunoside, neotame, benzamide derivatives, bernadame, canderel, carrelame and other guanidine-based sweeteners, vegetable fiber, corn sugar, coupling sugars, curculin, cyclamates, cyclocarioside I, demerara, dextran, dextrin, diastatic malt, dulcin, sucrol, valzin, dulcoside A, dulcoside B, emulin, enoxolone, maltodextrin, saccharin, estragole, ethyl maltol, glucin, gluconic acid, glucono-lactone, glucosamine, glucoronic acid, glycerol, glycine, glycyphillin, glycyrrhizin, golden sugar, yellow sugar, golden syrup, granulated sugar, gynostemma, hemandulcin, isomerized liquid sugars, jallab, chicory root dietary fiber, kynurenine derivatives (including N'-formyl-kynurenine, N'-acetyl-kynurenine, 6-chloro-kynurenine), galactitol, litesse, ligicane, lycasin, lugduname, guanidine, falemum, mabinlin I, mabinlin II, maltol, maltisorb, maltodextrin, maltotriol, mannosamine, miraculin, mizuame, mogrosides (including, for example, mogroside IV, mogroside V, and neomogroside), mukurozioside, nano sugar, naringin dihydrochalcone, neohesperidine dihydrochalcone, nib sugar, nigero-oligosaccharide, norbu, orgeat syrup, osladin, pekmez, pentadin, periandrin I, perillaldehyde, perillartine, petphyllum, phenylalanine, phlomisoside I, phlorodizin, phyllodulcin, polyglycitol syrups, polypodoside A, pterocaryoside A, pterocaryoside B, rebiana, refiners syrup, rub syrup, rubusoside, selligueain A, shugr, siamenoside I, siraitia grosvenorii, soybean oligosaccharide, Splenda, SRI oxime V, steviol glycoside, steviolbioside, stevioside, strogins 1, 2, and 4, sucronic acid, sucrononate, sugar, suosan, phloridzin, superaspartame, tetrasaccharide, threitol, treacle, trilobtain, tryptophan and derivatives (6-trifluoromethyl-tryptophan, 6-chloro-D-tryptophan), vanilla sugar, volemitol, birch syrup, aspartame-acesulfame, assugrin, and combinations or blends of any two or more thereof.

In still other embodiments, the sweetener can be a chemically or enzymatically modified natural high potency sweetener. Modified natural high potency sweeteners include glycosylated natural high potency sweetener such as glucosyl-, galactosyl-, or fructosyl-derivatives containing 1-50 glycosidic residues. Glycosylated natural high potency sweeteners may be prepared by enzymatic transglycosylation reaction catalyzed by various enzymes possessing transglycosylating activity. In some embodiments, the modified sweetener can be substituted or unsubstituted.

Additional sweeteners also include combinations of any two or more of any of the aforementioned sweeteners. In some embodiments, the sweetener may comprise combinations of two, three, four or five sweeteners as disclosed herein. In some embodiments, the sweetener may be a sugar. In some embodiments, the sweetener may be a combination of one or more sugars and other natural and artificial sweeteners.

One of skill in the art will recognize that any one or more of any of the aforementioned sweeteners can be combined in various ratios, amounts, or concentrations to yield a sweetener alone or a combination of two or more sweeteners, which is then combined with one or more flavor modifying compound.

One of skill in the art will recognize that the aforementioned sweeteners for use in a formulation comprising one or more sweetener and one or more flavor modifying compound are provided by way of example and are not intended to be limiting.

Some embodiments provide supplements, nutraceuticals, functional food products (e.g., any fresh or processed food claimed to have a health-promoting and/or disease-preventing properties beyond the basic nutritional function of supplying nutrients), pharmaceutical product, over the counter (OTC) product, oral care product, cosmetic products such as sweetened lip balms, and other personal care products including compounds as disclosed and described herein, individually or in combination.

In general, over the counter (OTC) product and oral care product generally refer to product for household and/or personal use which may be sold without a prescription and/or without a visit to a medical professional. Examples of the OTC products include, but are not limited to Vitamins and dietary supplements; Topical analgesics and/or anesthetic; Cough, cold and allergy remedies; Antihistamines and/or allergy remedies; and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anesthetic include any topical creams/ointments/gels used to alleviate superficial or deep-seated aches and pains, e.g. muscle pain; teething gel; patches with analgesic ingredient; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. Examples of oral care product include, but are not limited to mouth cleaning strips, toothpaste, toothbrushes, mouthwashes/dental rinses, denture care, mouth fresheners at-home teeth whiteners, dentifrices, and dental floss.

In at least one aspect, the disclosure provides formulations comprising one or more compounds of the first aspect (of any of the embodiments set forth above, or as any individual compounds of Tables 2-9, or combinations thereof) and one or more bitter compounds. The bitter compounds can come from any variety of sources. In some instances, the bitter compounds are components of certain natural products, such as caffeine, quinine, green tea, catechins, polyphenols, green *robusta* coffee extract, green coffee extract, menthol and other mint compounds, and the like. Thus, in some embodiments, the composition is a beverage product, such as a tea or coffee product that includes one or more compounds of the first aspect to reduce the bitter taste of such compounds in the beverage.

In some other embodiments, bitterness can arise from including certain proteins, such as protein isolates, into food products. Plant protein isolates can be especially bitter in some instances. Thus, in some embodiments, the compositions disclosed herein include one or more compounds of the first aspect and proteins, such as protein isolates. In some embodiments, the protein isolates are made from animal products, such as whey or casein. In other embodiments, the protein isolates are made from plant products like soy, hemp, chia seeds, rice, *quinoa*, beans, and the like. In some other embodiments, the protein is an algal protein, such as *spirulina*. In such cases, the compounds of the first aspect can block the bitter taste inherent to the protein, but can also block some of the astringency of the "fishy" or amine taste in the algal protein. In some other embodiments, the protein is a mycoprotein.

The compositions containing any of the foregoing proteins can be useful for making a variety of products. Non-limiting examples include protein mixes, energy bars, protein-based chips or cookies, cheese-replacement products, meat-replacement products (such as vegan chicken, vegan beef, etc.). Some such products may also include synthetic heme-based additives to simulate the taste of blood in red meat. One or more compounds of the first aspect are added to such products to offset the bitter taste of such heme-based additives.

In some other embodiments, bitterness can arise from compounds used to take the place of salt or monosodium glutamate (MSG). In many such instances, potassium chloride (KCl) is used. But KCl can impart a bitter taste. Thus, in some embodiments, the composition includes potassium chloride (KCl) in combination with one or more compounds of the first aspect.

In some embodiments, compounds as disclosed and described herein, individually or in combination may be included in food or beverage products or formulations. Examples of food and beverage products or formulations include, but are not limited to sweet coatings, frostings, or glazes for ingestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionery category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups).

The Dehydrated and Culinary Food Category usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee; tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionery category generally refers to edible product that is sweet to the taste. Examples of confectionery include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles. The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is not limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for ingestible compositions, particularly food and beverage products or formulations, are provided as follows. Illustrative ingestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary ingestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary ingestible compositions also include breakfast cereals, sweet beverages or solid or liquid concentrate compositions for preparing beverages, ideally so as to enable the reduction in concentration of previously known saccharide sweeteners, or artificial sweeteners.

Some embodiments provide a chewable composition that may or may not be intended to be swallowed. In some embodiments, the chewable composition may be gum, chewing gum, sugarized gum, sugar-free gum, functional gum, bubble gum including compounds as disclosed and described herein, individually or in combination.

Typically at least a sweet receptor modulating amount, a sweet receptor ligand modulating amount, a sweet flavor modulating amount, a sweet flavoring agent amount, a sweet flavor enhancing amount, or a therapeutically effective amount of one or more of the present compounds will be added to the ingestible composition, optionally in the presence of sweeteners so that the sweet flavor modified ingestible composition has an increased sweet taste as compared to the ingestible composition prepared without the compounds of the present invention, as judged by human beings or animals in general, or in the case of formulations testing, as judged by a majority of a panel of at least eight human taste testers, via procedures commonly known in the field.

In some embodiments, compounds as disclosed and described herein, individually or in combination, modulate the sweet taste or other taste properties of other natural or synthetic sweet tastants, and ingestible compositions made therefrom. In one embodiment, the compounds as disclosed and described herein, individually or in combination, may be used or provided in its ligand enhancing concentration(s). For example, the compounds as disclosed and described herein, individually or in combination, may be present in an amount of from about 0.001 ppm to 100 ppm, or narrower alternative ranges from about 0.1 ppm to about 10 ppm, from about 0.01 ppm to about 30 ppm, from about 0.05 ppm to about 10 ppm, from about 0.01 ppm to about 5 ppm, or from about 0.02 ppm to about 2 ppm, or from about 0.01 ppm to about 1 ppm.

Some embodiments provide a sweet enhancing composition. The sweet enhancing composition comprises a compound of the present invention in a sweet flavor enhancing amount in combination with a first amount of sweetener, wherein the sweetening is more than the sweetening provided by the first amount of sweetener without the compound. In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arabinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet *Stevia*-based glycosides, carrelame and other guanidine-based sweeteners. In some embodiments, the sweetener may combinations of two or more sweeteners as disclosed herein. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener may be a sugar. In some embodiments, the sugar is cane sugar. In some embodiments, the sugar is beet sugar. In some embodiments, the sweetener may be a combination of one or more sugars and other natural and artificial sweeteners. In some embodiments, the sugar may be sucrose, fructose, glucose or combinations thereof (for example, high fructose corn syrup). In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arabinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener may be sucralose.

In some embodiments, compounds as disclosed and described herein, individually or in combination, provide enhancement of potency of a sweetener at the T1R2/T1R3 taste receptor as measured by an enhancement ratio, defined as the ratio of $EC_{50}$ of the sweetener with and without the compound described herein. In some embodiments, compounds as disclosed and described herein, individually or in combination, provide enhancement ratio of greater than 1 and less than 10. In some embodiments, compounds as disclosed and described herein, individually or in combination, provide an enhancement ratio from 10 to 20. In some embodiments, compounds as disclosed and described herein, individually or in combination, provide an enhancement ratio greater than 20. In some embodiments, the sweetener may be common saccharide sweeteners, e.g., sucrose, fructose, glucose, and sweetener compositions comprising natural sugars, such as corn syrup (including high fructose corn syrup) or other syrups or sweetener concentrates derived from natural fruit and vegetable sources; rare natural sugars including D-allose, D-psicose, L-ribose, D-tagatose, L-glucose, L-fucose, L-arabinose, D-turanose, and D-leucrose; semi-synthetic "sugar alcohol" sweeteners such as erythritol, isomalt, lactitol, mannitol, sorbitol, xylitol, maltodextrin, and the like; and artificial sweeteners such as aspartame, saccharin, acesulfame-K, cyclamate, sucralose, and alitame. In some embodiments, the sweetener may be selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A and other sweet Stevia-based glycosides, carrelame and other guanidine-based sweeteners. In some embodiments, the sweetener may combinations of two or more sweeteners as disclosed herein. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener may be a sugar. In some embodiments, the sweetener may be a combination of one or more sugars and other natural and artificial sweeteners. In some embodiments, the sugar may be sucrose, fructose, glucose or combinations thereof (for example, high fructose corn syrup). In some embodiments, the sugar may be sucrose. In some embodiments, the sugar may be a combination of fructose and glucose. In some embodiments, the sugar may be a combination of about 55% fructose and about 42% glucose. In some embodiments, the sugar may be a combination of about 42% fructose and about 53% glucose. In some embodiments, the sugar may be a combination of about 90% fructose and about 10% glucose. In some embodiments, the sweetener may be a rare sugar. In some embodiments, the rare sugar is selected from the group consisting of D-allose, D-psicose, L-ribose, D-tagatose, L-glucose, L-fucose, L-arabinose, D-turanose, D-leucrose and combinations thereof. In some embodiments, the rare sugar is D-psicose. In some embodiments, the rare sugar is D-tagatose. In some embodiments, the sweetener is an artificial sweetener. In some embodiments, the artificial sweetener may be sucralose.

In some embodiments, compounds as disclosed and described herein, individually or in combination, may be provided in a flavoring concentrate formulation, e.g., suitable for subsequent processing to produce a ready-to-use (i.e., ready-to-serve) product. By "a flavoring concentrate formulation", it is meant a formulation which should be reconstituted with one or more diluting medium to become a ready-to-use composition. The term "ready-to-use composition" is used herein interchangeably with "ingestible composition", which denotes any substance that, either alone or together with another substance, can be taken by mouth whether intended for consumption or not. In one embodiment, the ready-to-use composition includes a composition that can be directly consumed by a human or animal. The flavoring concentrate formulation is typically used by mixing with or diluted by one or more diluting medium, e.g., any consumable or ingestible ingredient or product, to impart or modify one or more flavors to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a soft drink syrup concentrate can be reconstituted with water or other aqueous medium by a manufacturer in large industrial scales to produce the ready-to-use soft drinks. Since the flavoring concentrate formulation has the flavoring agent or flavor modifying agent in a concentration higher than the ready-to-use composition, the flavoring concentrate formulation is typically not suitable for being consumed directly without reconstitution. There are many benefits of using and producing a flavoring concentrate formulation. For example, one benefit is the reduction in weight and volume for transportation as the flavoring concentrate formulation can be reconstituted at the time of usage by the addition of suitable solvent, solid or liquid.

In one embodiment, the flavoring concentrate formulation comprises i) compounds as disclosed and described herein, individually or in combination; ii) a carrier; and iii) optionally at least one adjuvant. The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the flavoring concentrate formulation; and in other embodiments, the carrier is different from the diluting medium. The term "carrier" as used herein includes, but is not limited to, ingestibly acceptable carrier.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French vanilla, peanut butter, chai, or combinations thereof. In another embodiment, the at least one adjuvant comprises one or more sweeteners. The one or more sweeteners can be any of the sweeteners described in this application. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the content of which is hereby incorporated by reference in its entirety for all purposes.

In one embodiment, the present flavoring concentrate formulation can be in a form selected from the group consisting of liquid including solution and suspension, solid, foamy material, paste, gel, cream, and a combination thereof, such as a liquid containing certain amount of solid contents. In one embodiment, the flavoring concentrate formulation is in form of a liquid including aqueous-based and nonaqueous-based. In some embodiments, the present flavoring concentrate formulation can be carbonated or non-carbonated.

The flavoring concentrate formulation may further comprise a freezing point depressant, nucleating agent, or both as the at least one adjuvant. The freezing point depressant is an ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes an ingestibly acceptable compound or agent which is able to facilitate nucleation. The presence of nucleating agent in the flavoring concentrate formulation can improve the mouthfeel of the frozen Blushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In one embodiment, the flavoring concentrate formulation is formulated to have a low water activity for extended shelf life. Water activity is the ratio of the vapor pressure of water in a formulation to the vapor pressure of pure water at the same temperature. In one embodiment, the flavoring concentrate formulation has a water activity of less than about 0.85. In another embodiment, the flavoring concentrate formulation has a water activity of less than about 0.80. In another embodiment, the flavoring concentrate formulation has a water activity of less than about 0.75.

In one embodiment, the flavoring concentrate formulation has the present compound in a concentration that is at least 2 times of the concentration of the compound in a ready-to-use composition. In one embodiment, the flavoring concentrate formulation has the present compound in a concentration that is at least 5 times of the concentration of the compound in a ready-to-use composition. In one embodiment, the flavoring concentrate formulation has the present compound in a concentration that is at least 10 times of the concentration of the compound in a ready-to-use composition. In one embodiment, the flavoring concentrate formulation has the present compound in a concentration that is at least 15 times of the concentration of the compound in a ready-to-use composition. In one embodiment, the flavoring concentrate formulation has the present compound in a concentration that is at least 20 times of the concentration of the compound in a ready-to-use composition. In one embodiment, the flavoring concentrate formulation has the present compound in a concentration that is at least 30 times of the concentration of the compound in a ready-to-use composition. In one embodiment, the flavoring concentrate formulation has the present compound in a concentration that is at least 40 times of the concentration of the compound in a ready-to-use composition. In one embodiment, the flavoring concentrate formulation has the present compound in a concentration that is at least 50 times of the concentration of the compound in a ready-to-use composition. In one embodiment, the flavoring concentrate formulation has the present compound in a concentration that is at least 60 times of the concentration of the compound in a ready-to-use composition. In one embodiment, the flavoring concentrate formulation has the present compound in a concentration that is up to 100 times of the concentration of the compound in a ready-to-use composition.

In some embodiments, the disclosure provides pharmaceutical compositions comprising one or more compounds of the first aspect and one or more bitter compounds. In some embodiments, the bitter compounds are pharmaceutical APIs, such as antibiotics. Children often have much greater sensitivity to bitter tastes than adults, so the use of bitterness blockers can be especially useful in pharmaceutical compositions for pediatric administration.

In one embodiment, when administered to a patient, the compounds as disclosed and described herein and the optional pharmaceutically acceptable vehicles are sterile. In one embodiment, water is a preferred vehicle when a compound as disclosed and described herein is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used. In some instances, the pharmaceutical compositions are liquid solutions or suspensions, that include, among other things, flavorants, pH modulators, natural or artificial sweeteners, and the like.

Pharmaceutical compositions comprising a compound as disclosed and described herein may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the present invention into preparations which can be used pharmaceutically. Proper formulation is dependent upon the route of administration chosen.

In some embodiments, the pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule.

For topical administration a compound as disclosed and described herein may be formulated as solutions, gels, ointments, creams, suspensions, etc. as is well-known in the art.

In some embodiments, compounds as disclosed and described herein may be formulated in accordance with routine procedures as a pharmaceutical composition adapted for intravenous administration to human beings. Typically, compounds for intravenous administration are solutions in sterile isotonic aqueous buffer. For injection, a compound may be formulated in aqueous solutions, preferably in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optionally agents, for example, sweetening agents such as fructose, aspartame or saccharin; flavoring agents such as peppermint, oil of wintergreen, or cherry coloring agents and preserving agents, to provide a pharmaceutically palatable preparation.

Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds of the present invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM) etc. Additionally, flavoring agents, preservatives, coloring agents, bile salts, acylcarnitines and the like may be added.

Liquid drug formulations suitable for use with nebulizers and liquid spray devices and EHD aerosol devices will typically include a compound of the present invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art.

A compound as disclosed and described herein, and/or pharmaceutical composition thereof, will generally be used in an amount effective to achieve the intended purpose, i.e., bitterness masking. In general, the effective amount is an amount ranging from 5 to 2000 ppm, or from 5 to 1000 ppm, or from 5 to 800 ppm, or from 5 to 500 ppm, or from 5 to 400 ppm, or from 5 to 300 ppm, or from 5 to 200 ppm, based on the total weight of the composition.

Yet another embodiment of the invention generally pertains to a method of blocking bitterness by using any of the compositions discussed herein.

In illustrative embodiments compounds according to the invention will be used to block/reduce/modify biller taste associated with compounds that activate the hT2R54 receptor and/or which further activate the hTR6T, hT2R64 and/or hT2R75 taste receptors.

In specific exemplary embodiments compounds according to the invention will be used to block/reduce/modify biller taste associated with compounds that activate the hT2R54 receptor and/or the hTR61, hT2R64 and/or hT2R75 taste receptors such as acetaminophen, dextromethorphan, dequaliunium, chloroquine, and guaifenesin and their salts, hydrates, solvates or prodrug forms thereof.

Additionally the compounds of the present invention may be used in association with other biller taste blocker compounds such as are set forth in the following table.

TABLE 1

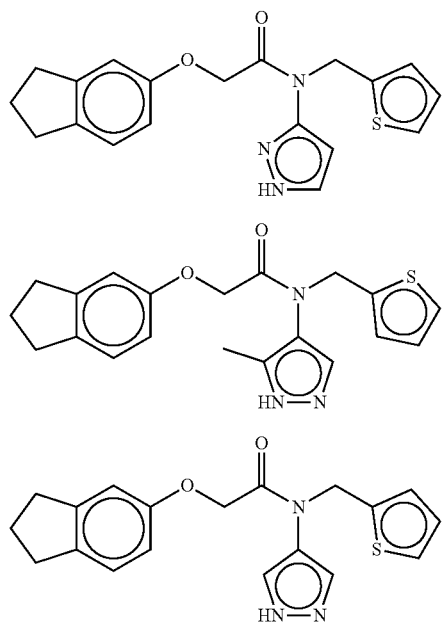

TABLE 1-continued
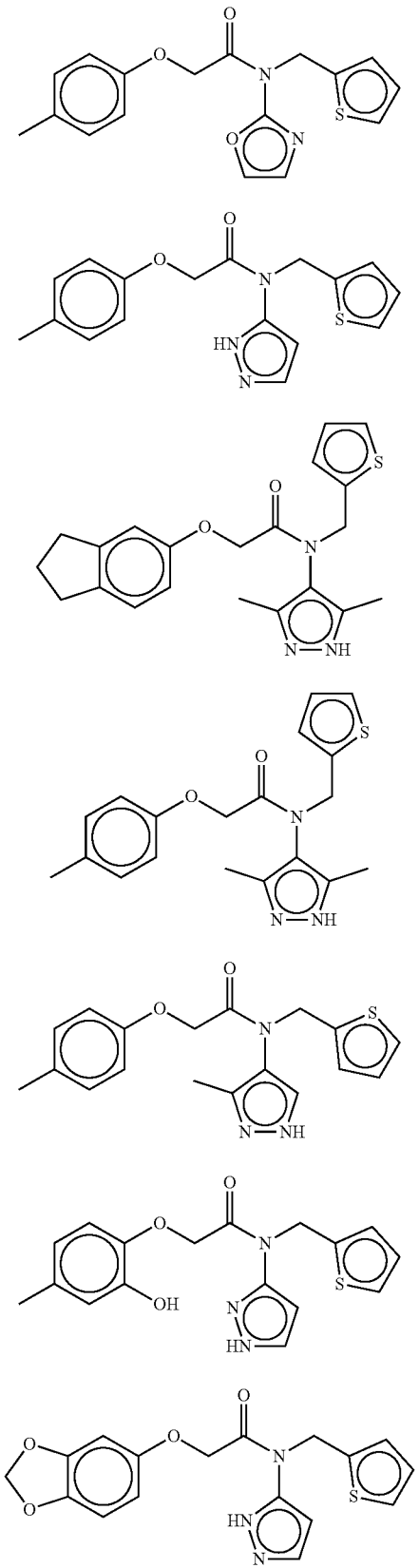
TABLE 1-continued
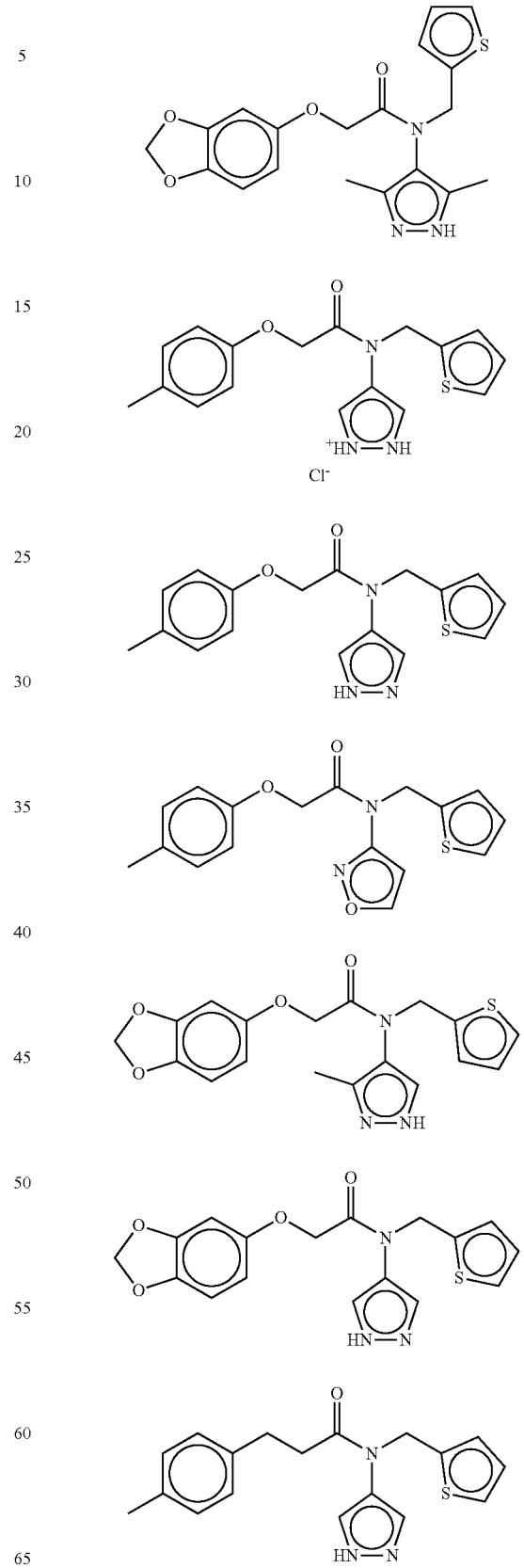

TABLE 1-continued
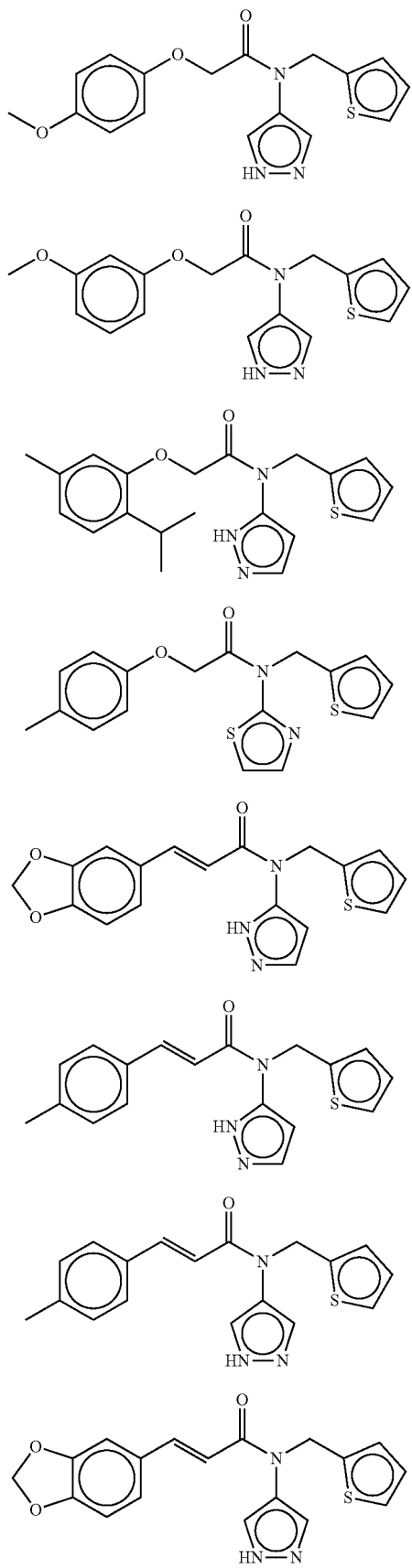
TABLE 1-continued
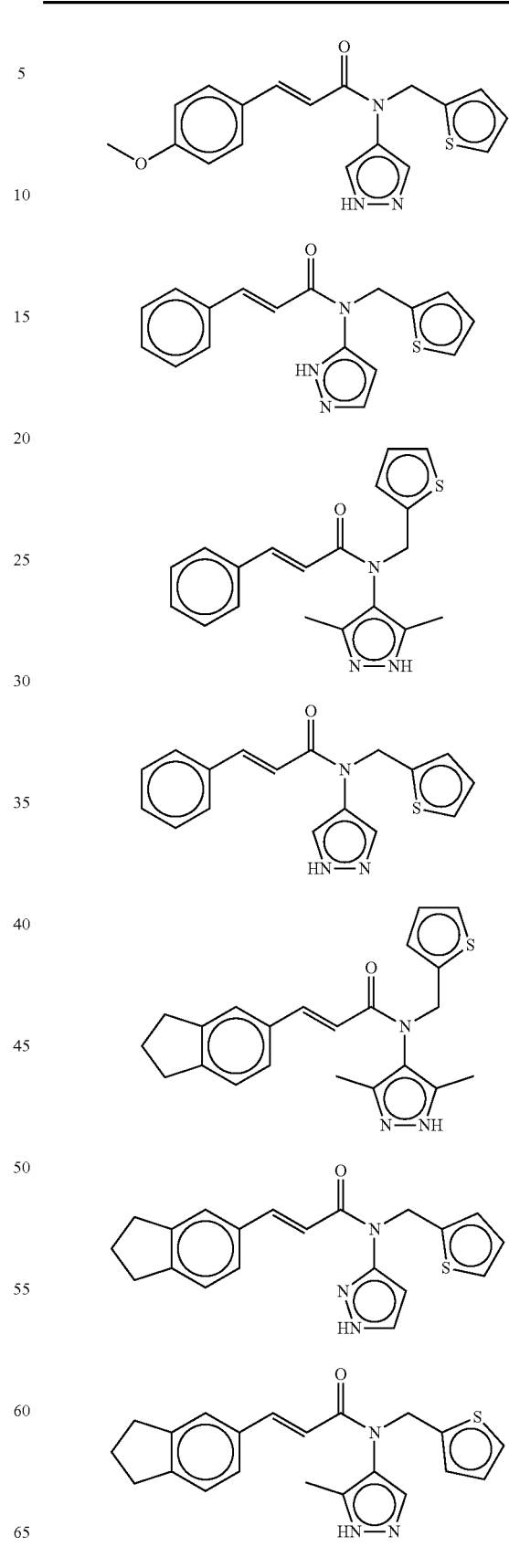

TABLE 1-continued

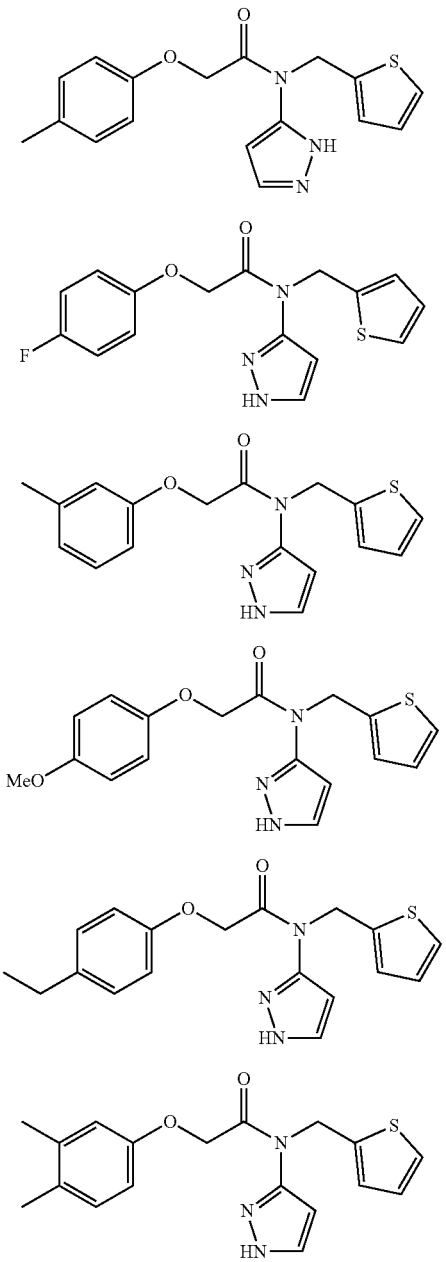

In some embodiments, the compositions for modifying bitter taste perception may additionally comprise one or more compounds described in PCT Publication No. WO 2014/130582, which is incorporated herein by reference in its entirety. In some embodiments, the compositions disclosed above may be used in combination with a cooling agent. Such cooling agents useful for combination with the compounds disclosed herein are known in the art, and include those described in U.S. 2013/0324557, WO 2014/130582, U.S. Pat. No. 7,923,585, U.S. 2008/0319055, U.S. Pat. No. 7,893,110, U.S. 2009/0105237, U.S. 2009/0098066, U.S. 2010/0035938, U.S. Pat. Nos. 8,263,046, 7,959,958, U.S. 2008/0300314, U.S. 2009/0312384, U.S. Pat. Nos. 8,309,598, 7,935,848, U.S. 2010/0297038, U.S. Pat. Nos. 8,377,422, 8,664,261, U.S. 2011/0091531, U.S. 2013/0323388, U.S. 2014/0341821, U.S. 2010/0086498, U.S. 2014/0186272, U.S. Pat. No. 6,884,906, U.S. 2011/0070329, U.S. Pat. Nos. 8,575,349, 5,725,865, 5,843,466, WO 2011/147455, U.S. Pat. No. 8,007,771, WO 2004/037764, U.S. Pat. No. 6,627,233, WO 2011/159935, U.S. Pat. Nos. 7,767,243, 7,662,576, 5,372,824, 5,009,893, 5,698,181, 7,189,760, 7,030,273, WO 02/091849, U.S. Pat. Nos. 5,286,500, 3,488,419, 6,515,188, 6,407,293, 4,459,425, 3,419,543, U.S. 2006/0210482, U.S. Pat. Nos. 6,328,982, 7,025,999, EP 1332772, U.S. Pat. No. 4,157,384, WO 2014/090293, U.S. 2008/0175800, U.S. Pat. Nos. 8,344,025, 8,927,605, U.S. 2011/0305657, U.S. 2013/0202543, and U.S. 2014/0335224, which are incorporated by reference herein in their entireties.

In certain embodiments the composition blocks bitterness associated with Acetaminophen, Dextromethorphan, Dequalinium, Chloroquine, and/or Guaifenesin, which activate T2R54 alone or T2R54 and other receptors.

In some embodiments, the composition comprises one or a combination of two or more of the compounds and compositions disclosed herein, may be further combined with one or more acids or sour flavorants. Representative sour flavorants include but are not limited to: ascorbic acid, benzoic acid, gallic acid, glucuronic acid, adipic acid, glutaric acid, malonic acid, succinic acid, malic acid, acetic acid, lactic acid, citric acid, tartaric acid, fumaric acid, phosphoric acid, pyrophosphoric acid, tannic acid, vinegar, lemon juice, lime juice, acidic fruit juices, and acidic fruit extracts.

In some embodiments, the composition comprises one or a combination of two or more of the compounds and compositions disclosed herein, may be further combined with one or more salts or salt flavor enhancers. Representative salts or salt flavor enhancers include but are not limited to: mineral salts, sodium chloride, potassium chloride, magnesium chloride, ammonium chloride, sodium gluconate, sodium phosphates, glycine, L-alanine, L-valine, L-leucine, L-isoleucine, L-phenylalanine, L-tyrosine, L-glutamine, L-glutamic acid, L-asparagine, L-aspartic acid, L-serine, L-threonine, L-cysteine, L-methionine, L-proline, L-lysine, L-arginine, L-tryptophan, L-histidine, L-pyrolysine, L-pyroglutamine, L-4-trans-hydroxyproline, L-3-cis-hydroxyproline, L-homoserine, L-homocysteine, L-cystine, L-ornithine and L-citrulline, L-glutamine, L-glutamic acid, L-asparagine, L-aspartic acid, L-valine, L-arginine and L-lysine.

In some embodiments, the composition comprises one or a combination of two or more of the compounds and compositions disclosed herein, which may be further combined with one or more umami flavor compounds or umami flavor enhancing compounds. Representative umami flavor compounds or umami flavor enhancing compounds include but are not limited to the compounds identified in U.S. Patent Application Publications 2005/0084506A1, U.S. 2009/0111834A1, U.S. 2012/0201763A1, U.S. 2015/0093339A1, U.S. 2006/0263411A1, U.S. 2012/0226047A1, and 2009/0220662A1. Additional representative umami flavor compounds or umami flavor enhancing compounds include but are not limited to: hydrolyzed soy protein, hydrolyzed corn protein, hydrolyzed wheat protein, anchovy, anchovy paste, fish sauce, yeast extract, nutritional yeast, hydrolyzed yeast extract, mushrooms, mushroom powder, dehydrated mushrooms, mushroom extract, kombucha, hydrolyzed vegetable protein, oyster sauce, soy sauce, soy extract, tamari, miso powder, miso paste, parmesan cheese, parmesan cheese solids, kombu powder, kombu, dehydrated kombu, kombu paste, nori, nori powder, nori paste, seaweed, dehydrated seaweed, seaweed powder, seaweed extract, tomato, dehydrated tomato, tomato powder, tomato extract, vegetable powder, vegetable extract, whey powder, whey solids, whey, collagen, gelatin, textured vegetable protein, sodium caseinate, calcium caseinate, magnesium caseinate, potassium caseinate, glyoxylic acid, 3-methyl-2-oxo-butanoic acid, 3-methyl-2-oxo-pentanoic acid, 4-methyl-2-oxo-pentanoic acid, 3-hydroxy-2-oxo-propanoic acid, oxalacetic acid, 2-oxo-glutaric acid, 2-oxo-3-phenyl-propanoic acid, 3-(4-hydroxyphenyl)-2-oxo-propanoic acid, 2-oxo-1H-indole-3-propanoic acid, 2-oxo-1H-imidazole-4-propanoic acid, 4-methylthio-2-oxo-butanoic acid, 3-mercapto-2-oxo-propanoic acid, 3-hydroxy-2-oxo-butanoic acid, 6-amino-2-oxo-hexanoic and 5-guanidino-2-oxo-pentanoic acid, 2-amino-butanoic acid, α-alanine, glycine, norvaline, valine, aspartic acid, norleucine, leucine, isoleucine, serine, threonine, glutamic acid, phenylalanine, tyrosine, cysteine, methionine, lysine, tryptophane, histidine, arginine, asparagine, glutamine, cystine, citrulline, theanine, γ-methylene-glutamic acid, isoeugenol, 2-propylphenol, p-vinylguaiacol, 2-acetylpyrazine, 2-ethyl-3,5-dimethylpyrazine, 2,3,5-trimethylpyrazine, 2,3-diethyl-5-methylpyrazine, 3-ethyl-2-methylpyrazine, dimethyl sulfide, dimethyl disulfide, dimethyl trisulfide, methylpropyl disulfide, 2-methylthiophenol, methional (3-methylthiopropanal), 2-octenal, 2,4-nonadienal, 2,4-decadienal, 2,4-undecadienal, 2-methoxybenzaldehyde, 2,4-dodecadienal, decenal, methyl 2-furanecarboxylate, 2-ethyl-4-hydroxy-3-methyl 5(2H)-furanone, 2,6-dimethylbenzenethiol 2-nonen-1-ol, 10-undecenoic acid, undecanoic acid, isodecanoic acid and isononanoic acid, 2-oxo-butanoic acid, oxalacetic acid, 3-methyl-2-oxo-butanoic acid, 3-methyl-2-oxo-pentanoic acid, 2-oxo-glutaric and 3-mercapto-2-oxo-propanoic acid, NaCl, KCl, MSG, guanosine monophosphate (GMP), inosin monophosphate (IMP), ribonucleotides such as disodium inosinate, disodium guanylate, N-(2-hydroxyethyl)-lact-amide, N-lactoyl-GMP, N-lactoyl tyramine, gamma amino butyric acid, allyl cysteine, 1-(2-hydroxy-4-methoxyphenyl)-3-(pyridine-2-yl)propan-1-one, arginine, potassium chloride, ammonium chloride, succinic acid, N-(2-methoxy-4-methyl benzyl)-N'-(2-(pyridin-2-yl)ethyl) oxalamide, N-(heptan-4-yl)benzo(D)(1,3)dioxole-5-carboxamide, N-(2,4-dimethoxybenzyl)-N'-(2-(pyridin-2-yl)ethyl) oxalamide, N-(2-methoxy-4-methyl benzyl)-N'-2(2-(5-methyl pyridin-2-yl)ethyl) oxalamide, cyclopropyl-E,Z-2,6-nonadienamide, glutamic acid, glutamate, monosodium glutamate, monopotassium glutamate, monoammonium glutamate, calcium diglutamate, magnesium diglutamate, L-asparagine or a salt thereof, 5'-ribonucleotides or their salts, calcium 5'-ribonucleotides, disodium 5'-ribonucleotides, dipotassium 5'-ribonucleotides, inosinic acid, guanylic acid, adenosinic acid, inosinates, guanylates, and adenylates, guanosine 5'-monophosphate, inosine 5'-monophosphate, 5'-adenylate, disodium guanylate, disodium inosinate, disodium adenylate; dipotassium guanylate, dipotassium inosinate, dipotassium adenylate, calcium guanylate, calcium inosinate, calcium adenylate, maltol, ethyl maltol, glycine, L-leucine, autolyzed or hydrolyzed proteins (e.g. autolyzed yeast, hydrolyzed yeast, hydrolyzed vegetable proteins), Koji-Aji (Ajinomoto Food Ingredients), fermented wheat gluten, Glutathione, Glutamyl Glutamic Acid, (Z)-6-Dodecen-4-olide, Inosinic acid, Dodec-Z6-en-4-olide, Glutamic Acid, L-Aconitic Acid, N-(1-deoxy-fructos-1-yl) glutamate, hydrolyzed vegetable protein, Methyl alpha-D-Glucoside, 2,3-Di-lysine, Methyl alpha-D-Glucoside 2,3-Di-omithine, L-Asparagine, L-a-glutamyl-L-a-glutamyl-L-Glutamic acid, L-a-aspartyl-L-a-glutamyl-Glutamyl valine, Wheat gluten hydrolyzate, Aspartic acid L-, L-a-aspartyl-L-a-aspartyl-L-a-aspartyl-Docosahexaenoic acid, and (4Z,7Z,10Z,13Z,16Z,19Z)-L-Theanine, allyl cysteine, propenyl cysteine, S-(α,β-dicarboxyethyl) γ-L-glutamyl-L-cysteinyl-glycine, S-(α,β-dicarboxyethyl) cysteine, 3-(carboxymethoxy)-alanine, S-carboxymethyl-glutathione (glutaramic acid), S-carboxymethyl-cysteinyl-glycine, (S-carboxymethyl)-lysyl-cysteine, S-dicarboxymethyl-glutathione, S-carboxymethyl-cysteine, S-(1,2-dicarboxyethyl)-glutathione, and S-(1,2-dicarboxyethyl)-cysteine, N-acetyl GMP, N-formyl GMP, N-propanoyl GMP, N-butanoyl GMP, N-pentanoyl GMP, N-hexanoyl GMP, N-heptanoyl GMP, N-octanoyl GMP, N-oxalyl GMP, N-succinyl GMP, N-glutaryl GMP, N-fumaryl GMP, N-maleyl GMP, N-adipyl GMP, N-citryl GMP, N-galloyl GMP, N-oxalacetyl-GMP, N-feruloyl GMP, N-pyruvyl GMP, N-benzoyl GMP, N-vanilloyl GMP, N-anthranoyl GMP, N-caffeoyl GMP, N-cinnamoyl GMP, N-acetyl AMP, N-formyl AMP, N-propanoyl AMP, N-butanoyl AMP, N-pentanoyl AMP, N-hexanoyl AMP, N-heptanoyl AMP, N-octanoyl AMP, N-oxalyl AMP, N-succinyl AMP, N-glutaryl AMP, N-fumaryl AMP, N-maleyl AMP, N-adipyl AMP, N-citryl AMP, N-galloyl AMP, N-oxalacetyl-AMP, N-feruloyl AMP, N-pyruvyl AMP, N-benzoyl AMP, N-vanilloyl AMP, N-anthranoyl AMP, N-caffeoyl AMP, N-cinnamoyl AMP, N-acetyl CMP, N-formyl CMP, N-propanoyl CMP, N-butanoyl CMP, N-pentanoyl CMP, N-hexanoyl CMP, N-heptanoyl CMP, N-octanoyl CMP, N-oxalyl CMP, N-succinyl CMP, N-glutaryl CMP, N-fumaryl CMP, N-maleyl CMP, N-adipyl CMP, N-citryl CMP, N-galloyl CMP, N-oxalacetyl-CMP, N-feruloyl CMP, N-pyruvyl CMP, N-benzoyl CMP, N-vanilloyl CMP, N-anthranoyl CMP, N-caffeoyl CMP, N-cinnamoyl CMP, N-acetyl GMP, N-formyl GMP, N-propanoyl GMP, N-butanoyl GMP, N-pentanoyl GMP, N-hexanoyl GMP, N-heptanoyl GMP, N-octanoyl GMP, N-oxalyl GMP, N-succinyl GMP, N-glutaryl GMP, N-fumaryl GMP, N-maleyl GMP, N-adipyl GMP, N-citryl GMP, N-galloyl GMP, N-oxalacetyl-GMP, N-feruloyl GMP, N-pyruvyl GMP, N-benzoyl GMP, N-vanilloyl GMP, N-anthranoyl GMP, N-caffeoyl GMP, N-cinnamoyl GMP, flavor modifiers created by maillard reactions, S-(α,β-dicarboxyethyl) γ-L-glutamyl-L-cysteinyl-glycine, S-(α,β-dicarboxyethyl) cysteine, 3-(carboxymethoxy)-alanine, S-carboxymethyl-glutathione (glutaramic acid), S-carboxymethyl-cysteinyl-glycine, (S-carboxymethyl)-lysyl-cysteine, S-dicarboxymethyl-glutathione, S-carboxymethyl-cysteine, S-(1,2-dicarboxyethyl)-glutathione, and S-(1,2-dicarboxyethyl)-cysteine, Gamma-L-glutamyl-L-cysteinyl-glycine or y-Glu-Cys-Gly, Rubemamine, rubemamide, rubescenamine, Rubescenamide, zanthosine, zanthosinamide, dioxamide, dioxamine, zanthomamine, and zanthomamide.

Umami flavor compounds or umami flavor enhancing compounds may also include peptides set forth in Nakata et al., Biosci. Biotechnol. Biochem. (1995) 59(4):689-93.

In some embodiments, the compounds and compositions described herein, are incorporated, either alone or in combination with one or more of the additional compounds described herein, into a smoking article or vapor inhalation ("e-cigarette") device. Such articles and devices are well known in the art, including but not limited to, cigars, cigarettes, loose pipe tobacco, flavored cigars, flavored cigarettes, rolling papers, pipes, water pipes, kretek cigarettes, bidis, mouthpieces (e.g., of a hookah), and electronic cigarettes. In some embodiments, the compounds and compositions described herein, which may be further combined with one or more cooling agents, may be applied directly to a smoking article at any time during or after the manufacture of the smoking article. In some further embodiments, the compounds and compositions described herein, may be provided as a liquid, solid, or concentrate to be applied to a smoking article or vaporizer fluid. In some further embodiments, the compounds and compositions described herein, can be incorporated into a vaporizer fluid. In some embodiments the vaporizer fluid further comprises propylene glycol, water, nicotine, glycerin, and/or polyethylene glycol. In some embodiments, the smoking article comprises tobacco. In some embodiments, the smoking article comprises tobacco, *cannabis*, cloves, and/or tendu or tembumi leaves.

In some embodiments, the compounds and compositions described herein, are incorporated, either alone or in combination with one or more of the additional compounds described herein, with *cannabis* or a *cannabis*-related or *cannabis*-derived or *cannabis*-containing product. Such *cannabis*-related or *cannabis*-derived or *cannabis*-containing products include, but are not limited to: dried *cannabis*; undried *cannabis*; *cannabis*-derived or *cannabis*-containing tinctures; *cannabis*-derived or *cannabis*-containing oils, e.g., hash oil; *cannabis*-derived topical preparations, e.g., ointments and balms containing or derived from *cannabis*; and concentrates, e.g., hash. Additionally, the compounds and compositions described herein, are incorporated, either alone or in combination with one or more of the additional compounds described herein, with edible products including but not limited to any of the ingestible and/or edible products discussed herein, e.g., foodstuffs and beverages, which may further contain *cannabis* or a *cannabis*-related or *cannabis*-derived products.

In some embodiments, the pharmaceutical composition disclosed herein may contain a *cannabis*-derived compound, e.g., any cannabinoid, tetrahydrocannabinol, (−)-trans-$\Delta^9$-tetrahydrocannabinol, or other isomers or related compounds derived from *cannabis* in addition to containing any of the compounds disclosed herein, which may further be combined with one or more cooling agents.

Methods of Preparation

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Some exemplary synthetic methods for preparing the present compounds are illustrated in Scheme 1 below.

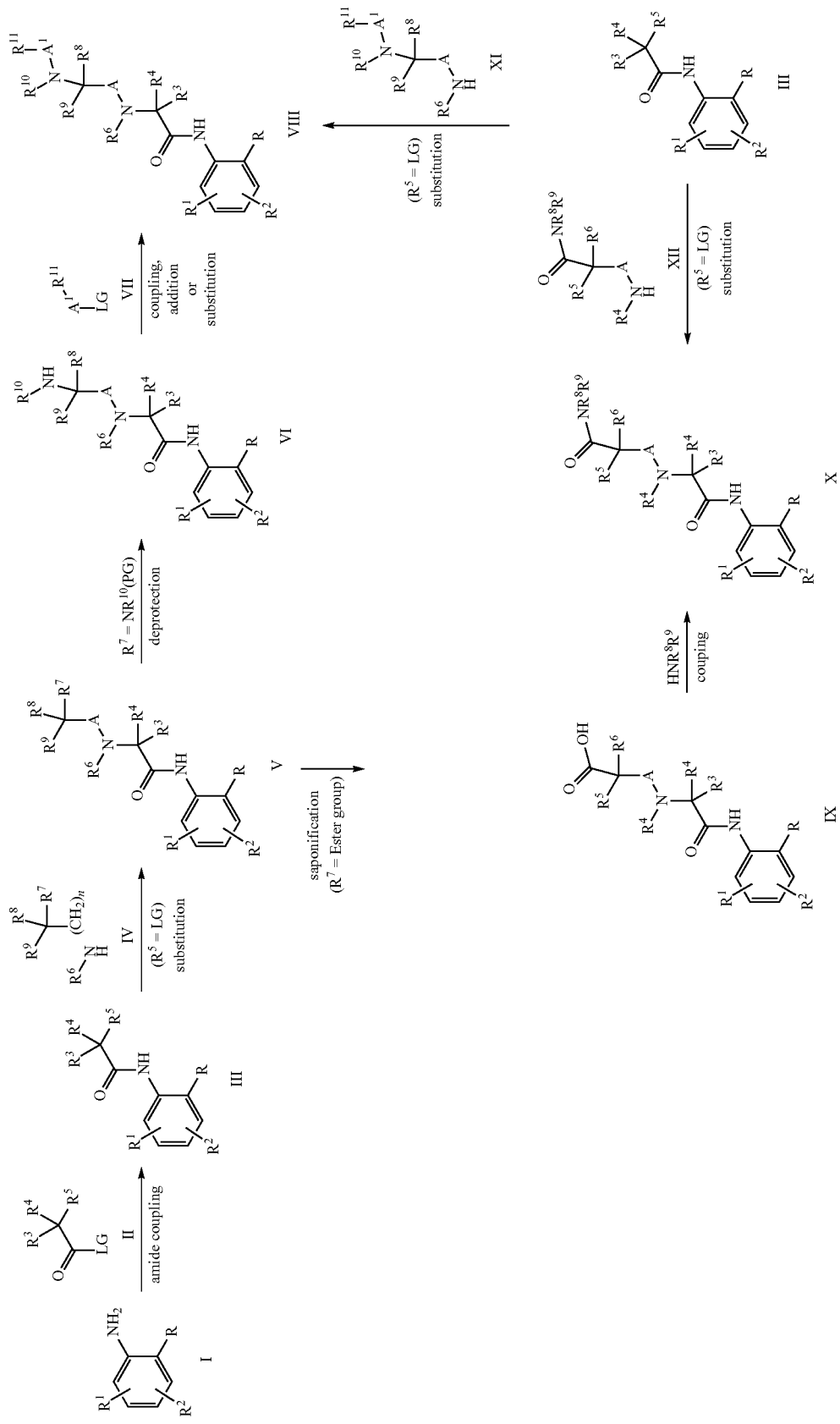

-continued

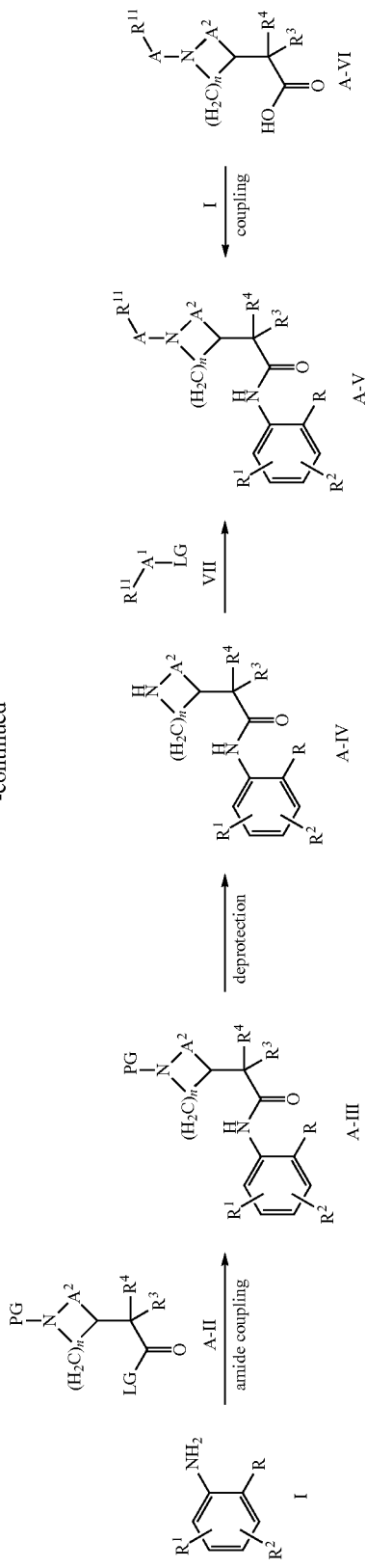

A, A$^1$, A$^2$ = O, S, NR$^{12}$R$^{13}$, CO, COO, SO$_2$, CONR$^{14}$, any fragment or substituted fragment
A, A$^1$, A$^2$ may combined with othe substituents or fragments to form cyclic, polycyclic or spiro analogs
R and R$^1$ through R$^{14}$ = any substituent and may alsobe combined with other substituents or fragments to form cyclic, polycyclic or spiro analogs
LG = leaving group
PG = Protecting group As depicted in Scheme 1, aniline building blocks I and activated carboxylic acids II and A-II can be allowed to react under various amide coupling conditions to yield either III or A-III. The species II and A-II can be generated in situ but may also be either commercially available or easily accessible as storable intermediates. Compounds III can be used either as final materials or as intermediates ($R^5$=leaving group). Thus, if $R^5$ is a leaving group (LG), III can be treated with amine building blocks of choice to form intermediates V. Subsequently, if substituent $R^7$ of compound V is a protected amine group, V can be submitted to conditions that allow for the removal of amine protecting groups to yield intermediates VI. Likewise, amine protecting groups of A-III can be removed under similar conditions to yield intermediates A-IV. These amine intermediates (VI & A-IV) can in turn be allow to react with various electrophiles under coupling, substitution, or addition conditions to furnish VIII and A-V, respectively.

However, if the substituent $R^7$ of intermediates V is an ester group, V can instead be submitted to saponification conditions to yield IX which in turn can be submitted to amide coupling conditions to yield compounds X. Alternatively, compounds VIII and X can also be prepared from intermediates III and building blocks XI and XII, respectively. On the other hand, compound A-V can also be generated from anilines I and acid building blocks A-VI. The latter building blocks (XI, XII, & A-VI) are either commercially available or can be synthesized using methods similar to those described above or in the literature.

Example 1—Synthesis of N-(6-Acetylbenzo[d][1,3] dioxol-5-yl)-2-(4-(3-methylbutanoyl)piperazin-1-yl) acetamide (1)

To a suspension of N-(6-acetylbenzo[d][1,3]dioxol-5-yl)-2-(piperazin-1-yl)acetamide dihydrochlorides (Example 1a) (38 mg, 0.1 mmol) and triethylamine (TEA) (40 mg, 0.4 mmol) in DMF (1 mL) was added 3-methylbutanoyl chloride (12 mg, 0.1 mmol). The mixture was irradiated in the microwave at 135° C. for 5 minutes. The solution was directly purified by reverse phase HPLC (water/acetonitrile gradient) to give the title compounds (20 mg, 50% yield) as a white solid. MS 390 (M+H$^+$).

Example 1a. N-(6-Acetylbenzo[d][1,3]dioxol-5-yl)-2-(piperazin-1-yl)acetamide Dihydrochloride

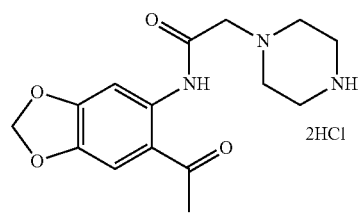 [SMILES: CC(=O)c1cc2c(cc1NC(=O)CN1CCNCC1)OCO2]

A solution of tert-butyl 4-(2-((6-acetylbenzo[d][1,3]dioxol-5-yl)amino)-2-oxoethyl)piperazine-1-carboxylate (Example 1b) (23.5 g, 58.0 mmol) in MeOH (220 mL) was treated with concentrate HCl (110 mL) and stirred overnight at room temperature. The solid was collected by filtration and washed with methanol to give (18.2 g, 48.1 mmol, 83% yield) of the title compound as a brown solid.

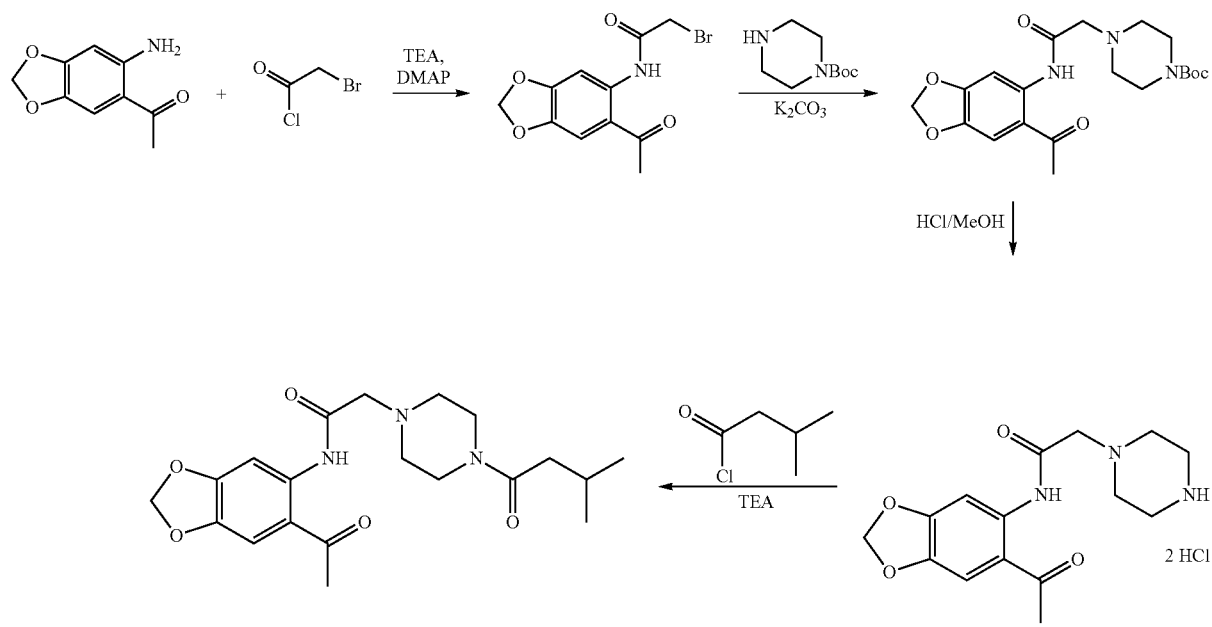

Example 1b. tert-Butyl 4-(2-((6-Acetylbenzo[d][1,3]dioxol-5-yl)amino)-2-oxoethyl)piperazine-1-carboxylate

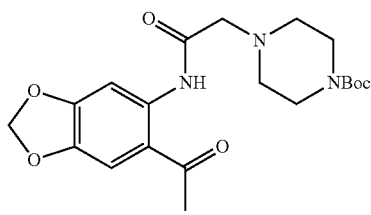 [SMILES: CC(=O)c1cc2c(cc1NC(=O)CN1CCN(C(=O)OC(C)(C)C)CC1)OCO2]

A mixture of N-(6-acetylbenzo[d][1,3]dioxol-5-yl)-2-bromoacetamide (Example 1c) (22 g, 73.3 mmol), tert-butyl piperazine-1-carboxylate (14 g, 73.3 mmol), and $K_2CO_3$ (21 g, 146.6 mmol) in dry ACN was heated to 85° C. and stirred overnight under nitrogen. The reaction was diluted with EtOAc and washed successively with water and brine. The organic layer was dried over $MgSO_4$, filtered, and evaporated to give the title compound (23.6 g, 58.2 mmol, 79% yield).

Example 1c. N-(6-Acetylbenzo[d][1,3]dioxol-5-yl)-2-bromoacetamide

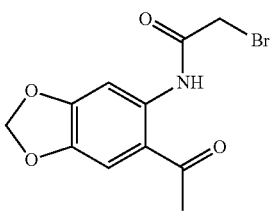 [SMILES: CC(=O)c1cc2c(cc1NC(=O)CBr)OCO2]

A solution of 1-(6-aminobenzo[d][1,3]dioxol-5-yl)ethanone (25 g, 139.5 mmol), TEA (29.2 mL, 209.3 mmol), and DMAP (1.2 g, 9.7 mmol) in dry THF (380 mL) was cooled to 0° C. and treated dropwise with bromo acetyl chloride (17.3 g, 209.3 mmol). The ice bath was then removed and the reaction was stirred overnight under nitrogen. The mixture was concentrated to about 150 mL of THF. The residual solution was diluted slowly with water. After stirring for 30 min the solid product was collected by filtration and dried to yield of title compound (41.0 g, 136.5 mmol, 98% yield) as a brown solid. $^1$H NMR (CDCl$_3$, 400 MHz): δ 2.58 (s, 3H), 3.97 (s, 1H), 4.16 (s, 1H), 6.04 (s, 2H), 7.25 (d, J=14.4 Hz, 1H), 8.34 (d, J=11.6 Hz, 1H), 12.68 (brs, 0.5H), 12.80 (bs, 0.5H). MS 301 (M+H$^+$).

Example 2—Synthesis of N-(6-Acetylbenzo[d][1,3]dioxol-5-yl)-2-(4-(5-fluoro-2-methoxybenzoyl)piperazin-1-yl)acetamide (2)

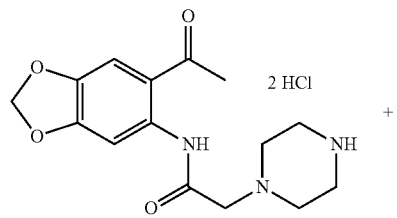

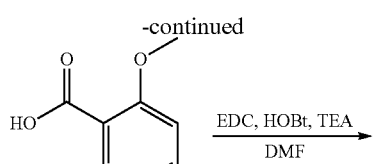

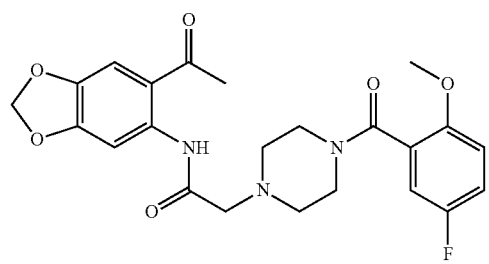

To a mixture of N-(6-acetylbenzo[d][1,3]dioxol-5-yl)-2-(piperazin-1-yl)acetamide dihydrochloride (Example 1a) (76 mg, 0.2 mmol), HOBt (30 mg, 0.2 mmol), EDC (38 mg, 0.2 mmol), and TEA (81 mg, 0.8 mmol) in DMF (1 mL) was added 5-fluoro-2-methoxybenzoic acid (34 mg, 0.2 mmol). The mixture was irradiated in the microwave at 150° C. for 5 minutes. The solution was directly purified by reverse phase HPLC (water/acetonitrile gradient) and the clean fractions were concentrated under reduced pressure and dried under vacuum to give 40 mg (44% yield) of the title compound. MS 458 (M+H$^+$).

Example 3—Synthesis of Propyl 4-(2-((6-Acetylbenzo[d][1,3]dioxol-5-yl)amino)-2-oxoethyl)piperazine-1-carboxylate (3)

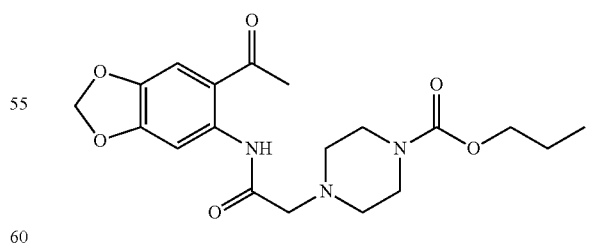

Prepared in a similar manner as in Example 1 from N-(6-acetylbenzo[d][1,3]dioxol-5-yl)-2-(piperazin-1-yl)acetamide dihydrochloride (Example 1a) (76 mg, 0.2 mmol), TEA (40 mg, 0.4 mmol), and propyl carbonochloridate (25 mg, 0.2 mmol) to give 16 mg (25% yield) of the title compound. MS 392 (M+H$^+$).

Example 4—Synthesis of 4-(2-((6-Acetylbenzo[d][1,3]dioxol-5-yl)amino)-2-oxoethyl)-N-isopropylpiperazine-1-carboxamide (4)

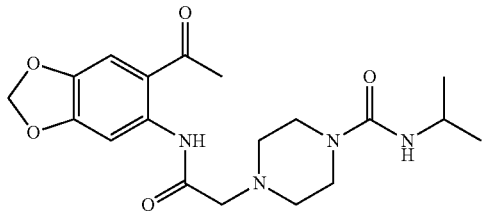 [SMILES: CC(=O)c1cc2c(cc1NC(=O)CN1CCN(C(=O)NC(C)C)CC1)OCO2]

Prepared in a similar manner as in Example 1 from N-(6-acetylbenzo[d][1,3]dioxol-5-yl)-2-(piperazin-1-yl)acetamide dihydrochloride (Example 1a) (76 mg, 0.2 mmol), TEA (40 mg, 0.4 mmol), and 2-isocyanatopropane (17 mg, 0.2 mmol) to give 23 mg (30% yield) of the title compound. MS 391 (M+H$^+$).

Example 5—Synthesis of N-(6-acetylbenzo[d][1,3]dioxol-5-yl)-2-(4-(isopropylsulfonyl)piperazin-1-yl)acetamide (5)

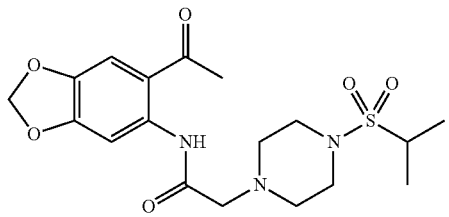

Prepared in a similar manner as in Example 1 from N-(6-acetylbenzo[d][1,3]dioxol-5-yl)-2-(piperazin-1-yl)acetamide dihydrochloride (76 mg, 0.2 mmol), TEA (40 mg, 0.4 mmol), and propane-2-sulfonyl chloride (28 mg, 0.2 mmol) to give 42 mg (10% yield) of the title compound. MS 412 (M+H$^+$).

Example 6—Synthesis of N-(6-Methoxybenzo[d][1,3]dioxol-5-yl)-2-(4-(3-methylbutanoyl)piperazin-1-yl)acetamide (6)

N-(6-Methoxybenzo[d][1,3]dioxol-5-yl)-2-(piperazin-1-yl)acetamide dihydrochloride (Example 6a) (73 mg, 0.2 mmol), HOBt (30 mg, 0.2 mmol), EDC (38 mg, 0.2 mmol), and TEA (81 mg, 0.8 mmol) were suspended in DMF (1 mL) followed by addition of 3-methylbutanoic acid (20 mg, 0.2 mmol). The mixture was irradiated in the microwave at 150° C. for 5 minutes. The solution was directly purified by reverse phase HPLC (water/acetonitrile gradient) to give 29 mg (38% yield) of the title compound. MS 378 (M+H$^+$).

Example 6a. N-(6-Methoxybenzo[d][1,3]dioxol-5-yl)-2-(piperazin-1-yl)acetamide Dihydrochlorides

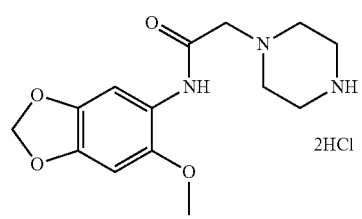 [SMILES: COc1cc2c(cc1NC(=O)CN1CCNCC1)OCO2]

Prepared in a similar manner as in Example 1a from tert-butyl 4-(2-((6-methoxybenzo[d][1,3]dioxol-5-yl)amino)-2-oxoethyl)piperazine-1-carboxylate (Example 6b) (1.29 g, 3.28 mmol) to afford the title compound as a yellow solid (1.20 g, quantitative yield).

Example 6b. tert-Butyl 4-(2-((6-methoxybenzo[d][1,3]dioxol-5-yl)amino)-2-oxoethyl)piperazine-1-carboxylate

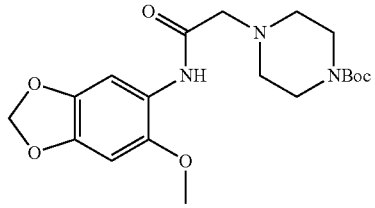 [SMILES: COc1cc2c(cc1NC(=O)CN1CCN(C(=O)OC(C)(C)C)CC1)OCO2]

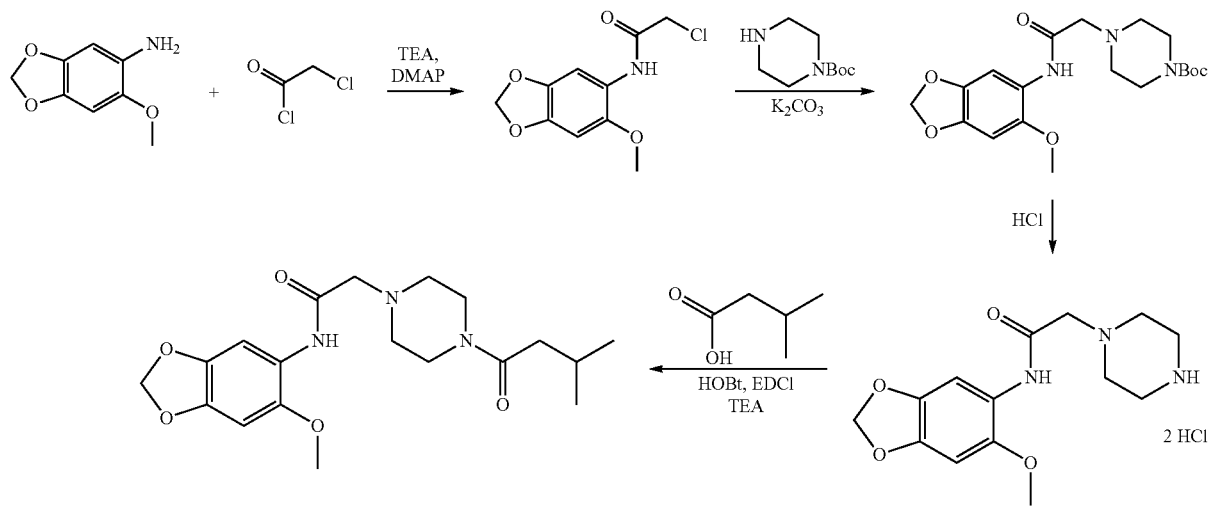

Prepared in a similar manner as in Example 1b from 2-bromo-N-(6-methoxybenzo[d][1,3]dioxol-5-yl)acetamide (Example 6c) (1.58 g, 5.5 mmol) and tert-butyl piperazine-1-carboxylate to afford the title compound as a yellowish solid (1.30 g, 3.30 mmol, 60% yield).

Example 6c. 2-Bromo-N-(6-methoxybenzo[d][1,3]dioxol-5-yl)acetamide

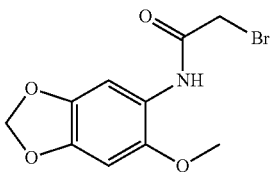 [SMILES: COc1cc2c(cc1NC(=O)CBr)OCO2]

Prepared in a similar manner as in Example 1c from 6-methoxybenzo[d][1,3]-dioxol-5-amine (0.92 g, 5.5 mmol) and bromoacetyl chloride to yield the desired product (1.60 g, quantitative yield) as a greyish solid. MS 289 (M+H⁺).

Compounds in Table 2 were prepared in a similar manner as in Example 1, Example 2, and/or Example 6 from the corresponding amine hydrochlorides described herein and commercially available electrophiles (e.g. carboxylic acids, acyl chlorides, chloroformates, isocyanates, and sulfonyl-chlorides).

TABLE 2

| SID | Structure | Obs. Mol Ion; MS (M + H⁺) | hT2R54 IC50 (uM) | $^1$H NMR (400 MHz) |
|---|---|---|---|---|
| 1 | 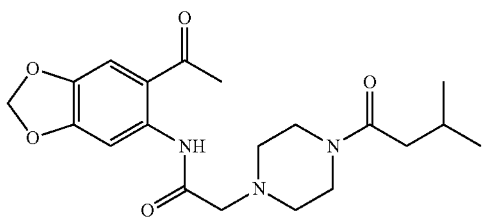 [SMILES: CC(=O)c1cc2c(cc1NC(=O)CN1CCN(C(=O)CC(C)C)CC1)OCO2] | 390 | 0.016 | (DMSO-$d_6$) δ 1.40 (d, J = 6.6 Hz, 6H), 2.52-2.61 (m, 1H), 2.69 (d, J = 6.8 Hz, 2H), 2.96-3.02 (m, 2H), 3.03-3.09 (m, 5H), 3.60 (s, 2H), 4.08-4.30 (m, 4H), 6.57 (s, 2H), 7.97 (s, 1H), 8.93 (s, 1H), 13.27 (s, 1H). |
| 2 | 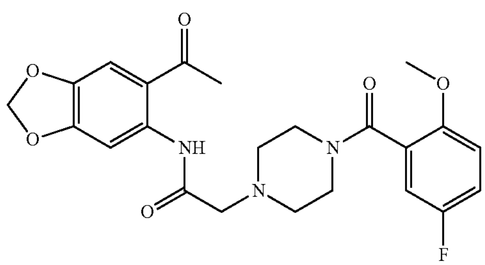 [SMILES: COc1ccc(F)cc1C(=O)N1CCN(CC(=O)Nc2cc3c(cc2C(C)=O)OCO3)CC1] | 458 | 0.027 | (DMSO-$d_6$) δ 2.42-2.50 (m, 2H), 2.53-2.60 (m, 5H), 3.18 (s, 2H), 3.23-3.32 (m, 2H), 3.70-3.85 (m, 5H), 6.14 (s, 2H), 7.05-7.18 (m, 2H), 7.23 (ddd, J = 9.1, 8.4, 3.2 Hz, 1H), 7.62 (s, 1H), 8.32 (s, 1H), 12.68 (s, 1H). |
| 3 | 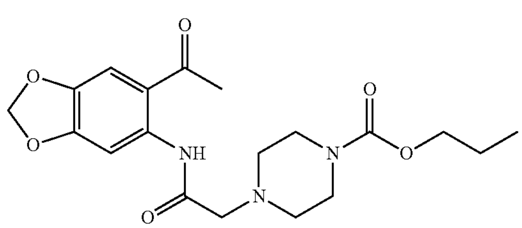 | 392 | 0.015 | (DMSO-$d_6$) δ 0.89 (t, J = 7.4 Hz, 3H), 1.58 (m, 2H), 2.48 (m, 4H), 2.57 (s, 3H), 3.16 (s, 2H), 3.52 (s, 4H), 3.96 (t, J = 6.6 Hz, 2H), 6.14 (s, 2H), 7.62 (s, 1H), 8.33 (s, 1H), 12.66 (s, 1H). |
| 4 | 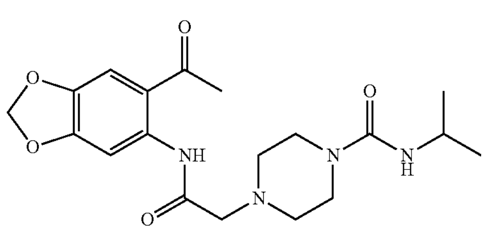 [SMILES: CC(=O)c1cc2c(cc1NC(=O)CN1CCN(C(=O)NC(C)C)CC1)OCO2] | 392 | 0.034 | (DMSO-$d_6$) δ 1.05 (d, J = 6.6 Hz, 6H), 2.45 (t, J = 4.9 Hz, 4H), 2.57 (s, 3H), 3.14 (s, 2H), 3.42 (t, J = 4.9 Hz, 4H), 3.69-3.82 (m, 1H), 6.14 (s, 1H), 6.19 (d, J = 7.5 Hz, 1H), 7.61 (s, 1H), 8.34 (s, 1H), 12.64 (s, 1H). |

TABLE 2-continued

| SID | Structure | Obs. Mol Ion; MS (M + H$^+$) | hT2R54 IC50 (uM) | $^1$H NMR (400 MHz) |
|---|---|---|---|---|
| 5 | 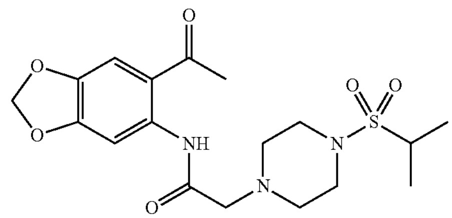 [SMILES: CC(=O)c1cc2c(cc1NC(=O)CN1CCN(S(=O)(=O)C(C)C)CC1)OCO2] | 412 | 0.130 | (DMSO-d$_6$) δ 1.26 (d, J = 6.8 Hz, 6H), 2.53-2.61 (m, 7H), 3.19 (s, 2H), 3.36-3.44 (m, 4H), 6.14 (s, 2H), 7.62 (s, 1H), 8.34 (s, 1H), 12.67 (s, 1H). |
| 6 | 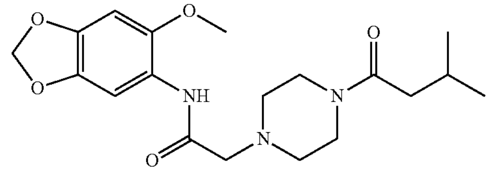 [SMILES: COc1cc2c(cc1NC(=O)CN1CCN(C(=O)CC(C)C)CC1)OCO2] | 378 | 0.49 | (DMSO-d$_6$) δ 0.90 (d, J = 6.6 Hz, 6H), 1.98 (m, 1H), 2.20 (d, J = 7.0 Hz, 2H), 2.43-2.58 (m, 2H), 3.13 (s, 2H), 3.48-3.54 (m, 4H), 3.82 (s, 3H), 5.95 (s, 2H), 6.91 (s, 1H), 7.77 (s, 1H), 9.52 (s, 1H). |
| 7 | 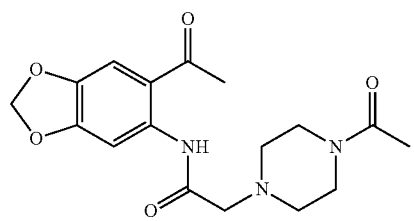 [SMILES: CC(=O)c1cc2c(cc1NC(=O)CN1CCN(C(C)=O)CC1)OCO2] | 348 | 0.09 | (DMSO-d$_6$) δ 2.01 (s, 3H), 2.40-2.48 (m, 2H), 2.50-2.55 (m, 2H), 2.58 (s, 3H), 3.16 (s, 2H), 3.53-3.63 (m, 4H), 6.14 (s, 2H), 7.62 (s, 1H), 8.34 (s, 1H), 12.68 (s, 1H). |
| 8 | 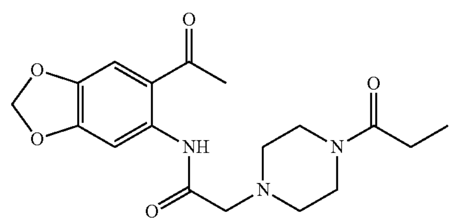 [SMILES: CCC(=O)N1CCN(CC(=O)Nc2cc3c(cc2C(C)=O)OCO3)CC1] | 362 | 0.05 | (DMSO-d$_6$) δ 0.99 (t, J = 7.4 Hz, 3H), 2.34 (q, J = 7.3 Hz, 2H), 2.46 (br. s, 4H), 2.57 (s, 3H), 3.17 (br. s, 2H), 3.58 (br. s, 4H), 6.15 (s, 2H), 7.61 (s, 1H), 8.32 (br. s, 1H), 12.66 (br. s, 1H). |
| 9 | 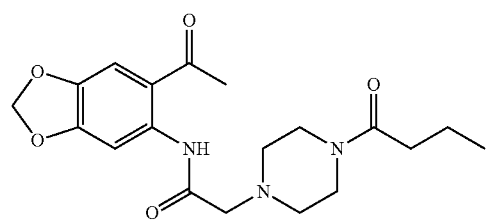 [SMILES: CCCC(=O)N1CCN(CC(=O)Nc2cc3c(cc2C(C)=O)OCO3)CC1] | 376 | 0.029 | (DMSO-d$_6$) δ 0.89 (t, J = 7.4 Hz, 3H), 1.51 (h, J = 7.4 Hz, 2H), 2.30 (t, J = 7.4 Hz, 2H), 2.39-2.48 (m, 2H), 2.52-2.54 (m, 2H), 2.57 (s, 3H), 3.16 (s, 2H), 3.59 (m, 4H), 6.14 (s, 2H), 7.62 (s, 1H), 8.34 (s, 1H), 12.67 (s, 1H). |
| 10 | 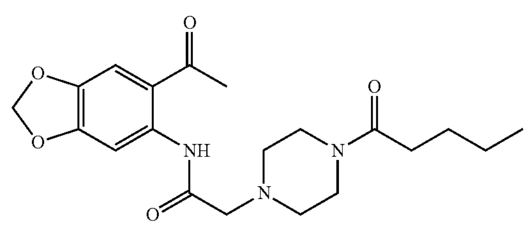 | 390 | 0.009 | (DMSO-d$_6$) δ 0.88 (t, J = 7.3 Hz, 3H), 1.25-1.34 (m, 2H), 1.44-1.51 (m, 2H), 2.31 (t, J = 7.2 Hz, 2H), 2.45 (t, J = 4.3 Hz, 2H), 2.53 (m, 2H), 2.57 (s, 3H), 3.16 (s, 2H), 3.59 (m, 4H), 6.14 (s, 2H), 7.62 (s, 1H), 8.33 (s, 1H), 12.67 (s, 1H). |
| 11 | 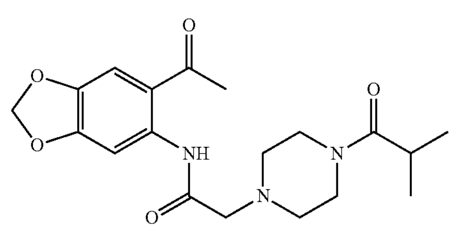 [SMILES: CC(=O)c1cc2c(cc1NC(=O)CN1CCN(C(=O)C(C)C)CC1)OCO2] | 376 | 0.04 | (DMSO-d$_6$) δ 1.00 (d, J = 6.7 Hz, 6H), 2.45-2.47 (m, 2H), 2.53-2.54 (m, 2H), 2.58 (s, 3H), 2.88 (hept, J = 6.7 Hz, 1H), 3.17 (s, 2H), 3.61-3.65 (m, 4H), 6.14 (s, 2H), 7.62 (s, 1H), 8.33 (s, 1H), 12.68 (s, 1H). |

TABLE 2-continued

| SID | Structure | Obs. Mol Ion; MS (M + H⁺) | hT2R54 IC50 (uM) | ¹H NMR (400 MHz) |
|---|---|---|---|---|
| 12 | 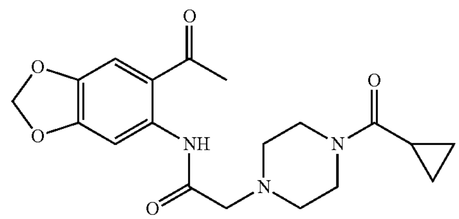 [SMILES: CC(=O)c1cc2c(cc1NC(=O)CN1CCN(C(=O)C3CC3)CC1)OCO2] | 374 | 0.04 | (DMSO-d₆) δ 0.68-0.76 (m, 4H), 1.99 (tt, J = 7.7, 4.8 Hz, 1H), 2.47 (br. s, 2H), 2.56 (br. s, 2H), 2.58 (s, 3H), 3.18 (s, 2H), 3.61 (br. s, 2H), 3.83 (br. s, 2H), 6.14 (s, 2H), 7.62 (s, 1H), 8.34 (s, 1H), 12.69 (s, 1H). |
| 13 | 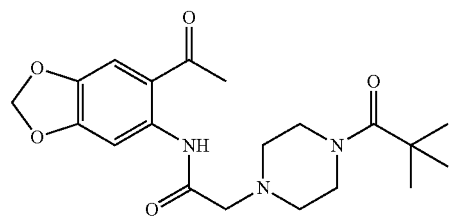 [SMILES: CC(=O)c1cc2c(cc1NC(=O)CN1CCN(C(=O)C(C)(C)C)CC1)OCO2] | 390 | 0.023 | (DMSO-d₆) δ 1.20 (s, 9H), 2.48 (br., s, 4H), 2.58 (s, 3H), 3.16 (s, 2H), 3.69 (br. s, 4H), 6.14 (s, 2H), 7.62 (s, 1H), 8.34 (s, 1H), 12.69 (s, 1H). |
| 14 | 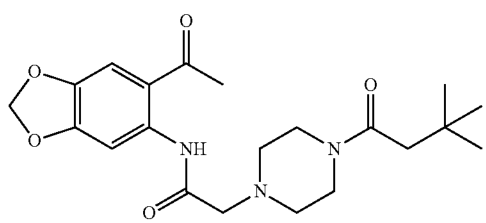 [SMILES: CC(=O)c1cc2c(cc1NC(=O)CN1CCN(C(=O)CC(C)(C)C)CC1)OCO2] | 404 | 0.08 | (DMSO-d₆) δ 0.99 (s, 9H), 2.24 (s, 2H), 2.44-2.47 (m, 2H), 2.52 (m, 2H), 2.57 (s, 3H), 3.16 (s, 2H), 3.64 (m, 4H), 6.14 (s, 2H), 7.61 (s, 1H), 8.33 (s, 1H), 12.66 (s, 1H). |
| 15 | 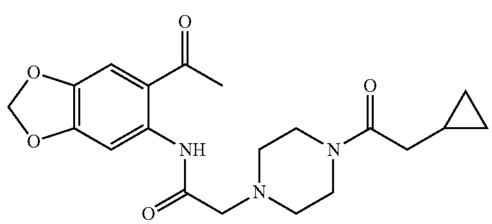 [SMILES: CC(=O)c1cc2c(cc1NC(=O)CN1CCN(C(=O)CC3CC3)CC1)OCO2] | 388 | 0.024 | (DMSO-d₆) δ 0.97-0.13 (m, 2H), 0.43-0.47 (m, 2H), 0.90-1.00 (m, 1H), 2.27 (d, J = 6.8 Hz, 2H), 2.45-2.47 (m, 2H), 2.52 (m, 2H), 2.57 (s, 3H), 3.16 (s, 2H), 3.57-3.62 (m, 4H), 6.14 (s, 2H), 7.62 (s, 1H), 8.34 (s, 1H), 12.67 (s, 1H). |
| 16 | 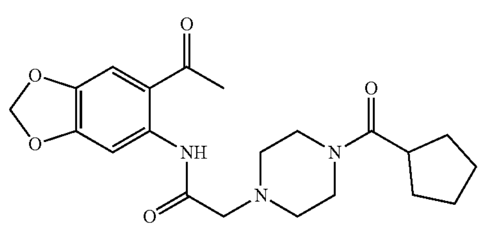 [SMILES: CC(=O)c1cc2c(cc1NC(=O)CN1CCN(C(=O)C3CCCC3)CC1)OCO2] | 402 | 0.029 | (DMSO-d₆) δ 1.47-1.82 (m, 8H), 2.42-2.48 (m, 2H), 2.49-2.55 (m, 2H), 2.58 (s, 3H), 2.90-3.05 (m, 1H), 3.16 (s, 2H), 3.55-3.70 (m, 4H), 6.14 (s, 2H), 7.62 (s, 1H), 8.34 (s, 1H), 12.68 (s, 1H). |
| 17 | 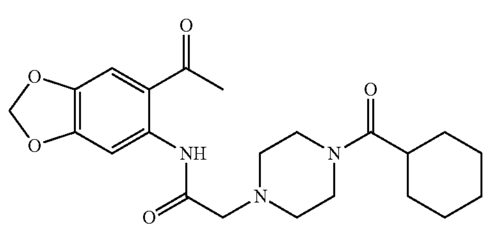 [SMILES: CC(=O)c1cc2c(cc1NC(=O)CN1CCN(C(=O)C3CCCCC3)CC1)OCO2] | 416 | 0.15 | (DMSO-d₆) δ 1.10-1.16 (m, 1H), 1.24-1.38 (m, 4H), 1.62-1.70 (m, 5H), 2.45 (m, 2H), 2.52 (m, 2H), 2.57 (s, 3H), 2.61 (m, 1H), 3.16 (s, 2H), 3.60-3.63 (m, 4H), 6.14 (s, 2H), 7.62 (s, 1H), 8.33 (s, 1H), 12.67 (s, 1H). |

TABLE 2-continued

| SID | Structure | Obs. Mol Ion; MS (M + H+) | hT2R54 IC50 (uM) | 1H NMR (400 MHz) |
|---|---|---|---|---|
| 18 | 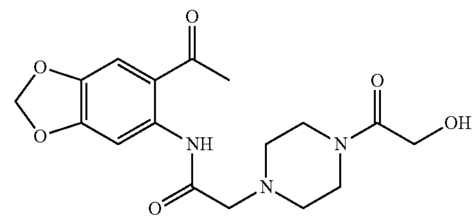 [SMILES: CC(=O)c1cc2c(cc1NC(=O)CN1CCN(C(=O)CO)CC1)OCO2] | 364 | 0.216 | (DMSO-d6) δ 2.45-2.52 (m, 4H), 2.58 (s, 3H), 3.17 (s, 2H), 3.48-3.50 (m, 2H), 3.61-3.64 (m, 2H), 4.10 (d, J = 5.3 Hz, 2H), 4.58 (t, J = 5.5 Hz, 1H), 6.14 (s, 2H), 7.62 (s, 1H), 8.33 (s, 1H), 12.68 (s, 1H). |
| 19 | 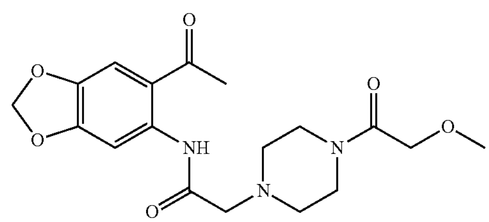 | 378 | 0.06 | (DMSO-d6) δ 2.47-2.48 (m, 2H), 2.52 (m, 2H), 2.58 (s, 3H), 3.16 (s, 2H), 3.29 (s, 3H), 3.53 (m, 2H), 3.60 (m, 2H), 4.10 (s, 2H), 6.14 (s, 2H), 7.62 (s, 1H), 8.33 (s, 1H), 12.68 (s, 1H). |
| 20 | 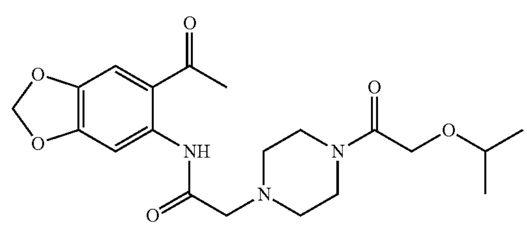 [SMILES: CC(=O)c1cc2c(cc1NC(=O)CN1CCN(C(=O)COC(C)C)CC1)OCO2] | 406 | 0.17 | (DMSO-d6) δ 1.10 (d, J = 6.1 Hz, 6H), 2.47 (m, 2H), 2.54 (m, 2H), 2.58 (s, 3H), 3.17 (2H), 3.56-3.63 (m, 5H), 4.10 (s, 2H), 6.14 (s, 2H), 7.62 (s, 1H), 8.34 (s, 1H), 12.68 (s, 1H). |
| 21 | 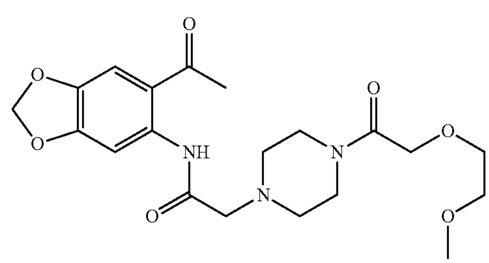 [SMILES: COCCOCC(=O)N1CCN(CC(=O)Nc2cc3c(cc2C(C)=O)OCO3)CC1] | 422 | 0.179 | (DMSO-d6) δ 2.48 (m, 2H), 2.52 (m, 2H), 2.58 (s, 3H), 3.16 (s, 2H), 3.25 (s, 2H), 3.46 (dd, J = 6.2, 3.3 Hz, 2H), 3.55-3.59 (m, 6H), 4.16 (s, 2H), 6.14 (s, 2H), 7.62 (s, 1H), 8.33 (s, 1H), 12.68 (s, 1H). |
| 22 | 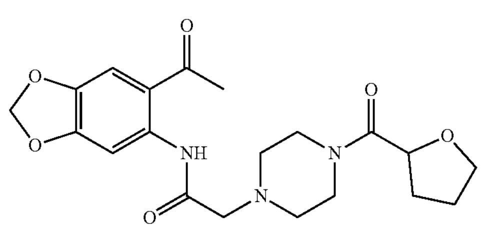 | 404 | 0.021 | (DMSO-d6)) δ 1.74-1.89 (m, 2H), 1.92-2.10 (m, 2H), 2.43-2.56 (m, 4H), 2.58 (s, 3H), 3.16 (s, 2H), 3.56-3.81 (m, 6H), 4.67 (dd, J = 7.7, 5.6 Hz, 1H), 6.14 (s, 2H), 7.62 (s, 1H), 8.33 (s, 1H), 12.68 (s, 1H). |
| 23 | 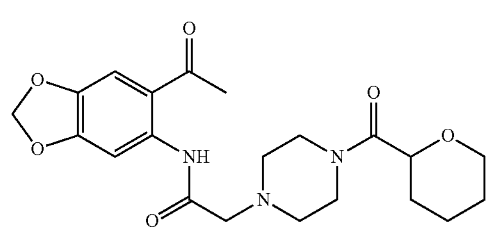 [SMILES: CC(=O)c1cc2c(cc1NC(=O)CN1CCN(C(=O)C3CCCCO3)CC1)OCO2] | 418 | 0.018 | (DMSO-d6) δ 1.48-1.83 (m, 6H), 2.46-2.54 (m, 4H), 2.58 (s, 3H), 3.16 (s, 2H), 3.43-3.49 (m, 1H), 3.60-3.65 (m, 4H), 3.84-3.87 (m, 1H), 4.14 (dd, J = 9.3, 3.3 Hz, 1H), 6.14 (s, 2H), 7.62 (s, 1H), 8.34 (s, 1H), 12.68 (s, 1H). |

TABLE 2-continued

| SID | Structure | Obs. Mol Ion; MS (M + H⁺) | hT2R54 IC50 (uM) | ¹H NMR (400 MHz) |
|---|---|---|---|---|
| 24 | 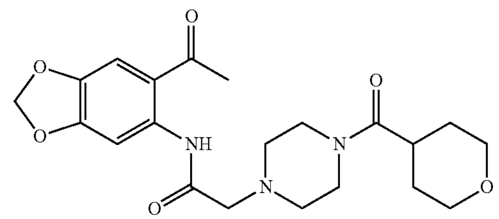 [SMILES: CC(=O)c1cc2c(cc1NC(=O)CN1CCN(C(=O)C3CCOCC3)CC1)OCO2] | 418 | 0.336 | (DMSO-d$_6$) δ 1.44-1.66 (m, 4H), 2.44 (m, 2H), 2.51 (m, 2H), 2.56 (s, 3H), 2.80-2.93 (m, 1H), 3.15 (s, 2H), 3.36 (td, J = 11.5, 2.6 Hz, 2H), 3.55-3.62 (m, 2H), 3.62-3.70 (m, 2H), 3.82 (ddd, J = 11.1, 3.8, 1.8 Hz, 2H), 6.12 (s, 2H), 7.60 (s, 1H), 8.31 (s, 1H), 12.65 (s, 1H). |
| 25 | 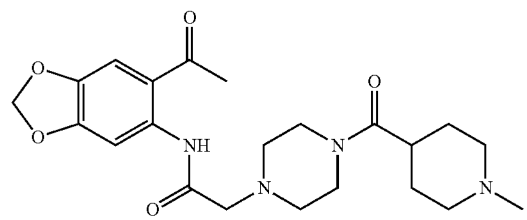 [SMILES: CC(=O)c1cc2c(cc1NC(=O)CN1CCN(C(=O)C3CCN(C)CC3)CC1)OCO2] | 431 | 4.36 | |
| 26 | 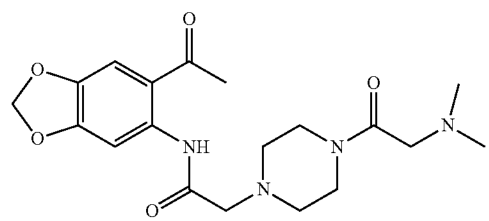 [SMILES: CC(=O)c1cc2c(cc1NC(=O)CN1CCN(C(=O)CN(C)C)CC1)OCO2] | 491 | 2.06 | |
| 27 | 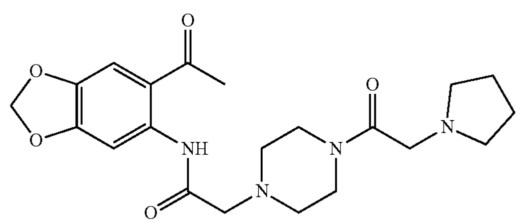 [SMILES: CC(=O)c1cc2c(cc1NC(=O)CN1CCN(C(=O)CN3CCCC3)CC1)OCO2] | 418 | 0.176 | (DMSO-d$_6$) δ 1.66-1.77 (m, 4H), 2.43-2.49 (m, 2H), 2.53 (m, 2H), 2.58 (s, 3H), 2.61 (m, 4H), 3.16 (s, 2H), 3.44 (s, 2H), 3.56-3.62 (m, 2H), 3.62-3.68 (m, 2H), 6.14 (s, 2H), 7.62 (s, 1H), 8.33 (s, 1H), 12.67 (s, 1H). |
| 28 | 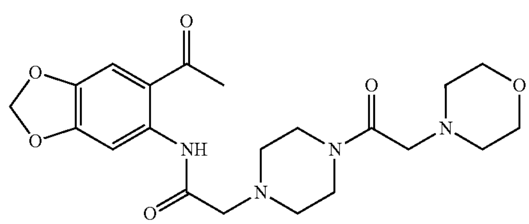 [SMILES: CC(=O)c1cc2c(cc1NC(=O)CN1CCN(C(=O)CN3CCOCC3)CC1)OCO2] | 433 | 0.107 | (DMSO-d$_6$) δ 2.40 (br t, J = 4.9 Hz, 4H), 2.46 (br t, J = 4.9 Hz, 2H), 2.54 (br t, J = 5.2 Hz, 2H), 2.58 (s, 3H), 3.16 (s, 4H), 3.50-3.63 (m, 6H), 3.70 (t, J = 4.9 Hz, 2H), 6.14 (s, 2H), 7.62 (s, 1H), 8.33 (s, 1H), 12.67 (s, 1H). |
| 29 | 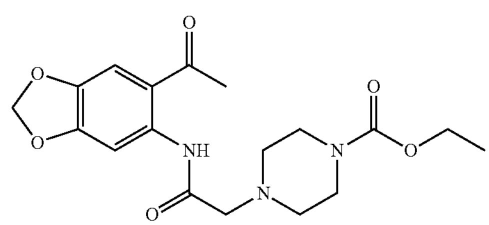 [SMILES: CCOC(=O)N1CCN(CC(=O)Nc2cc3c(cc2C(C)=O)OCO3)CC1] | 378 | 0.311 | (DMSO-d$_6$) δ 1.02-1.22 (m, 5H), 1.66 (d, J = 13.1 Hz, 2H), 1.87-2.02 (m, 1H), 2.31 (d, J = 7.1 Hz, 2H), 2.57 (s, 3H), 2.66-2.89 (m, 2H), 3.90-4.06 (m, 4H), 6.14 (s, 2H), 7.56 (s, 1H), 8.11 (s, 1H), 11.81 (s, 1H). |

TABLE 2-continued

| SID | Structure | Obs. Mol Ion; MS (M + H⁺) | hT2R54 IC50 (uM) | $^1$H NMR (400 MHz) |
|---|---|---|---|---|
| 30 | 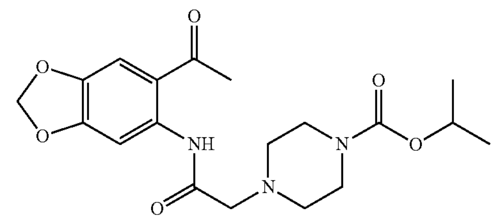 [SMILES: CC(=O)c1cc2c(cc1NC(=O)CN1CCN(C(=O)OC(C)C)CC1)OCO2] | 392 | 0.04 | (DMSO-d$_6$) δ 1.19 (d, J = 6.2 Hz, 6H), 2.47-2.48 (m, 4H), 2.57 (s, 3H), 3.16 (s, 2H), 3.50 (t, J = 4.8 Hz, 4H), 4.78 (m, 1H), 6.14 (s, 2H), 7.62 (s, 1H), 8.33 (s, 1H), 12.65 (s, 1H). |
| 31 | 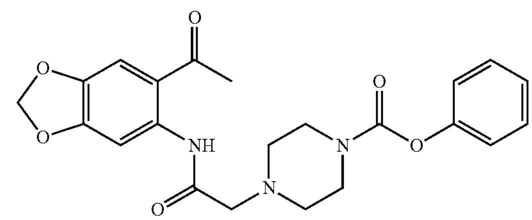 [SMILES: CC(=O)c1cc2c(cc1NC(=O)CN1CCN(C(=O)Oc3ccccc3)CC1)OCO2] | 426 | 0.262 | (DMSO-d$_6$) δ 2.60 (m, 7H), 3.22 (s, 2H), 3.60 (br. s, 2H), 3.75 (br. s, 2H), 6.14 (s, 2H), 7.07-7.19 (m, 2H), 7.22 (tt, J = 7.0, 1.1 Hz, 1H), 7.35-7.44 (m, 2H), 7.63 (s, 1H), 8.35 (s, 1H), 12.70 (s, 1H). |
| 32 | 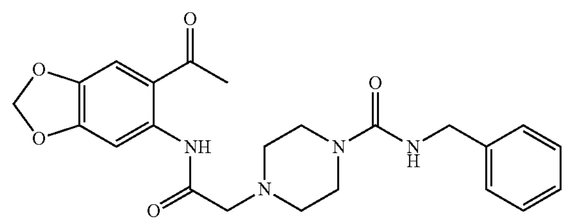 [SMILES: CC(=O)c1cc2c(cc1NC(=O)CN1CCN(C(=O)NCc3ccccc3)CC1)OCO2] | 440 | 0.021 | (DMSO-d$_6$) δ 2.47-2.48 (m, 4H), 2.57 (s, 3H), 3.15 (s, 2H), 3.47-3.50 (m, 4H), 4.25 (d, J = 5.8 Hz, 2H), 6.14 (s, 2H), 7.12 (t, J = 5.8 Hz, 1H), 7.16-7.33 (m, 5H), 7.61 (s, 1H), 8.34 (s, 1H), 12.65 (s, 1H). |
| 33 | 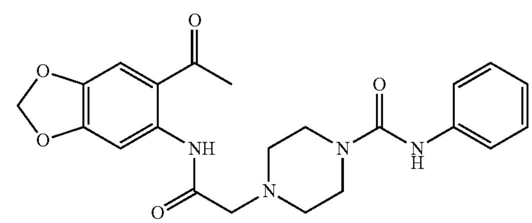 [SMILES: CC(=O)c1cc2c(cc1NC(=O)CN1CCN(C(=O)Nc3ccccc3)CC1)OCO2] | 425 | 0.05 | (DMSO-d$_6$) δ 2.54 (t, J = 4.7 Hz, 4H), 2.59 (s, 3H), 3.19 (s, 2H), 3.60 (t, J = 4.7 Hz, 4H), 6.14 (s, 2H), 6.93 (tt, J = 7.4, 1.2 Hz, 1H), 7.18-7.28 (m, 2H), 7.41-7.49 (m, 2H), 7.63 (s, 1H), 8.35 (s, 1H), 8.55 (s, 1H), 12.68 (s, 1H). |
| 34 | 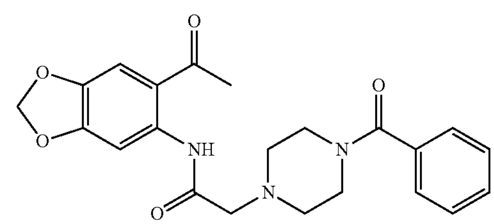 [SMILES: CC(=O)c1cc2c(cc1NC(=O)CN1CCN(C(=O)c3ccccc3)CC1)OCO2] | 410 | 0.02 | (DMSO-d$_6$) δ 2.52-2.55 (m, 4H), 2.58 (s, 3H), 3.18 (s, 2H), 3.49 (br. s, 2H), 3.78 (br. s, 2H), 6.14 (s, 2H), 7.40-7.46 (m, 5H), 7.62 (s, 1H), 8.33 (s, 1H), 12.68 (s, 1H). |
| 35 | 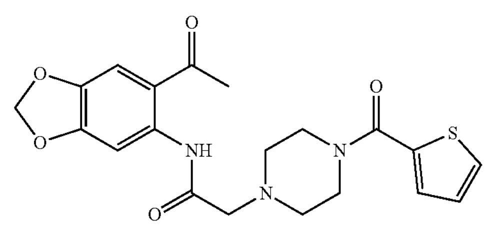 [SMILES: CC(=O)c1cc2c(cc1NC(=O)CN1CCN(C(=O)c3cccs3)CC1)OCO2] | 416 | 0.04 | (DMSO-d$_6$) δ 2.53-2.64 (m, 7H), 3.20 (s, 0H), 3.74-3.86 (m, 4H), 6.14 (s, 1H), 7.13 (dd, J = 5.0, 3.7 Hz, 1H), 7.44 (dd, J = 3.7, 1.1 Hz, 1H), 7.63 (s, 1H), 7.76 (dd, J = 5.0, 1.1 Hz, 1H), 8.34 (s, 1H), 12.71 (s, 1H). |

TABLE 2-continued

| SID | Structure | Obs. Mol Ion; MS (M + H+) | hT2R54 IC50 (uM) | ¹H NMR (400 MHz) |
|---|---|---|---|---|
| 36 | 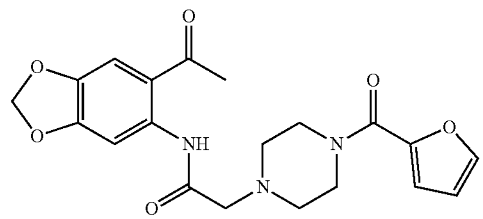 [SMILES: CC(=O)c1cc2c(cc1NC(=O)CN1CCN(C(=O)c3ccco3)CC1)OCO2] | 400 | 0.004 | (DMSO-d₆) δ 2.53-2.62 (m, 7H), 3.19 (s, 2H), 3.66-3.91 (m, 4H), 6.14 (s, 2H), 6.63 (dd, J = 3.5, 1.8 Hz, 1H), 7.01 (dd, J = 3.5, 0.8 Hz, 1H), 7.63 (s, 1H), 7.84 (dd, J = 1.8, 0.8 Hz, 1H), 8.34 (s, 1H), 12.71 (s, 1H). |
| 37 | 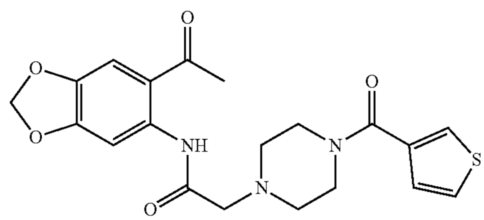 | 416 | 0.023 | (DMSO-d₆) δ 2.50-2.65 (m, 7H), 3.18 (s, 3H), 3.47-3.92 (m, 4H), 6.14 (s, 3H), 7.19-7.26 (m, 1H), 7.58-7.67 (m, 3H), 7.81 (dd, J = 2.9, 1.3 Hz, 1H), 8.33 (s, 1H), 12.70 (s, 1H). |
| 38 | 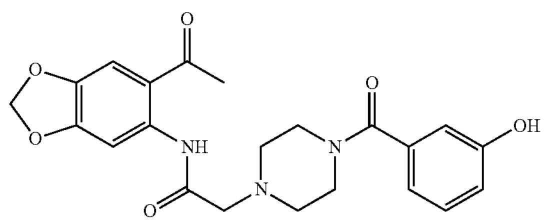 [SMILES: CC(=O)c1cc2c(cc1NC(=O)CN1CCN(C(=O)c3cccc(O)c3)CC1)OCO2] | 426 | 0.05 | (DMSO-d₆) δ 2.58 (m, 7H), 3.18 (s, 2H), 3.48 (br. s, 2H), 3.74 (br. s, 2H), 6.14 (s, 2H), 6.75 (dd, J = 2.5, 1.5 Hz, 1H), 6.81 (ddt, J = 13.2, 7.5, 1.3 Hz, 2H), 7.23 (t, J = 7.6 Hz, 1H), 7.62 (s, 1H), 8.33 (s, 1H), 9.70 (s, 1H), 12.68 (s, 1H). |
| 39 | 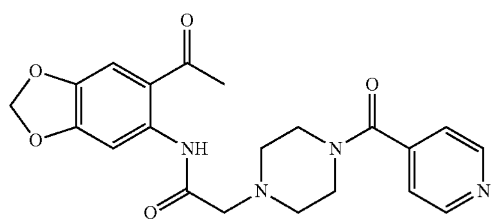 [SMILES: CC(=O)c1cc2c(cc1NC(=O)CN1CCN(C(=O)c3ccncc3)CC1)OCO2] | 411 | 0.07 | (DMSO-d₆) δ 2.50-2.55 (m, 2H), 2.57-2.64 (m, 5H), 3.19 (s, 2H), 3.38-3.48 (m, 2H), 3.75-3.86 (m, 2H), 6.14 (s, 2H), 7.38-7.46 (m, 2H), 7.62 (s, 1H), 8.32 (s, 1H), 8.64-8.70 (m, 2H), 12.68 (s, 1H). |
| 40 | 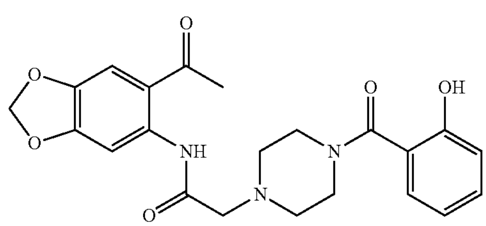 [SMILES: CC(=O)c1cc2c(cc1NC(=O)CN1CCN(C(=O)c3ccccc3O)CC1)OCO2] | 426 | 0.08 | (DMSO-d₆) δ 2.53 (m, 4H), 2.58 (s, 3H), 3.18 (s, 2H), 3.77 (br. s, 4H), 6.13 (s, 2H), 6.82-6.88 (m, 2H), 7.13 (dd, J = 7.5, 1.8 Hz, 1H), 7.22 (ddd, J = 8.2, 7.3, 1.8 Hz, 1H), 7.62 (s, 1H), 8.33 (s, 1H), 9.80 (s, 1H), 12.68 (s, 1H). |
| 41 | 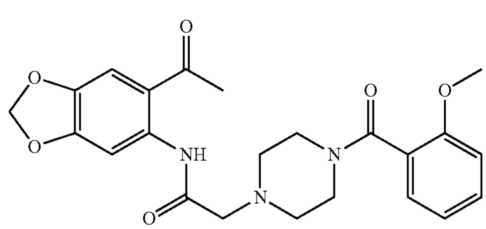 [SMILES: COc1ccccc1C(=O)N1CCN(CC(=O)Nc2cc3c(cc2C(C)=O)OCO3)CC1] | 440 | 0.04 | (DMSO-d₆) δ 2.42-2.50 (m, 2H), 2.55-2.58 (m, 5H), 3.17 (s, 2H), 3.25-3.30 (m, 2H), 3.76-3.81 (m, 5H), 6.13 (s, 2H), 7.00 (td, J = 7.4, 0.9 Hz, 1H), 7.08 (dd, J = 8.5, 0.9 Hz, 1H), 7.19 (dd, J = 7.4, 1.7 Hz, 1H), 7.39 (ddd, J = 8.4, 7.4, 1.8 Hz, 1H), 7.61 (s, 1H), 8.32 (s, 1H), 12.67 (s, 1H). |

TABLE 2-continued

| SID | Structure | Obs. Mol Ion; MS (M + H+) | hT2R54 IC50 (uM) | 1H NMR (400 MHz) |
|---|---|---|---|---|
| 42 | 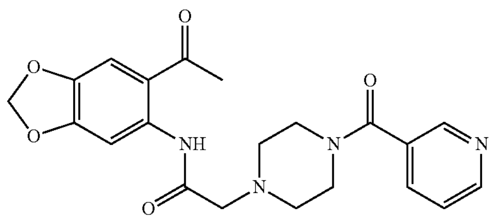 [SMILES: CC(=O)c1cc2c(cc1NC(=O)CN1CCN(C(=O)c3cccnc3)CC1)OCO2] | 411 | 0.06 | (DMSO-d6) δ 2.54 (br. s, 2H), 2.58-2.61 (m, 5H), 3.19 (s, 2H), 3.49 (br. s, 2H), 3.80 (br. s, 2H), 6.14 (s, 2H), 7.48 (ddd, J = 7.8, 4.9, 0.9 Hz, 1H), 7.62 (s, 1H), 7.86 (ddd, J = 7.8, 2.2, 1.7 Hz, 1H), 8.33 (s, 1H), 8.63 (dd, J = 2.2, 0.9 Hz, 1H), 8.65 (dd, J = 4.9, 1.7 Hz, 1H), 12.68 (s, 1H). |
| 43 | 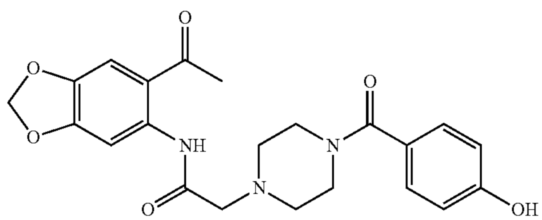 [SMILES: CC(=O)c1cc2c(cc1NC(=O)CN1CCN(C(=O)c3ccc(O)cc3)CC1)OCO2] | 426 | 0.08 | (DMSO-d6) δ 2.53 (m, 4H), 2.58 (s, 3H), 3.17 (s, 2H), 3.64 (br. s, 4H), 6.14 (s, 2H), 6.79 (d, J = 8.6 Hz, 2H), 7.27 (d, J = 8.6 Hz, 2H), 7.62 (s, 1H), 8.33 (s, 1H), 9.87 (br. s, 1H), 12.68 (s, 1H). |
| 44 | 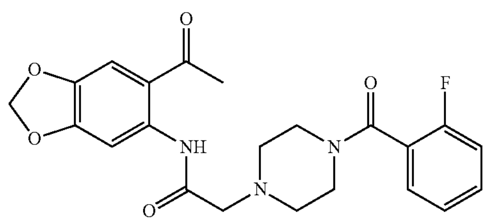 [SMILES: CC(=O)c1cc2c(cc1NC(=O)CN1CCN(C(=O)c3ccccc3F)CC1)OCO2] | 428 | 0.05 | (DMSO-d6) δ 2.48-2.50 (m, 2H), 2.58-2.61 (m, 5H), 3.19 (s, 2H), 3.35-3.43 (m, 2H), 3.74-3.86 (m, 2H), 6.14 (s, 2H), 7.26-7.35 (m, 2H), 7.39-7.46 (m, 1H), 7.51 (m, 1H), 7.62 (s, 1H), 8.33 (s, 1H), 12.68 (s, 1H). |
| 45 | 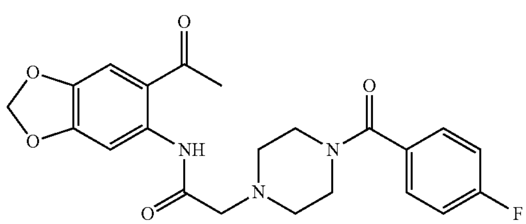 [SMILES: CC(=O)c1cc2c(cc1NC(=O)CN1CCN(C(=O)c3ccc(F)cc3)CC1)OCO2] | 428 | 0.028 | (DMSO-d6) δ 2.54-2.58 (m, 7H), 3.18 (s, 2H), 3.50 (br. s, 2H), 3.76 (br. s, 2H), 6.14 (s, 2H), 7.28 (t, J = 8.9 Hz, 2H), 7.49 (dd, J = 8.8, 5.5 Hz, 2H), 7.62 (s, 1H), 8.33 (s, 1H), 12.68 (s, 1H). |
| 46 | 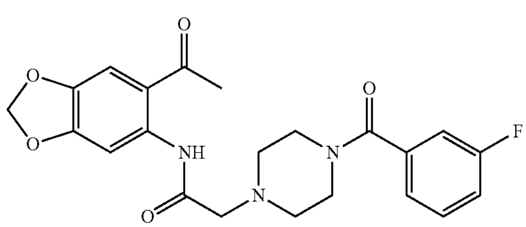 [SMILES: CC(=O)c1cc2c(cc1NC(=O)CN1CCN(C(=O)c3cccc(F)c3)CC1)OCO2] | 428 | 0.026 | (DMSO-d6) δ 2.58 (m, 7H), 3.18 (s, 2H), 3.46 (br. s, 2H), 3.78 (br. s, 2H), 6.14 (s, 2H), 7.17-7.37 (m, 3H), 7.42-7.55 (m, 1H), 7.62 (s, 1H), 8.32 (s, 1H), 12.68 (s, 1H). |
| 47 | 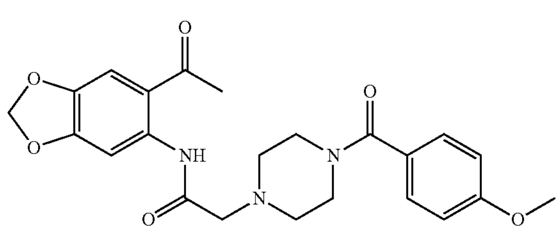 [SMILES: COc1ccc(C(=O)N2CCN(CC(=O)Nc3cc4c(cc3C(C)=O)OCO4)CC2)cc1] | 440 | 0.021 | (DMSO-d6) δ 2.51-2.57 (m, 4H), 2.58 (s, 3H), 3.18 (s, 2H), 3.45-3.74 (m, 4H), 3.79 (s, 3H), 6.14 (s, 2H), 6.94-7.03 (m, 2H), 7.34-7.43 (m, 2H), 7.62 (s, 1H), 8.33 (s, 1H), 12.69 (s, 1H). |

TABLE 2-continued

| SID | Structure | Obs. Mol Ion; MS (M + H⁺) | hT2R54 IC50 (uM) | ¹H NMR (400 MHz) |
|---|---|---|---|---|
| 48 | 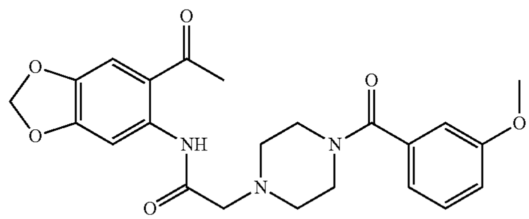 [SMILES: COc1cccc(C(=O)N2CCN(CC(=O)Nc3cc4c(cc3C(C)=O)OCO4)CC2)c1] | 440 | 0.013 | (DMSO-d₆) δ 2.58 (m, 7H), 3.18 (s, 2H), 3.48 (br. s, 2H), 3.78 (m, 5H), 6.14 (s, 2H), 6.92-6.97 (m, 2H), 6.98-7.05 (m, 1H), 7.36 (t, J = 7.6 Hz, 1H), 7.62 (s, 1H), 8.32 (s, 1H), 12.68 (s, 1H). |
| 49 | 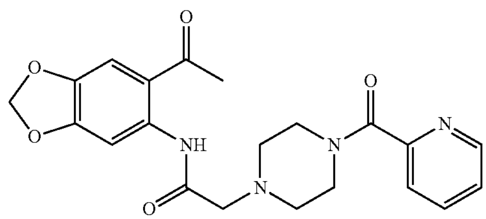 [SMILES: CC(=O)c1cc2c(cc1NC(=O)CN1CCN(C(=O)c3ccccn3)CC1)OCO2] | 411 | 0.1 | (DMSO-d₆) δ 2.50-2.53 (m, 2H), 2.57 (s, 3H), 2.60 (t, J = 4.8 Hz, 2H), 3.17 (s, 2H), 3.53 (t, J = 5.0 Hz, 2H), 3.80 (t, J = 4.9 Hz, 2H), 6.12 (s, 2H), 7.46 (ddd, J = 7.6, 4.9, 1.2 Hz, 1H), 7.57 (dt, J = 7.8, 1.1 Hz, 1H), 7.60 (s, 1H), 7.91 (td, J = 7.7, 1.8 Hz, 1H), 8.31 (s, 1H), 8.57 (ddd, J = 4.9, 1.8, 1.0 Hz, 1H), 12.69 (s, 1H). |
| 50 | 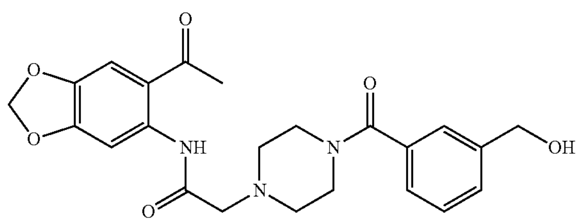 [SMILES: CC(=O)c1cc2c(cc1NC(=O)CN1CCN(C(=O)c3cccc(CO)c3)CC1)OCO2] | 440 | 0.402 | (DMSO-d₆) δ 2.49-2.64 (m, 5H), 3.14-3.21 (m, 3H), 3.28-3.34 (m, 1H), 3.49 (br s, 2H), 3.78 (br s, 2H), 4.53 (d, J = 5.2 Hz, 2H), 5.23-5.31 (m, 1H), 6.14 (s, 2H), 7.23-7.30 (m, 1H), 7.33-7.45 (m, 3H), 7.62 (s, 1H), 8.33 (s, 1H), 12.69 (s, 1H). |
| 51 | 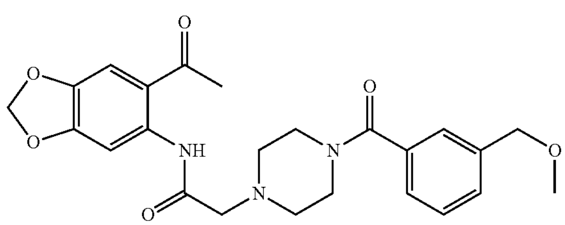 [SMILES: COCc1cccc(C(=O)N2CCN(CC(=O)Nc3cc4c(cc3C(C)=O)OCO4)CC2)c1] | 454 | 0.234 | (DMSO-d₆) δ 2.39-2.63 (m, 8H), 3.18 (s, 2H), 3.30 (s, 3H), 3.48 (br s, 1.5H), 3.78 (br s, 1.5H), 4.45 (s, 2H), 6.14 (s, 2H), 7.30-7.37 (m, 2H), 7.37-7.48 (m, 2H), 7.61 (s, 1H), 8.33 (s, 1H), 12.68 (s, 1H). |
| 52 | 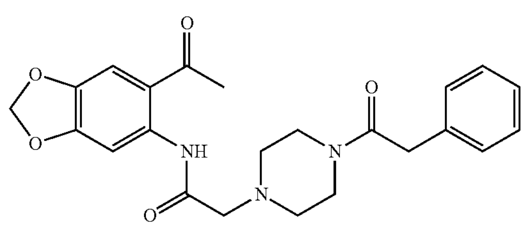 [SMILES: CC(=O)c1cc2c(cc1NC(=O)CN1CCN(C(=O)Cc3ccccc3)CC1)OCO2] | 424 | 0.051 | (DMSO-d₆) δ 2.39-2.48 (m, 4H), 2.56 (s, 3H), 3.13 (s, 2H), 3.7-3.68 (m, 4H), 3.74 (s, 2H), 6.14 (s, 2H), 7.18-7.36 (m, 5H), 7.61 (s, 1H), 8.33 (s, 1H), 12.66 (s, 1H). |
| 53 | 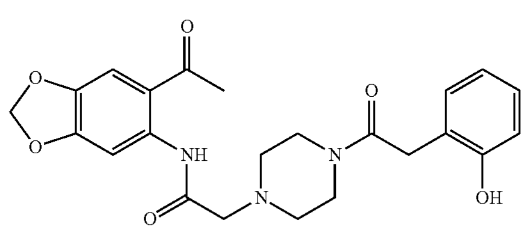 [SMILES: CC(=O)c1cc2c(cc1NC(=O)CN1CCN(C(=O)Cc3ccccc3O)CC1)OCO2] | 440 | 0.018 | (DMSO-d₆) δ 2.45-2.46 (m, 4H), 2.57 (s, 3H), 3.14 (s, 2H), 3.60 (s, 2H), 3.64 (m, 4H), 6.14 (s, 2H), 6.74 (td, J = 7.4, 1.2 Hz, 1H), 6.80 (dd, J = 8.5, 1.2 Hz, 1H), 6.97-7.13 (m, 2H), 7.61 (s, 1H), 8.33 (s, 1H), 9.53 (br. s, 1H), 12.66 (s, 1H). |

TABLE 2-continued

| SID | Structure | Obs. Mol Ion; MS (M + H⁺) | hT2R54 IC50 (uM) | ¹H NMR (400 MHz) |
|---|---|---|---|---|
| 54 | 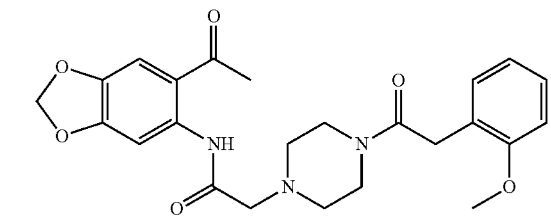 [SMILES: COc1ccccc1CC(=O)N1CCN(CC(=O)Nc2cc3c(cc2C(C)=O)OCO3)CC1] | 454 | 0.024 | (DMSO-d₆) δ 2.46-2.47 (m, 4H), 2.58 (s, 3H), 3.15 (s, 2H), 3.62 (m, 6H), 3.77 (s, 3H), 6.14 (s, 2H), 6.89 (td, J = 7.4, 1.1 Hz, 1H), 6.97 (dd, J = 8.3, 1.1 Hz, 1H), 7.11 (dd, J = 7.5, 1.7 Hz, 1H), 7.23 (ddd, J = 8.2, 7.4, 1.8 Hz, 1H), 7.62 (s, 1H), 8.33 (s, 1H), 12.67 (s, 1H). |
| 55 | 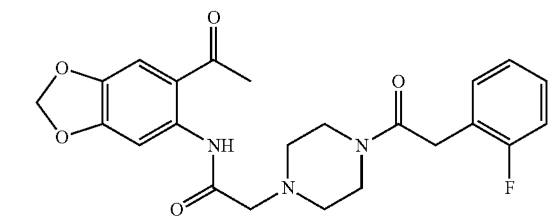 [SMILES: CC(=O)c1cc2c(cc1NC(=O)CN1CCN(C(=O)Cc3ccccc3F)CC1)OCO2] | 442 | 0.07 | (DMSO-d₆) δ 2.48 (m, 2H), 2.52-2.57 (m, 2H), 2.58 (s, 3H), 3.18 (s, 2H), 3.59-3.66 (m, 2H), 3.66-3.73 (m, 2H), 3.76 (s, 2H), 6.14 (s, 2H), 7.09-7.20 (m, 2H), 7.22-7.34 (m, 2H), 7.62 (s, 1H), 8.34 (s, 1H), 12.68 (s, 1H). |
| 56 | 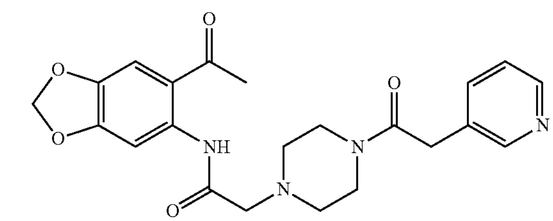 [SMILES: CC(=O)c1cc2c(cc1NC(=O)CN1CCN(C(=O)Cc3cccnc3)CC1)OCO2] | 425 | 0.08 | (DMSO-d₆) δ 2.48 (m, 2H), 2.51-2.54 (m, 2H), 2.57 (s, 3H), 3.17 (s, 2H), 3.63 (m, 2H), 3.70 (m, 2H), 3.79 (s, 2H), 6.14 (s, 2H), 7.33 (ddd, J = 7.8, 4.8, 0.9 Hz, 1H), 7.59-7.67 (m, 2H), 8.33 (s, 1H), 8.43-8.44 (m, 2H), 12.67 (s, 1H). |
| 57 | 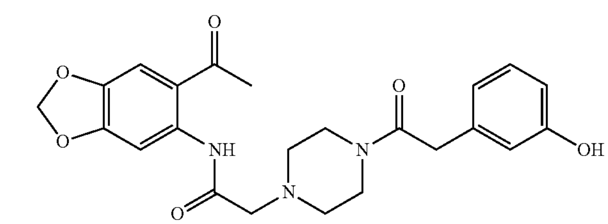 [SMILES: CC(=O)c1cc2c(cc1NC(=O)CN1CCN(C(=O)Cc3cccc(O)c3)CC1)OCO2] | 440 | 0.1 | (DMSO-d₆) δ 2.38-2.48 (m, 4H), 2.56 (s, 3H), 3.13 (s, 2H), 3.61-3.64 (s, 6H), 6.13 (s, 2H), 6.56-6.72 (m, 4H), 7.09 (t, J = 8.0 Hz, 1H), 7.61 (s, 1H), 8.32 (s, 1H), 9.33 (s, 1H), 12.65 (s, 1H). |
| 58 | 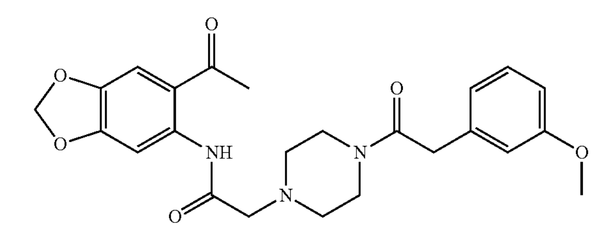 [SMILES: COc1cccc(CC(=O)N2CCN(CC(=O)Nc3cc4c(cc3C(C)=O)OCO4)CC2)c1] | 454 | 0.06 | (DMSO-d₆) δ 2.44 (m, 4H), 2.56 (s, 3H), 3.14 (s, 2H), 3.63 (q, J = 4.1 Hz, 4H), 3.71 (s, 2H), 3.73 (s, 3H), 6.13 (s, 2H), 6.80-6.82 (m, 3H), 7.16-7.28 (m, 1H), 7.61 (s, 1H), 8.32 (s, 1H), 12.65 (s, 1H). |
| 59 | 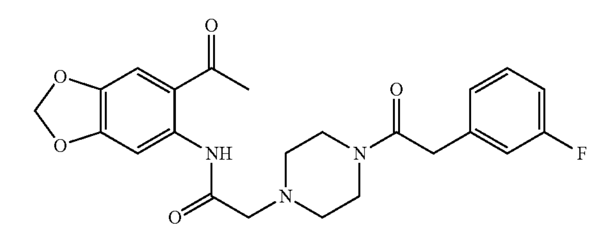 [SMILES: CC(=O)c1cc2c(cc1NC(=O)CN1CCN(C(=O)Cc3cccc(F)c3)CC1)OCO2] | 442 | 0.2 | (DMSO-d₆) δ 2.43-2.49 (m, 4H), 2.57 (s, 3H), 3.15 (s, 2H), 3.64 (dt, J = 13.8, 5.0 Hz, 4H), 3.77 (s, 2H), 6.14 (s, 2H), 7.01-7.11 (m, 3H), 7.30-7.40 (m, 1H), 7.62 (s, 1H), 8.33 (s, 1H), 12.67 (s, 1H). |

TABLE 2-continued

| SID | Structure | Obs. Mol Ion; MS (M + H⁺) | hT2R54 IC50 (uM) | ¹H NMR (400 MHz) |
|---|---|---|---|---|
| 60 | 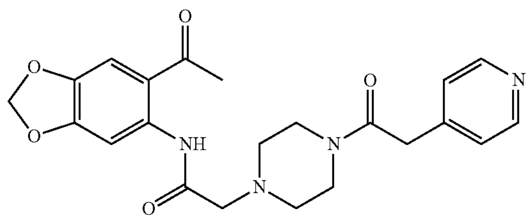 [SMILES: CC(=O)c1cc2c(cc1NC(=O)CN1CCN(C(=O)Cc3ccncc3)CC1)OCO2] | 425 | 0.08 | (DMSO-d$_6$) δ 2.47-2.48 (m, 4H), 2.57 (s, 3H), 3.16 (s, 3H), 3.65 (m, 4H), 3.80 (s, 2H), 6.14 (s, 2H), 7.22-7.29 (m, 2H), 7.61 (s, 1H), 8.33 (s, 1H), 8.44-8.54 (m, 2H), 12.66 (s, 1H). |
| 61 | 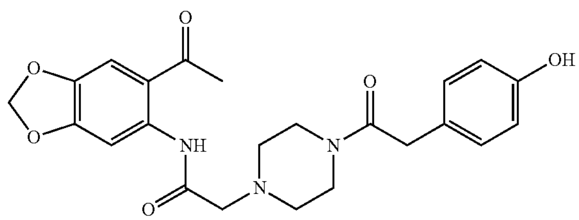 [SMILES: CC(=O)c1cc2c(cc1NC(=O)CN1CCN(C(=O)Cc3ccc(O)cc3)CC1)OCO2] | 440 | 0.05 | (DMSO-d$_6$) δ 2.42 (dt, J = 14.5, 4.8 Hz, 4H), 2.56 (s, 3H), 3.13 (s, 2H), 3.56-3.65 (m, 4H), 6.14 (s, 2H), 6.65-6.73 (m, 2H), 6.98-7.06 (m, 2H), 7.61 (s, 1H), 8.33 (s, 1H), 9.26 (s, 1H), 12.65 (s, 1H). |
| 62 | 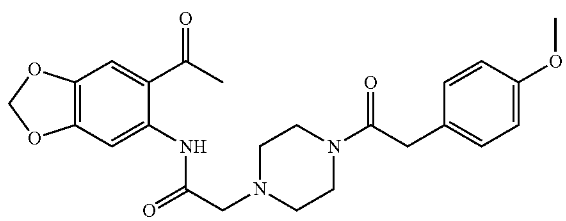 [SMILES: COc1ccc(CC(=O)N2CCN(CC(=O)Nc3cc4c(cc3C(C)=O)OCO4)CC2)cc1] | 454 | 0.2 | (DMSO-d$_6$) δ 2.41-2.46 (m, 4H), 2.46 (s, 3H), 3.13 (s, 2H), 3.60-3.65 (m, 6H), 3.73 (s, 3H), 6.13 (s, 2H), 6.87 (d, J = 8.7 Hz, 2H), 7.15 (d, J = 8.7 Hz, 2H), 7.61 (s, 1H), 8.32 (s, 1H), 12.65 (s, 1H). |
| 63 | 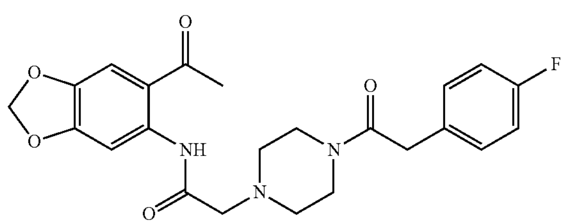 [SMILES: CC(=O)c1cc2c(cc1NC(=O)CN1CCN(C(=O)Cc3ccc(F)cc3)CC1)OCO2] | 442 | 0.4 | (DMSO-d$_6$) δ 2.42-2.48 (m, 4H), 2.57 (s, 3H), 3.15 (s, 2H), 3.64 (dt, J = 13.5, 4.7 Hz, 4H), 3.73 (s, 2H), 6.14 (s, 2H), 7.13 (t, J = 8.9 Hz, 2H), 7.26 (dd, J = 8.9, 5.6 Hz, 2H), 7.61 (s, 1H), 8.33 (s, 1H), 12.66 (s, 1H). |
| 64 | 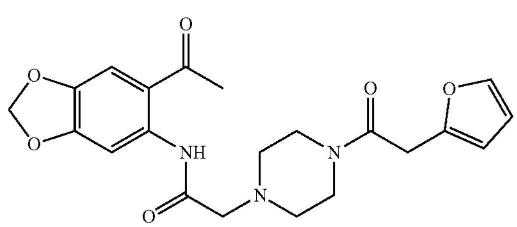 [SMILES: CC(=O)c1cc2c(cc1NC(=O)CN1CCN(C(=O)Cc3ccco3)CC1)OCO2] | 414 | 0.1 | (DMSO-d$_6$) δ 2.46-2.49 (m, 4H), 2.57 (s, 3H), 3.16 (s, 2H), 3.61 (t, J = 4.9 Hz, 2H), 3.66 (t, J = 5.0 Hz, 2H), 3.80 (s, 2H), 6.14 (s, 2H), 6.21 (dd, J = 3.2, 0.8 Hz, 1H), 6.39 (dd, J = 3.1, 1.9 Hz, 1H), 7.56 (dd, J = 1.9, 0.9 Hz, 1H), 7.62 (s, 1H), 8.33 (s, 1H), 12.67 (s, 1H). |
| 65 | 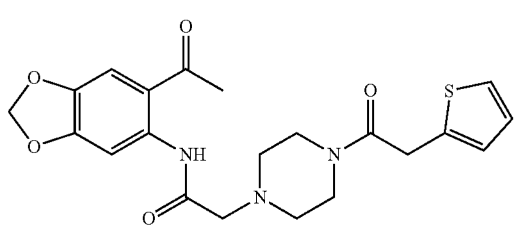 [SMILES: CC(=O)c1cc2c(cc1NC(=O)CN1CCN(C(=O)Cc3cccs3)CC1)OCO2] | 430 | 0.03 | (DMSO-d$_6$) δ 2.43-2.49 (m, 4H), 2.57 (s, 3H), 3.15 (s, 2H), 3.62 (t, J = 4.7 Hz, 2H), 3.68 (t, J = 4.9 Hz, 2H), 3.97 (s, 2H), 6.14 (s, 2H), 6.93 (m, 1H), 6.96 (dd, J = 5.1, 3.4 Hz, 1H), 7.38 (dd, J = 5.1, 1.3 Hz, 1H), 7.61 (s, 1H), 8.33 (s, 1H), 12.67 (s, 1H). |

TABLE 2-continued

| SID | Structure | Obs. Mol Ion; MS (M + H⁺) | hT2R54 IC50 (uM) | ¹H NMR (400 MHz) |
|---|---|---|---|---|
| 66 | 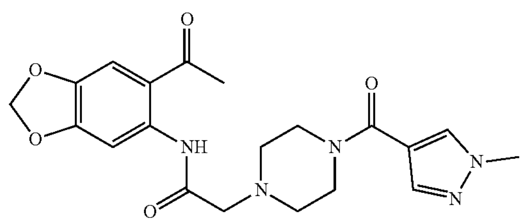 [SMILES: CC(=O)c1cc2c(cc1NC(=O)CN1CCN(C(=O)c3cnn(C)c3)CC1)OCO2] | 414 | 0.017 | (DMSO-d$_6$) δ 2.54 (t, J = 4.9 Hz, 4H), 2.59 (s, 3H), 3.18 (s, 2H), 3.76 (m, 4H), 3.85 (s, 3H), 6.14 (s, 2H), 7.62 (s, 1H), 7.67 (d, J = 0.7 Hz, 1H), 8.07 (s, 1H), 8.34 (s, 1H), 12.71 (s, 1H). |
| 67 | 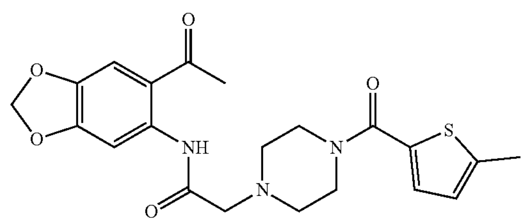 [SMILES: CC(=O)c1cc2c(cc1NC(=O)CN1CCN(C(=O)c3ccc(C)s3)CC1)OCO2] | 430 | 0.015 | (DMSO-d$_6$) δ 2.46 (s, 3H), 2.53-2.58 (m, 4H), 2.59 (s, 3H), 3.19 (s, 2H), 3.79 (s, 4H), 6.14 (s, 2H), 6.82 (dd, J = 3.6, 1.1 Hz, 1H), 7.24 (d, J = 3.5 Hz, 1H), 7.62 (s, 1H), 8.34 (s, 1H), 12.70 (s, 1H). |
| 68 | 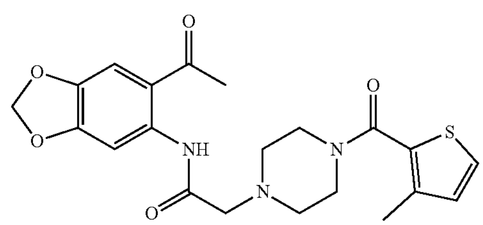 [SMILES: CC(=O)c1cc2c(cc1NC(=O)CN1CCN(C(=O)c3sccc3C)CC1)OCO2] | 430 | 0.03 | (DMSO-d$_6$) δ 2.21 (s, 3H), 2.52-2.57 (m, 4H), 2.58 (s, 3H), 3.19 (s, 3H), 3.64 (br s, 4H), 6.14 (s, 2H), 6.94 (d, J = 4.9 Hz, 1H), 7.58 (d, J = 5.0 Hz, 1H), 7.62 (s, 1H), 8.33 (s, 1H), 12.68 (s, 1H). |
| 69 | 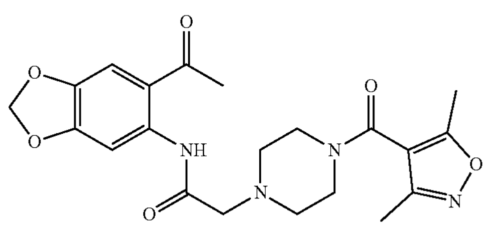 [SMILES: CC(=O)c1cc2c(cc1NC(=O)CN1CCN(C(=O)c3c(C)noc3C)CC1)OCO2] | 429 | 0.04 | (DMSO-d$_6$) δ 2.20 (s, 3H), 2.39 (s, 3H), 2.55 (br s, 4H), 2.58 (s, 3H), 3.19 (s, 2H), 3.62 (m, 4H), 6.14 (s, 2H), 7.62 (s, 1H), 8.32 (s, 1H), 12.66 (s, 1H). |
| 70 | 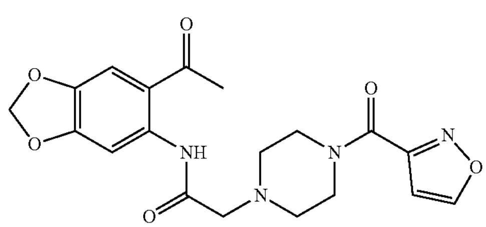 [SMILES: CC(=O)c1cc2c(cc1NC(=O)CN1CCN(C(=O)c3ccon3)CC1)OCO2] | 401 | 0.02 | (DMSO-d$_6$) δ 2.55-2.58 (m, 5H), 2.60-2.63 (m, 2H), 3.20 (s, 2H), 3.68-3.70 (m, 2H), 3.81-3.83 (m, 2H), 6.14 (s, 2H), 6.85 (d, J = 1.7 Hz, 1H), 7.62 (s, 1H), 8.33 (s, 1H), 9.09 (d, J = 1.7 Hz, 1H), 12.70 (s, 1H). |
| 71 | 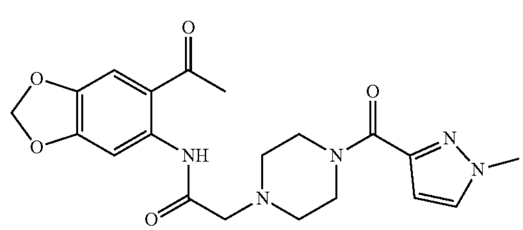 [SMILES: CC(=O)c1cc2c(cc1NC(=O)CN1CCN(C(=O)c3ccn(C)n3)CC1)OCO2] | 414 | 0.05 | (DMSO-d$_6$) δ 2.55 (br s, 4H), 2.59 (s, 3H), 3.18 (s, 2H), 3.77 (br. s, 2H), 3.88 (s, 3H), 4.07 (br s, 2H), 6.14 (s, 2H), 6.55 (d, J = 2.2 Hz, 1H), 7.62 (s, 1H), 7.76 (d, J = 2.2 Hz, 1H), 8.34 (s, 1H), 12.71 (s, 1H). |

TABLE 2-continued
| SID | Structure | Obs. Mol Ion; MS (M + H⁺) | hT2R54 IC50 (uM) | ¹H NMR (400 MHz) |
|---|---|---|---|---|
| 72 | 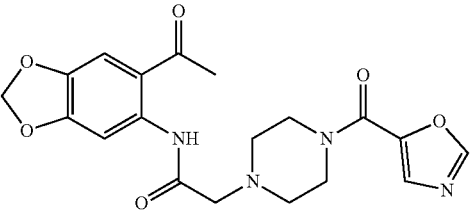 [SMILES: CC(=O)c1cc2c(cc1NC(=O)CN1CCN(C(=O)c3cnco3)CC1)OCO2] | 401 | 0.06 | (DMSO-d₆) δ 2.56-2.62 (m, 7H), 3.20 (s, 2H), 3.81 (br s, 4H), 6.14 (s, 2H), 7.63 (s, 1H), 7.74 (s, 1H), 8.34 (s, 1H), 8.56 (s, 1H), 12.71 (s, 1H). |
| 73 | 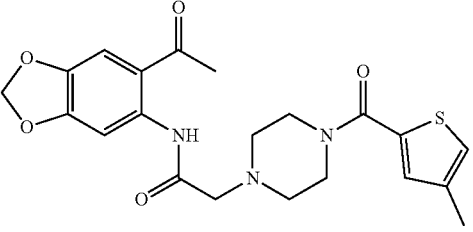 [SMILES: CC(=O)c1cc2c(cc1NC(=O)CN1CCN(C(=O)c3cc(C)cs3)CC1)OCO2] | 430 | 0.08 | (DMSO-d₆) δ 2.22 (d, J = 1.0 Hz, 3H), 2.58 (m, 7H), 3.19 (s, 2H), 3.71-3.86 (m, 4H), 6.14 (s, 2H), 7.26 (d, J = 1.4 Hz, 1H), 7.31-7.38 (m, 1H), 7.62 (s, 1H), 8.34 (s, 1H), 12.71 (s, 1H). |
| 74 | 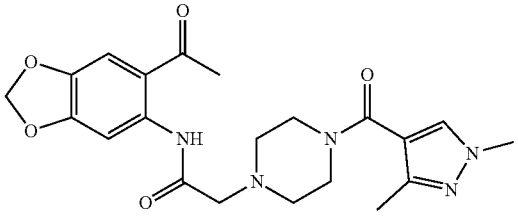 [SMILES: CC(=O)c1cc2c(cc1NC(=O)CN1CCN(C(=O)c3cn(C)nc3C)CC1)OCO2] | 428 | 0.2 | (DMSO-d₆) δ 2.18 (s, 3H), 2.52-2.54 (m, 4H), 2.58 (s, 3H), 3.18 (s, 2H), 3.62-3.72 (m, 4H), 3.75 (s, 3H), 6.14 (s, 2H), 7.62 (s, 1H), 7.86 (s, 1H), 8.34 (s, 1H), 12.69 (s, 1H). |
| 75 | 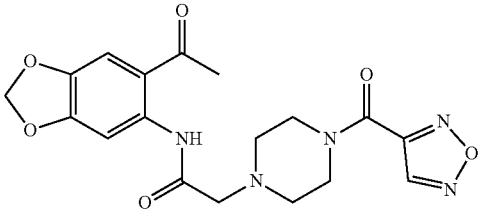 [SMILES: CC(=O)c1cc2c(cc1NC(=O)CN1CCN(C(=O)c3cnon3)CC1)OCO2] | 402 | 0.1 | (DMSO-d₆) δ 2.54-2.61 (m, 7H), 3.19 (s, 2H), 3.70-3.73 (m, 4H), 6.14 (s, 2H), 7.62 (s, 1H), 8.33 (s, 1H), 12.69 (s, 1H). |
| 76 | 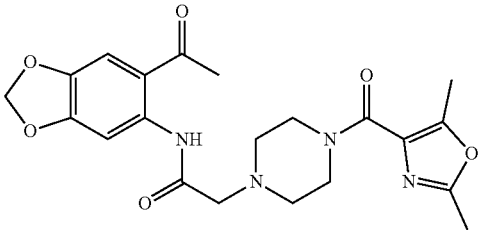 [SMILES: CC(=O)c1cc2c(cc1NC(=O)CN1CCN(C(=O)c3nc(C)oc3C)CC1)OCO2] | 429 | 0.07 | (DMSO-d₆) δ 2.38 (s, 3H), 2.41 (s, 3H), 2.52-2.57 (m, 4H), 2.58 (s, 3H), 3.18 (s, 2H), 3.72 (br s, 2H), 3.97 (br s, 2H), 6.14 (s, 2H), 7.62 (s, 1H), 8.34 (s, 1H), 12.69 (s, 1H). |
| 77 | 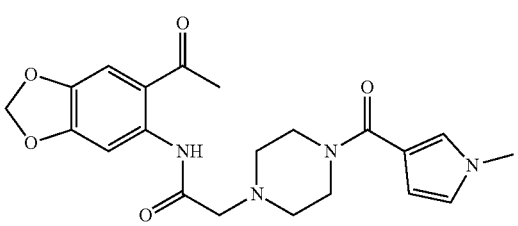 [SMILES: CC(=O)c1cc2c(cc1NC(=O)CN1CCN(C(=O)c3ccn(C)c3)CC1)OCO2] | 413 | 0.03 | (DMSO-d₆) δ 2.51-2.53 (m, 4H), 2.58 (s, 3H), 3.17 (s, 2H), 3.62 (s, 3H), 3.76 (m, 4H), 6.14 (s, 2H), 6.21 (dd, J = 2.8, 1.7 Hz, 1H), 6.72 (t, J = 2.4 Hz, 1H), 7.11 (t, J = 1.9 Hz, 1H), 7.62 (s, 1H), 8.34 (s, 1H), 12.70 (s, 1H). |

TABLE 2-continued

| SID | Structure | Obs. Mol Ion; MS (M + H+) | hT2R54 IC50 (uM) | 1H NMR (400 MHz) |
|---|---|---|---|---|
| 78 | 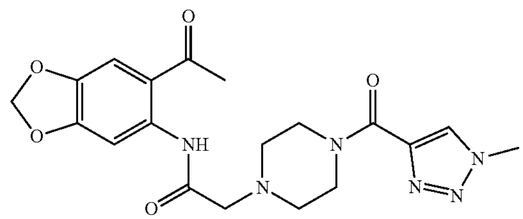 [SMILES: CC(=O)c1cc2c(cc1NC(=O)CN1CCN(C(=O)c3cn(C)nn3)CC1)OCO2] | 415 | 0.03 | (DMSO-d6) δ 2.58-2.60 (m, 7H), 3.19 (s, 2H), 3.79 (br s, 2H), 4.08 (s, 3H), 4.16 (br s, 2H), 6.14 (s, 2H), 7.63 (s, 1H), 8.34 (s, 1H), 8.49 (s, 1H), 12.72 (s, 1H). |
| 79 | 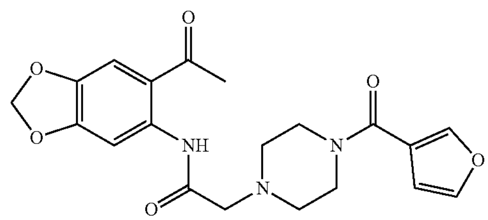 [SMILES: CC(=O)c1cc2c(cc1NC(=O)CN1CCN(C(=O)c3ccoc3)CC1)OCO2] | 400 | 0.03 | (DMSO-d6) δ 2.54 (t, J = 5.0 Hz, 4H), 2.58 (s, 3H), 3.18 (s, 2H), 3.63-3.79 (m, 4H), 6.14 (s, 2H), 6.68 (dd, J = 1.9, 0.8 Hz, 1H), 7.62 (s, 1H), 7.74 (t, J = 1.7 Hz, 1H), 8.06 (dd, J = 1.6, 0.9 Hz, 1H), 8.34 (s, 1H), 12.70 (s, 1H). |
| 80 | 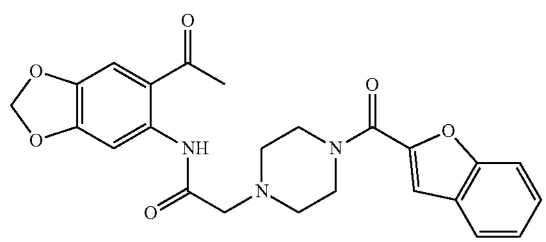 [SMILES: CC(=O)c1cc2c(cc1NC(=O)CN1CCN(C(=O)c3cc4ccccc4o3)CC1)OCO2] | 450 | 0.5 | (DMSO-d6) δ 2.60 (s, 3H), 2.62 (t, J = 4.9 Hz, 4H), 3.22 (s, 2H), 3.88 (br. s, 4H), 6.14 (s, 2H), 7.33 (ddd, J = 8.0, 7.2, 1.0 Hz, 1H), 7.41-7.48 (m, 2H), 7.63 (s, 1H), 7.67 (dq, J = 8.4, 0.9 Hz, 1H), 7.75 (ddd, J = 7.8, 1.4, 0.7 Hz, 1H), 8.34 (s, 1H), 12.73 (s, 1H). |
| 81 | 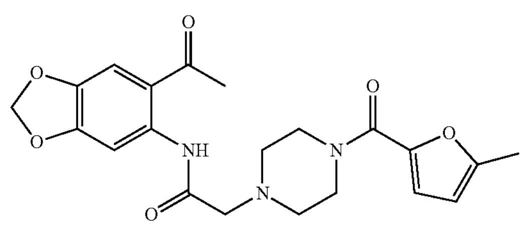 [SMILES: CC(=O)c1cc2c(cc1NC(=O)CN1CCN(C(=O)c3ccc(C)o3)CC1)OCO2] | 414 | 0.004 | (DMSO-d6) δ 2.32 (s, 3H), 2.55-2.59 (m, 7H), 3.19 (s, 2H), 3.81 (br s, 4H), 6.14 (s, 2H), 6.24-6.25 (m, 1H), 6.90 (d, J = 3.3 Hz, 1H), 7.63 (s, 1H), 8.34 (s, 1H), 12.71 (s, 1H). |
| 82 | 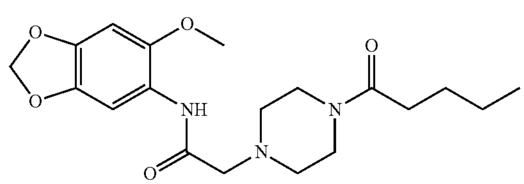 [SMILES: CCCCC(=O)N1CCN(CC(=O)Nc2cc3c(cc2OC)OCO3)CC1] | 378 | 0.54 | (DMSO-d6) δ 0.88 (t, J = 7.3 Hz, 3H), 1.23-1.36 (m, 2H), 1.40-1.53 (m, 2H), 2.31 (t, J = 7.6 Hz, 2H), 2.46 (t, J = 5.2 Hz, 2H), 2.53 (m, 2H), 3.13 (s, 2H), 3.45-3.55 (m, 4H), 3.82 (s, 3H), 5.95 (s, 2H), 6.91 (s, 1H), 7.78 (s, 1H), 9.53 (s, 1H). |
| 83 | 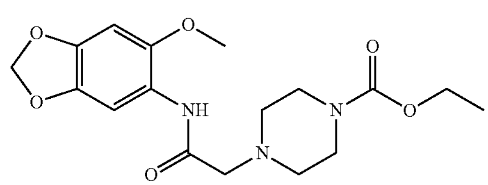 [SMILES: CCOC(=O)N1CCN(CC(=O)Nc2cc3c(cc2OC)OCO3)CC1] | 366 | 0.52 | (DMSO-d6) δ 1.19 (t, J = 7.1 Hz, 3H), 2.49-2.51 (m, 4H), 3.13 (s, 2H), 3.42-3.45 (m, 4H), 3.82 (s, 3H), 4.05 (q, J = 7.1 Hz, 2H), 5.95 (s, 2H), 6.91 (s, 1H), 7.79 (s, 1H), 9.51 (s, 1H). |
| 84 | 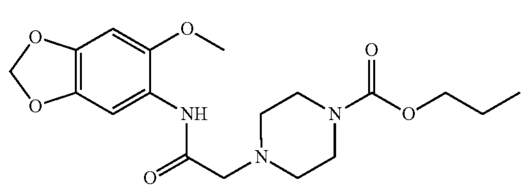 [SMILES: CCCOC(=O)N1CCN(CC(=O)Nc2cc3c(cc2OC)OCO3)CC1] | 380 | 0.24 | (DMSO-d6) δ 0.89 (t, J = 7.4 Hz, 3H), 1.58 (h, J = 7.4 Hz, 2H), 3.13 (s, 2H), 3.43 (m, 4H), 3.82 (s, 3H), 3.96 (t, J = 6.6 Hz, 2H), 5.95 (s, 2H), 6.91 (s, 1H), 7.78 (s, 1H), 9.51 (s, 1H). |

TABLE 2-continued

| SID | Structure | Obs. Mol Ion; MS (M + H+) | hT2R54 IC50 (uM) | ¹H NMR (400 MHz) |
|---|---|---|---|---|
| 85 | 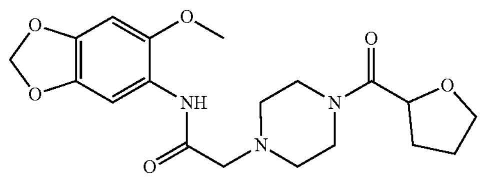 [SMILES: COc1cc2c(cc1NC(=O)CN1CCN(C(=O)C3CCCO3)CC1)OCO2] | 392 | 1.16 | (DMSO-d$_6$) δ 1.77-1.89 (m, 2H), 1.94-2.08 (m, 2H), 2.52-2.55 (m, 4H), 3.13 (s, 2H), 3.51-3.64 (m, 4H), 3.70-3.78 (m, 2H), 3.82 (s, 3H), 4.66 (dd, J = 7.6, 5.7 Hz, 1H), 5.95 (s, 2H), 6.91 (s, 1H), 7.78 (s, 1H), 9.53 (s, 1H). |
| 86 | 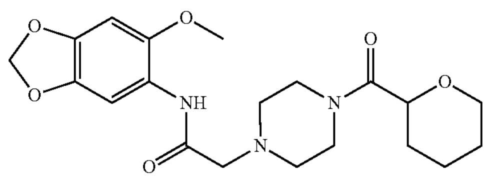 [SMILES: COc1cc2c(cc1NC(=O)CN1CCN(C(=O)C3CCCCO3)CC1)OCO2] | 406 | 1.14 | (DMSO-d$_6$) δ 1.46-1.57 (m, 6H), 2.51 (m, 4H), 3.11 (s, 2H), 3.44-3.53 (m, 6H), 3.80 (s, 3H), 4.11 (dd, J = 9.1, 3.5 Hz, 1H), 5.93 (s, 2H), 6.89 (s, 1H), 7.76 (s, 1H), 9.51 (s, 1H). |
| 87 | 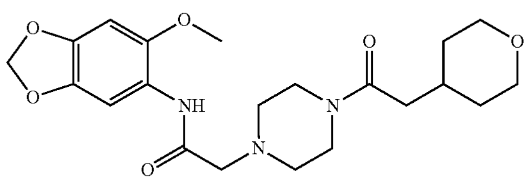 | 420 | 1.04 | (DMSO-d$_6$) δ 1.19 (qd, J = 12.0, 4.3 Hz, 2H), 1.52-1.64 (m, 2H), 1.91 (m, 1H), 2.26 (d, J = 6.9 Hz, 2H), 2.42-2.53 (m, 4H), 3.13 (s, 2H), 3.25-3.30 (m, 2H), 3.51-3.53 (m, 4H), 3.79 (m, 2H), 3.82 (s, 3H), 5.95 (s, 2H), 6.91 (s, 1H), 7.77 (s, 1H), 9.52 (s, 1H). |
| 88 | 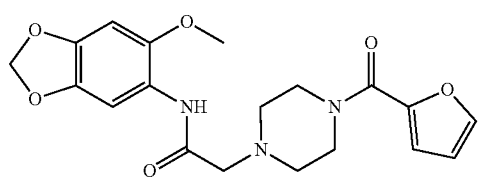 [SMILES: COc1cc2c(cc1NC(=O)CN1CCN(C(=O)c3ccco3)CC1)OCO2] | 388 | 0.13 | (DMSO-d$_6$) δ 2.58-2.60 (m, 4H), 3.16 (s, 2H), 3.73 (br s, 4H), 3.83 (s, 3H), 5.95 (s, 2H), 6.63 (dd, J = 3.5, 1.8 Hz, 1H), 6.92 (s, 1H), 7.01 (dd, J = 3.5, 0.8 Hz, 1H), 7.78 (s, 1H), 7.85 (dd, J = 1.8, 0.8 Hz, 1H), 9.54 (s, 1H). |
| 89 | 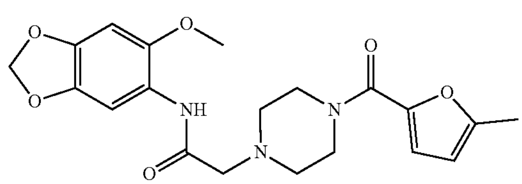 | 402 | 0.08 | (DMSO-d$_6$) δ 2.32 (s, 3H), 2.56-2.59 (m, 4H), 3.16 (s, 2H), 3.73 (br s, 4H), 3.83 (s, 3H), 5.95 (s, 2H), 6.25 (dd, J = 3.3, 1.0 Hz, 1H), 6.90 (d, J = 3.3 Hz, 1H), 6.91 (s, 1H), 7.78 (s, 1H), 9.54 (s, 1H). |
| 90 | 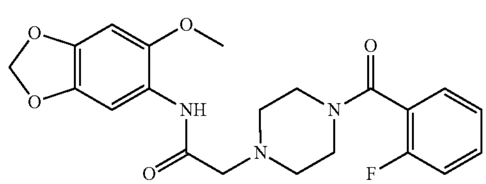 [SMILES: COc1cc2c(cc1NC(=O)CN1CCN(C(=O)c3ccccc3F)CC1)OCO2] | 416 | 0.20 | (DMSO-d$_6$) δ 2.58 (m, 2H), 2.60-2.62 (m, 2H), 3.16 (s, 2H), 3.28-3.30 (m, 2H), 3.71-3.73 (m, 2H), 3.82 (s, 3H), 5.95 (s, 2H), 6.91 (s, 1H), 7.28-7.33 (m, 2H), 7.42 (td, J = 7.2, 1.8 Hz, 1H), 7.48-7.54 (m, 1H), 7.76 (s, 1H), 9.51 (s, 1H). |
| 91 | 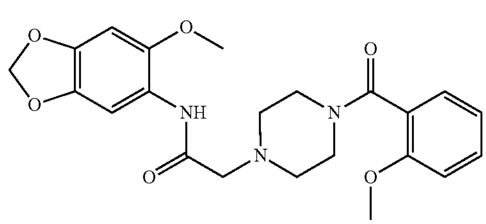 [SMILES: COc1cc2c(cc1NC(=O)CN1CCN(C(=O)c3ccccc3OC)CC1)OCO2] | 428 | 0.28 | (DMSO-d$_6$) δ 2.44-2.47 (m, 2H), 2.58 (t, J = 5.1 Hz, 2H), 3.14 (d, J = 2.1 Hz, 2H), 3.19 (m, 2H), 3.68-3.70 (m, 2H), 3.80 (s, 3H), 3.82 (s, 3H), 5.95 (s, 2H), 6.91 (s, 1H), 7.00 (td, J = 7.4, 0.9 Hz, 1H), 7.09 (d, J = 7.6 Hz, 1H), 7.19 (dd, J = 7.4, 1.7 Hz, 1H), 7.39 (ddd, J = 8.3, 7.4, 1.8 Hz, 1H), 7.76 (s, 1H), 9.52 (s, 1H). |
| 92 | 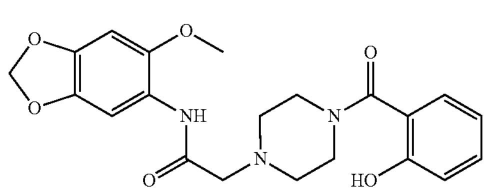 [SMILES: COc1cc2c(cc1NC(=O)CN1CCN(C(=O)c3ccccc3O)CC1)OCO2] | 414 | 0.44 | (DMSO-d$_6$) δ 2.54 (br s, 4H), 3.14 (s, 2H), 3.65 (br s, 4H), 3.82 (s, 3H), 5.95 (s, 2H), 6.82-6.88 (m, 2H), 6.91 (s, 1H), 7.12 (dd, J = 7.5, 1.7 Hz, 1H), 7.22 (ddd, J = 8.2, 7.3, 1.7 Hz, 1H), 7.77 (s, 1H), 9.54 (s, 1H), 9.83 (br s, 1H). |

TABLE 2-continued

| SID | Structure | Obs. Mol Ion; MS (M + H+) | hT2R54 IC50 (uM) | 1H NMR (400 MHz) |
|---|---|---|---|---|
| 93 | 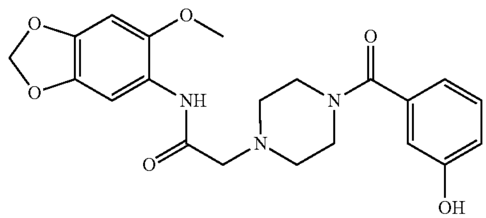 [SMILES: COc1cc2c(cc1NC(=O)CN1CCN(C(=O)c3cccc(O)c3)CC1)OCO2] | 414 | 0.43 | (DMSO-d6) δ 2.55 (br. s, 4H), 3.15 (s, 2H), 3.65 (br s, 4H), 3.83 (s, 3H), 5.95 (s, 2H), 6.75 (dd, J = 2.4, 1.5 Hz, 1H), 6.79 (dt, J = 7.5, 1.3 Hz, 1H), 6.83 (ddd, J = 8.2, 2.5, 1.0 Hz, 1H), 6.91 (s, 1H), 7.23 (t, J = 7.6 Hz, 1H), 7.77 (s, 1H), 9.53 (s, 1H), 9.76 (br s, 1H). |
| 94 | 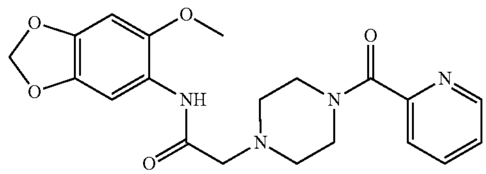 [SMILES: COc1cc2c(cc1NC(=O)CN1CCN(C(=O)c3ccccn3)CC1)OCO2] | 399 | 1.51 | (DMSO-d6) δ 2.50-2.53 (m, 2H), 2.60-2.62 (m, 2H), 3.14 (s, 2H), 3.45 (t, J = 5.0 Hz, 2H), 3.70-3.72 (m, 2H), 3.81 (s, 3H), 5.93 (s, 2H), 6.89 (s, 1H), 7.47 (ddd, J = 7.6, 4.9, 1.2 Hz, 1H), 7.57 (dt, J = 7.8, 1.1 Hz, 1H), 7.75 (s, 1H), 7.92 (td, J = 7.7, 1.7 Hz, 1H), 8.57 (ddd, J = 4.9, 1.8, 1.0 Hz, 1H), 9.51 (s, 1H). |
| 95 | 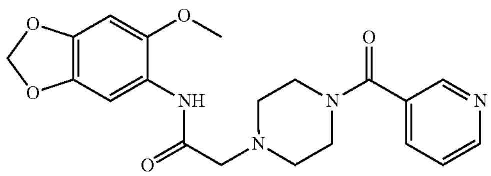 [SMILES: COc1cc2c(cc1NC(=O)CN1CCN(C(=O)c3cccnc3)CC1)OCO2] | 399 | 1.34 | (DMSO-d6) δ 2.55 (br s, 2H), 2.61 (br s, 2H), 3.16 (s, 2H), 3.40 (br s, 2H), 3.71 (br s, 2H), 3.83 (s, 3H), 5.95 (s, 2H), 6.91 (s, 1H), 7.49 (ddd, J = 7.8, 4.9, 0.9 Hz, 1H), 7.77 (s, 1H), 7.85 (dt, J = 7.8, 1.9 Hz, 1H), 8.63 (dd, J = 2.3, 0.9 Hz, 1H), 8.65 (dd, J = 4.9, 1.7 Hz, 1H), 9.52 (s, 1H). |
| 96 | 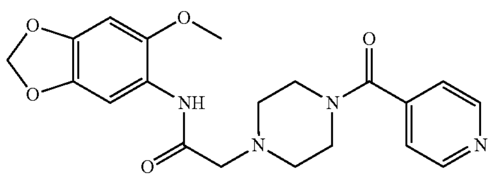 | 399 | 1.44 | (DMSO-d6) δ 2.52 (m, 2H), 2.61-2.64 (m, 2H), 3.16 (s, 2H), 3.43 (br s, 2H), 3.71 (br s, 2H), 3.83 (s, 3H), 5.95 (s, 2H), 6.91 (s, 1H), 7.40-7.41 (m, 2H), 7.76 (s, 1H), 8.67-8.68 (m, 2H), 9.51 (s, 1H). |
| 97 | 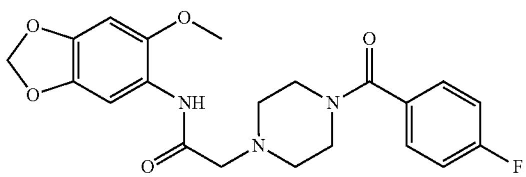 [SMILES: COc1cc2c(cc1NC(=O)CN1CCN(C(=O)c3ccc(F)cc3)CC1)OCO2] | 416 | <1 | (DMSO-d6) δ 2.50-2.61 (m, 3H), 3.13 (s, 2H), 3.18-3.74 (m, 5H), 3.81 (s, 3H), 5.93 (s, 2H), 6.89 (s, 1H), 7.21-7.35 (m, 2H), 7.42-7.52 (m, 1H), 7.75 (s, 1H), 7.93-8.03 (m, 1H), 9.51 (s, 1H). |
| 98 | 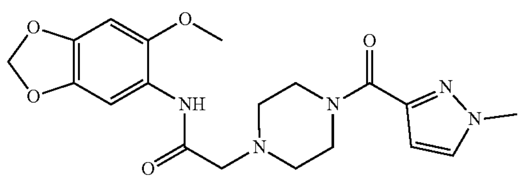 [SMILES: COc1cc2c(cc1NC(=O)CN1CCN(C(=O)c3ccn(C)n3)CC1)OCO2] | 402 | 1.08 | (DMSO-d6) δ 2.54-2.56 (m, 4H), 3.15 (s, 2H), 3.66 (m, 4H), 3.83 (s, 3H), 3.85 (s, 3H), 5.95 (s, 2H), 6.92 (s, 1H), 7.67 (d, J = 0.7 Hz, 1H), 7.78 (s, 1H), 8.06 (s, 1H), 9.54 (s, 1H). |
| 99 | 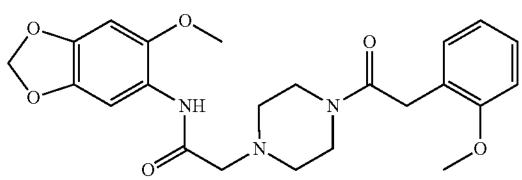 [SMILES: COc1ccccc1CC(=O)N1CCN(CC(=O)Nc2cc3c(cc2OC)OCO3)CC1] | 442 | 0.60 | (DMSO-d6) δ 2.44-2.53 (m, 4H), 3.12 (s, 2H), 3.50-3.59 (m, 4H), 3.62 (s, 2H), 3.76 (s, 3H) 3.82 (s, 3H), 5.95 (s, 2H), 6.83-7.00 (m, 3H), 7.03-7.28 (m, 2H), 7.77 (s, 1H), 9.52 (s, 1H). |
| 100 | 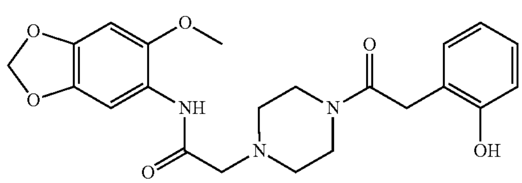 [SMILES: COc1cc2c(cc1NC(=O)CN1CCN(C(=O)Cc3ccccc3O)CC1)OCO2] | 428 | 0.43 | (DMSO-d6) δ 2.46 (m, 4H), 3.11 (s, 2H), 3.55 (m, 4H), 3.59 (s, 2H), 3.81 (s, 3H), 5.95 (s, 2H), 6.51 (m, 1H), 6.70-6.77 (m, 1H), 6.80 (dd, J = 8.5, 1.3 Hz, 1H), 6.91 (s, 1H), 7.04 (d, J = 7.1 Hz, 1H), 7.76 (s, 1H), 8.31 (s, 1H), 9.51 (s, 1H). |

TABLE 2-continued

| SID | Structure | Obs. Mol Ion; MS (M + H+) | hT2R54 IC50 (uM) | 1H NMR (400 MHz) |
|---|---|---|---|---|
| 282 | 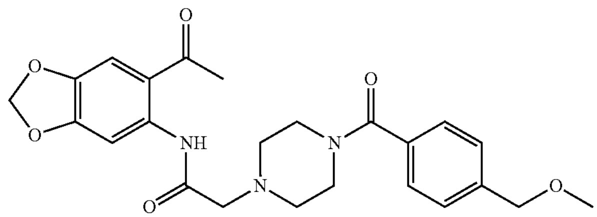 [SMILES: COCc1ccc(C(=O)N2CCN(CC(=O)Nc3cc4c(cc3C(C)=O)OCO4)CC2)cc1] | 454 | 0.038 | (DMSO-d6) δ 2.50-2.62 (m, 4H), 2.58 (s, 3H), 3.18 (s, 2H), 3.31 (d, J = 0.6 Hz, 3H), 3.39 (br s, 2H), 3.77 (br s, 2H), 4.45 (s, 2H), 6.14 (s, 2H), 7.36-7.42 (m, 4H), 7.62 (s, 1H), 8.33 (d, J = 0.5 Hz, 1H), 12.69 (s, 1H). |
| 283 | 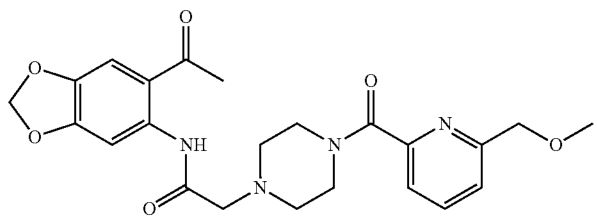 [SMILES: COCc1cccc(C(=O)N2CCN(CC(=O)Nc3cc4c(cc3C(C)=O)OCO4)CC2)n1] | 455 | 0.125 | (DMSO-d6) δ 2.50-2.54 (m, 2H), 2.59 (s, 3H), 2.59-2.64 (m, 2H), 3.19 (s, 2H), 3.37 (s, 3H), 3.50-3.55 (m, 2H), 3.77-3.83 (m, 2H), 4.51 (s, 2H), 6.14 (s, 2H), 7.48 (dd, J = 7.8, 0.7 Hz, 2H), 7.62 (s, 1H), 7.94 (t, J = 7.8 Hz, 1H), 8.33 (s, 1H), 12.71 (s, 1H). |
| 284 | 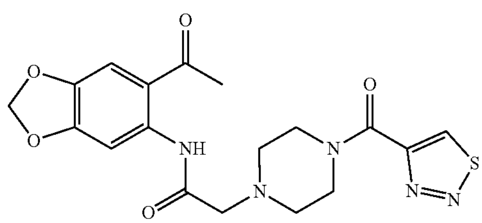 [SMILES: CC(=O)c1cc2c(cc1NC(=O)CN1CCN(C(=O)c3csnn3)CC1)OCO2] | 418 | 0.030 | (DMSO-d6) δ 2.54-2.61 (m, 2H), 2.59 (s, 3H), 2.62-2.69 (m, 2H), 3.22 (s, 2H), 3.67-3.74 (m, 2H), 3.85-3.92 (m, 2H), 6.14 (s, 2H), 7.63 (s, 1H), 8.34 (s, 1H), 9.60 (d, J = 0.5 Hz, 1H), 12.72 (s, 1H). |
| 285 | 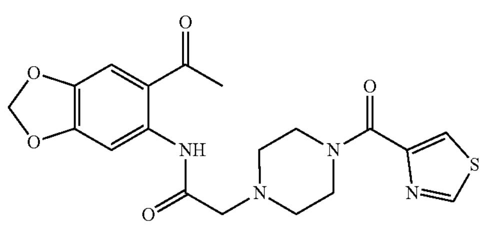 | 417 | 0.034 | (DMSO-d6) δ 2.52-2.64 (m, 4H), 2.58 (s, 3H), 3.19 (s, 2H), 3.77-3.84 (m, 4H), 6.14 (s, 2H), 7.62 (s, 1H), 8.19 (d, J = 2.0 Hz, 1H), 8.34 (s, 1H), 9.17 (d, J = 2.0 Hz, 1H), 12.71 (s, 1H). |
| 286 | 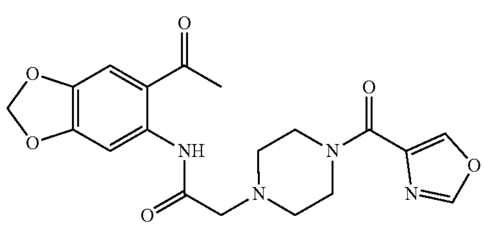 | 401 | 0.108 | (DMSO-d6) δ 2.54-2.62 (m, 4H), 2.58 (s, 3H), 3.19 (s, 2H), 3.76 (br s, 2H), 4.02 (br s, 2H), 6.14 (s, 2H), 7.62 (s, 1H), 8.34 (s, 1H), 8.50-8.51 (m, 1H), 8.59-8.60 (m, 1H), 12.71 (s, 1H). |
| 287 | 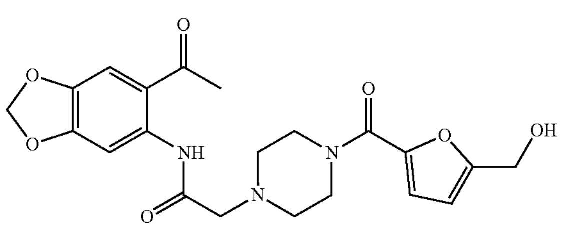 [SMILES: CC(=O)c1cc2c(cc1NC(=O)CN1CCN(C(=O)c3ccc(CO)o3)CC1)OCO2] | 430 | 0.23 | (DMSO-d6) 2.58 (m, 76H), 3.19 (s, 2H), 3.83 (br, 4H), 4.37-4.46 (m, 2H), 5.38 (m, 1H), 6.14 (s, 2H), 6.43 (d, J = 3.4 Hz, 1H), 6.94 (d, J = 3.4 Hz, 1H), 7.63 (s, 1H), 8.34 (s, 1H), 12.72 (s, 1H). |

TABLE 2-continued

| SID | Structure | Obs. Mol Ion; MS (M + H⁺) | hT2R54 IC50 (uM) | ¹H NMR (400 MHz) |
|---|---|---|---|---|
| 288 | 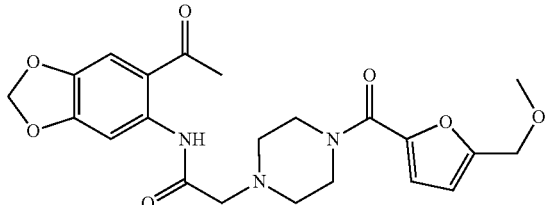 | 444 | 0.065 | (DMSO-d₆) δ δ 2.59 (m, 7H), 3.19 (br, 2H), 3.25-3.27 s, 3H), 3.81 (br, 4H), 4.40 (s, 2H), 6.15 (s, 2H), 6.58 (d, J = 3.3 Hz, 1H), 6.97 (d, J = 3.4 Hz, 1H), 7.63 (s, 1H), 8.34 (br, 1H), 12.72 (br, 1H). |
| 289 | 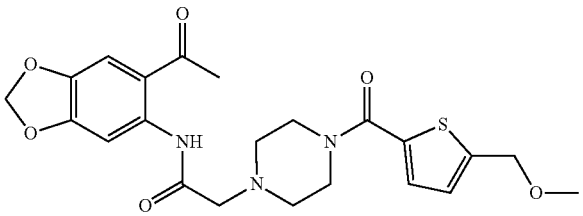 [SMILES: COCc1ccc(C(=O)N2CCN(CC(=O)Nc3cc4c(cc3C(C)=O)OCO4)CC2)s1] | 460 | 0.021 | (DMSO-d₆) δ 2.54-2.62 (, 7H), 3.19 (s, 2H), 3.30 (d, J = 1.1 Hz, 3H), 3.75-3.83 (m, 4H), 4.58 (s, 2H), 6.14 (d, J = 1.1 Hz, 2H), 7.02-7.05 (m, 1H), 7.31 (dd, J = 3.7, 1.1 Hz, 1H), 7.62 (d, J = 1.1 Hz, 1H), 8.33 (d, J = 1.1 Hz, 1H), 12.70 (s, 1H). |
| 290 | 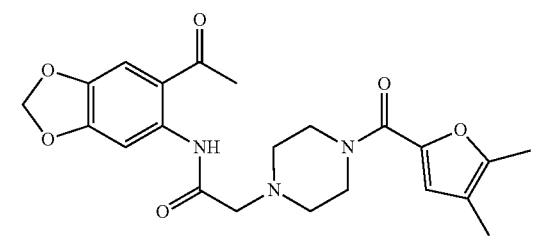 [SMILES: CC(=O)c1cc2c(cc1NC(=O)CN1CCN(C(=O)c3cc(C)c(C)o3)CC1)OCO2] | 428 | 0.01 | (DMSO-d₆) δ 1.94 (s, 3H), 2.23 (s, 3H), 2.55 (t, J = 5.0 Hz, 4H), 2.59 (s, 3H), 3.18 (s, 2H), 3.80 (m, 4H), 6.14 (s, 2H), 6.81 (s, 1H), 7.63 (s, 1H), 8.34 (s, 1H), 12.71 (s, 1H). |
| 291 | 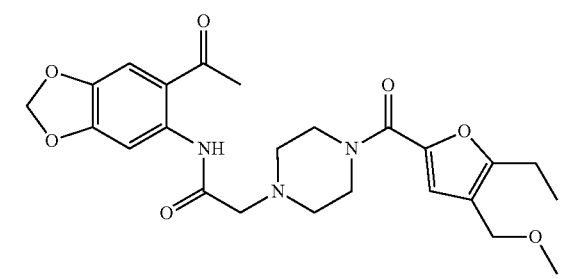 [SMILES: CCc1oc(C(=O)N2CCN(CC(=O)Nc3cc4c(cc3C(C)=O)OCO4)CC2)cc1COC] | 472 | 0.049 | (DMSO-d₆) δ 1.16 (td, J = 7.5, 1.3 Hz, 3H), 2.54-2.61 (m, 7H), 2.65-2.73 (m, 2H), 3.19 (s, 2H), 3.22 (d, J = 1.3 Hz, 3H), 3.81 (br s, 4H), 4.23 (d, J = 1.2 Hz, 2H), 6.14 (d, J = 1.3 Hz, 2H), 6.91 (d, J = 1.2 Hz, 1H), 7.62 (d, J = 1.2 Hz, 1H), 8.34 (d, J = 1.3 Hz, 1H), 12.71 (s, 1H). |
| 292 | 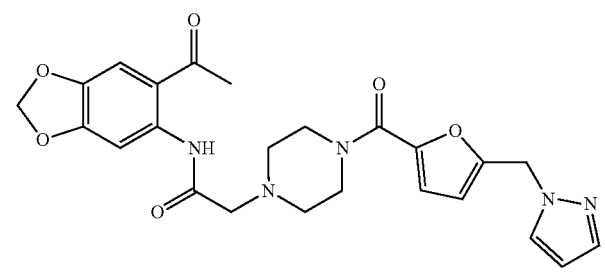 [SMILES: CC(=O)c1cc2c(cc1NC(=O)CN1CCN(C(=O)c3ccc(Cn4cccn4)o3)CC1)OCO2] | 480 | 0.006 | (DMSO-d₆) δ 2.52-2.57 (m, 4H), 2.59 (s, 3H), 3.18 (s, 2H), 3.76 (br s, 4H), 5.42 (s, 2H), 6.14 (s, 2H), 6.25-6.30 (m, 1H), 6.51-6.53 (m, 1H), 6.95 (d, J = 3.4 Hz, 1H), 7.46 (dd, J = 1.8, 0.7 Hz, 1H), 7.63 (s, 1H), 7.80 (dd, J = 2.3, 0.7 Hz, 1H), 8.34 (s, 1H), 12.70 (s, 1H). |
| 293 | 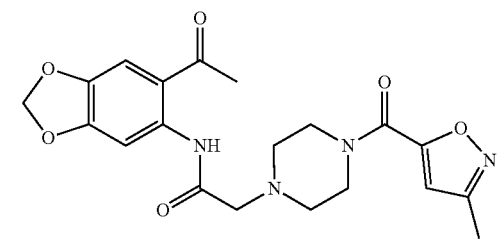 [SMILES: CC(=O)c1cc2c(cc1NC(=O)CN1CCN(C(=O)c3cc(C)no3)CC1)OCO2] | 415 | 0.008 | (DMSO-d₆) δ 2.29 (s, 3H), 2.53-2.63 (m, 4H), 2.59 (s, 3H), 3.20 (s, 2H), 3.69 (br s, 2H), 3.78 (br s, 2H), 6.14 (s, 2H), 6.82 (s, 1H), 7.63 (s, 1H), 8.33 (s, 1H), 12.70 (s, 1H). |

TABLE 2-continued

| SID | Structure | Obs. Mol Ion; MS (M + H+) | hT2R54 IC50 (uM) | 1H NMR (400 MHz) |
|---|---|---|---|---|
| 294 | 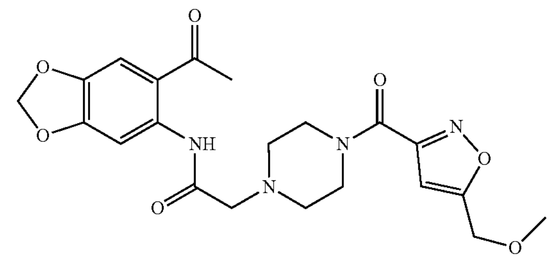 [SMILES: COCc1cc(C(=O)N2CCN(CC(=O)Nc3cc4c(cc3C(C)=O)OCO4)CC2)no1] | 445 | 0.07 | (DMSO-d6) δ 2.53-2.66 (m, 7H), 3.20 (s, 2H), 3.3 (s, 3H), 3.67-3.73 (m, 2H), 3.81 (s, 2H), 4.60 (d, J = 0.6 Hz, 2H), 6.14 (s, 2H), 6.74-6.79 (m, 1H), 7.63 (s, 1H), 8.33 (s, 1H), 12.71 (s, 1H). |
| 295 | 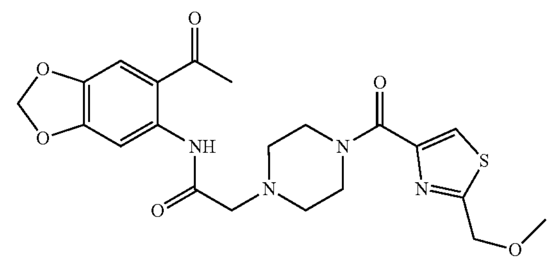 [SMILES: COCc1nc(C(=O)N2CCN(CC(=O)Nc3cc4c(cc3C(C)=O)OCO4)CC2)cs1] | 461 | 0.020 | (DMSO-d6) δ 2.52-2.61 (m, 4H), 2.59 (s, 3H), 3.19 (s, 2H), 3.41 (s, 3H), 3.79 (br s, 4H), 4.73 (s, 2H), 6.14 (s, 2H), 7.62 (s, 1H), 8.12 (d, J = 0.4 Hz, 1H), 8.34 (s, 1H), 12.71 (s, 1H). |
| 296 | 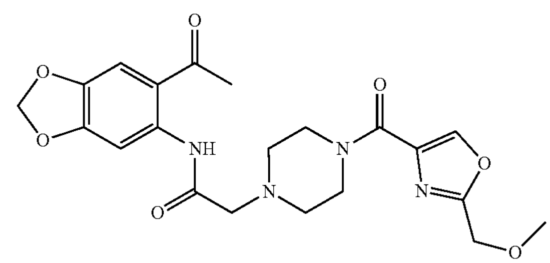 [SMILES: COCc1nc(C(=O)N2CCN(CC(=O)Nc3cc4c(cc3C(C)=O)OCO4)CC2)co1] | 445 | 0.053 | (DMSO-d6) δ 2.54-2.62 (m, 7H), 3.19 (s, 2H), 3.32 (d, J = 0.8 Hz, 3H), 3.76 (br s, 2H), 4.02 (br s, 2H), 4.53 (d, J = 0.8 Hz, 2H), 6.14 (s, 2H), 7.62 (d, J = 0.8 Hz, 1H), 8.33 (d, J = 0.8 Hz, 1H), 8.58 (d, J = 0.8 Hz, 1H), 12.70 (s, 1H). |
| 297 | 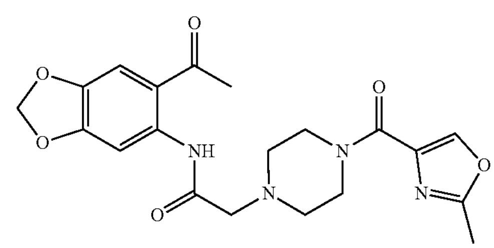 [SMILES: CC(=O)c1cc2c(cc1NC(=O)CN1CCN(C(=O)c3coc(C)n3)CC1)OCO2] | 415 | 0.023 | (DMSO-d6) δ 2.45 (s, 3H), 2.56 (t, J = 5.0 Hz, 4H), 2.58 (s, 3H), 3.18 (s, 2H), 3.74 (br s, 2H), 4.05 (br s, 2H), 6.14 (s, 2H), 7.62 (s, 1H), 8.33 (d, J = 0.5 Hz, 1H), 8.42 (d, J = 0.5 Hz, 1H), 12.70 (s, 1H). |
| 298 | 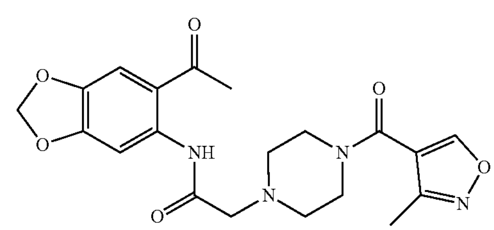 [SMILES: CC(=O)c1cc2c(cc1NC(=O)CN1CCN(C(=O)c3conc3C)CC1)OCO2] | 415 | 0.091 | (DMSO-d6) δ 2.29 (s, 3H), 2.53-2.58 (m, 4H), 2.58 (s, 3H), 3.19 (s, 2H), 3.56-3.83 (m, 4H), 6.14 (s, 2H), 7.63 (s, 1H), 8.34 (s, 1H), 9.16 (s, 1H), 12.70 (s, 1H). |
| 299 | 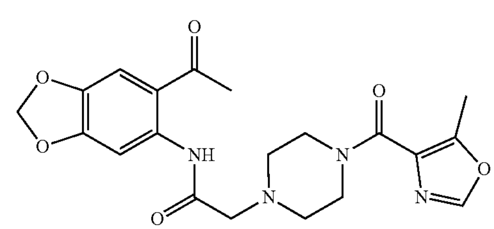 | 415 | 0.058 | (DMSO-d6) δ 2.46 (d, J = 0.9 Hz, 3H), 2.54-2.59 (m, 7H), 3.18 (s, 2H), 3.74 (br s, 2H), 3.94 (br s, 2H), 6.14 (d, J = 1.0 Hz, 2H), 7.62 (d, J = 0.9 Hz, 1H), 8.32 (d, J = 0.9 Hz, 1H), 8.33 (d, J = 0.9 Hz, 1H), 12.70 (s, 1H). |

TABLE 2-continued

| SID | Structure | Obs. Mol Ion; MS (M + H+) | hT2R54 IC50 (uM) | ¹H NMR (400 MHz) |
|---|---|---|---|---|
| 300 | 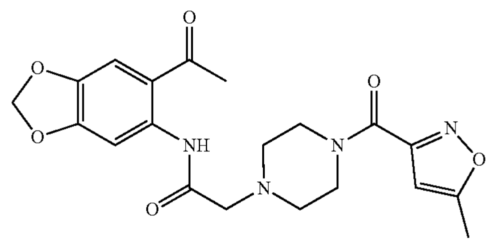 [SMILES: CC(=O)c1cc2c(cc1NC(=O)CN1CCN(C(=O)c3cc(C)on3)CC1)OCO2] | 415 | 0.04 | (DMSO-d₆) δ 2.45 (s, 3H), 2.53-2.61 (m, 7H), 3.20 (s, 2H), 3.64-3.85 (m, 4H), 6.14 (s, 2H), 6.48 (dd, J = 1.4, 0.8 Hz, 1H), 7.62 (s, 1H), 8.33 (s, 1H), 12.70 (s, 1H). |
| 301 | 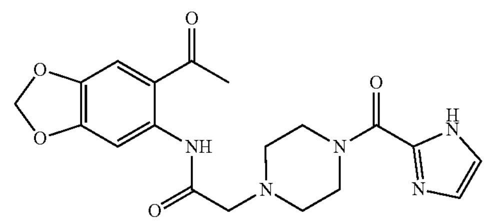 [SMILES: CC(=O)c1cc2c(cc1NC(=O)CN1CCN(C(=O)c3ncc[nH]3)CC1)OCO2] | 400 | 0.02 | (DMSO-d₆) δ 2.56-2.65 (m, 7H), 3.19 (s, 2H), 3.80 (s, 2H), 4.61 (s, 2H), 6.14 (s, 2H), 7.07 (dd, J = 1.6, 1.1 Hz, 1H), 7.25 (dd, J = 2.4, 1.1 Hz, 1H), 7.63 (s, 1H), 8.34 (s, 1H), 12.72, s, 1H), 12.93 (s, 1H). |
| 302 | 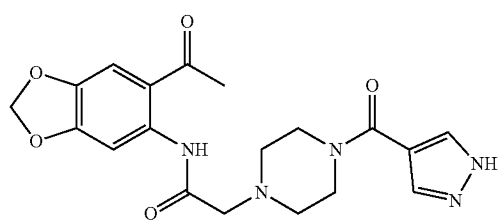 [SMILES: CC(=O)c1cc2c(cc1NC(=O)CN1CCN(C(=O)c3cn[nH]c3)CC1)OCO2] | 400 | 0.8 | (DMSO-d₆) δ 2.56 (m, 7H), 3.18 (s, 2H), 3.78 (br, 2H), 4.08 (br, 2H), 6.14 (s, 2H), 6.58 (d, J = 2.2 Hz, 1H), 7.62 (s, 1H), 7.81 (s, 1H), 8.34 (s, 1H), 12.71 (s, 1H). |
| 303 | 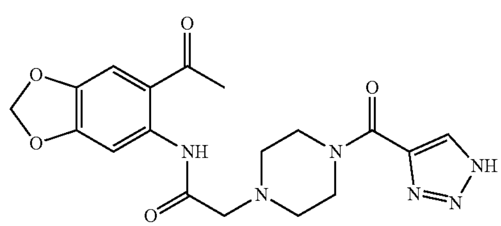 [SMILES: CC(=O)c1cc2c(cc1NC(=O)CN1CCN(C(=O)c3c[nH]nn3)CC1)OCO2] | 401 | 0.06 | (DMSO-d₆) δ 2.59 (m, 7H), 3.19 (s, 2H), 3.80 (m, 2H), 4.07 (m, 2H), 6.14 (s, 2H), 7.63 (s, 1H), 8.34 (m, 2H), 12.72 (s, 1H). |
| 304 | 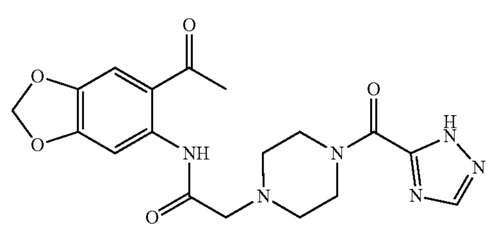 | 401 | 0.08 | (DMSO-d₆) δ 2.47-2.64 (m, 7H), 3.19 (d, J = 4.9 Hz, 2H), 3.48-3.61 (m, 2H), 3.81 (m, 1H), 3.98 (m, 1H), 6.14 (s, 2H), 7.62 (d, J = 0.7 Hz, 1H), 8.34 (s, 1H), 12.70 (d, J = 12.0 Hz, 1H). |
| 305 | 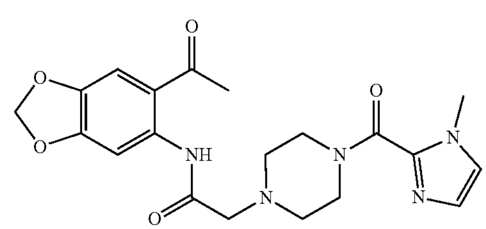 [SMILES: CC(=O)c1cc2c(cc1NC(=O)CN1CCN(C(=O)c3nccn3C)CC1)OCO2] | 414 | 0.031 | (DMSO-d₆) δ 2.55-2.62 (m, 4H), 2.58 (s, 3H), 3.19 (s, 2H), 3.76 (s, 3H), 3.76-3.82 (m, 2H), 4.00-4.06 (m, 2H), 6.14 (s, 2H), 6.97 (d, J = 1.1 Hz, 1H), 7.30 (d, J = 1.1 Hz, 1H), 7.62 (s, 1H), 8.34 (s, 1H), 12.72 (s, 1H). |

| SID | Structure | Obs. Mol Ion; MS (M + H⁺) | hT2R54 IC50 (uM) | ¹H NMR (400 MHz) |
|---|---|---|---|---|
| 306 | 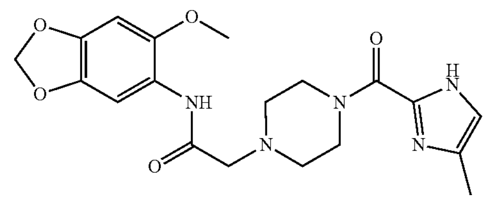 [SMILES: COc1cc2c(cc1NC(=O)CN1CCN(C(=O)c3nc(C)c[nH]3)CC1)OCO2] | 402 | 0.077 | (DMSO-d₆) δ 2.15 (s, 1.5H), 2.18 (s, 1.5H), 2.59 (br s, 4H), 3.15 (s, 2H), 3.69 (br s, 2H), 3.83 (s, 3H), 4.55 (br s, 2H), 5.95 (s, 2H), 6.77 (s, 0.5H), 6.92 (s, 1H), 6.95 (s, 0.5H), 7.79 (s, 1H), 9.58 (s, 1H), 12.62 (s, 0.5H), 12.69 (s, 0.5H). |
| 307 | 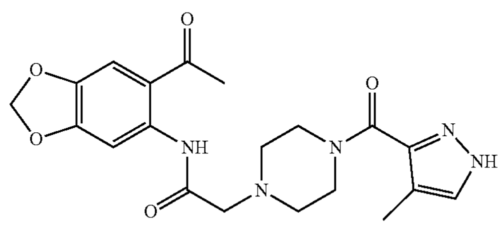 [SMILES: CC(=O)c1cc2c(cc1NC(=O)CN1CCN(C(=O)c3n[nH]cc3C)CC1)OCO2] | 414 | 0.09 | (DMSO-d₆) δ 2.06 (s, 3H), 2.58 (m, 7H), 3.18 (s, 2H), 3.80 (m, 4H), 6.14 (s, 2H), 7.59 (s, 1H), 7.62 (s, 1H), 8.34 (s, 1H), 12.71 (s, 1H), 12.84 (s, 1H). |
| 308 | 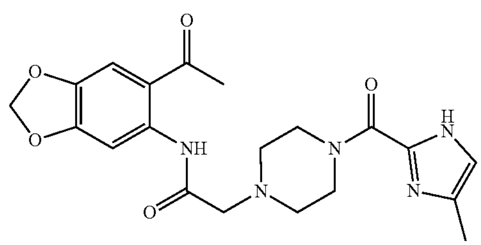 [SMILES: CC(=O)c1cc2c(cc1NC(=O)CN1CCN(C(=O)c3nc(C)c[nH]3)CC1)OCO2] | 414 | 0.009 | (DMSO-d₆) δ 2.16 (dd, J = 16.6, 0.9 Hz, 3H), 2.56-2.61 (m, 7H), 3.18 (d, J = 1.3 Hz, 2H), 3.78 (br, 2H), 4.62 (br, 2H), 6.14 (s, 2H), 6.76 (m, 0.5H), 6.95 (m, 0.5H), 7.63 (s, 1H), 8.34 (s, 1H), 12.72 (s, 1H). |
| 309 | 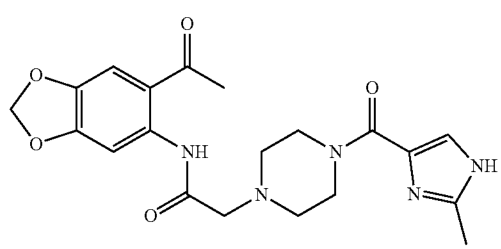 [SMILES: CC(=O)c1cc2c(cc1NC(=O)CN1CCN(C(=O)c3c[nH]c(C)n3)CC1)OCO2] | 414 | 0.2 | (DMSO-d₆) δ 2.27 (s, 3H), 2.53 (m, 4H), 2.59 (s, 3H), 3.17 (s, 2H), 3.8-4.4 (br, 4H), 6.14 (s, 2H), 7.48 (s, 1H), 7.62 (s, 1H), 8.34 (s, 1H), 12.20 (m, 1H), 12.71 (s, 1H). |
| 310 | 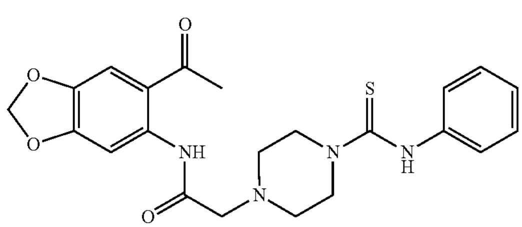 | 441 | 0.8 | (DMSO-d₆) δ 2.55 (m, 4H), 2.59 (s, 3H), 3.19 (s, 2H), 3.60 (m, 4H), 6.14 (s, 2H), 6.88-6.97 (m, 1H), 7.19-7.26 (m, 2H), 7.42-7.48 (m, 2H), 7.63 (s, 1H), 8.35 (s, 1H), 8.55 (s, 1H), 12.68 (s, 1H). |
| 311 | 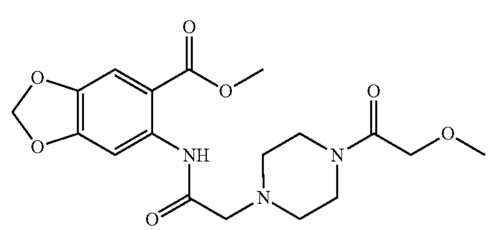 [SMILES: COCC(=O)N1CCN(CC(=O)Nc2cc3c(cc2C(=O)OC)OCO3)CC1] | 394 | 0.082 | (DMSO-d₆) δ 2.46-2.50 (m, 2H), 2.51-2.54 (m, 2H), 3.18 (s, 2H), 3.28 (s, 3H), 3.47-3.54 (m, 2H), 3.54-3.61 (m, 2H), 3.84 (s, 3H), 4.10 (s, 2H), 6.13 (s, 2H), 7.41 (s, 1H), 8.29 (s, 1H), 12.05 (s, 1H). |

TABLE 2-continued

| SID | Structure | Obs. Mol Ion; MS (M + H⁺) | hT2R54 IC50 (uM) | ¹H NMR (400 MHz) |
|---|---|---|---|---|
| 312 | 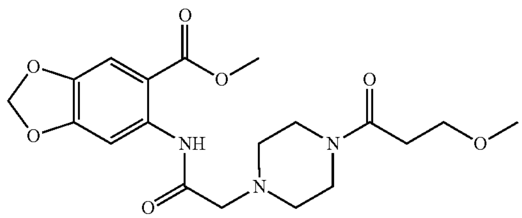 [SMILES: COCCC(=O)N1CCN(CC(=O)Nc2cc3c(cc2C(=O)OC)OCO3)CC1] | 408 | 0.157 | (DMSO-d$_6$) δ 2.44-2.49 (m, , 2H), 2.51-2.55 (m, 2H), 2.58 (t, J = 6.6 Hz, 2H), 3.18 (s, 2H), 3.22 (s, 3H), 3.54 (t, J = 6.6 Hz, 2H), 3.56-3.62 (m, 4H), 3.84 (s, 3H), 6.13 (s, 2H), 7.42 (s, 1H), 8.30 (s, 1H), 12.05 (s, 1H). |
| 313 | 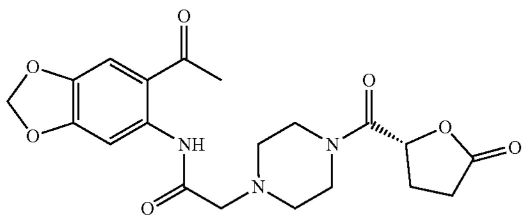 [SMILES: CC(=O)c1cc2c(cc1NC(=O)CN1CCN(C(=O)[C@H]3CCC(=O)O3)CC1)OCO2] | 418 | 0.06 | (DMSO-d$_6$) 2.11-2.24 (m, 1H), 2.36-2.48 (m, 3H), 2.58 (m, 7H), 3.19 (d, J = 1.6 Hz, 2H), 3.64 (m, 4H), 5.51 (m, 1H), 6.14 (s, 2H), 7.63 (s, 1H), 8.33 (s, 1H), 12.68 (s, 1H). |
| 314 | 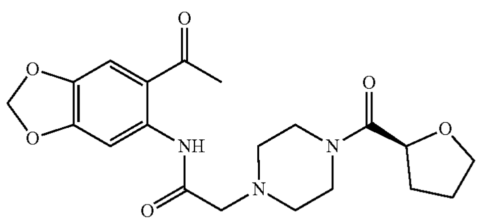 [SMILES: CC(=O)c1cc2c(cc1NC(=O)CN1CCN(C(=O)[C@@H]3CCCO3)CC1)OCO2] | 404 | 0.06 | (DMSO-d$_6$) δ 1.78-1.87 (m, 2H), 1.96-2.07 (m, 2H), 2.48-2.53 (m, 4H), 2.58 (s, 3H), 3.16 (s, 2H), 3.61-3.78 (m, 6H), 4.67 (dd, J = 7.7, 5.6 Hz, 1H), 6.14 (s, 2H), 7.62 (s, 1H), 8.34 (s, 1H), 12.68 (s, 1H). |
| 315 | 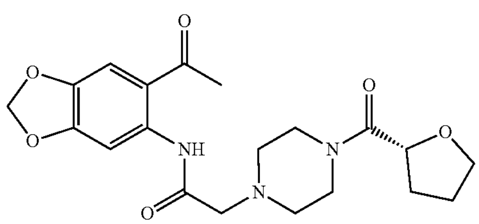 [SMILES: CC(=O)c1cc2c(cc1NC(=O)CN1CCN(C(=O)[C@H]3CCCO3)CC1)OCO2] | 404 | 0.13 | (DMSO-d$_6$) δ 1.77-1.88 (m, 2H), 1.94-2.07 (m, 2H), 2.48-2.53 (m, 4H), 2.58 (s, 3H), 3.16 (s, 2H), 3.61-3.80 (m, 6H), 4.67 (dd, J = 7.6, 5.6 Hz, 1H), 6.14 (s, 2H), 7.62 (s, 1H), 8.34 (s, 1H), 12.69 (s, 1H). |
| 316 | 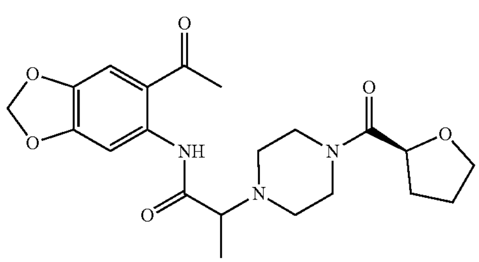 [SMILES: CC(=O)c1cc2c(cc1NC(=O)C(C)N1CCN(C(=O)[C@@H]3CCCO3)CC1)OCO2] | 418 | 0.08 | (DMSO-d$_6$) δ 1.15 (d, J = 7.0 Hz, 3H), 1.78-1.87 (m, 2H), 1.93-2.06 (m, 2H), 2.45 (br. s, 2H), 2.58 (s, 3H), 3.37-3.40 (m, 2H), 3.61-3.80 (m, 5H), 4.66 (dd, J = 7.6, 5.7 Hz, 1H), 6.13 (s, 2H), 7.61 (s, 1H), 8.35 (s, 1H), 12.80 (s, 1H). |
| 317 | 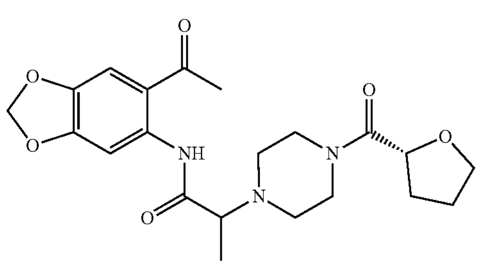 [SMILES: CC(=O)c1cc2c(cc1NC(=O)C(C)N1CCN(C(=O)[C@H]3CCCO3)CC1)OCO2] | 418 | 0.2 | (DMSO-d$_6$) δ 1.15 (d, J = 7.0 Hz, 2H), 1.79-1.87 (m, 2H), 1.96-2.06 (m, 2H), 2.46 (br. s, 2H), 2.57 (s, 3H), 3.37-3.39 (m, 2H), 3.61-3.80 (m, 5H), 4.66 (dd, J = 7.6, 5.6 Hz, 1H), 6.13 (m, 1H), 7.61 (s, 1H), 8.35 (s, 1H), 12.80 (s, 1H). |

TABLE 2-continued

| SID | Structure | Obs. Mol Ion; MS (M + H+) | hT2R54 IC50 (uM) | 1H NMR (400 MHz) |
|---|---|---|---|---|
| 318 | 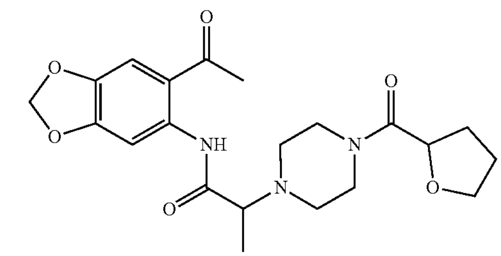 [SMILES: CC(=O)c1cc2c(cc1NC(=O)C(C)N1CCN(C(=O)C3CCCO3)CC1)OCO2] | 418 | 0.06 | (DMSO-d6) δ 1.15 (d, J = 7.0 Hz, 3H), 1.79-1.87 (m, 2H), 1.97-2.06 (m, 2H), 2.45 (m, 4H), 2.58 (s, 3H), 3.37-3.38 (m, 1H), 3.61-3.68 (m, 4H), 3.73-3.78 (m, 2H), 4.66 (dd, J = 7.7, 5.6 Hz, 1H), 6.13 (s, 2H), 7.61 (s, 1H), 8.35 (s, 1H), 12.81 (s, 1H). |
| 319 | 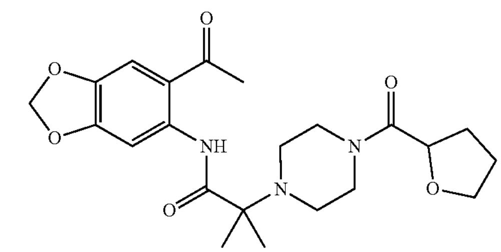 [SMILES: CC(=O)c1cc2c(cc1NC(=O)C(C)(C)N1CCN(C(=O)C3CCCO3)CC1)OCO2] | 432 | 1.0 | (DMSO-d6) δ 1.16 (s, 6H), 1.79-1.85 (m, 2H), 1.95-2.05 (m, 2H), 2.37-2.47 (m, 4H), 2.58 (s, 3H), 3.57-3.71 (m, 4H), 3.73-3.80 (m, 2H), 4.65 (dd, J = 7.7, 5.6 Hz, 1H), 6.13 (s, 2H), 7.61 (s, 1H), 8.34 (s, 1H), 12.84 (s, 1H). |
| 320 | 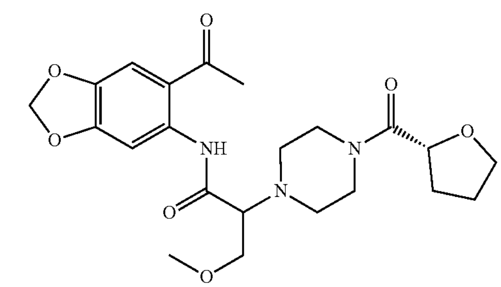 [SMILES: COCC(C(=O)Nc1cc2c(cc1C(C)=O)OCO2)N1CCN(C(=O)[C@H]2CCCO2)CC1] | 448 | 1.6 | (Methanol-d4) δ 1.90-2.07 (m, 3H), 2.16-2.22 (m, 1H), 2.57 (s, 3H), 2.67-2.70 (m, 2H), 2.79-2.83 (m, 2H), 3.31 (s, 3H), 3.39-3.41 (m, 1H), 3.76-3.87 (m, 7H), 3.94 (q, J = 7.2 Hz, 1H), 4.73 (dd, J = 7.9, 5.8 Hz, 1H), 6.05 (s, 2H), 7.48 (s, 1H), 8.33 (s, 1H). |
| 321 | 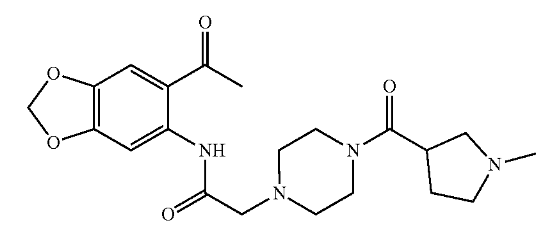 [SMILES: CC(=O)c1cc2c(cc1NC(=O)CN1CCN(C(=O)C3CCN(C)C3)CC1)OCO2] | 417 | 1 | (DMSO-d6) δ 1.87-2.10 (m, 3H), 2.39 (s, 3H), 2.47-2.53 (m, 4H), 2.55-2.61 (m, 4H), 2.75 (m, 2H), 2.93 (t, J = 8.9 Hz, 1H), 3.26-3.40 (m, 2H), 3.62 (m, 4H), 6.14 (s, 2H), 7.62 (s, 1H), 8.33 (s, 1H), 12.67 (s, 1H). |
| 322 | 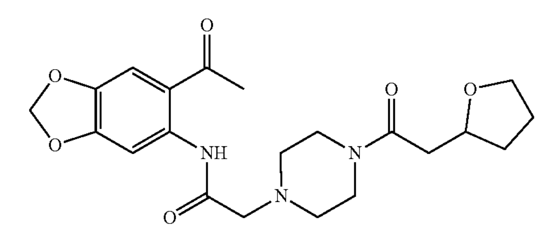 [SMILES: CC(=O)c1cc2c(cc1NC(=O)CN1CCN(C(=O)CC3CCCO3)CC1)OCO2] | 418 | 0.07 | (DMSO-d6) δ 1.47 (m, , 21H), 1.81 (m, 2H), 2.00 (m, 2H), 2.36-2.48 (m, 4H), 2.58 (s, 3H), 2.66 (m, 1H), 3.16 (s, 2H), 3.49-3.64 (m, 4H), 3.73 (m, 1H), 4.05-4.17 (m, 1H), 6.14 (s, 2H), 7.62 (s, 1H), 8.34 (s, 1H), 12.68 (s, 1H). |
| 323 | 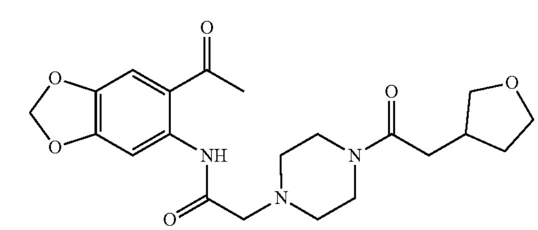 [SMILES: CC(=O)c1cc2c(cc1NC(=O)CN1CCN(C(=O)CC3CCOC3)CC1)OCO2] | 418 | 0.2 | (DMSO-d6) δ 1.48 (m, 1H), 2.00 (m, 1H), 2.34-2.49 (m, 6H), 2.57 (s, 3H), 3.16 (s, 2H), 3.24 (dd, J = 8.3, 6.0 Hz, 1H), 3.51-3.64 (m, 6H), 3.71 (m, 1H), 3.82 (m, 1H), 6.14 (s, 2H), 7.62 (s, 1H), 8.34 (s, 1H), 12.67 (s, 1H). |

TABLE 2-continued

| SID | Structure | Obs. Mol Ion; MS (M + H⁺) | hT2R54 IC50 (uM) | ¹H NMR (400 MHz) |
|---|---|---|---|---|
| 324 | 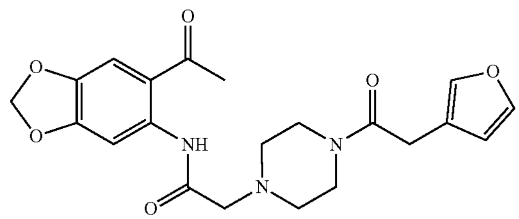 [SMILES: CC(=O)c1cc2c(cc1NC(=O)CN1CCN(C(=O)Cc3ccoc3)CC1)OCO2] | 414 | 0.08 | (DMSO-d₆) δ 2.48 (m, , 4H), 2.56-2.60 (s, 3H), 3.16 (s, 2H), 3.57-3.71 (m, 4H), 3.80 (s, 2H), 6.14 (d, J = 1.4 Hz, 2H), 6.22 (dt, J = 3.2, 0.8 Hz, 1H), 6.39 (dd, J = 3.1, 1.9 Hz, 1H), 7.56 (dd, J = 1.9, 0.9 Hz, 1H), 7.62 (d, J = 2.7 Hz, 1H), 8.33 (d, J = 0.7 Hz, 1H), 12.68 (s, 1H). |
| 325 | 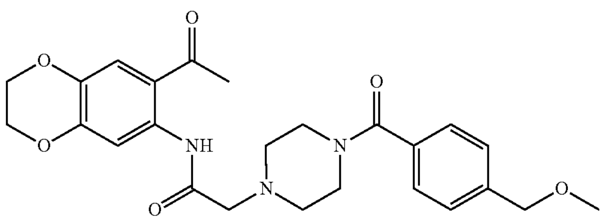 [SMILES: COCc1ccc(C(=O)N2CCN(CC(=O)Nc3cc4c(cc3C(C)=O)OCCO4)CC2)cc1] | 468 | 0.045 | (DMSO-d₆) δ 2.51-2.61 (m, 4H), 2.57 (s, 3H), 3.16 (s, 2H), 3.31 (s, 3H), 3.48 (br s, 2H), 3.77 (br s, 2H), 4.25-4.29 (m, 2H), 4.32-4.36 (m, 2H), 4.44 (s, 2H), 7.36-7.42 (m, 4H), 7.57 (s, 1H), 8.26 (s, 1H), 12.39 (s, 1H). |
| 326 | 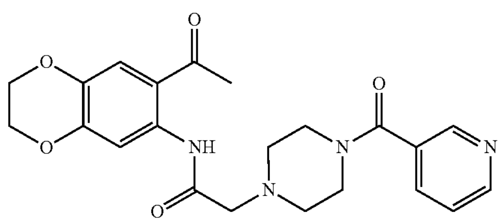 [SMILES: CC(=O)c1cc2c(cc1NC(=O)CN1CCN(C(=O)c3cccnc3)CC1)OCCO2] | 425 | 0.04 | |
| 327 | 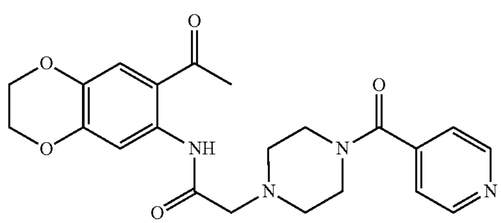 [SMILES: CC(=O)c1cc2c(cc1NC(=O)CN1CCN(C(=O)c3ccncc3)CC1)OCCO2] | 425 | 0.07 | (DMSO-d₆) 2.52 (m, 2H), 2.57 (s, 3H), 2.61 (m, 2H), 3.17 (s, 2H), 3.38-3.47 (m, 2H), 3.79 (m, 2H), 4.30 (m, 4H), 7.37-7.46 (m, 2H), 7.57 (s, 1H), 8.26 (s, 1H), 8.67 (d, J = 5.4 Hz, 2H), 12.38 (s, 1H). |
| 328 | 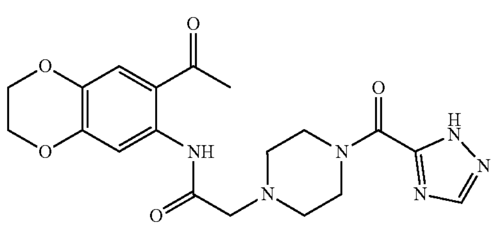 [SMILES: CC(=O)c1cc2c(cc1NC(=O)CN1CCN(C(=O)c3ncn[nH]3)CC1)OCCO2] | 415 | 0.06 | 2.56 (m, 7H), 3.15 (d, J = 5.7 Hz, 2H), 3.79 (m, 4H), 4.21-4.37 (m, 4H), 7.56 (s, 1H), 8.25 (s, 1H), 8.64 (s, 1H), 12.40 (s, 1H). |
| 329 | 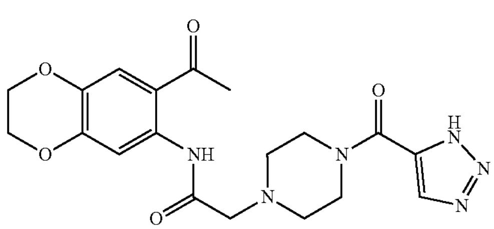 [SMILES: CC(=O)c1cc2c(cc1NC(=O)CN1CCN(C(=O)c3cnn[nH]3)CC1)OCCO2] | 415 | 0.05 | |

TABLE 2-continued
| SID | Structure | Obs. Mol Ion; MS (M + H+) | hT2R54 IC50 (uM) | 1H NMR (400 MHz) |
|---|---|---|---|---|
| 330 | 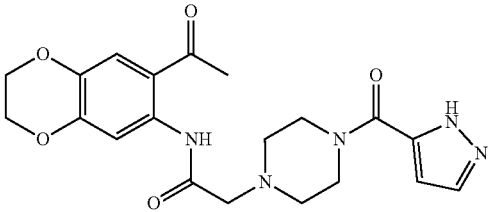 [SMILES: CC(=O)c1cc2c(cc1NC(=O)CN1CCN(C(=O)c3ccn[nH]3)CC1)OCCO2] | 414 | 0.09 | |
| 331 | 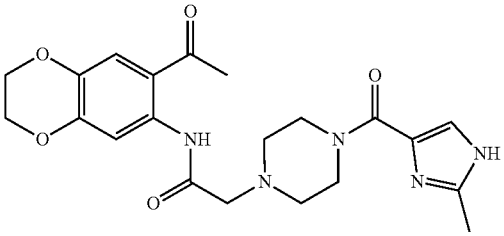 [SMILES: CC(=O)c1cc2c(cc1NC(=O)CN1CCN(C(=O)c3c[nH]c(C)n3)CC1)OCCO2] | 428 | 0.2 | (DMSO-d6) 2.28 (s, 3H), 2.39-2.58 (m, 7H), 3.15 (s, 2H), 3.34 (br, 2H), 3.77 (br, 2H), 4.31 (m, 4H), 7.48 (s, 1H), 7.58 (d, J = 1.7 Hz, 1H), 8.17 (s, H), 8.28 (d, J = 1.6 Hz, 1H), 12.41 (s, 1H). |
| 332 | 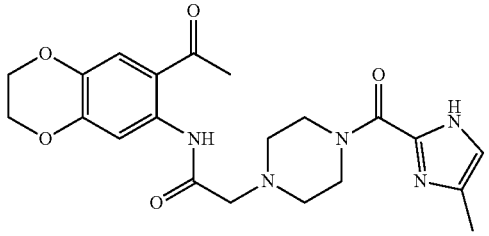 [SMILES: CC(=O)c1cc2c(cc1NC(=O)CN1CCN(C(=O)c3nc(C)c[nH]3)CC1)OCCO2] | 428 | 0.2 | (DMSO-d6) 2.16 (dd, J = 16.7, 0.9 Hz, 3H), 2.56-2.60 (m, 7H), 3.16 (d, J = 1.4 Hz, 2H), 3.78 (s, 2H), 4.24-4.38 (m, 4H), 4.62 (s, 2H), 6.76 (s, 0.5H), 6.95 (s, 0.5H), 7.58 (d, J = 1.0 Hz, 1H), 8.27 (d, J = 0.9 Hz, 1H), 12.42 (s, 1H), 12.6 (br, 1H) |
| 333 | 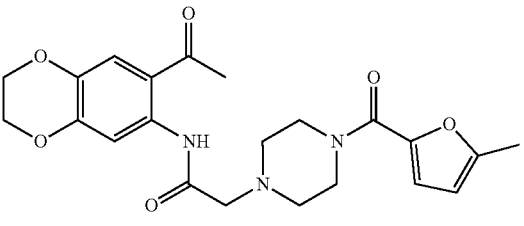 [SMILES: CC(=O)c1cc2c(cc1NC(=O)CN1CCN(C(=O)c3ccc(C)o3)CC1)OCCO2] | 428 | 0.08 | (DMSO-d6) 2.32 (dd, J = 1.0, 0.5 Hz, 3H), 2.57 (m, 7H), 3.17 (s, 2H), 3.81 (br, 4H), 4.23-4.41 (m, 4H), 6.25 (dt, J = 3.3, 1.0 Hz, 1H), 6.90 (dd, J = 3.3, 0.6 Hz, 1H), 7.58 (s, 1H), 8.27 (s, 1H), 12.42 (s, 1H). |
| 334 | 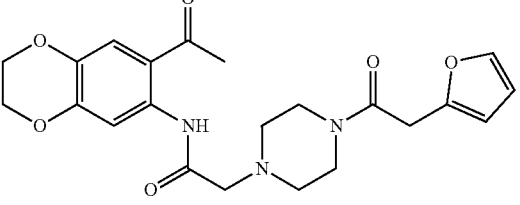 | 428 | 0.05 | (DMSO-d6) δ 2.42-2.49 (m, 4H), 2.57 (s, 3H), 3.14 (s, 2H), 3.56-3.68 (m, 4H), 3.80 (s, 2H), 4.23-4.38 (m, 4H), 6.19-6.41 (m, 2H), 7.54-7.60 (m, 2H), 8.26 (s, 1H), 12.38 (s, 1H). |
| 335 | 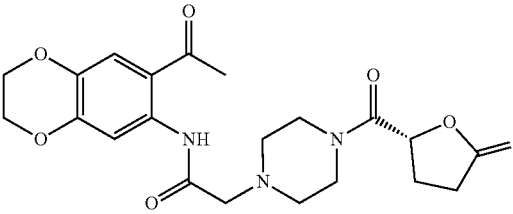 | 431 | 0.05 | (DMSO-d6) 2.08-2.22 (m, 1H), 2.36-2.48 (m, 3H), 2.57 (m, 7H), 3.13-3.19 (m, 2H), 3.47-3.73 (m, 4H), 4.24-4.38 (m, 4H), 5.51 (m, 1H), 7.58 (s, 1H), 8.26 (s, 1H), 12.38 (s, 1H). |

TABLE 2-continued

| SID | Structure | Obs. Mol Ion; MS (M + H+) | hT2R54 IC50 (uM) | 1H NMR (400 MHz) |
|---|---|---|---|---|
| 336 | 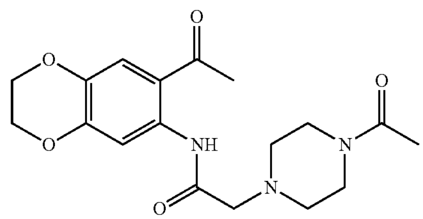 [SMILES: CC(=O)c1cc2c(cc1NC(=O)CN1CCN(C(C)=O)CC1)OCCO2] | 362 | 0.05 | (DMSO-d6) δ 1.99 (s, 3H), 2.43 (m, 2H), 2.50 (m, 2H), 2.55 (s, 3H), 3.12 (s, 2H), 3.56 (m, 4H), 4.25 (m, 2H), 4.32 (m, 2H), 7.55 (s, 1H), 8.25 (s, 1H), 12.35 (s, 1H). |
| 337 | 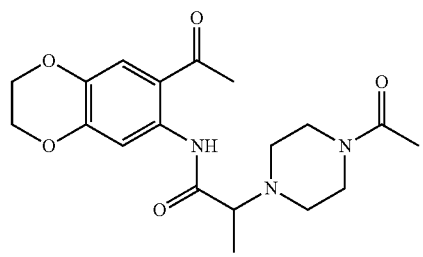 [SMILES: CC(=O)c1cc2c(cc1NC(=O)C(C)N1CCN(C(C)=O)CC1)OCCO2] | 376 | 0.06 | (DMSO-d6) δ 1.15 (d, J = 7.0 Hz, 3H), 2.01 (s, 3H), 2.43 (m, 4H), 2.57 (s, 3H), 3.31-3.37 (m, 1H), 3.58 (q, J = 5.3 Hz, 4H), 4.26-4.29 (m, 2H), 4.33-4.36 (m, 2H), 7.57 (s, 1H), 8.28 (s, 1H), 12.50 (s, 1H). |
| 338 | 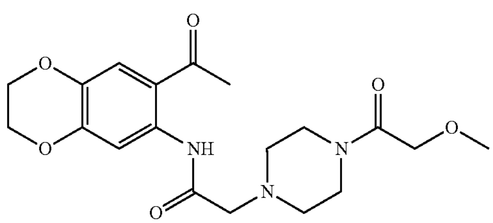 [SMILES: COCC(=O)N1CCN(CC(=O)Nc2cc3c(cc2C(C)=O)OCCO3)CC1] | 392 | 0.06 | |
| 339 | 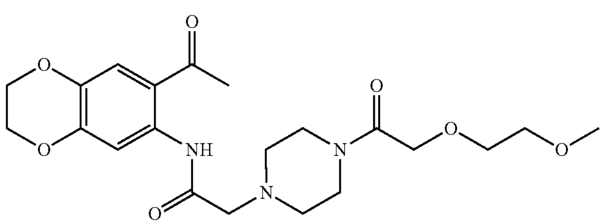 [SMILES: COCCOCC(=O)N1CCN(CC(=O)Nc2cc3c(cc2C(C)=O)OCCO3)CC1] | 436 | 0.08 | |
| 340 | 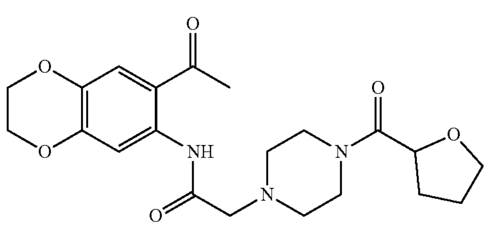 | 418 | 0.09 | (DMSO-d6) 1.74-2.08 (m, 4H), 2.47 (m, 4H), 2.57 (s, 3H), 3.14 (s, 2H), 3.60 (m, 2H), 3.64-3.85 (m, 4H), 4.22-4.39 (m, 4H), 4.67 (m, 1H), 7.57 (s, 1H), 8.27 (s, 1H), 12.39 (s, 1H). |
| 341 | 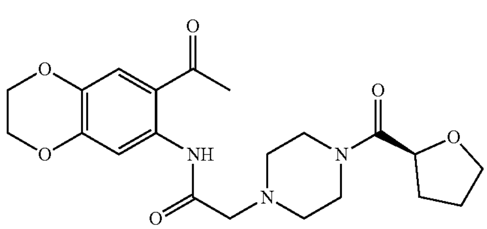 [SMILES: CC(=O)c1cc2c(cc1NC(=O)CN1CCN(C(=O)[C@@H]3CCCO3)CC1)OCCO2] | 418 | 1.8 | (DMSO-d6) δ 1.78-1.87 (m, 2H), 1.97-2.07 (m, 2H), 2.46-2.53 (m, 4H), 2.57 (s, 3H), 3.14 (s, 2H), 3.60-3.80 (m, 6H), 4.27 (dt, J = 3.9, 2.5 Hz, 2H), 4.34 (dt, J = 4.2, 2.6 Hz, 2H), 4.67 (dd, J = 7.7, 5.7 Hz, 1H), 7.57 (s, 1H), 8.27 (s, 1H), 12.38 (s, 1H). |

TABLE 2-continued

| SID | Structure | Obs. Mol Ion; MS (M + H⁺) | hT2R54 IC50 (uM) | ¹H NMR (400 MHz) |
|---|---|---|---|---|
| 342 | 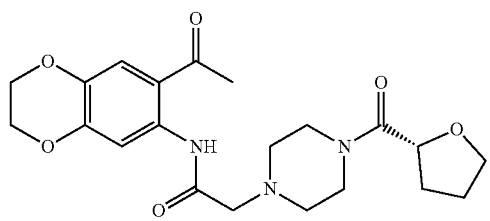 [SMILES: CC(=O)c1cc2c(cc1NC(=O)CN1CCN(C(=O)[C@H]3CCCO3)CC1)OCCO2] | 418 | 0.07 | (DMSO-d$_6$) δ 1.77-1.89 (m, 2H), 1.94-2.09 (m, 2H), 2.48-2.53 (m, 4H), 2.58 (s, 3H), 3.15 (s, 2H), 3.61-3.81 (m, 6H), 4.28 (dt, J = 4.0, 2.6 Hz, 2H), 4.35 (dt, J = 4.2, 2.6 Hz, 2H), 4.68 (dd, J = 7.6, 5.6 Hz, 1H), 7.58 (s, 1H), 8.27 (s, 1H), 12.39 (s, 1H). |
| 343 | 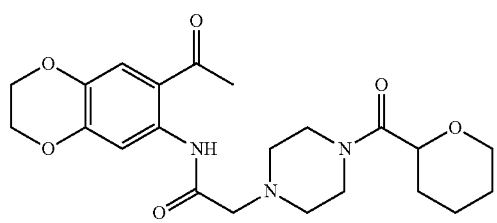 [SMILES: CC(=O)c1cc2c(cc1NC(=O)CN1CCN(C(=O)C3CCCCO3)CC1)OCCO2] | 432 | 0.03 | |
| 344 | 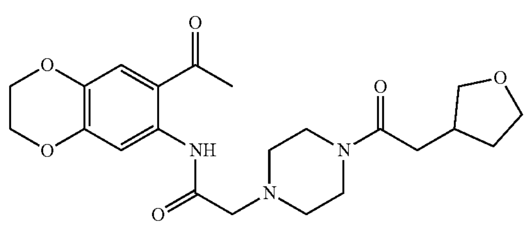 [SMILES: CC(=O)c1cc2c(cc1NC(=O)CN1CCN(C(=O)CC3CCOC3)CC1)OCCO2] | 432 | 0.05 | |
| 345 | 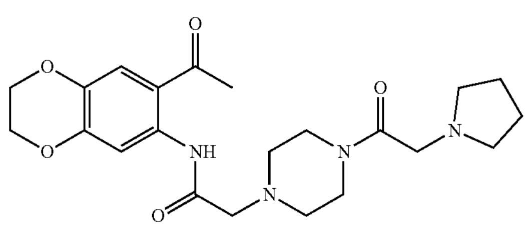 [SMILES: CC(=O)c1cc2c(cc1NC(=O)CN1CCN(C(=O)CN3CCCC3)CC1)OCCO2] | 431 | >10 | |
| 346 | 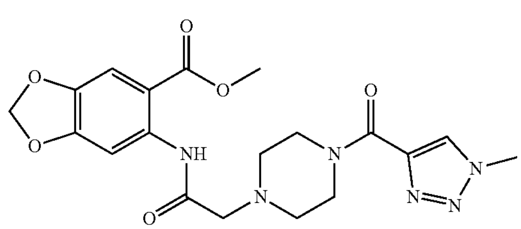 [SMILES: COC(=O)c1cc2c(cc1NC(=O)CN1CCN(C(=O)c3cn(C)nn3)CC1)OCO2] | 431 | 0.023 | (DMSO-d$_6$) δ 2.60 (t, J = 5.0 Hz, 4H), 3.21 (s, 2H), 3.77 (br s, 2H), 3.85 (s, 3H), 4.08 (s, 3H), 4.15 (br s, 2H), 6.13 (s, 2H), 7.42 (s, 1H), 8.30 (s, 1H), 8.49 (s, 1H), 12.10 (s, 1H). |
| 347 | 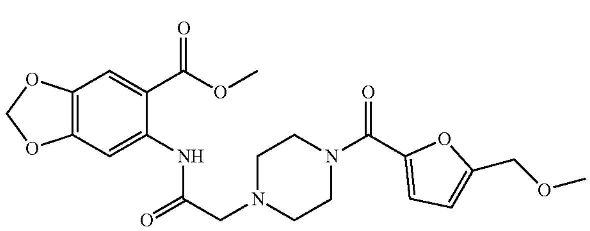 [SMILES: COCc1ccc(C(=O)N2CCN(CC(=O)Nc3cc4c(cc3C(=O)OC)OCO4)CC2)o1] | 460 | 0.083 | (DMSO-d$_6$) δ 2.59 (t, J = 4.9 Hz, 4H), 3.21 (s, 2H), 3.26 (s, 3H), 3.79 (br s, 4H), 3.85 (s, 3H), 4.40 (s, 2H), 6.13 (s, 2H), 6.58 (d, J = 3.4 Hz, 1H), 6.96 (d, J = 3.4 Hz, 1H), 7.42 (s, 1H), 8.30 (s, 1H), 12.08 (s, 1H). |

TABLE 2-continued

| SID | Structure | Obs. Mol Ion; MS (M + H+) | hT2R54 IC50 (uM) | ¹H NMR (400 MHz) |
|---|---|---|---|---|
| 348 | 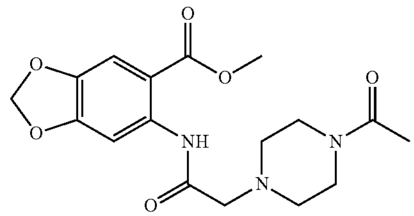 [SMILES: COC(=O)c1cc2c(cc1NC(=O)CN1CCN(C(C)=O)CC1)OCO2] | 364 | 0.166 | (DMSO-d₆) δ 2.01 (s, 3H), 2.43-2.49 (m, 2H), 2.52-2.57 (m, 2H), 3.18 (s, 2H), 3.51-3.60 (m, 4H), 3.84 (s, 3H), 6.12 (s, 2H), 7.41 (s, 1H), 8.29 (s, 1H), 12.04 (s, 1H). |
| 349 | 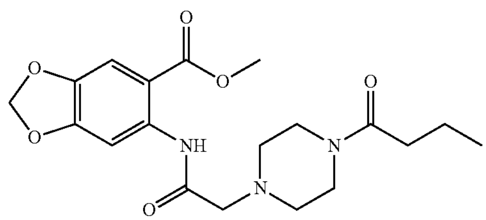 [SMILES: CCCC(=O)N1CCN(CC(=O)Nc2cc3c(cc2C(=O)OC)OCO3)CC1] | 392 | 0.244 | (DMSO-d₆) δ 0.89 (t, J = 7.4 Hz, 3H), 1.45-1.56 (m, 2H), 2.29 (t, J = 7.4 Hz, 2H), 2.44-2.49 (m, 2H), 2.51-2.55 (m, 2H), 3.18 (s, 2H), 3.54-3.61 (m, 4H), 3.84 (s, 3H), 6.13 (s, 2H), 7.42 (s, 1H), 8.29 (s, 1H), 12.04 (s, 1H). |
| 350 | 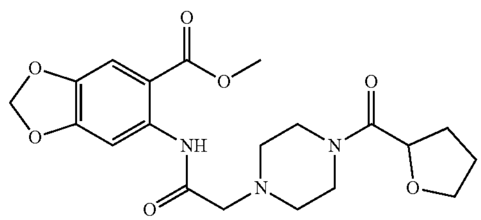 [SMILES: COC(=O)c1cc2c(cc1NC(=O)CN1CCN(C(=O)C3CCCO3)CC1)OCO2] | 420 | 0.299 | (DMSO-d₆) δ 1.74-1.91 (m, 2H), 1.92-2.09 (m, 2H), 2.46-2.50 (m, 2H), 2.52-2.58 (m, 2H), 3.18 (d, J = 1.1 Hz, 2H), 3.55-3.67 (m, 4H), 3.69-3.80 (m, 2H), 3.84 (d, J = 1.1 Hz, 3H), 4.64-4.69 (m, 1H), 6.13 (d, J = 1.1 Hz, 2H), 7.42 (d, J = 1.1 Hz, 1H), 8.29 (d, J = 1.1 Hz, 1H), 12.05 (s, 1H). |
| 351 | 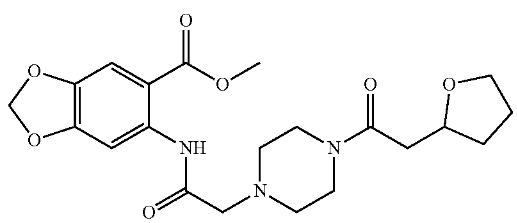 [SMILES: COC(=O)c1cc2c(cc1NC(=O)CN1CCN(C(=O)CC3CCCO3)CC1)OCO2] | 434 | 0.439 | (DMSO-d₆) δ 1.42-1.52 (m, 1H), 1.72-1.88 (m, 2H), 1.95-2.05 (m, 1H), 2.37-2.48 (m, 3H), 2.51-2.56 (m, 2H), 2.62-2.70 (m, 1H), 3.18 (s, 2H), 3.52-3.62 (m, 5H), 3.69-3.76 (m, 1H), 3.84 (s, 3H), 4.05-4.13 (m, 1H), 6.13 (s, 2H), 7.42 (s, 1H), 8.29 (s, 1H), 12.04 (s, 1H). |
| 352 | 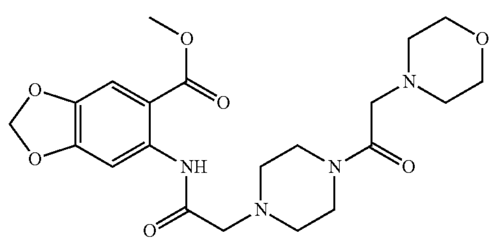 [SMILES: COC(=O)c1cc2c(cc1NC(=O)CN1CCN(C(=O)CN3CCOCC3)CC1)OCO2] | 449 | 0.74 | (DMSO-d₆) δ 2.36-2.43 (m, 4H), 2.44-2.49 (m, 2H), 2.53-2.59 (m, 2H), 3.17 (d, J = 9.0 Hz, 4H), 3.52-3.61 (m, 6H), 3.63-3.71 (m, 2H), 3.84 (s, 3H), 6.13 (s, 2H), 7.42 (s, 1H), 8.29 (s, 1H), 12.05 (s, 1H). |
| 353 | 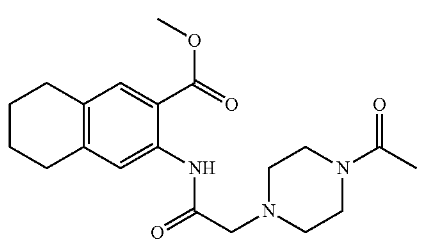 [SMILES: COC(=O)c1cc2c(cc1NC(=O)CN1CCN(C(C)=O)CC1)CCCC2] | 374 | 2.1 | (DMSO-d₆) δ 1.69-1.76 (m, 4H), 2.01 (s, 3H), 2.46 (t, J = 5.1 Hz, 2H), 2.53 (t, J = 4.9 Hz, 2H), 2.67-2.77 (m, 4H), 3.16 (s, 2H), 3.52-3.60 (m, 4H), 3.86 (s, 3H), 7.69 (s, 1H), 8.39 (s, 1H), 11.73 (s, 1H). |

TABLE 2-continued

| SID | Structure | Obs. Mol Ion; MS (M + H⁺) | hT2R54 IC50 (uM) | ¹H NMR (400 MHz) |
|---|---|---|---|---|
| 354 | 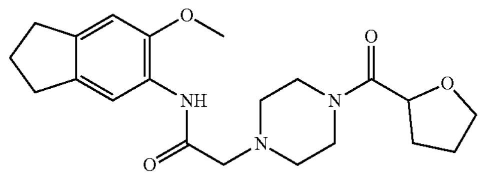 [SMILES: COc1cc2c(cc1NC(=O)CN1CCN(C(=O)C3CCCO3)CC1)CCC2] | 388 | 1.9 | |
| 355 | 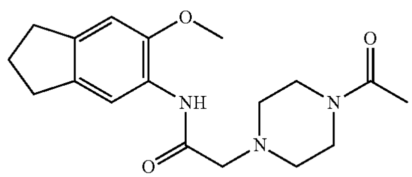 [SMILES: COc1cc2c(cc1NC(=O)CN1CCN(C(C)=O)CC1)CCC2] | 332 | 2.5 | |
| 356 | 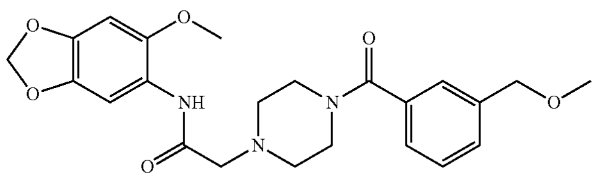 [SMILES: COCc1cccc(C(=O)N2CCN(CC(=O)Nc3cc4c(cc3OC)OCO4)CC2)c1] | 442 | 0.156 | (DMSO-d₆) δ 2.51-2.64 (m, 4H), 3.15 (s, 2H), 3.30 (s, 3H), 3.35-3.49 (m, 2H), 3.59-3.75 (m, 2H), 3.83 (s, 3H), 4.45 (s, 2H), 5.95 (s, 2H), 6.91 (s, 1H), 7.29-7.36 (m, 2H), 7.37-7.47 (m, 2H), 7.77 (s, 1H), 9.53 (s, 1H). |
| 357 | 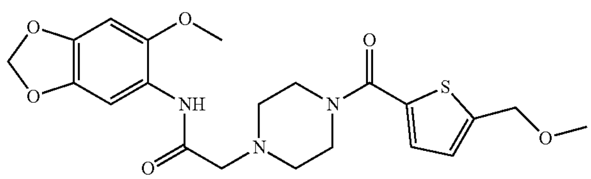 [SMILES: COCc1ccc(C(=O)N2CCN(CC(=O)Nc3cc4c(cc3OC)OCO4)CC2)s1] | 448 | 0.208 | (DMSO-d₆) δ 2.55-2.63 (, 4H), 3.16 (s, 2H), 3.30 (d, J = 0.9 Hz, 3H), 3.67-3.75 (m, 4H), 3.84 (d, J = 0.9 Hz, 3H), 4.58 (s, 2H), 5.95 (d, J = 0.9 Hz, 2H), 6.91 (d, J = 0.9 Hz, 1H), 7.04 (dd, J = 3.6, 0.9 Hz, 1H), 7.31 (dd, J = 3.7, 0.9 Hz, 1H), 7.77 (d, J = 0.9 Hz, 1H), 9.53 (s, 1H). |
| 358 | 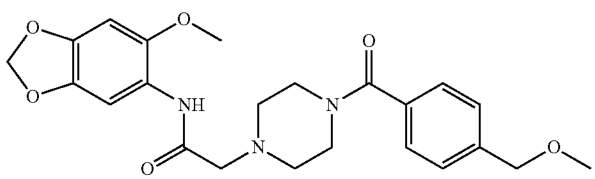 [SMILES: COCc1ccc(C(=O)N2CCN(CC(=O)Nc3cc4c(cc3OC)OCO4)CC2)cc1] | 442 | 0.148 | (DMSO-d₆) δ 2.51-2.63 (m, 4H), 3.15 (s, 2H), 3.31 (s, 3H), 3.43 (br s, 2H), 3.68 (br s, 2H), 3.83 (s, 3H), 4.45 (s, 2H), 5.95 (s, 2H), 6.91 (s, 1H), 7.36-7.42 (m, 4H), 7.77 (s, 1H), 9.53 (s, 1H). |
| 359 | 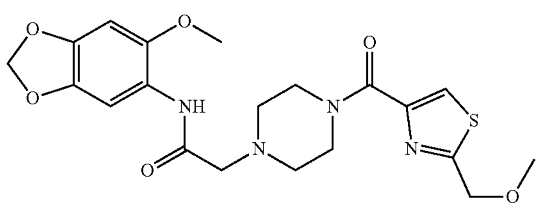 [SMILES: COCc1nc(C(=O)N2CCN(CC(=O)Nc3cc4c(cc3OC)OCO4)CC2)cs1] | 449 | 0.261 | (DMSO-d₆) δ 2.58 (br s, 4H), 3.15 (s, 2H), 3.41 (s, 3H), 3.71 (br s, 4H), 3.83 (s, 3H), 4.73 (s, 2H), 5.95 (s, 2H), 6.91 (s, 1H), 7.77 (s, 1H), 8.12 (s, 1H), 9.54 (s, 1H). |
| 360 | 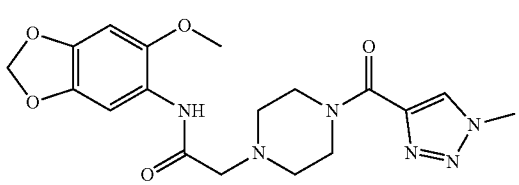 [SMILES: COc1cc2c(cc1NC(=O)CN1CCN(C(=O)c3cn(C)nn3)CC1)OCO2] | 403 | 0.735 | (DMSO-d₆) δ 2.60 (t, J = 5.0 Hz, 4H), 3.16 (s, 2H), 3.70 (br s, 2H), 3.83 (s, 3H), 4.08 (s, 3H), 4.09 (br s, 2H), 5.95 (s, 2H), 6.92 (s, 1H), 7.78 (s, 1H), 8.49 (s, 1H), 9.56 (s, 1H). |
| 361 | 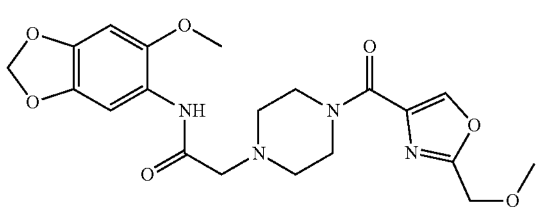 [SMILES: COCc1nc(C(=O)N2CCN(CC(=O)Nc3cc4c(cc3OC)OCO4)CC2)co1] | 433 | 0.546 | (DMSO-d₆) δ 2.59 (t, J = 4.9 Hz, 4H), 3.16 (s, 2H), 3.33 (d, J = 1.7 Hz, 3H), 3.67 (br s, 2H), 3.83 (d, J = 1.4 Hz, 3H), 3.94 (br s, 2H), 4.53 (d, J = 1.4 Hz, 2H), 5.95 (d, J = 1.4 Hz, 2H), 6.91 (d, J = 1.4 Hz, 1H), 7.78 (d, J = 1.4 Hz, 1H), 8.58 (d, J = 1.7 Hz, 1H), 9.54 (s, 1H). |

TABLE 2-continued

| SID | Structure | Obs. Mol Ion; MS (M + H+) | hT2R54 IC50 (uM) | 1H NMR (400 MHz) |
|---|---|---|---|---|
| 362 | 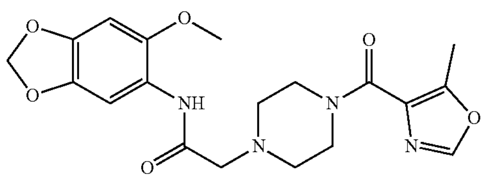 [SMILES: COc1cc2c(cc1NC(=O)CN1CCN(C(=O)c3ncoc3C)CC1)OCO2] | 403 | 0.567 | (DMSO-d6) δ 2.46 (d, J = 0.9 Hz, 3H), 2.53-2.60 (m, 7H), 3.19 (d, J = 0.9 Hz, 2H), 3.74 (br s, 2H), 3.94 (br s, 2H), 6.14 (d, J = 0.7 Hz, 2H), 7.62 (d, J = 0.9 Hz, 1H), 8.32 (d, J = 1.0 Hz, 1H), 8.34 (d, J = 0.9 Hz, 1H), 12.70 (s, 1H). |
| 363 | 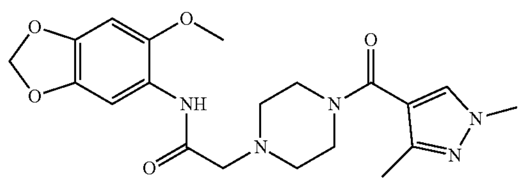 [SMILES: COc1cc2c(cc1NC(=O)CN1CCN(C(=O)c3cn(C)nc3C)CC1)OCO2] | 416 | 0.600 | (DMSO-d6) δ 2.17 (s, 3H), 2.51-2.57 (m, 4H), 3.15 (s, 2H), 3.56-3.63 (m, 4H), 3.76 (s, 3H), 3.83 (s, 3H), 5.95 (s, 2H), 6.91 (s, 1H), 7.78 (s, 1H), 7.85 (s, 1H), 9.53 (s, 1H). |
| 364 | 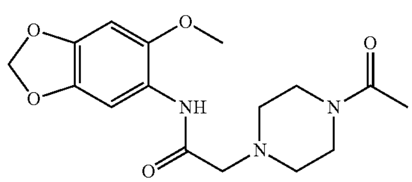 [SMILES: COc1cc2c(cc1NC(=O)CN1CCN(C(C)=O)CC1)OCO2] | 336 | 1.56 | (DMSO-d6) δ 2.01 (s, 3H), 2.44-2.48 (m, 2H), 2.51-2.56 (m, 2H), 3.13 (s, 2H), 3.43-3.54 (m, 4H), 3.82 (s, 3H), 5.95 (s, 2H), 6.91 (s, 1H), 7.78 (s, 1H), 9.53 (s, 1H). |
| 365 | 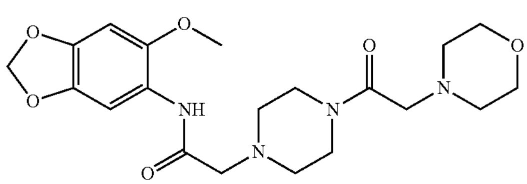 [SMILES: COc1cc2c(cc1NC(=O)CN1CCN(C(=O)CN3CCOCC3)CC1)OCO2] | 421 | 2.64 | (DMSO-d6) δ 2.34-2.43 (m, 4H), 2.44-2.49 (m, 2H), 2.53-2.58 (m, 2H), 3.14 (dd, J = 9.8, 4.6 Hz, 4H), 3.43-3.66 (m, 8H), 3.82 (d, J = 5.4 Hz, 3H), 5.95 (d, J = 5.4 Hz, 2H), 6.91 (d, J = 5.4 Hz, 1H), 7.78 (d, J = 5.4 Hz, 1H), 9.53 (d, J = 4.4 Hz, 1H). |
| 366 | 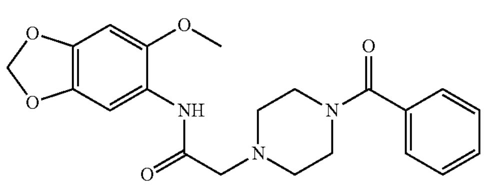 [SMILES: COc1cc2c(cc1NC(=O)CN1CCN(C(=O)c3ccccc3)CC1)OCO2] | 416 | 0.2 | (DMSO-d6) δ 2.56 (s, 4H), 3.15 (s, 2H), 3.54 (m, 4H), 3.83 (s, 3H), 5.95 (s, 2H), 6.91 (s, 1H), 7.42-7.55 (m, 2H), 7.77 (s, 1H), 7.94-8.05 (m, 2H), 13.07 (br, 1H). |
| 367 | 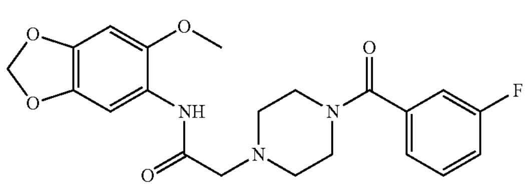 [SMILES: COc1cc2c(cc1NC(=O)CN1CCN(C(=O)c3cccc(F)c3)CC1)OCO2] | 416 | 0.6 | (DMSO-d6) δ 2.55-2.67 (m, 4H), 3.15 (s, 2H), 3.36 (m, 2H), 3.67 (m, 2H), 3.83 (s, 3H), 5.95 (s, 2H), 6.91 (s, 1H), 7.20-7.35 (m, 3H), 7.44-7.60 (m, 1H), 7.77 (s, 1H), 9.53 (s, 1H). |
| 368 | 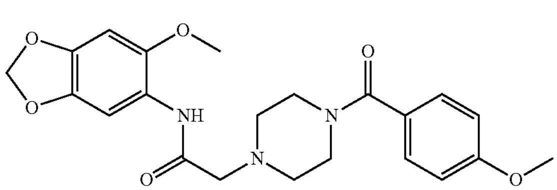 [SMILES: COc1ccc(C(=O)N2CCN(CC(=O)Nc3cc4c(cc3OC)OCO4)CC2)cc1] | 428 | 0.6 | (DMSO-d6) δ 2.52-2.60 (m, 4H), 3.15 (s, 2H), 3.62 (br, 4H), 3.79 (s, 3H), 3.82 (s, 3H), 3.83 (s, 2H), 5.95 (s, 2H), 6.91 (s, 1H), 7.33-7.42 (m, 2H), 7.78 (s, 1H), 7.84-7.93 (m, 2H), 9.54 (s, 1H). |
| 369 | 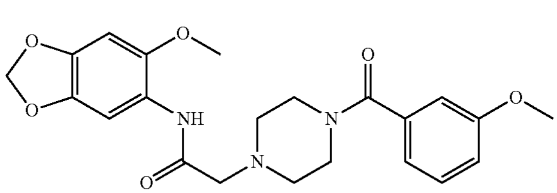 [SMILES: COc1cccc(C(=O)N2CCN(CC(=O)Nc3cc4c(cc3OC)OCO4)CC2)c1] | 428 | 0.3 | (DMSO-d6) δ 2.57 (m, 4H), 3.15 (s, 2H), 3.40 (br, 2H), 3.56-3.74 br, 2H), 3.78 (s, 3H), 3.80 (s, 3H), 5.95 (s, 2H), 6.91 (s, 1H), 7.02 (m, 1H), 7.18 (m, 1H), 7.42-7.45 (m, 1H), 7.52 (m, 1H), 7.77 (s, 1H), 9.52 (s, 1H). |

TABLE 2-continued

| SID | Structure | Obs. Mol Ion; MS (M + H+) | hT2R54 IC50 (uM) | 1H NMR (400 MHz) |
|---|---|---|---|---|
| 370 | 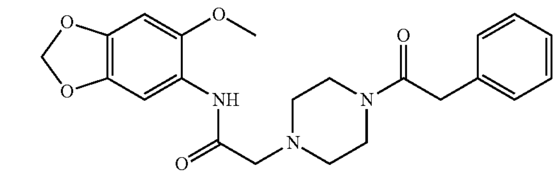 [SMILES: COc1cc2c(cc1NC(=O)CN1CCN(C(=O)Cc3ccccc3)CC1)OCO2] | 412 | 0.4 | (DMSO-d6) δ 2.45 (m, 4H), 3.10 (s, 2H), 3.55 (m, 4H), 3.73 (s, 2H), 3.79 (s, 3H), 5.59 (s, 2H), 6.90 (s, 1H), 7.27-7.34 (m, 5H), 7.76 (s, 1H), 12.32 (s, 1H). |
| 371 | 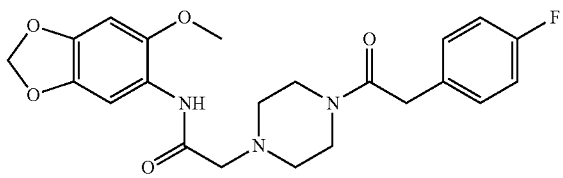 [SMILES: COc1cc2c(cc1NC(=O)CN1CCN(C(=O)Cc3ccc(F)cc3)CC1)OCO2] | 430 | 0.9 | (DMSO-d6) δ 2.42-2.48 (m, 4H), 3.11 (s, 2H), 3.49-3.59 (m, 4H), 3.73 (s, 2H), 3.80 (s, 3H), 5.95 (s, 2H), 6.91 (s, 1H), 7.22-7.32 (m, 4H), 7.76 (s, 1H), 12.37 (br, 1H) |
| 372 | 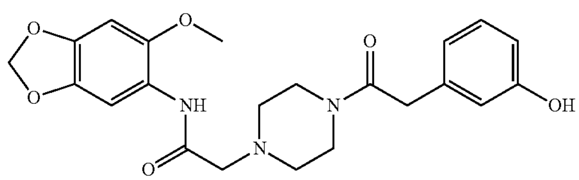 [SMILES: COc1cc2c(cc1NC(=O)CN1CCN(C(=O)Cc3cccc(O)c3)CC1)OCO2] | 428 | 0.4 | (DMSO-d6) δ 2.39-2.49 (m, 4H), 3.10 (s, 2H), 3.52 (m, 4H), 3.63 (s, 2H), 3.79 (s, 3H), 5.95 (s, 2H), 6.56-6.68 (m, 3H), 6.90 (s, 1H), 7.09 (t, J = 8.0 Hz, 1H), 8.14 (s, 1H), 9.49 (s, 1H). |
| 373 | 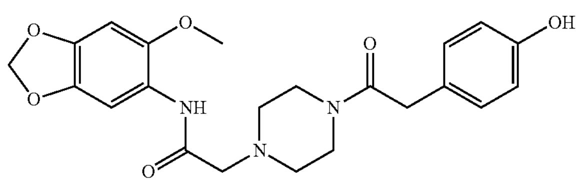 [SMILES: COc1cc2c(cc1NC(=O)CN1CCN(C(=O)Cc3ccc(O)cc3)CC1)OCO2] | 428 | 0.7 | (DMSO-d6) δ 2.37-2.48 (m, 4H), 3.09 (s, 2H), 3.51 (m, 4H), 3.59 (s, 2H), 3.79 (s, 3H), 5.95 (s, 2H), 6.64-6.73 (m, 2H), 6.90 (s, 1H), 6.97-7.04 (m, 2H), 7.76 (s, 1H), 9.50 (s, 1H). |
| 374 | 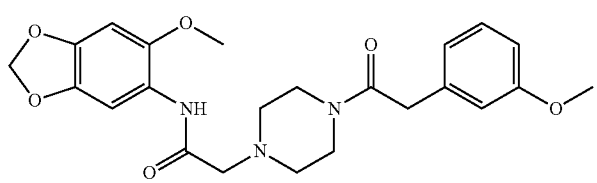 [SMILES: COc1cccc(CC(=O)N2CCN(CC(=O)Nc3cc4c(cc3OC)OCO4)CC2)c1] | 442 | 0.3 | (DMSO-d6) δ 2.37-2.48 (m, 4H), 3.10 (s, 2H), 3.54 (m, 4H), 3.70 (s, 2H), 3.73 (s, 3H), 3.79 (s, 3H), 5.95 (s, 2H), 6.74-6.83 (m, 3H), 6.90 (s, 1H), 7.17-7.26 (m, 1H), 7.76 (s, 1H), 9.50 (s, 1H). |
| 375 | 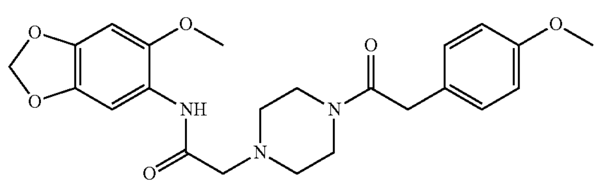 [SMILES: COc1ccc(CC(=O)N2CCN(CC(=O)Nc3cc4c(cc3OC)OCO4)CC2)cc1] | 442 | 1 | (DMSO-d6) δ 2.45 (m, 4H), 3.10 (s, 2H), 3.55 (m, 4H), 3.65 (s, 2H), 3.73 (s, 3H), 3.79 (s, 3H), 5.95 (s, 2H), 6.81-6.94 (m, 2H), 7.10-7.19 (m, 2H), 7.76 (s, 1H), 9.49 (s, 1H). |
| 376 | 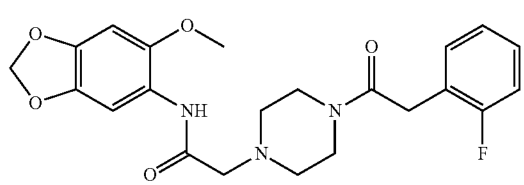 [SMILES: COc1cc2c(cc1NC(=O)CN1CCN(C(=O)Cc3ccccc3F)CC1)OCO2] | 430 | 0.2 | (DMSO-d6) δ 2.60 (m, 4H), 3.14 (s, 2H), 3.62 (m, 4H), 3.76 (s, 2H), 3.82 (s, 3H), 5.95 (s, 2H), 6.91 (s, 1H), 7.09-7.19 (m, 2H), 7.21-7.35 (m, 2H), 7.77 (s, 1H), 9.53 (s, 1H). |
| 377 | 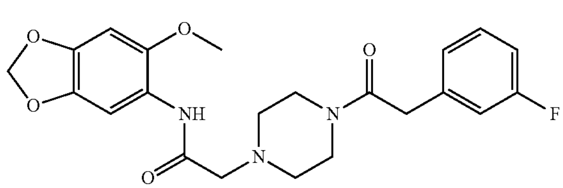 [SMILES: COc1cc2c(cc1NC(=O)CN1CCN(C(=O)Cc3cccc(F)c3)CC1)OCO2] | 430 | 0.2 | (DMSO-d6) δ 2.47 (m, 4H), 3.12 (s, 2H), 3.55 (m, 4H), 3.77 (s, 2H), 3.80 (s, 3H), 5.95 (s, 2H), 6.91 (s, 1H), 7.01-7.07 (m, 1H), 7.08 (s, 1H), 7.27-7.43 (m, 1H), 7.76 (s, 1H), 9.50 (s, 1H). |

TABLE 2-continued

| SID | Structure | Obs. Mol Ion; MS (M + H+) | hT2R54 IC50 (uM) | 1H NMR (400 MHz) |
|---|---|---|---|---|
| 378 | 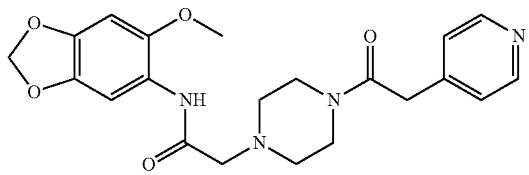 [SMILES: COc1cc2c(cc1NC(=O)CN1CCN(C(=O)Cc3ccncc3)CC1)OCO2] | 413 | 1.1 | |
| 379 | 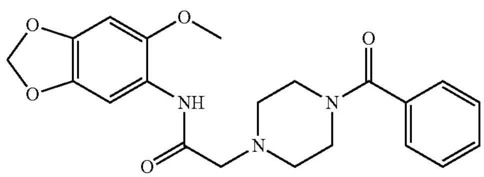 [SMILES: COc1cc2c(cc1NC(=O)CN1CCN(C(=O)c3ccccc3)CC1)OCO2] | 398 | 0.4 | (DMSO-d6) δ 2.55 (br, 4H), 3.15 (s, 2H), 3.67 (br, 4H), 3.83 (s, 3H), 5.95 (s, 2H), 6.91 (s, 1H), 7.31-7.55 (m, 5H), 7.77 (s, 1H), 9.53 (s, 1H). |
| 380 | 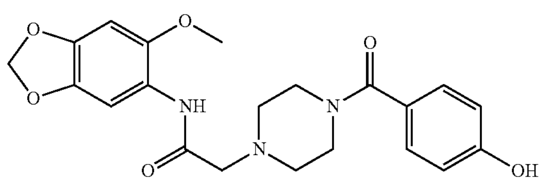 [SMILES: COc1cc2c(cc1NC(=O)CN1CCN(C(=O)c3ccc(O)cc3)CC1)OCO2] | 414 | 0.8 | (DMSO-d6) δ 2.55 (m, 4H), 3.14 (s, 2H), 3.56 (m, 4H), 3.83 (s, 3H), 5.95 (s, 2H), 6.71-6.85 (m, 2H), 6.91 (s, 1H), 7.21-7.32 (m, 2H), 7.78 (s, 1H), 9.54 (s, 1H), 9.86 (s, 1H). |
| 381 | 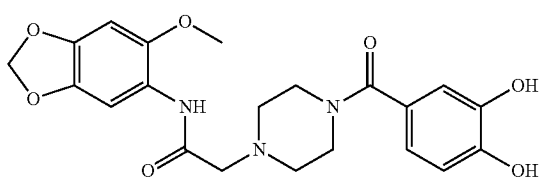 [SMILES: COc1cc2c(cc1NC(=O)CN1CCN(C(=O)c3ccc(O)c(O)c3)CC1)OCO2] | 430 | 5 | |
| 382 | 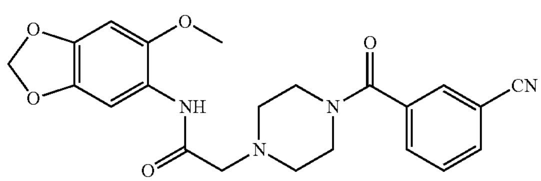 [SMILES: COc1cc2c(cc1NC(=O)CN1CCN(C(=O)c3cccc(C#N)c3)CC1)OCO2] | 423 | 0.4 | (DMSO-d6) δ 2.61 (m, 4H), 3.16 (s, 2H), 3.37 (m, 2H), 3.70 (m, 2H), 3.83 (s, 3H), 5.95 (s, 2H), 6.91 (s, 1H), 7.67 (t, J = 7.7 Hz, 1H), 7.77 (s, 1H), 7.87-7.98 (m, 2H), 9.52 (s, 1H). |
| 383 | 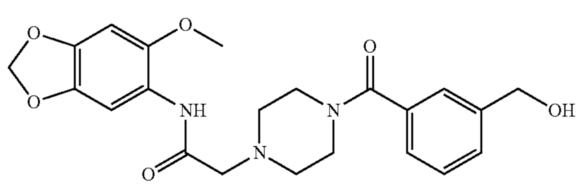 [SMILES: COc1cc2c(cc1NC(=O)CN1CCN(C(=O)c3cccc(CO)c3)CC1)OCO2] | 428 | 0.6 | (DMSO-d6) δ 2.55 (m, 4H), 3.15 (s, 2H), 3.36 (m, 2H), 3.67 (m, 2H), 3.83 (s, 3H), 4.53 (s, 2H), 5.95 (s, 2H), 6.91 (s, 1H), 7.26 (m, 1H), 7.35 (m, 1H), 7.37-7.44 (m, 2H), 7.77 (s, 1H), 8.19 (s, 1H), 9.53 (s, 1H). |
| 384 | 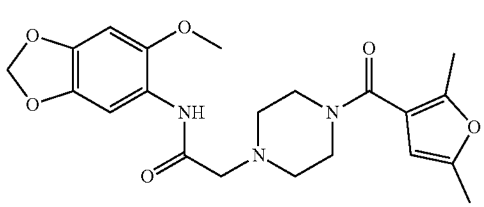 [SMILES: COc1cc2c(cc1NC(=O)CN1CCN(C(=O)c3cc(C)oc3C)CC1)OCO2] | 416 | 0.2 | (DMSO-d6) δ 2.26 (s, 3H), 2.45 (s, 3H), 2.54 (m, 4H), 3.14 (s, 2H), 3.56 (br, 4H), 3.83 (s, 3H), 5.95 (s, 2H), 6.10 (d, J = 1.3 Hz, 1H), 6.91 (s, 1H), 7.77 (s, 1H), 12.38 (s, 1H). |
| 385 | 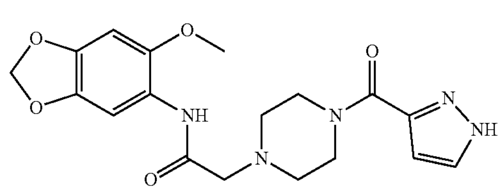 [SMILES: COc1cc2c(cc1NC(=O)CN1CCN(C(=O)c3cc[nH]n3)CC1)OCO2] | 388 | 0.7 | (DMSO-d6) δ 2.52-2.63 (m, 4H), 3.15 (s, 2H), 3.69 (br, 2H), 3.83 (d, J = 3.5 Hz, 3H), 3.98 (br, 2H), 5.95 (s, 2H), 6.58 (d, J = 2.2 Hz, 1H), 6.91 (d, J = 0.8 Hz, 1H), 7.78 (d, J = 6.2 Hz, 1H), 7.81 (s, 1H), 8.02 (s, H), 9.54 (d, J = 19.2 Hz, 1H). |

TABLE 2-continued

| SID | Structure | Obs. Mol Ion; MS (M + H+) | hT2R54 IC50 (uM) | 1H NMR (400 MHz) |
|---|---|---|---|---|
| 386 | 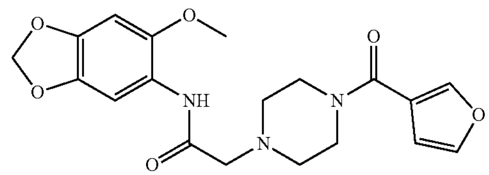 [SMILES: COc1cc2c(cc1NC(=O)CN1CCN(C(=O)c3ccoc3)CC1)OCO2] | 388 | 0.2 | (DMSO-d6) δ 2.53-2.60 (m, 4H), 3.15 (s, 2H), 3.64 (m, 4H), 3.83 (s, 3H), 5.95 (s, 2H), 6.67 (dd, J = 1.9, 0.9 Hz, 1H), 6.92 (s, 1H), 7.74-7.76 (m, 1H), 7.78 (s, 1H), 8.05 (dd, J = 1.6, 0.8 Hz, 1H), 9.53 (s, 1H). |
| 387 | 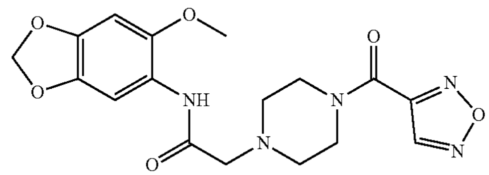 [SMILES: COc1cc2c(cc1NC(=O)CN1CCN(C(=O)c3cnon3)CC1)OCO2] | 390 | >10 | |
| 388 | 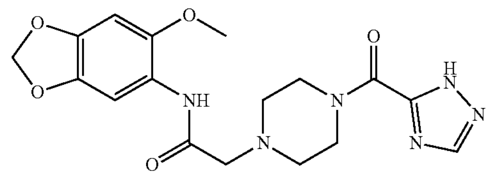 [SMILES: COc1cc2c(cc1NC(=O)CN1CCN(C(=O)c3ncn[nH]3)CC1)OCO2] | 389 | 2.6 | (DMSO-d6) δ 2.47 (m, 4H), 3.16 (d, J = 5.4 Hz, 2H), 3.44 (m, 2H), 3.72 (m, 2H), 3.83 (s, 3H), 5.95 (s, 2H), 6.91 (s, 1H), 7.77 (d, J = 1.1 Hz, 1H), 8.02 (s, 1H), 9.52 (br, 1H), 9.54 (br, 1H). |
| 389 | 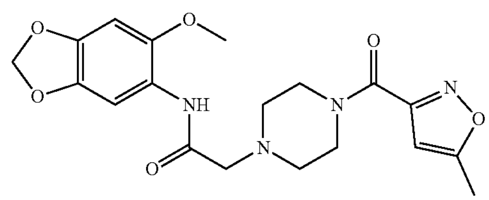 [SMILES: COc1cc2c(cc1NC(=O)CN1CCN(C(=O)c3cc(C)on3)CC1)OCO2] | 403 | 0.4 | (DMSO-d6) δ 2.46 (s, 3H), 2.52-2.62 (m, 4H), 3.16 (s, 2H), 3.56-3.74 (m, 4H), 3.83 (s, 3H), 5.95 (s, 2H), 6.47 (t, J = 0.9 Hz, 1H), 6.91 (s, 1H), 7.76 (s, 1H), 9.51 (s, 1H). |
| 390 | 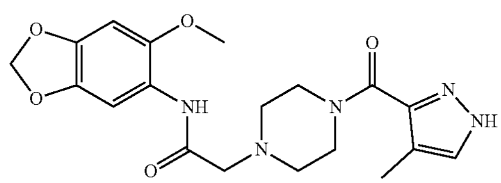 [SMILES: COc1cc2c(cc1NC(=O)CN1CCN(C(=O)c3n[nH]cc3C)CC1)OCO2] | 402 | 2.7 | (DMSO-d6) δ 2.06 (s, 3H), 2.56-(m, 4H), 3.15 (s, 2H), 3.64 (m, 4H), 3.83 (s, 3H), 5.95 (s, 2H), 6.91 (s, 1H), 7.59 (s, 1H), 7.78 (s, 1H), 9.55 (s, 1H), 12.85 (s, 1H). |
| 391 | 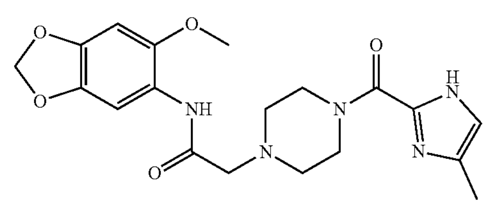 [SMILES: COc1cc2c(cc1NC(=O)CN1CCN(C(=O)c3nc(C)c[nH]3)CC1)OCO2] | 402 | 0.2 | (DMSO-d6) δ 2.47-2.66 (m, 7H), 3.16 (d, J = 5.4 Hz, 2H), 3.44 (m, 2H), 3.72 (m, 2H), 3.83 (d, J = 2.7 Hz, 3H), 5.95 (s, 2H), 6.91 (s, 1H), 7.77 (d, J = 1.1 Hz, 1H), 8.02 (s, 1H), 9.52 (s, 1H), 9.54 (s, 1H) |
| 392 | 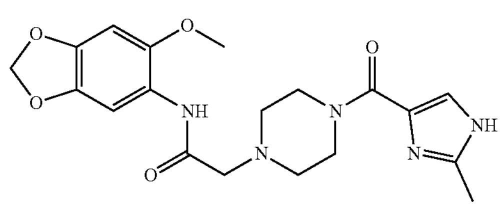 [SMILES: COc1cc2c(cc1NC(=O)CN1CCN(C(=O)c3c[nH]c(C)n3)CC1)OCO2] | 402 | 1.3 | 2.28 (s, 3H), 2.47 (m, 1H), 2.52-2.61 (m, 3H), 3.14 (d, J = 8.1 Hz, 2H), 3.44 (m, 2H), 3.69 (m, 1H), 3.78-3.89 (m, 3H), 4.28 (m, 1H), 5.95 (s, 2H), 6.88-6.96 (m, 1H), 7.78 (dd, J = 10.3, 0.7 Hz, 1H), 8.02 (s, 1H), 9.49-9.64 (m, 1H). |
| 393 | 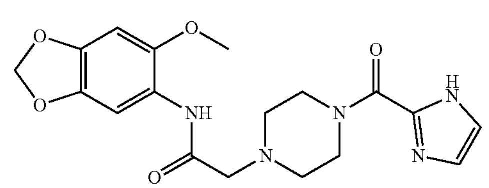 [SMILES: COc1cc2c(cc1NC(=O)CN1CCN(C(=O)c3ncc[nH]3)CC1)OCO2] | 388 | 0.2 | (DMSO-d6) δ 2.61 (m, 4H), 3.15 (d, J = 2.2 Hz, 2H), 3.71 (m, 2H), 3.83 (d, J = 5.2 Hz, 3H), 4.55 (m, 2H), 5.95 (s, 2H), 6.92 (d, J = 2.5 Hz, 1H), 7.08 (d, J = 1.4 Hz, 1H), 7.25 (d, J = 2.2 Hz, 1H), 7.78 (d, J = 7.2 Hz, 1H), 9.58 (s, 1H), 12.94 (s, 1H). |

TABLE 2-continued

| SID | Structure | Obs. Mol Ion; MS (M + H⁺) | hT2R54 IC50 (uM) | ¹H NMR (400 MHz) |
|---|---|---|---|---|
| 394 | 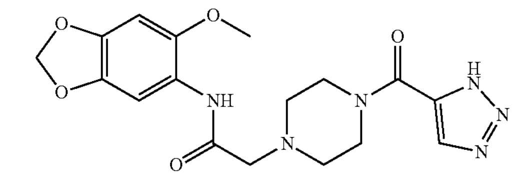 [SMILES: COc1cc2c(cc1NC(=O)CN1CCN(C(=O)c3cnn[nH]3)CC1)OCO2] | 388 | 1.3 | |
| 395 | 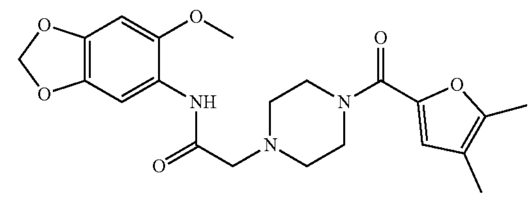 [SMILES: COc1cc2c(cc1NC(=O)CN1CCN(C(=O)c3cc(C)c(C)o3)CC1)OCO2] | 416 | 0.1 | (DMSO-d₆) δ 1.91-1.96 (s, 3H), 2.21-2.26 (s, 3H), 2.54-2.61 (m, 4H), 3.15 (s, 2H), 3.72, (m, 4H), 3.83 (s, 3H), 5.95 (s, 2H), 6.81 (d, J = 0.5 Hz, 1H), 6.92 (s, 1H), 7.78 (s, 1H), 9.54 (s, 1H). |
| 396 | 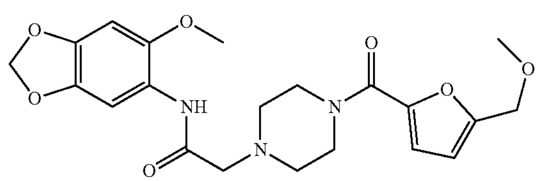 [SMILES: COCc1ccc(C(=O)N2CCN(CC(=O)Nc3cc4c(cc3OC)OCO4)CC2)o1] | 432 | 0.1 | (DMSO-d₆) δ 2.59 (m, 4H), 3.16 (s, 2H), 3.26 (s, 3H), 3.73 (m, 4H), 3.83 (s, 3H), 4.40 (s, 2H), 5.95 (s, 2H), 6.58 (d, J = 3.3 Hz, 1H), 6.92 (s, 1H), 6.96 (d, J = 3.4 Hz, 1H), 7.78 (s, 1H), 9.53 (s, 1H). |
| 397 | 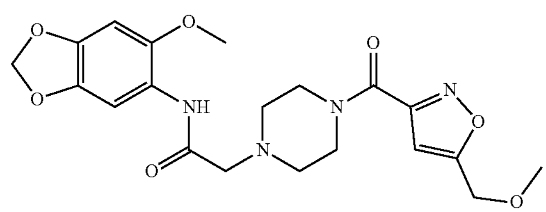 [SMILES: COCc1cc(C(=O)N2CCN(CC(=O)Nc3cc4c(cc3OC)OCO4)CC2)no1] | 433 | 0.77 | (DMSO-d₆) δ 2.52-2.59 (m, 4H), 3.17 (s, 2H), 3.32 (s, 3H), 3.58-3.76 (m, 4H), 3.83 (s, 3H), 4.60 (s, 2H), 5.95 (s, 2H), 6.75 (t, J = 0.6 Hz, 1H), 6.91 (s, 1H), 7.76 (s, 1H), 9.52 (s, 1H). |
| 398 | 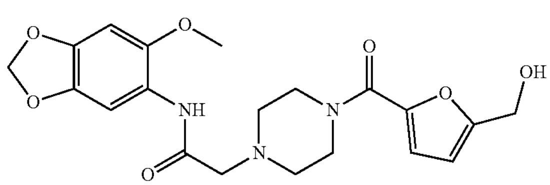 [SMILES: COc1cc2c(cc1NC(=O)CN1CCN(C(=O)c3ccc(CO)o3)CC1)OCO2] | 418 | 0.63 | (DMSO-d₆) δ 2.56-2.62 (m, 4H), 3.16 (d, J = 4.9 Hz, 2H), 3.44 (m, 1H), 3.74 (m, 3H), 3.83 (d, J = 5.4 Hz, 3H), 4.43 (dt, J = 5.9, 0.5 Hz, 2H), 5.38 (t, J = 5.9 Hz, 1H), 5.95 (s, 2H), 6.43 (m, 1H), 6.91 (d, J = 1.2 Hz, 1H), 6.94 (d, J = 3.3 Hz, 1H), 7.78 (s, 1H), 9.54 (s, 1H). |
| 399 | 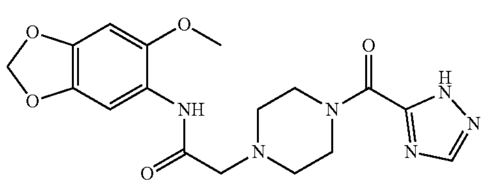 [SMILES: COc1cc2c(cc1NC(=O)CN1CCN(C(=O)c3ncn[nH]3)CC1)OCO2] | 389 | 1.4 | |
| 400 | 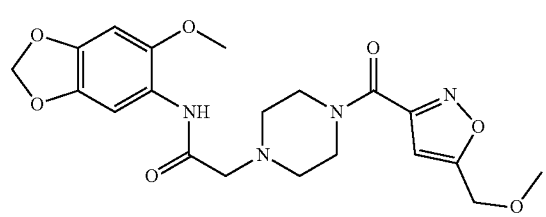 [SMILES: COCc1cc(C(=O)N2CCN(CC(=O)Nc3cc4c(cc3OC)OCO4)CC2)no1] | 433 | 0.3 | (DMSO-d₆) δ 2.60 (m, 4H), 3.17 (s, 2H), 3.33 (s, 3H), 3.44 (d, J = 7.3 Hz, 2H), 3.62 (m, 4H), 3.83 (s, 3H), 5.95 (d, J = 1.8 Hz, 2H), 6.75 (s, 1H), 6.91 (d, J = 1.1 Hz, 1H), 7.76 (s, 1H), 9.51 (s, 1H). |
| 401 | 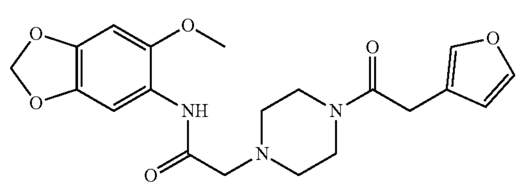 [SMILES: COc1cc2c(cc1NC(=O)CN1CCN(C(=O)Cc3ccoc3)CC1)OCO2] | 402 | 0.13 | (DMSO-d₆) δ 2.48 (m, 4H), 3.13 (s, 2H), 3.47-3.61 (m, 4H), 3.79 (s, 2H), 3.82 (s, 3H), 5.95 (s, 2H), 6.22 (dd, J = 3.1, 0.9 Hz, 1H), 6.39 (dd, J = 3.1, 1.8 Hz, 1H), 6.91 (s, 1H), 7.56 (dd, J = 1.9, 0.9 Hz, 1H), 7.77 (s, 1H), 9.52 (s, 1H). |

TABLE 2-continued
| SID | Structure | Obs. Mol Ion; MS (M + H⁺) | hT2R54 IC50 (uM) | ¹H NMR (400 MHz) |
|---|---|---|---|---|
| 402 | 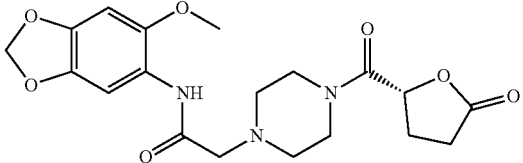 [SMILES: COc1cc2c(cc1NC(=O)CN1CCN(C(=O)[C@H]3CCC(=O)O3)CC1)OCO2] | 406 | 1.1 | |
| 403 | 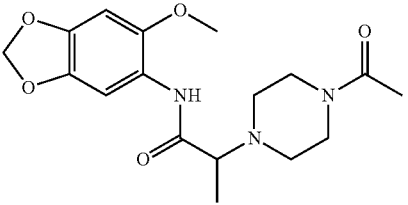 [SMILES: COc1cc2c(cc1NC(=O)C(C)N1CCN(C(C)=O)CC1)OCO2] | 350 | 1.4 | (DMSO-d₆) δ 1.14 (d, J = 6.9 Hz, 3H), 2.01 (s, 3H), 2.42-2.49 (m, 4H), 3.36-3.39 (m, 1H), 3.48-3.51 (m, 4H), 3.82 (s, 3H), 5.95 (s, 2H), 6.91 (s, 1H), 7.77 (s, 1H), 9.71 (s, 1H). |
| 404 | 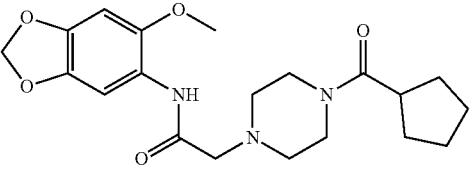 [SMILES: COc1cc2c(cc1NC(=O)CN1CCN(C(=O)C3CCCC3)CC1)OCO2] | 390 | 0.3 | (DMSO-d₆) δ 1.44-1.81 (m, 8H), 2.47-2.56 (m, 4H), 2.89-3.06 (m, 1H), 3.13 (s, 2H), 3.55 (m, 4H), 3.82 (s, 3H), 5.95 (s, 2H), 6.91 (s, 1H), 7.78 (s, 1H), 9.53 (s, 1H). |
| 405 | 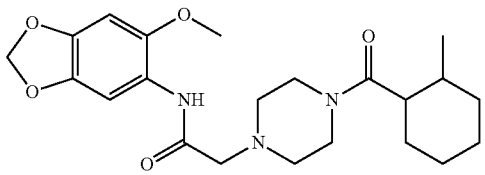 [SMILES: COc1cc2c(cc1NC(=O)CN1CCN(C(=O)C3CCCCC3C)CC1)OCO2] | 418 | 1 | (DMSO-d₆) δ 0.81 (d, J = 7.1 Hz, 3H), 1.18-1.50 (m, 5H), 1.51-1.72 (m, 5H), 1.87-1.99 (m, 1H), 2.31-2.49 (m, 3H), 2.59 (s, 1H), 2.77 (m, 1H), 3.13 (s, 2H), 3.37-3.73 (m, 4H), 3.82 (s, 3H), 5.95 (s, 2H), 6.91 (s, 1H), 7.77 (s, 1H), 9.53 (s, 1H). |
| 406 | 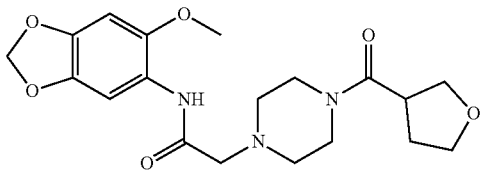 [SMILES: COc1cc2c(cc1NC(=O)CN1CCN(C(=O)C3CCOC3)CC1)OCO2] | 392 | 1.8 | (DMSO-d₆) δ 1.91-2.10 (m, 2H), 2.48-2.54 (m, 4H), 3.14 (s, 2H), 3.41-3.48 (m, 1H), 3.50-3.62 (m, 4H), 3.62-3.74 (m, 3H), 3.82 (s, 3H), 3.86 (t, J = 8.1 Hz, 1H), 5.95 (s, 2H), 6.91 (s, 1H), 7.77 (s, 1H), 9.52 (s, 1H). |
| 407 | 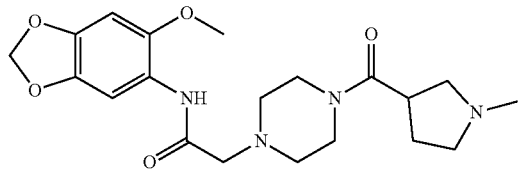 [SMILES: COc1cc2c(cc1NC(=O)CN1CCN(C(=O)C3CCN(C)C3)CC1)OCO2] | 405 | >10 | |
| 408 | 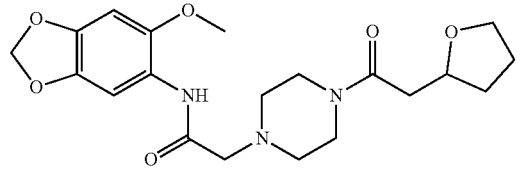 [SMILES: COc1cc2c(cc1NC(=O)CN1CCN(C(=O)CC3CCCO3)CC1)OCO2] | 406 | 0.88 | (DMSO-d₆) δ 1.47 (m, 1H), 1.72-1.89 (m, 2H), 2.00 (m, 1H), 2.36-2.48 (m, 3H), 2.53, (m, 4H), 2.66 (dd, J = 15.1, 6.5 Hz, 1H), 3.13 (s, 2H), 3.52 (m, 4H), 3.58 (m, 1H), 3.73 (m, 1H), 3.82 (s, 3H), 4.09 (p, J = 6.6 Hz, 1H), 5.95 (s, 2H), 6.91 (s, 1H), 7.77 (s, 1H), 9.53 (s, 1H). |

TABLE 2-continued

| SID | Structure | Obs. Mol Ion; MS (M + H+) | hT2R54 IC50 (uM) | 1H NMR (400 MHz) |
|---|---|---|---|---|
| 409 | 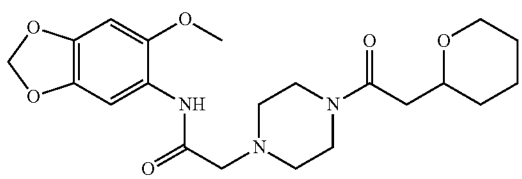 [SMILES: COc1cc2c(cc1NC(=O)CN1CCN(C(=O)CC3CCCCO3)CC1)OCO2] | 420 | 0.5 | (DMSO-d6) δ 1.10-1.28 (m, 2H), 1.33-1.56 (m, 4H), 1.68 (dd, J = 50.8, 12.1 Hz, 3H), 2.31 (dd, J = 15.1, 5.3 Hz, 2H), 2.46 (m, 2H), 2.57 (m, 2H), 3.12 (s, 2H), 3.29 (m, 2H), 3.52 (m, 4H), 3.57-3.69 (m, 1H), 3.79 (m, 1H), 3.82 (s, 3H), 5.95 (s, 2H), 6.91 (s, 1H), 7.77 (s, 1H), 9.52 (s, 1H). |
| 410 | 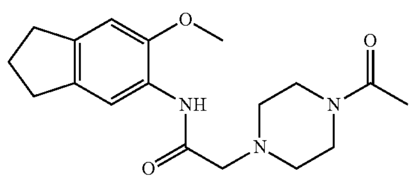 [SMILES: COc1cc2c(cc1NC(=O)CN1CCN(C(C)=O)CC1)CCC2] | 332 | 1.142 | (DMSO-d6) δ 1.94-2.04 (m, 5H), 2.47 (t, J = 5.1 Hz, 2H), 2.53 (t, J = 4.8 Hz, 2H), 2.80 (dt, J = 14.9, 7.3 Hz, 4H), 3.14 (d, J = 1.2 Hz, 2H), 3.46-3.53 (m, 4H), 3.84 (d, J = 1.2 Hz, 3H), 6.94 (s, 1H), 8.04 (s, 1H), 9.59 (s, 1H). |
| 411 | 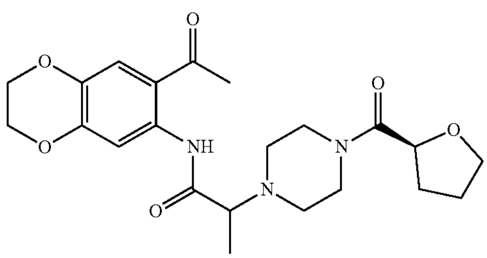 [SMILES: CC(=O)c1cc2c(cc1NC(=O)C(C)N1CCN(C(=O)[C@@H]3CCCO3)CC1)OCCO2] | 432 | 0.17 | (DMSO-d6) δ 1.14 (d, J = 7.0 Hz, 3H), 1.76-1.84 (m, 2H), 1.98-2.06 (m, 2H), 2.44 (m, 4H), 2.57 (s, 3H), 3.34-3.40 (m, 2H), 3.60-3.66 (m, 3H), 3.72-3.78 (m, 2H), 4.26-4.28 (m, 2H), 4.33-4.35 (m, 2H), 4.66 (dd, J = 7.6, 5.6 Hz, 1H), 7.57 (s, 1H), 8.28 (s, 1H), 12.50 (s, 1H). |
| 412 | 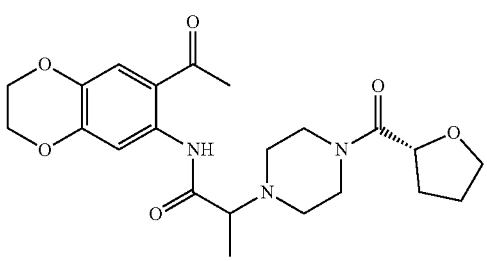 [SMILES: CC(=O)c1cc2c(cc1NC(=O)C(C)N1CCN(C(=O)[C@H]3CCCO3)CC1)OCCO2] | 432 | 0.17 | (DMSO-d6) δ 1.14 (d, J = 7.0 Hz, 3H), 1.79-1.87 (m, 2H), 1.97-2.06 (m, 2H), 2.45 (m, 4H), 2.57 (s, 3H), 3.35 (m, 1H), 3.54-3.80 (m, 6H), 4.26-4.28 (m, 2H), 4.33-4.34 (m, 2H), 4.66 (dd, J = 7.6, 5.6 Hz, 1H), 7.57 (s, 1H), 8.28 (s, 1H), 12.51 (s, 1H). |
| 413 | 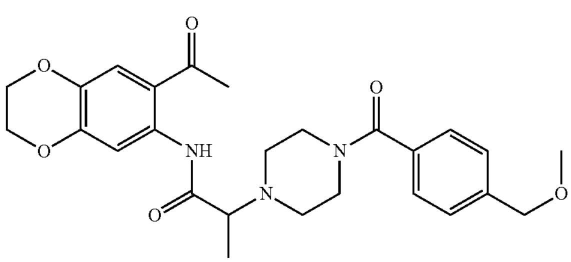 [SMILES: COCc1ccc(C(=O)N2CCN(C(C)C(=O)Nc3cc4c(cc3C(C)=O)OCCO4)CC2)cc1] | 482 | 0.19 | (DMSO-d6) δ 1.16 (d, J = 7.0 Hz, 3H), 2.54 (br. s, 4H), 2.57 (s, 3H), 3.30 (s, 3H), 3.38 (m, 1H), 3.48 (br. s, 2H), 3.78 (br. s, 2H), 4.25-4.28 (m, 2H), 4.32-4.38 (m, 2H), 4.44 (s, 2H), 7.39 (m, 4H), 7.57 (s, 1H), 8.27 (s, 1H), 12.51 (s, 1H). |
| 414 | 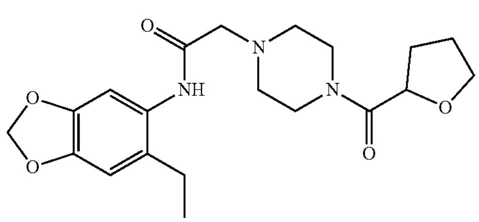 [SMILES: CCc1cc2c(cc1NC(=O)CN1CCN(C(=O)C3CCCO3)CC1)OCO2] | 390 | 7.6 | |

Compounds with hT2R54 IC50 of 1 μM or lower are considered especially potent.

Example 7—Synthesis of N-(6-acetylbenzo[d][1,3]dioxol-5-yl)-2-(4-benzylpiperazin-1-yl)acetamide (101)

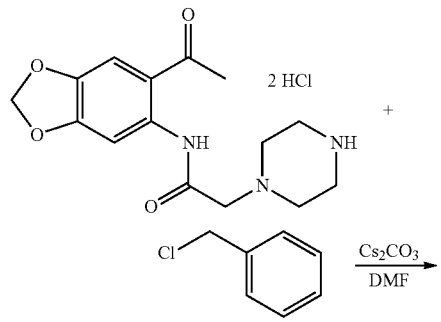

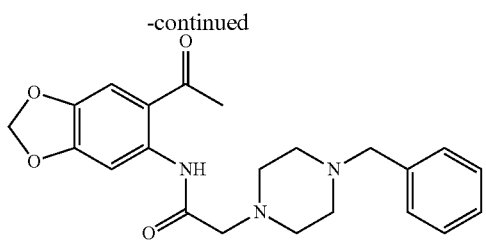

To a mixture of N-(6-acetylbenzo[d][1,3]dioxol-5-yl)-2-(piperazin-1-yl)acetamide dihydrochloride (Example 1a) (76 mg, 0.2 mmol), TEA (40 mg, 0.4 mmol), and $Cs_2CO_3$ (76 mg, 0.4 mmol) in DMF (1 mL) was added (chloromethyl)benzene (25 mg, 0.2 mmol). The mixture was irradiated in the microwave at 150 NC for 10 minutes, diluted with methanol (1 mL), filtered, and the filtrate was purified by reverse phase HPLC (water/acetonitrile gradient) to give 20 mg of the title compound. MS 396 (M+H$^+$).

Compounds in Table 3 were prepared in a similar manner as described in Example 7 from N-(6-acetylbenzo[d][1,3]dioxol-5-yl)-2-(piperazin-1-yl)acetamide dihydrochloride (Example 1a) and the corresponding commercially available electrophiles.

TABLE 3

| SID | Structure | Obs. Mol Ion; MS (M + H)$^+$ | hT2R54 IC50 (uM) | $^1$H NMR (400 MHz) |
|---|---|---|---|---|
| 101 | 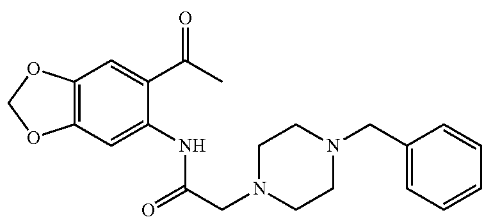 [SMILES: CC(=O)c1cc2c(cc1NC(=O)CN1CCN(Cc3ccccc3)CC1)OCO2] | 396 | 1.06 | (DMSO-d$_6$) δ 2.53 (m, 5H), 2.57 (s, 3H), 3.12 (s, 2H), 3.51 (s, 2H), 6.13 (s, 2H), 7.24 (m, 1H), 7.32 (d, J = 4.4 Hz, 4H), 7.61 (s, 1H), 8.14 (s, 1H), 8.31 (s, 1H), 12.54 (s, 1H). MS 396 (M+ H+). |
| 102 | 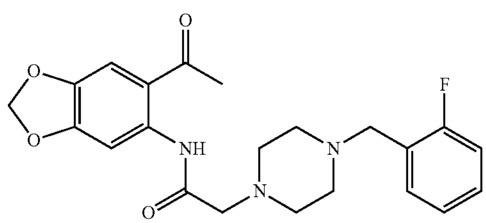 [SMILES: CC(=O)c1cc2c(cc1NC(=O)CN1CCN(Cc3ccccc3F)CC1)OCO2] | 414 | 0.5 | |
| 103 | 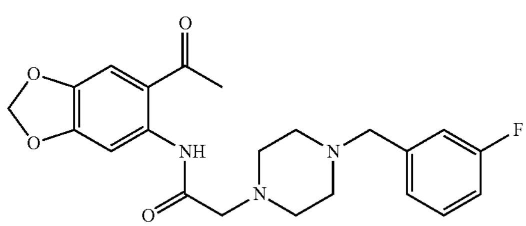 [SMILES: CC(=O)c1cc2c(cc1NC(=O)CN1CCN(Cc3cccc(F)c3)CC1)OCO2] | 414 | 0.5 | |
| 104 | 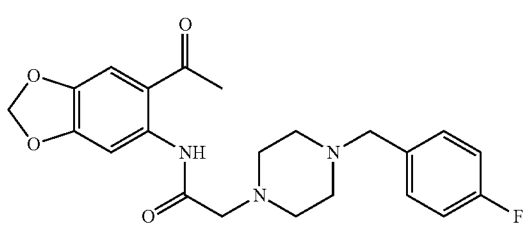 [SMILES: CC(=O)c1cc2c(cc1NC(=O)CN1CCN(Cc3ccc(F)cc3)CC1)OCO2] | 414 | 0.6 | |

TABLE 3-continued

| SID | Structure | Obs. Mol Ion; MS (M + H)+ | hT2R54 IC50 (uM) | 1H NMR (400 MHz) |
|---|---|---|---|---|
| 105 | 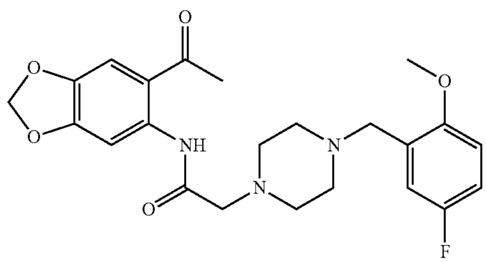 [SMILES: COc1ccc(F)cc1CN1CCN(CC(=O)Nc2cc3c(cc2C(C)=O)OCO3)CC1] | 444 | 0.09 | (DMSO-d6) δ 2.50-2.60 (m, 12H), 3.12 (s, 2H), 3.50 (s, 2H), 3.77 (s, 3H), 6.13 (s, 2H), 6.93-7.09 (m, 2H), 7.13 (dd, J = 9.5, 3.2 Hz, 1H), 7.60 (s, 1H), 8.32 (s, 1H), 12.55 (s, 1H). |
| 106 | 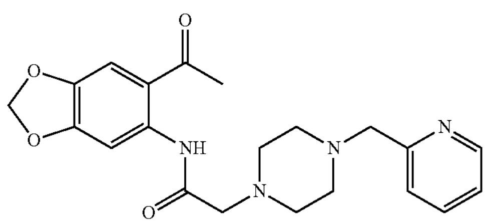 [SMILES: CC(=O)c1cc2c(cc1NC(=O)CN1CCN(Cc3ccccn3)CC1)OCO2] | 397 | 0.3 | |
| 107 | 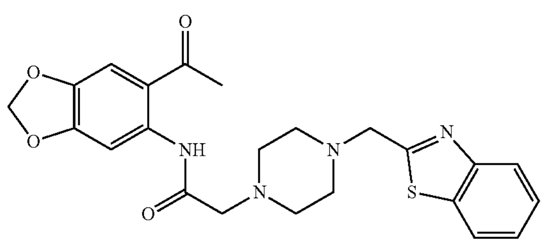 [SMILES: CC(=O)c1cc2c(cc1NC(=O)CN1CCN(Cc3nc4ccccc4s3)CC1)OCO2] | 453 | 4.18 | |
| 108 | 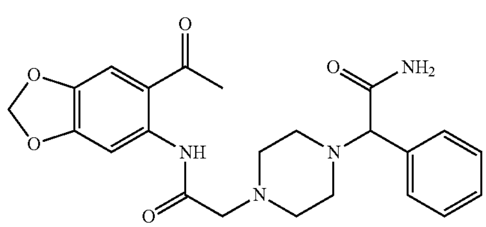 [SMILES: CC(=O)c1cc2c(cc1NC(=O)CN1CCN(C(C(N)=O)c3ccccc3)CC1)OCO2] | 439 | 1.76 | |
| 415 | 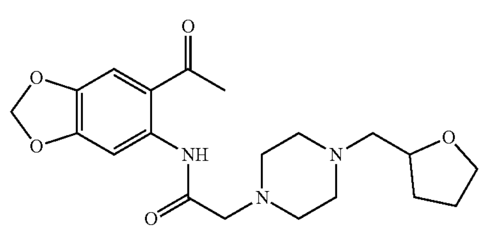 [SMILES: CC(=O)c1cc2c(cc1NC(=O)CN1CCN(CC3CCCO3)CC1)OCO2] | 390 | 1.3 | |
| 416 | 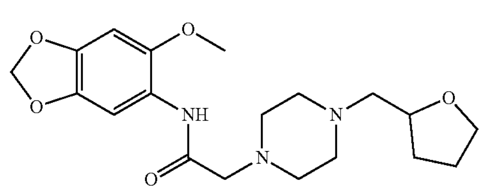 [SMILES: COc1cc2c(cc1NC(=O)CN1CCN(CC3CCCO3)CC1)OCO2] | 378 | 4 | |

Compounds with hT2R54 IC50 of 1 μM or lower are considered especially potent.

Example 8—Synthesis of N-(6-acetylbenzo[d][1,3]dioxol-5-yl)-2-morpholinoacetamide (109)

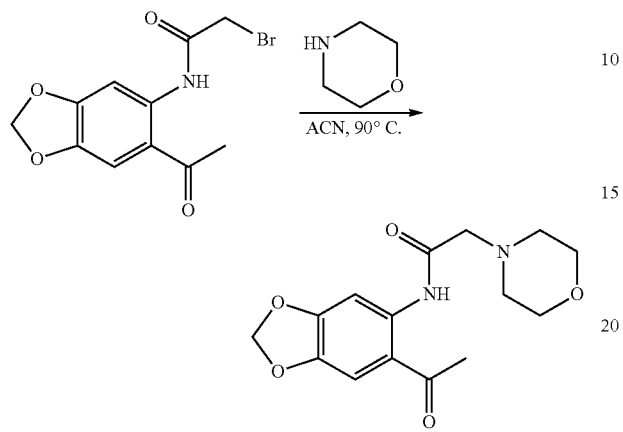

A solution of N-(6-acetylbenzo[d][1,3]dioxol-5-yl)-2-bromoacetamide (Example 1c) (2.5 g, 8.56 mmol) and morpholine (2.3 mL, 25.7 mmol) in acetonitrile (100 mL) was heated to 90° C. and stirred for 1 hour. The mixture was cooled to room temperature and concentrated under vacuum. The residue was stirred in a mixture of EtOAc (15 mL) and water (20 mL) for about 30 min, the solid product collected by filtration and recrystallized from EtOH/H$_2$O to give the title compound (2.2 g, 84% yield) as a light brown solid. MS (M+H$^+$) 307.

Example 9—Synthesis of N-(6-Acetylbenzo[d][1,3]dioxol-5-yl)-2-morpholinopropanamide (110)

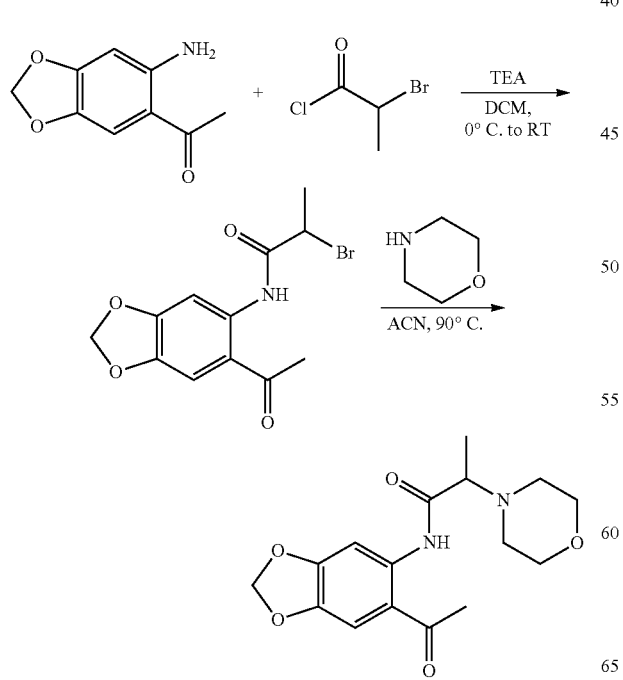

To a solution of N-(6-acetylbenzo[d][1,3]dioxol-5-yl)-2-bromopropanamide (Example 9a) (55 mg, 0.175 mmol) in ACN was added morpholine (45 uL, 0.525 mmol). The solution was heated at 90° C. for 2 hours and concentrated under vacuum. The residue was purified by silica gel column chromatography (0-50% EtOAc/Hexanes gradient) to afford the title compound as a white solid (48.9 mg, 87% yield). MS 321 (M+H$^+$).

Example 9a. N-(6-Acetylbenzo[d][1,3]dioxol-5-yl)-2-bromopropanamide

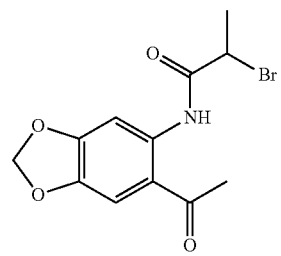 [SMILES: CC(=O)c1cc2c(cc1NC(=O)C(C)Br)OCO2]

Prepared in a similar manner as in Example 1c from 1-(6-aminobenzo[d][1,3]-dioxol-5-yl)ethan-1-one (185 mg, 1.033 mmol), TEA (288 uL, 2.065 mmol), and 2-bromopropionyl chloride (114 uL, 1.136 mmol) to afford the title compound as an orange solid (282 mg, 87% yield). $^1$H NMR (400 MHz, DMSO-d$_6$) δ 1.78 (d, J=6.4 Hz, 3H), 2.59 (s, 3H), 4.84 (q, J=6.8 Hz, 1H), 6.16 (s, 2H), 7.63 (s, 1H), 8.06 (s, 1H), 12.25 (s, 1H). MS 314 (M+H$^+$).

Example 10—Synthesis of N-(6-Acetylbenzo[d][1,3]dioxol-5-yl)-2-methyl-2-morpholinopropanamide (111)

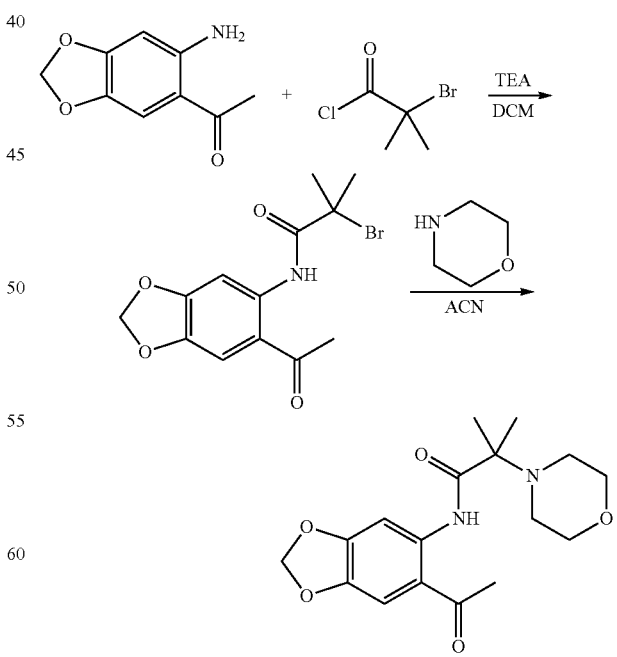

Prepared in a similar manner as in Example 9 from N-(6-acetylbenzo[d][1,3]dioxol-5-yl)-2-bromo-2-methylpropanamide (Example 10a) (60 mg, 0.183 mmol) and morpholine (47 uL, 0.549 mmol) to afford the title compound as a white solid (13.2 mg, 22% yield). MS 335 (M+H$^+$).

Example 10a. N-(6-Acetylbenzo[d][1,3]dioxol-5-yl)-2-bromo-2-methylpropanamide

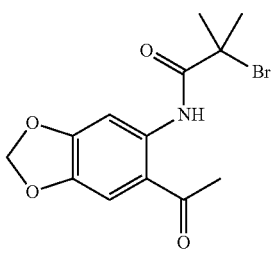 [SMILES: CC(=O)c1cc2c(cc1NC(=O)C(C)(C)Br)OCO2]

Prepared in a similar manner as in Example 1c from 1-(6-aminobenzo[d][1,3]-dioxol-5-yl)ethan-1-one (250 mg, 1.40 mmol), TEA (389 uL, 2.79 mmol), and 2-bromo-2-methylpropanoyl chloride (285 mg, 1.54 mmol) to afford the title compound as a yellow solid (272 mg, 59% yield). MS 329 (M+H$^+$).

Example 11—Synthesis of Ethyl (2-((6-acetylbenzo [d][1,3]dioxol-5-yl)amino)-2-oxoethyl)-L-prolinate (112)

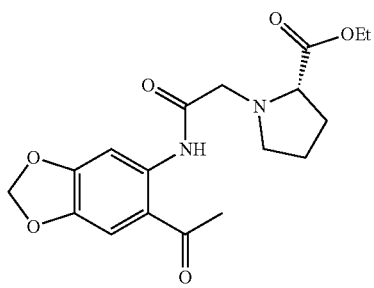 [SMILES: CCOC(=O)[C@@H]1CCCN1CC(=O)Nc1cc2c(cc1C(C)=O)OCO2]

Prepared in a similar manner as in Example 1b from N-(6-acetylbenzo[d][1,3]-dioxol-5-yl)-2-bromoacetamide (Example 1c) (84 mg, 0.280 mmol), L-proline ethyl ester HCl salt (55 mg, 0.308 mmol), and K$_2$C$_{O3}$ (116 mg, 0.840 mmol) in dry DMF (3 mL) at room temperature to afford the title compound as an orange powder (47.1 mg, 46% yield). MS 363 (M+H$^+$).

Example 12—Synthesis of Ethyl 1-(2-((6-Acetyl-benzo[d][1,3]dioxol-5-yl)amino)-2-oxoethyl)piperidine-2-carboxylate (113)

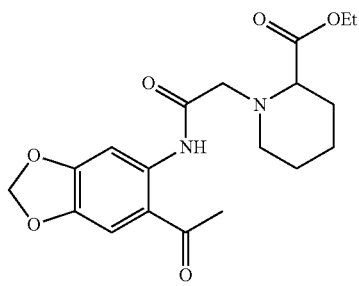 [SMILES: CCOC(=O)C1CCCCN1CC(=O)Nc1cc2c(cc1C(C)=O)OCO2]

Prepared in a similar manner as in Example 1b from N-(6-acetylbenzo[d][1,3]-dioxol-5-yl)-2-bromoacetamide (Example 1c) (75 mg, 0.250 mmol) and ethyl pipecolinate HCl salt (53 mg, 0.275 mmol) to afford the title compound as an off-white solid (55.8 mg, 59% yield). MS 377 (M+H$^+$).

Example 13—Synthesis of Ethyl 1-(2-((6-acetyl-benzo[d][1,3]dioxol-5-yl)amino)-2-oxoethyl)pyrrolidine-3-carboxylate (114)

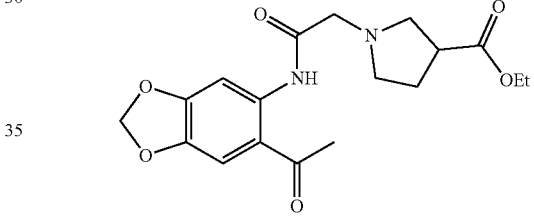

Prepared in a similar manner as in Example 1b from N-(6-acetylbenzo[d][1,3]-dioxol-5-yl)-2-bromoacetamide (Example 1c) (120 mg, 0.400 mmol) and ethyl pyrrolidine-3-carboxylate HCl salt (79 mg, 0.440 mmol) to afford the title compound as an orange solid (14.5 mg, 10% yield). MS 363 (M+H$^+$).

Example 14—Synthesis of Ethyl 1-(2-((6-Acetyl-benzo[d][1,3]dioxol-5-yl)amino)-2-oxoethyl)piperidine-3-carboxylate (115)

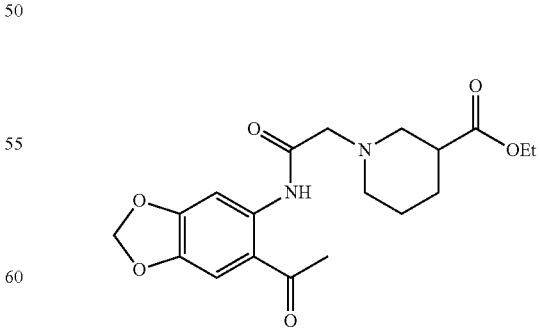

Prepared in a similar manner as in Example 1b from N-(6-acetylbenzo[d][1,3]-dioxol-5-yl)-2-bromoacetamide (Example 1c) (77 mg, 0.257 mmol) and ethyl nipecotate (44 uL, 0.283 mmol) to afford the title compound as a yellowish solid (62.8 mg, 65% yield). MS 377 (M+H⁺). Alternatively, the title was synthesized in a similar manner as in Example 1b from N-(6-acetylbenzo[d][1,3]dioxol-5-yl)-2-chloroacetamide (Example 14a) (5.0 g, 20.0 mmol) and ethyl nipecotate (3.5 g, 22.0 mmol) to afford the title compound as a whitish solid (5.3 g, 70% yield). MS 377 (M+H⁺).

Example 14a. N-(6-Acetylbenzo[d][1,3]dioxol-5-yl)-2-chloroacetamide

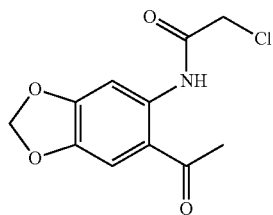 [SMILES: CC(=O)c1cc2c(cc1NC(=O)CCl)OCO2]

Prepared in a similar manner as in Example 1c from 1-(6-aminobenzo[d][1,3]-dioxol-5-yl)ethan-1-one (3.6 g, 20 mmol) and acetyl chloride, (2.4 mL, 30 mmol), and TEA (4.1 mL, 30 mmol) to yield the desired product 5.6 g (quantitative yield). $^1$H NMR (400 MHz, DMSO-$d_6$) δ 2.58 (s, 3H), 4.42 (s, 2H), 6.16 (s, 2H), 7.63 (s, 1H), 8.13 (s, 1H), 12.45 (s, 1H). MS 256 (M+H⁺).

Example 15—Synthesis of Ethyl 1-(2-((6-acetylbenzo[d][1,3]dioxol-5-yl)amino)-2-oxoethyl)piperidine-4-carboxylate (116)

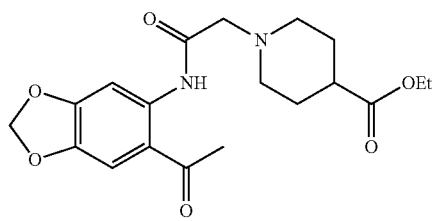 [SMILES: CCOC(=O)C1CCN(CC(=O)Nc2cc3c(cc2C(C)=O)OCO3)CC1]

Prepared in a similar manner as in Example 1b from N-(6-acetylbenzo[d][1,3]-dioxol-5-yl)-2-bromoacetamide (Example 1c) (75 mg, 0.250 mmol) and ethyl piperidine-4-carboxylate HCl salt (53 mg, 0.275 mmol) to afford the title compound as an orange solid (10.9 mg, 12% yield). MS 377 (M+H⁺).

Example 16—Synthesis of Ethyl 1-(2-((6-Methoxybenzo[d][1,3]dioxol-5-yl)amino)-2-oxoethyl)piperidine-3-carboxylate (117)

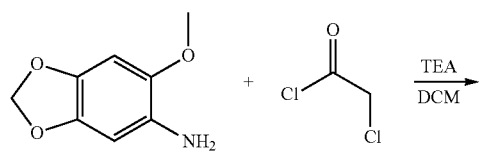

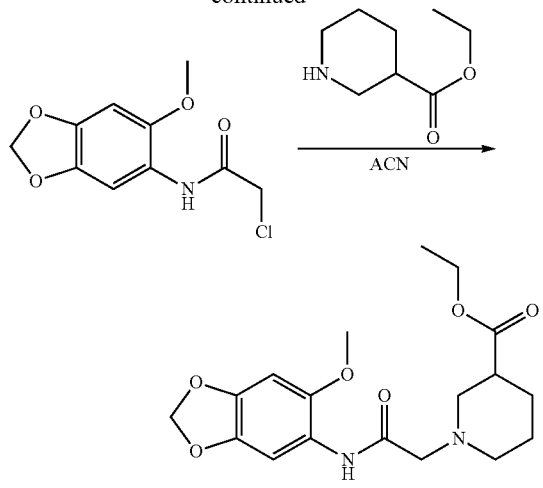

Prepared in a similar manner as in Example 9 from 2-chloro-N-(6-methoxybenzo-[d][1,3]dioxol-5-yl)acetamide (Example 16a) (100 mg, 0.4 mmol) and ethyl piperidine-3-carboxylate (63 mg, 0.4 mmol) to give 55 mg (30% yield) of the title compound as an off white gel. MS 365 (M+H⁺).

Example 16a. 2-Chloro-N-(6-methoxybenzo[d][1,3]dioxol-5-yl)acetamide

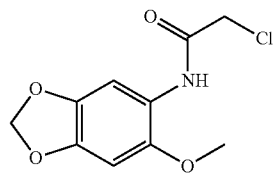 [SMILES: COc1cc2c(cc1NC(=O)CCl)OCO2]

Prepared in a similar manner as in Example 1c from 6-methoxybenzo[d][1,3]-dioxol-5-amine (84 mg, 0.5 mmol) and acetyl chloride (56 mg, 0.5 mmol) to yield the desired product as a greyish solid (100 mg, 82% yield). MS 244 (M+H⁺).

Example 17—Synthesis of Ethyl 1-(2-((7-Acetyl-2,3-dihydrobenzo[b][1,4]dioxin-6-yl)amino)-2-oxoethyl)piperidine-3-carboxylate (118)

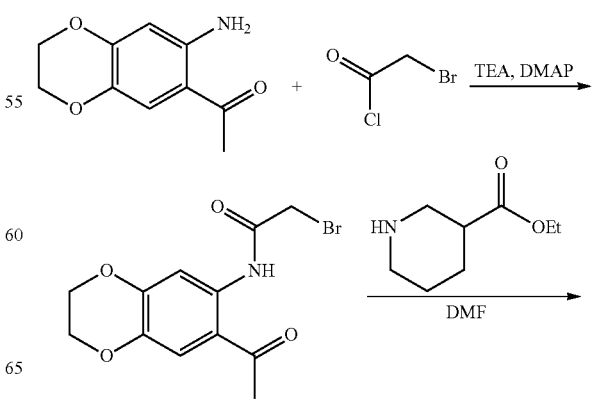

-continued

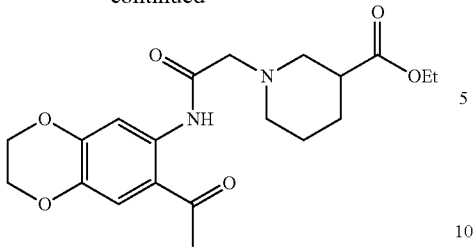

Prepared in a similar manner as in Example 9 from N-(7-acetyl-2,3-dihydrobenzo[b][1,4]dioxin-6-yl)-2-bromoacetamide (Example 17a) (200 mg, 0.64 mmol) and ethyl piperidine-3-carboxylate (148 µL, 0.96 mmol) to give the desired product as a yellowish oil (75 mg, 30% yield). MS 391 (M+H⁺).

Example 17a. N-(7-Acetyl-2,3-dihydrobenzo[b][1,4]dioxin-6-yl)-2-chloroacetamide

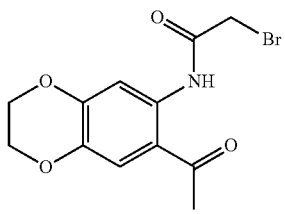 [SMILES: CC(=O)c1cc2c(cc1NC(=O)CBr)OCCO2]

Prepared in similar manner as in Example 1c from 1-(7-amino-2,3-dihydrobenzo[b][1,4]dioxin-6-yl)ethan-1-one (11 g, 56.94 mmol) and 2-bromoacetyl chloride (7.08 m, 85.40 mmol) to yield the desired product as a brown solid (17.8 g, 99% yield). MS 315 (M+H⁺).

Compounds in Table 4 were prepared in a similar manner as in Example 1b and/or Example 9 from the corresponding 2-chloro- and 2-bromo-acetamides synthesized as described herein and commercially available amine nucleophiles.

TABLE 4

| SID | Structure | Obs Mol Ion MS; (M + H⁺) | hT2R54 IC50 (uM) | ¹H NMR (400 MHz) |
|---|---|---|---|---|
| 109 | 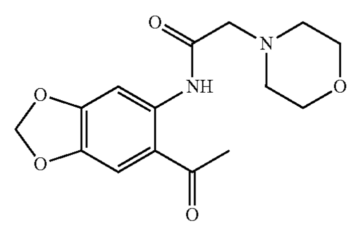 [SMILES: CC(=O)c1cc2c(cc1NC(=O)CN1CCOCC1)OCO2] | 307 | 0.588 | (DMSO-d$_6$) δ 2.48 (m, 4H), 2.56 (s, 3H), 3.11 (s, 2H), 3.71 (t, J = 4.4 Hz, 4H), 6.11 (s, 2H), 7.59 (s, 1H), 8.30 (s, 1H), 12.62 (s, 1H). |
| 110 | 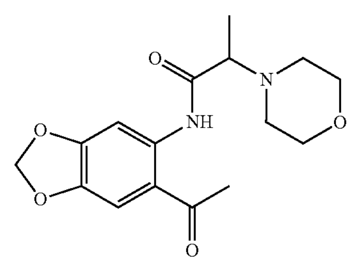 [SMILES: CC(=O)c1cc2c(cc1NC(=O)C(C)N1CCOCC1)OCO2] | 321 | 0.359 | (DMSO-d$_6$) δ 1.18 (d, J = 7.2 Hz, 3H), 2.47 (m, 4H), 2.58 (s, 3H), 3.25 (q, J = 7.2 Hz, 1H), 3.73 (t, J = 4.4 Hz, 4H), 6.13 (s, 2H), 7.61 (s, 1H), 8.33 (s, 1H), 12.74 (s, 1H). |
| 111 | 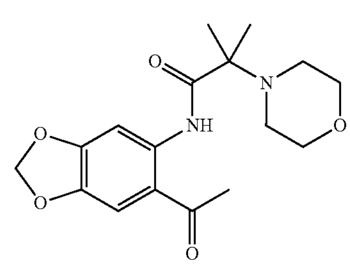 [SMILES: CC(=O)c1cc2c(cc1NC(=O)C(C)(C)N1CCOCC1)OCO2] | 335 | 0.207 | (DMSO-d$_6$) δ 1.16 (s, 6H), 2.44 (t, J = 4.4 Hz, 4H), 2.58 (s, 3H), 3.71 (t, J = 4.4 Hz, 4H), 6.12 (s, 2H), 7.60 (s, 1H), 8.32 (s, 1H), 12.81 (s, 1H). |

TABLE 4-continued

| SID | Structure | Obs Mol Ion MS; (M + H+) | hT2R54 IC50 (uM) | ¹H NMR (400 MHz) |
|---|---|---|---|---|
| 112 | 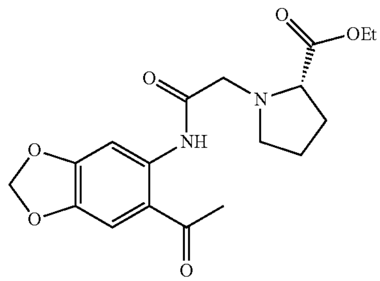 [SMILES: CCOC(=O)[C@@H]1CCCN1CC(=O)Nc1cc2c(cc1C(C)=O)OCO2] | 363 | 0.206 | (DMSO-d₆) δ 1.09 (t, J = 6.8 Hz, 3H), 1.87-1.99 (m, 3H), 2.18-2.19 (m, 1H), 2.55 (s, 3H), 2.66-2.67 (m, 1H), 3.03-3.06 (m, 1H), 3.50-3.65 (m, 3H), 3.97-4.05 (m, 2H), 6.14 (s, 2H), 7.60 (s, 1H), 8.31 (s, 1H), 12.59 (s, 1H). |
| 113 | 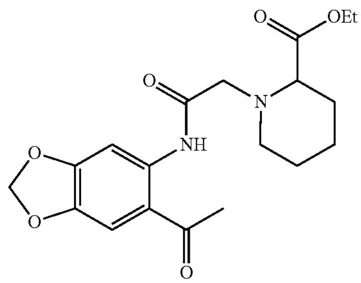 [SMILES: CCOC(=O)C1CCCCN1CC(=O)Nc1cc2c(cc1C(C)=O)OCO2] | 377 | 0.078 | (DMSO-d₆) δ 1.17 (t, J = 7.2 Hz, 3H), 1.29-1.35 (m, 1H), 1.52-1.72 (m, 3H), 1.93-2.07 (m, 2H), 2.58 (s, 3H), 2.67 (m, 2H), 3.26 (s, 2H), 3.54 (t, J = 4.8 Hz, 1H), 4.04-4.14 (m, 2H), 6.14 (s, 2H), 7.62 (s, 1H), 8.36 (s, 1H), 12.66 (s, 1H). |
| 114 | 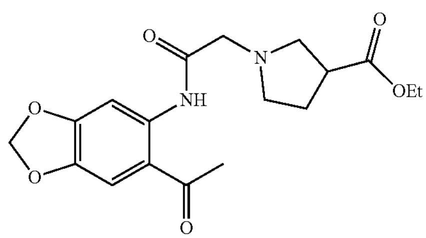 [SMILES: CCOC(=O)C1CCN(CC(=O)Nc2cc3c(cc2C(C)=O)OCO3)C1] | 363 | 0.061 | (DMSO-d₆) δ 1.18 (t, J = 7.2 Hz, 3H), 2.05-2.14 (m, 2H), 2.55 (s, 3H), 2.60-2.62 (m, 1H), 2.73-2.77 (m, 2H), 2.97 (t, J = 8.4 Hz, 1H), 3.09-3.15 (m, 1H), 3.28 (s, 2H), 4.07 (q, J = 7.2 Hz, 2H), 6.14 (s, 2H), 7.60 (s, 1H), 8.30 (s, 1H), 12.53 (s, 1H). |
| 115 | 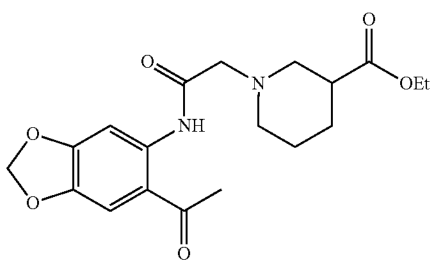 [SMILES: CCOC(=O)C1CCCN(CC(=O)Nc2cc3c(cc2C(C)=O)OCO3)C1] | 377 | 0.009 | (DMSO-d₆) δ 1.15 (t, J = 7.2 Hz, 3H), 1.31-1.41 (m, 1H), 1.67-1.74 (m, 2H), 1.91-1.94 (m, 1H), 2.16 (td, J = 10.8, 3.9 Hz, 1H), 2.29 (t, J = 10.8 Hz, 1H), 2.70-2.78 (m, 2H), 2.92 (d, J = 11.6 Hz, 1H), 3.14 (d, J = 4.0 Hz, 2H), 4.01-4.07 (m, 2H), 6.14 (s, 2H), 7.61 (s, 1H), 8.33 (s, 1H), 12.57 (s, 1H). |
| 116 | 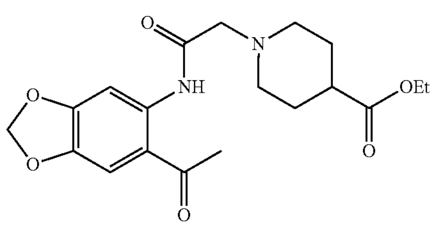 [SMILES: CCOC(=O)C1CCN(CC(=O)Nc2cc3c(cc2C(C)=O)OCO3)CC1] | 377 | 0.103 | (DMSO-d₆) δ 1.19 (t, J = 7.2 Hz, 3H), 1.81-1.86 (m, 4H), 2.19-2.25 (m, 2H), 2.32-2.36 (m, 1H), 2.57 (s, 3H), 2.77-2.80 (m, 2H), 3.09 (s, 2H), 4.07 (q, J = 7.1 Hz, 2H), 6.13 (s, 2H), 7.61 (s, 1H), 8.33 (s, 1H), 12.56 (s, 1H). |
| 117 | 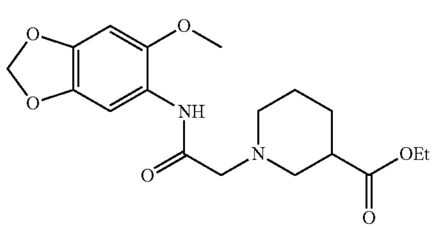 [SMILES: CCOC(=O)C1CCCN(CC(=O)Nc2cc3c(cc2OC)OCO3)C1] | 365 | 0.188 | (DMSO-d₆) δ 1.14 (t, J = 7.1 Hz, 3H), 1.40-1.60 (m, 2H), 1.63-1.73 (m, 1H), 1.73-1.85 (m, 1H), 2.21-2.31 (m, 1H), 2.54-2.66 (m, 1H), 2.83-2.92 (m, 1H), 3.09 (s, 2H), 3.81 (s, 3H), 4.06 (q, J = 7.1 Hz, 2H), 5.94 (s, 2H), 6.90 (s, 1H), 7.78 (s, 1H), 9.49 (s, 1H). |

TABLE 4-continued

| SID | Structure | Obs Mol Ion MS; (M + H+) | hT2R54 IC50 (uM) | 1H NMR (400 MHz) |
|---|---|---|---|---|
| 118 | 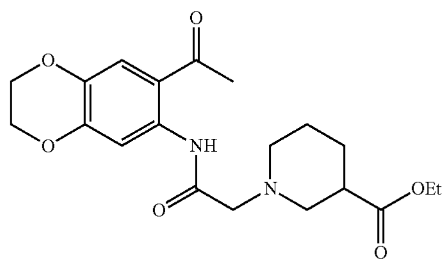 [SMILES: CCOC(=O)C1CCCN(CC(=O)Nc2cc3c(cc2C(C)=O)OCCO3)C1] | 391 | 0.024 | 1H NMR (400 MHz, DMSO-d6) δ 1.13-1.19 (m, 4H), 1.33-1.38 (m, 1H), 1.67-1.70 (m, 2H), 1.90-2.08 (m, 1H), 2.13-2.19 (m, 1H), 2.28 (t, J = 10.8 Hz, 1H), 2.56 (s, 3H), 2.69-2.79 (m, 1H), 2.91-2.95 (dd, J = 11.1, 3.7 Hz, 1H), 3.12 (d, J = 2.4 Hz, 2H), 4.00-4.07 (m, 2H), 4.22-4.38 (m, 4H), 7.56 (s, 1H), 8.26 (s, 1H), 12.27 (s, 1H). |
| 119 | 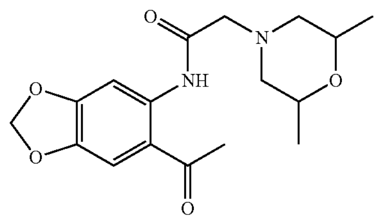 [SMILES: CC(=O)c1cc2c(cc1NC(=O)CN1CC(C)OC(C)C1)OCO2] | 335 | 0.246 | (DMSO-d6) δ 1.05 (d, J = 6.3 Hz, 5H), 1.88 (dd, J = 11.3, 10.1 Hz, 2H), 2.57 (s, 3H), 2.73 (d, J = 10.4 Hz, 2H), 3.10 (s, 2H), 3.85 (m, 2H), 6.13 (s, 2H), 7.60 (s, 1H), 8.33 (s, 1H), 12.63 (s, 1H). |
| 120 | 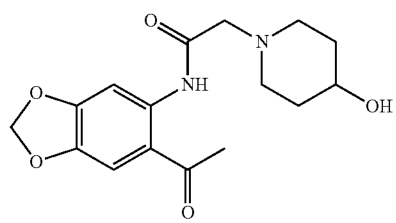 [SMILES: CC(=O)c1cc2c(cc1NC(=O)CN1CCC(O)CC1)OCO2] | 321 | <0.01 | (DMSO-d6) δ 1.55-1.70 (m, 2H), 1.70-1.84 (m, 2H), 2.23 (td, J = 11.7, 10.6, 2.9 Hz, 2H), 2.57 (s, 3H), 2.65-2.75 (m, 2H), 3.07 (s, 2H), 3.52 (br-s, 1H), 4.61 (br-s, 1H), 6.13 (s, 2H), 7.60 (s, 1H), 8.33 (s, 1H), 12.58 (s, 1H). |
| 121 | 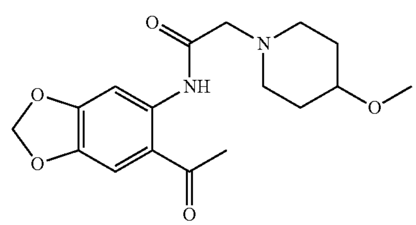 [SMILES: COC1CCN(CC(=O)Nc2cc3c(cc2C(C)=O)OCO3)CC1] | 335 | 0.065 | (DMSO-d6) δ 1.67 (ddt, J = 13.4, 9.0, 4.5 Hz, 2H), 1.86-1.93 (m, 2H), 2.23-2.34 (m, 2H), 2.57 (s, 3H), 2.63-2.76 (m, 2H), 3.09 (s, 2H), 3.19-3.24 (m, 1H), 3.24 (s, 3H), 6.13 (s, 2H), 7.61 (s, 1H), 8.34 (s, 1H), 12.61 (s, 1H). |
| 122 | 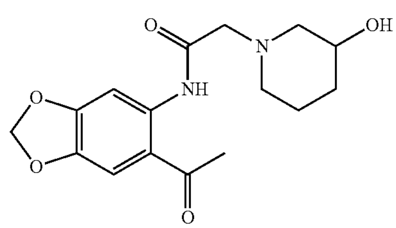 [SMILES: CC(=O)c1cc2c(cc1NC(=O)CN1CCCC(O)C1)OCO2] | 321 | <0.02 | |
| 123 | 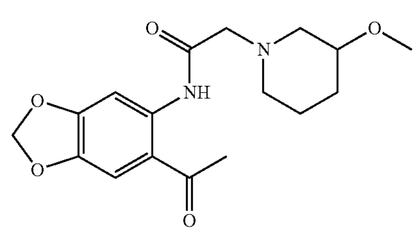 [SMILES: COC1CCCN(CC(=O)Nc2cc3c(cc2C(C)=O)OCO3)C1] | 335 | 0.002 | (DMSO-d6) δ 1.03 (qd, J = 11.8, 5.2 Hz, 1H), 1.61-1.76 (m, 2H), 1.92 (t, J = 10.0 Hz, 1H), 2.05 (td, J = 11.0, 4.1 Hz, 2H), 2.57 (s, 3H), 2.67-2.73 (m, 1H), 3.00-3.06 (m, 1H), 3.13 (d, J = 1.1 Hz, 2H), 3.24 (s, 3H), 3.46 (tt, J = 9.5, 4.2 Hz, 1H), 6.13 (s, 2H), 7.60 (s, 1H), 8.32 (s, 1H), 12.51 (s, 1H). |

TABLE 4-continued

| SID | Structure | Obs Mol Ion MS; (M + H⁺) | hT2R54 IC50 (uM) | ¹H NMR (400 MHz) |
|---|---|---|---|---|
| 124 | 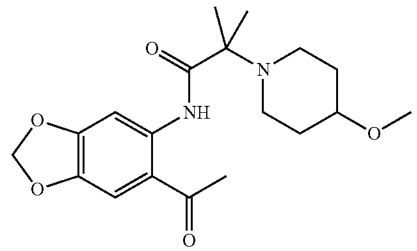 [SMILES: COC1CCN(C(C)(C)C(=O)Nc2cc3c(cc2C(C)=O)OCO3)CC1] | 362 | 2.143 | (DMSO-d₆) δ 1.14 (s, 6H), 1.60 (q, J = 10.0, 9.5 Hz, 2H), 1.87 (d, J = 12.2 Hz, 2H), 2.22 (t, J = 10.4 Hz, 2H), 2.57 (s, 3H), 2.58-2.69 (m, 2H), 3.14-3.25 (m, 4H), 6.12 (s, 2H), 7.59 (s, 1H), 8.34 (s, 1H), 12.77 (s, 1H). |
| 125 | 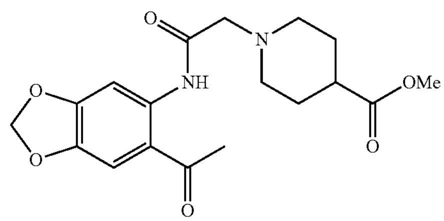 [SMILES: COC(=O)C1CCN(CC(=O)Nc2cc3c(cc2C(C)=O)OCO3)CC1] | 363 | 0.100 | ¹H NMR (400 MHz, DMSO-d₆) δ 1.81-1.86 (m, 4H), 2.19-2.25 (m, 2H), 2.33-2.41 (m, 1H), 2.57 (s, 3H), 2.77 (m, 2H), 3.09 (s, 2H), 3.62 (s, 3H), 6.13 (s, 2H), 7.61 (s, 1H), 8.33 (s, 1H), 12.56 (s, 1H). |
| 126 | 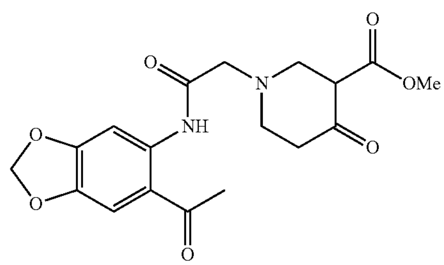 [SMILES: COC(=O)C1CN(CC(=O)Nc2cc3c(cc2C(C)=O)OCO3)CCC1=O] | 377 | 0.154 | |
| 127 | 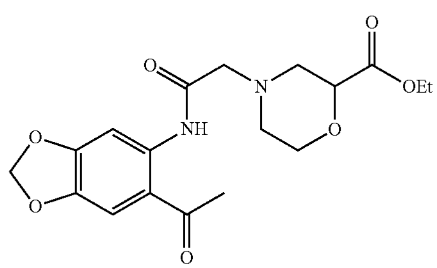 | 379 | 0.013 | (DMSO-d₆) δ 1.17 (t, J = 7.1 Hz, 3H), 1.20-1.25 (m, 1H), 2.37-2.44 (m, 1H), 2.53-2.64 (m, 1H), 2.57 (s, 3H), 2.83-2.94 (m, 1H), 3.19 (d, J = 2.4 Hz, 2H), 3.76 (ddd, J = 11.5, 9.0, 2.7 Hz, 1H), 3.95 (dt, J = 11.3, 3.4 Hz, 1H), 4.11 (qd, J = 7.1, 4.4 Hz, 2H), 4.38 (dd, J = 8.5, 3.0 Hz, 1H), 6.14 (s, 2H), 7.61 (s, 1H), 8.30 (s, 1H), 12.60 (s, 1H). |
| 128 | 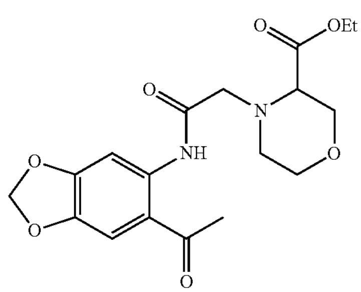 | 379 | 0.079 | (DMSO-d₆, rotamers) δ 1.13-1.29 (m, 3H), 2.43-2.50 (m, 1H), 2.53-2.62 (m, 3H), 3.02-3.12 (m, 1H), 3.30-3.52 (m, 2H), 3.61-3.66 (m, 1H), 3.70-3.90 (m, 2H), 3.91-4.09 (m, 2H), 4.09-4.18 (m, 2H), 6.14 (two s, 2H), 7.63 (two s, 1H), 8.36 (two s, 1H), 12.71 (br. s, 1H). |
| 129 | 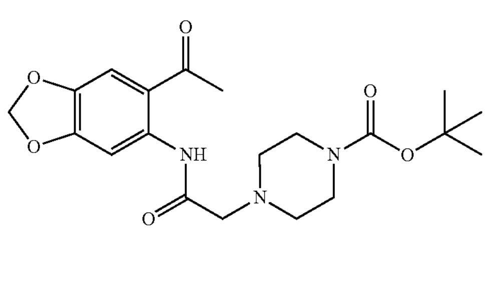 | 406 | <1 | |

TABLE 4-continued

| SID | Structure | Obs Mol Ion MS; (M + H⁺) | hT2R54 IC50 (uM) | ¹H NMR (400 MHz) |
|---|---|---|---|---|
| 130 | 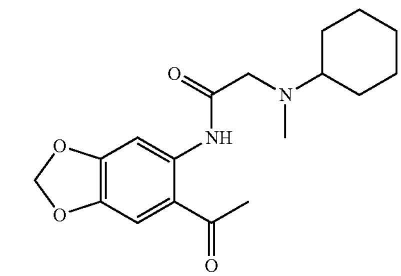 [SMILES: CC(=O)c1cc2c(cc1NC(=O)CN(C)C1CCCCC1)OCO2] | 333 | 0.312 | (DMSO-d₆) δ 0.99-1.13 (m, 1H), 1.13-1.29 (m, 4H), 1.57 (br d, J = 12.4 Hz, 1H), 1.68-1.80 (m, 2H), 1.82-1.91 (m, 2H), 2.27 (s, 3H), 2.38-2.47 (m, 1H), 2.55 (s, 3H), 3.14 (s, 2H), 6.13 (s, 2H), 7.59 (s, 1H), 8.34 (s, 1H), 12.68 (s, 1H). |
| 131 | 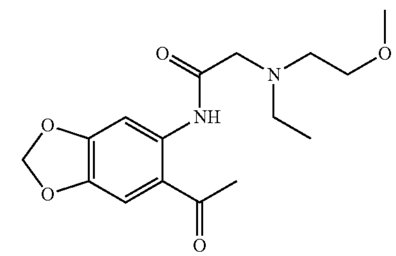 [SMILES: CCN(CCOC)CC(=O)Nc1cc2c(cc1C(C)=O)OCO2] | 323 | 2.0 | |
| 132 | 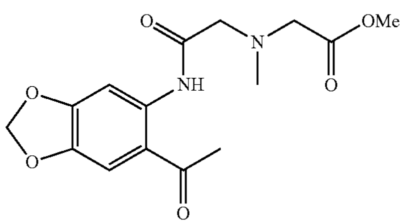 [SMILES: COC(=O)CN(C)CC(=O)Nc1cc2c(cc1C(C)=O)OCO2] | 323 | 0.659 | (DMSO-d₆) δ 2.45 (s, 3H), 2.56 (s, 3H), 3.37 (s, 2H), 3.56 (s, 2H), 3.63 (s, 3H), 6.14 (s, 2H), 7.60 (s, 1H), 8.29 (s, 1H), 12.58 (s, 1H). |
| 133 | 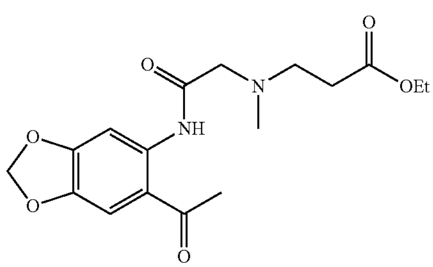 [SMILES: CCOC(=O)CCN(C)CC(=O)Nc1cc2c(cc1C(C)=O)OCO2] | 351 | 0.113 | (DMSO-d₆) δ 1.14 (t, J = 7.1 Hz, 3H), 2.28 (s, 3H), 2.52-2.63 (m, 5H), 2.74 (t, J = 7.2 Hz, 2H), 3.15 (s, 2H), 4.02 (q, J = 7.1 Hz, 2H), 6.13 (s, 2H), 7.60 (s, 1H), 8.30 (s, 1H), 12.51 (s, 1H). |
| 134 | 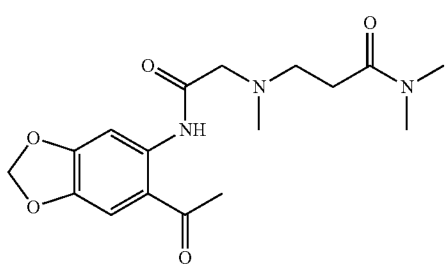 [SMILES: CC(=O)c1cc2c(cc1NC(=O)CN(C)CCC(=O)N(C)C)OCO2] | 350 | 0.96 | (DMSO-d6) δ 2.30 (s, 3H), 2.56 (s, 3H), 2.56-2.62 (m, 2H), 2.64-2.73 (m, 2H), 2.77 (s, 3H), 2.96 (s, 3H), 3.16 (s, 2H), 6.13 (s, 2H), 7.59 (s, 1H), 8.30 (s, 1H), 12.53 (s, 1H). |

TABLE 4-continued

| SID | Structure | Obs Mol Ion MS; (M + H⁺) | hT2R54 IC50 (uM) | ¹H NMR (400 MHz) |
|---|---|---|---|---|
| 135 | 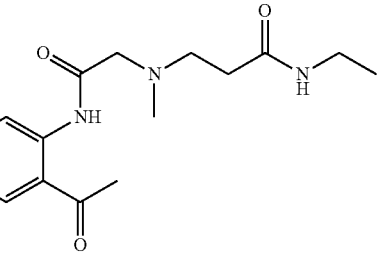 | 350 | 0.50 | (DMSO-d$_6$) δ 0.97 (t, J = 7.2 Hz, 3H), 2.28 (s, 3H), 2.32 (dd, J = 8.3, 6.8 Hz, 2H), 2.56 (s, 3H), 2.70 (dd, J = 8.5, 6.7 Hz, 2H), 3.02 (qd, J = 7.2, 5.4 Hz, 2H), 3.13 (s, 2H), 6.13 (s, 2H), 7.60 (s, 1H), 7.83 (t, J = 4.9 Hz, 1H), 8.30 (s, 1H), 12.51 (s, 1H). |
| 136 | 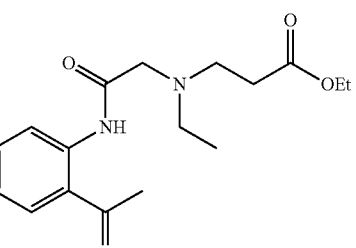 | 365 | 0.179 | (DMSO-d$_6$) δ 1.02 (t, J = 7.1 Hz, 3H), 1.12 (t, J = 7.1 Hz, 3H), 2.51-2.61 (m, 7H), 2.81 (t, J = 7.2 Hz, 2H), 3.18 (s, 2H), 3.98 (q, J = 7.1 Hz, 2H), 6.13 (s, 2H), 7.59 (s, 1H), 8.33 (s, 1H), 12.53 (s, 1H). |
| 137 | 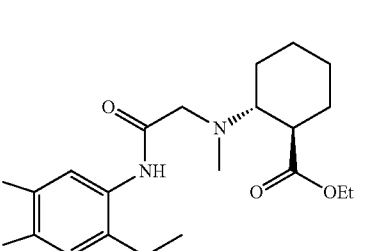 | 405 | 2.826 | (DMSO-d$_6$) δ 1.05 (t, J = 7.1 Hz, 3H), 1.11-1.30 (m, 3H), 1.33-1.48 (m, 1H), 1.60 (d, J = 11.8 Hz, 1H), 1.68-1.86 (m, 2H), 1.91 (d, J = 6.6 Hz, 1H), 2.29 (s, 3H), 2.46 (dd, J = 11.3, 3.6 Hz, 1H), 2.54 (s, 3H), 2.75 (dt, J = 11.1, 5.5 Hz, 1H), 2.99 (d, J = 17.0 Hz, 1H), 3.37 (d, J = 17.0 Hz, 1H), 3.89 (m, 2H), 6.13 (s, 2H), 7.58 (s, 1H), 8.25 (s, 1H), 12.21 (s, 1H). |
| 138 | 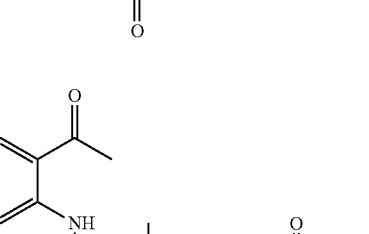 | 434 | 0.15 | (DMSO-d$_6$) δ 0.70-0.90 (m, 1H), 1.18-1.52 (m, 11H), 1.64-1.76 (m, 1H), 1.92 (br d, J = 12.1 Hz, 1H), 2.32 (s, 3H), 2.37-2.50 (m, 1H), 2.56 (s, 3H), 2.59-2.86 (m, 1H), 3.15-3.29 (m, 2H), 3.79 (br d, J = 13.0 Hz, 1H), 4.07 (br d, J = 12.4 Hz, 1H), 6.13 (s, 2H), 7.60 (s, 1H), 8.34 (s, 1H), 12.69 (s, 1H). |
| 139 | 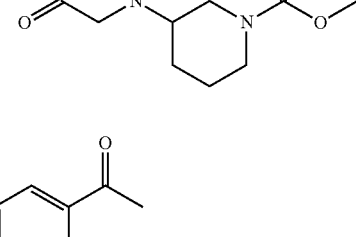 | 420 | 0.176 | (DMSO-d$_6$) δ 1.13-1.25 (m, 2H), 1.38 (s, 9H), 1.77-1.86 (m, 2H), 2.55 (s, 4H), 2.62-2.70 (m, 1H), 2.77 (br-s, 2H), 3.29 (d, J = 5.8 Hz, 2H), 3.84 (d, J = 13.2 Hz, 2H), 6.13 (s, 2H), 7.59 (s, 1H), 8.36 (s, 1H), 12.66 (s, 1H). |

TABLE 4-continued

| SID | Structure | Obs Mol Ion MS; (M + H⁺) | hT2R54 IC50 (uM) | ¹H NMR (400 MHz) |
|---|---|---|---|---|
| 140 | 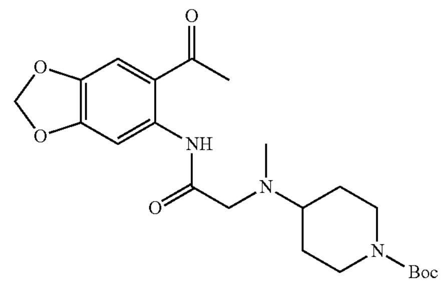 [SMILES: CC(=O)c1cc2c(cc1NC(=O)CN(C)C1CCN(C(=O)OC(C)(C)C)CC1)OCO2] | 434 | 0.433 | (DMSO-d$_6$) δ 1.27-1.44 (m, 2H), 1.39 (s, 9H), 1.80 (d, J = 12.4 Hz, 2H), 2.27 (s, 3H), 2.55 (s, 3H), 2.57-2.76 (m, 3H), 3.17 (s, 2H), 3.98 (d, J = 13.2 Hz, 2H), 6.13 (s, 2H), 7.60 (s, 1H), 8.33 (s, 1H), 12.68 (s, 1H). |
| 141 | 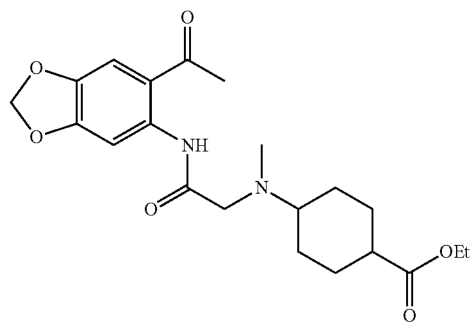 [SMILES: CCOC(=O)C1CCC(N(C)CC(=O)Nc2cc3c(cc2C(C)=O)OCO3)CC1] | 405 | 0.168 | (DMSO-d$_6$) δ 1.07-1.60 (m, 8H), 1.63-1.76 (m, 2H), 1.85-1.99 (m, 1H), 2.02-2.17 (m, 2H), 2.21-2.30 (m, 3H), 2.40-2.60 (m, 5H), 3.07-3.16 (m, 2H), 4.00-4.11 (m, 2H), 6.13 (s, 2H), 7.59 (s, 1H), 8.33 (s, 1H), 12.66 (s, 1H). |
| 142 | 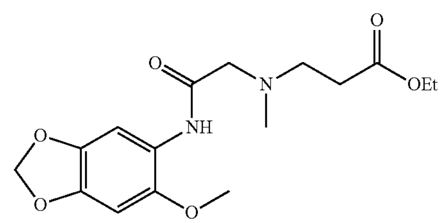 [SMILES: CCOC(=O)CCN(C)CC(=O)Nc1cc2c(cc1OC)OCO2] | 339 | 0.23 | (DMSO-d$_6$) δ 1.14 (t, J = 7.0 Hz, 3H), 2.28 (s, 3H), 2.50-2.57 (m, 2H), 2.73 (t, J = 7.0 Hz, 2H), 3.11 (s, 2H), 3.78 (d, J = 0.9 Hz, 3H), 3.96-4.11 (m, 2H), 5.94 (s, 2H), 6.89 (d, J = 0.8 Hz, 1H), 7.78 (d, J = 0.8 Hz, 1H), 9.28 (s, 1H). |
| 143 | 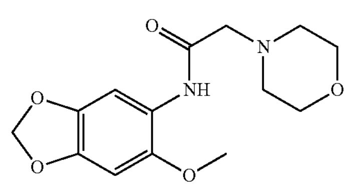 [SMILES: COc1cc2c(cc1NC(=O)CN1CCOCC1)OCO2] | 295 | 0.142 | (DMSO-d$_6$) δ 2.50-2.55 (m, 4H), 3.10 (s, 2H), 3.65 (t, J = 4.6 Hz, 4H), 3.82 (s, 3H), 5.95 (s, 2H), 6.91 (s, 1H), 7.79 (s, 1H), 9.56 (s, 1H). |
| 144 | 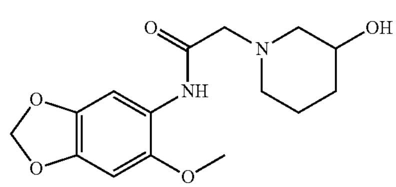 [SMILES: COc1cc2c(cc1NC(=O)CN1CCCC(O)C1)OCO2] | 309 | <2 | |
| 145 | 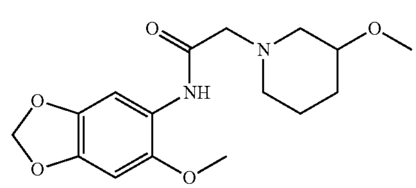 [SMILES: COc1cc2c(cc1NC(=O)CN1CCCC(OC)C1)OCO2] | 323 | 0.575 | (DMSO-d$_6$) δ 1.09-1.29 (m, 1H), 1.41-1.53 (m, 1H), 1.68-1.77 (m, 1H), 1.85-1.99 (m, 1H), 2.04-2.28 (m, 2H), 2.58-2.67 (m, 1H), 2.92 (br d, J = 11.2 Hz, 1H), 3.08 (s, 2H), 3.22-3.31 (m, 4H), 3.82 (s, 3H), 5.95 (s, 2H), 6.91 (s, 1H), 7.81 (s, 1H), 9.54 (s, 1H). |

TABLE 4-continued

| SID | Structure | Obs Mol Ion MS; (M + H+) | hT2R54 IC50 (uM) | ¹H NMR (400 MHz) |
|---|---|---|---|---|
| 146 | 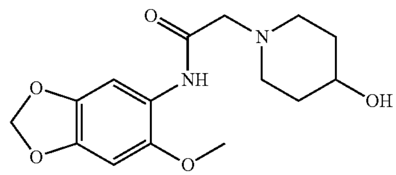 [SMILES: COc1cc2c(cc1NC(=O)CN1CCC(O)CC1)OCO2] | 309 | <2 | (DMSO-d₆) δ 1.40-1.52 (m, 2H), 1.72-1.81 (m, 2H), 2.20-2.33 (m, 2H), 2.67-2.78 (m, 2H), 3.04 (s, 2H), 3.45-3.56 (m, 1H), 3.82 (s, 3H), 4.63 (d, J = 4.2 Hz, 1H), 5.95 (s, 2H), 6.91 (s, 1H), 7.82 (s, 1H), 9.63 (s, 1H). |
| 147 | 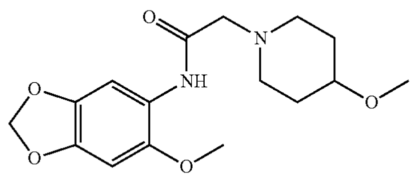 [SMILES: COc1cc2c(cc1NC(=O)CN1CCC(OC)CC1)OCO2] | 323 | 0.448 | (DMSO-d₆) δ 1.40-1.59 (m, 2H), 1.87-1.92 (m, 2H), 2.25-2.39 (m, 2H), 2.64-2.78 (m, 2H), 3.06 (s, 2H), 3.18-3.27 (m, 4H), 3.81 (s, 3H), 5.95 (s, 2H), 6.91 (s, 1H), 7.81 (s, 1H), 9.59 (s, 1H). |
| 148 | 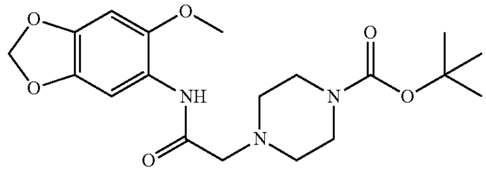 [SMILES: COc1cc2c(cc1NC(=O)CN1CCN(C(=O)OC(C)(C)C)CC1)OCO2] | 394 | <2 | |
| 149 | 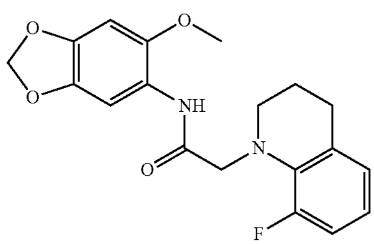 [SMILES: COc1cc2c(cc1NC(=O)CN1CCCc3cccc(F)c31)OCO2] | 359 | 0.885 | |
| 150 | 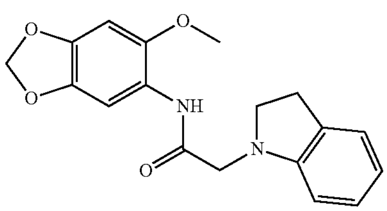 [SMILES: COc1cc2c(cc1NC(=O)CN1CCc3ccccc31)OCO2] | 327 | 0.393 | |
| 151 | 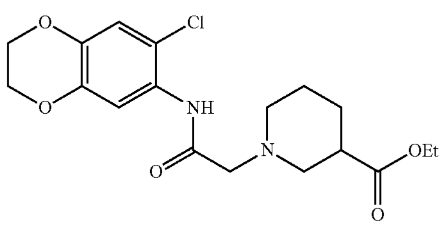 [SMILES: CCOC(=O)C1CCCN(CC(=O)Nc2cc3c(cc2Cl)OCCO3)C1] | 383 | 0.152 | |
| 152 | 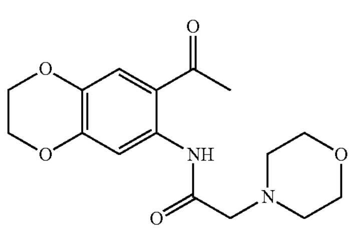 [SMILES: CC(=O)c1cc2c(cc1NC(=O)CN1CCOCC1)OCCO2] | 321 | 0.63 | ¹H NMR (400 MHz, CDCl₃) δ2.57 (s, 3H), 6.61 (m, 4H), 2.27 (s, 2H), 3.89 (m, 4H), 4.27 (m, 2H), 4.33 (m, 2H), 7.40 (s, 1H), 8.40 (s, 1H), 12.49 (br s, 1H). |

TABLE 4-continued

| SID | Structure | Obs Mol Ion MS; (M + H⁺) | hT2R54 IC50 (uM) | ¹H NMR (400 MHz) |
|---|---|---|---|---|
| 153 | 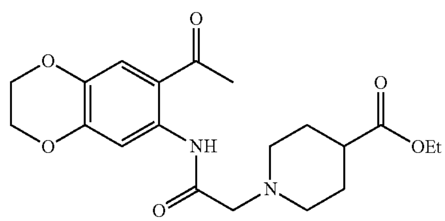 [SMILES: CCOC(=O)C1CCN(CC(=O)Nc2cc3c(cc2C(C)=O)OCCO3)CC1] | 391 | 0.024 | ¹H NMR (400 MHz, DMSO-d₆) δ 1.19 (t, J = 7.2 Hz, 3H), 1.78-1.86 (m, 4H), 2.18-2.24 (m, 2H), 2.32-2.35 (m, 1H), 2.56 (s, 3H), 2.76 (m, 2H), 3.07 (s, 2H), 4.08 (q, J = 7.1 Hz, 2H), 4.26-4.35 (m, 4H), 7.56 (s, 1H), 8.26 (s, 1H), 12.26 (s, 1H). |
| 417 | 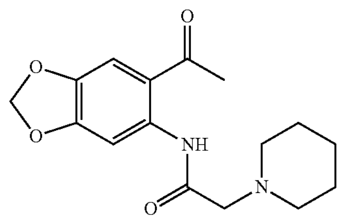 [SMILES: CC(=O)c1cc2c(cc1NC(=O)CN1CCCCC1)OCO2] | 305 | 0.439 | (DMSO-d₆) δ 1.37-1.49 (m, 2H), 1.61-1.69 (m, 4H), 2.39-2.47 (m, 4H), 2.57 (s, 3H), 3.05 (s, 2H), 6.13 (s, 2H), 7.60 (s, 1H), 8.34 (s, 1H), 12.59 (s, 1H). |
| 418 | 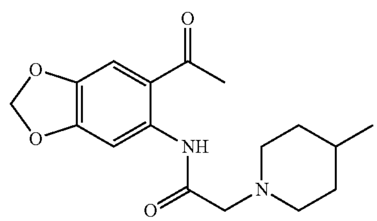 [SMILES: CC(=O)c1cc2c(cc1NC(=O)CN1CCC(C)CC1)OCO2] | 319 | 0.183 | (DMSO-d₆) δ 0.93 (d, J = 5.8 Hz, 3H), 1.30-1.50 (m, 3H), 1.54-1.62 (m, 2H), 2.07-2.17 (m, 2H), 2.56 (s, 3H), 2.73-2.81 (m, 2H), 3.07 (s, 2H), 6.13 (s, 2H), 7.60 (s, 1H), 8.32 (s, 1H), 12.54 (s, 1H). |
| 419 | 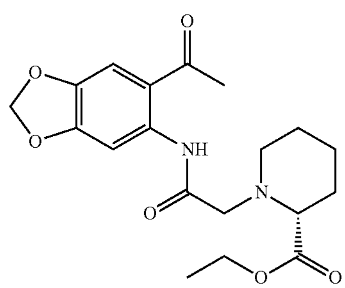 [SMILES: CCOC(=O)[C@H]1CCCCN1CC(=O)Nc1cc2c(cc1C(C)=O)OCO2] | 377 | 0.135 | (DMSO-d₆) δ 1.17 (t, J = 7.1 Hz, 3H), 1.26-1.40 (m, 1H), 1.48-1.67 (m, 2H), 1.68-1.80 (m, 1H), 1.85-1.99 (m, 1H), 1.99-2.11 (m, 1H), 2.41-2.48 (m, 1H), 2.58 (s, 3H), 2.85-2.95 (m, 1H), 3.26 (s, 2H), 3.54 (t, J = 4.9 Hz, 1H), 4.00-4.18 (m, 2H), 6.13 (s, 2H), 7.61 (s, 1H), 8.36 (s, 1H), 12.66 (s, 1H). |
| 420 | 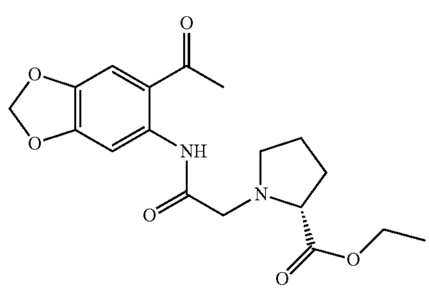 [SMILES: CCOC(=O)[C@H]1CCCN1CC(=O)Nc1cc2c(cc1C(C)=O)OCO2] | 363 | 0.1 | (DMSO-d₆) δ 1.09 (t, J = 7.1 Hz, 3H), 1.85-2.01 (m, 3H), 2.16-2.23 (m, 1H), 2.55 (s, 3H), 2.64-2.68 (m, 1H), 3.02-3.07 (m, 1H), 3.50-3.54 (m, 2H), 3.55-3.58 (m, 1H), 3.97-4.04 (m, 2H), 6.13 (s, 2H), 7.60 (s, 1H), 8.31 (s, 1H), 12.59 (s, 1H). |
| 421 | 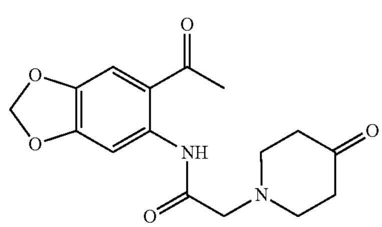 [SMILES: CC(=O)c1cc2c(cc1NC(=O)CN1CCC(=O)CC1)OCO2] | 319 | 0.187 | (DMSO-d₆) δ 2.46-2.52 (m, 4H), 2.58 (s, 3H), 2.86 (t, J = 6.0 Hz, 4H), 3.31 (s, 2H), 6.15 (s, 2H), 7.63 (s, 1H), 8.36 (s, 1H), 12.81 (s, 1H). |

TABLE 4-continued

| SID | Structure | Obs Mol Ion MS; (M + H⁺) | hT2R54 IC50 (uM) | ¹H NMR (400 MHz) |
|---|---|---|---|---|
| 422 | 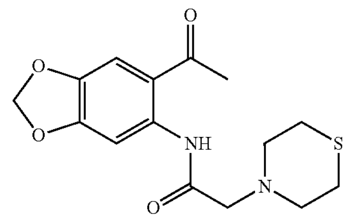 [SMILES: CC(=O)c1cc2c(cc1NC(=O)CN1CCSCC1)OCO2] | 322 | 0.05 | 2.59 (s, 3H), 2.76 (dd, J = 6.0, 3.8 Hz, 8H), 3.13 (s, 2H), 6.14 (s, 2H), 7.62 (s, 1H), 8.34 (s, 1H), 12.61 (s, 1H). |
| 423 | 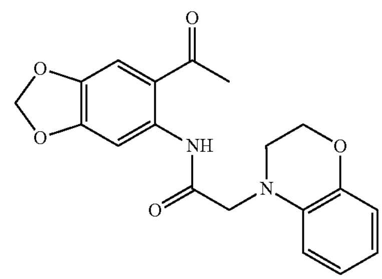 [SMILES: CC(=O)c1cc2c(cc1NC(=O)CN1CCOc3ccccc31)OCO2] | 355 | 1 | (DMSO-d₆) δ 2.50 (s, 3H), 3.48-3.50 (m, 2H), 3.97 (s, 2H), 4.44-4.46 (m, 2H), 6.14 (s, 2H), 6.46 (dd, J = 8.5, 1.4 Hz, 1H), 6.55-6.67 (m 1H), 6.67-6.79 (m, 2H), 7.59 (s, 1H), 8.34 (s, 1H), 12.59 (s, 1H). |
| 424 | 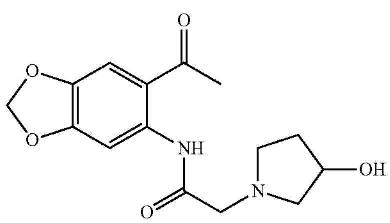 [SMILES: CC(=O)c1cc2c(cc1NC(=O)CN1CCC(O)C1)OCO2] | 307 | 1.592 | (DMSO-d₆) δ 1.59-1.71 (m, 1H), 2.03-2.14 (m, 1H), 2.37 (dd, J = 9.6, 4.2 Hz, 1H), 2.55 (s, 3H), 2.60-2.75 (m, 2H), 3.01 (dd, J = 9.6, 6.1 Hz, 1H), 3.20-3.31 (m, 2H), 4.26-4.34 (m, 1H), 4.71 (d, J = 4.9 Hz, 1H), 6.13 (s, 2H), 7.59 (s, 1H), 8.30 (s, 1H), 12.54 (s, 1H). |
| 425 | 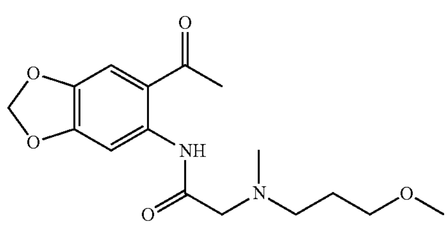 [SMILES: COCCCN(C)CC(=O)Nc1cc2c(cc1C(C)=O)OCO2] | 323 | 0.643 | (DMSO-d₆) δ 1.69-1.77 (m, 2H), 2.26 (s, 3H), 2.45-2.49 (m, 2H), 2.56 (d, J = 1.2 Hz, 3H), 3.11 (s, 2H), 3.19 (d, J = 1.1 Hz, 3H), 3.41 (td, J = 6.4, 1.2 Hz, 2H), 6.13 (d, J = 1.3 Hz, 2H), 7.60 (d, J = 1.2 Hz, 1H), 8.32 (d, J = 1.1 Hz, 1H), 12.54 (s, 1H). |
| 426 | 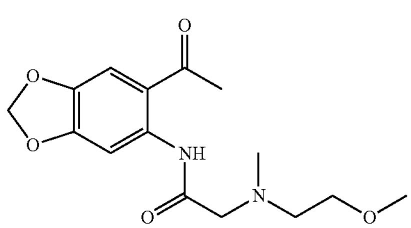 [SMILES: COCCN(C)CC(=O)Nc1cc2c(cc1C(C)=O)OCO2] | 309 | 1.146 | (DMSO-d₆) δ 2.33 (d, J = 1.2 Hz, 3H), 2.57 (d, J = 1.2 Hz, 3H), 2.67 (td, J = 6.0, 1.2 Hz, 2H), 3.18 (s, 2H), 3.21 (d, J = 1.2 Hz, 3H), 3.53 (td, J = 5.9, 1.2 Hz, 2H), 6.13 (d, J = 1.2 Hz, 2H), 7.60 (d, J = 1.2 Hz, 1H), 8.31 (d, J = 1.2 Hz, 1H), 12.55 (s, 1H). |
| 427 | 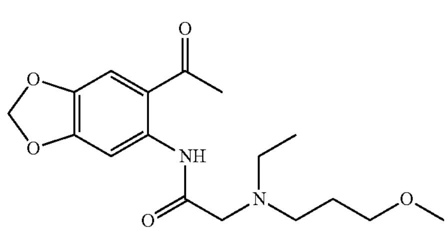 [SMILES: CCN(CCCOC)CC(=O)Nc1cc2c(cc1C(C)=O)OCO2] | 337 | 0.373 | (DMSO-d₆) δ 1.02 (t, J = 7.0 Hz, 3H), 1.63-1.73 (m, 2H), 2.51-2.60 (m, 7H), 3.14 (s, 2H), 3.16 (d, J = 0.9 Hz, 3H), 3.36 (t, J = 6.4 Hz, 2H), 6.13 (d, J = 0.9 Hz, 2H), 7.59 (d, J = 0.9 Hz, 1H), 8.34 (d, J = 0.9 Hz, 1H), 12.57 (s, 1H). |

TABLE 4-continued

| SID | Structure | Obs Mol Ion MS; (M + H⁺) | hT2R54 IC50 (uM) | ¹H NMR (400 MHz) |
|---|---|---|---|---|
| 428 | 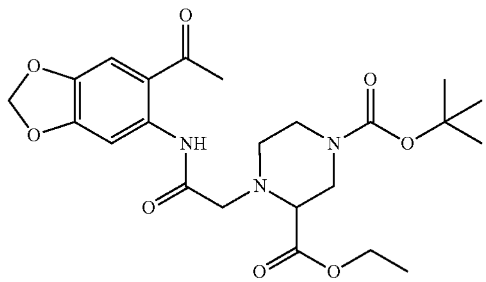 [SMILES: CCOC(=O)C1CN(C(=O)OC(C)(C)C)CCN1CC(=O)Nc1cc2c(cc1C(C)=O)OCO2] | 478 | 0.650 | (DMSO-d₆) δ 1.20 (br s, 3H), 1.39 (s, 9H), 2.58 (s, 3H), 2.98-3.07 (m, 1H), 3.23 (br s, 1H), 3.31 (s, 1H), 3.35 (s, 1H), 3.39-3.56 (m, 2H), 3.69 (s, 1H), 3.80 (br s, 1H), 4.00-4.24 (m, 3H), 6.14 (s, 2H), 7.62 (s, 1H), 8.35 (s, 1H), 12.70 (s, 1H). |
| 429 | 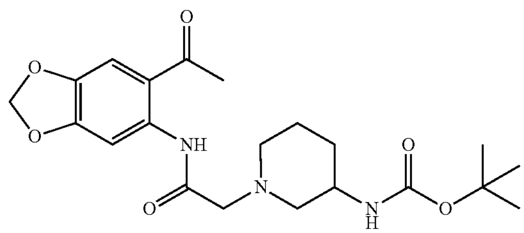 [SMILES: CC(=O)c1cc2c(cc1NC(=O)CN1CCCC(NC(=O)OC(C)(C)C)C1)OCO2] | 420 | 1.279 | (DMSO-d₆) δ 1.19-1.33 (m, 2H), 1.36 (s, 9H), 1.62-1.73 (m, 3H), 2.10-2.25 (m, 2H), 2.59 (s, 3H), 2.68-2.77 (m, 1H), 3.01-3.15 (m, 2H), 3.61-3.73 (m, 1H), 6.14 (s, 2H), 6.82 (d, J = 8.6 Hz, 1H), 7.62 (s, 1H), 8.34 (s, 1H), 12.69 (s, 1H). |
| 430 | 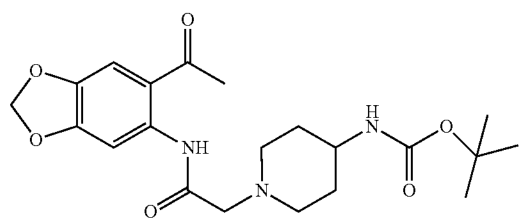 [SMILES: CC(=O)c1cc2c(cc1NC(=O)CN1CCC(NC(=O)OC(C)(C)C)CC1)OCO2] | 420 | 0.162 | (DMSO-d₆) δ 1.38 (s, 9H), 1.57-1.70 (m, 2H), 1.70-1.79 (m, 2H), 2.14-2.24 (m, 2H), 2.57 (s, 3H), 2.72-2.81 (m, 2H), 3.09 (s, 2H), 3.17-3.28 (m, 1H), 6.13 (s, 2H), 6.90 (d, J = 7.1 Hz, 1H), 7.60 (s, 1H), 8.31 (s, 1H), 12.52 (s, 1H). |
| 431 | 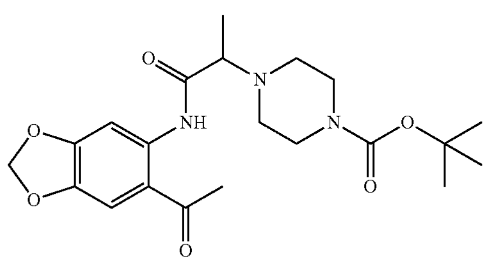 [SMILES: CC(=O)c1cc2c(cc1NC(=O)C(C)N1CCN(C(=O)OC(C)(C)C)CC1)OCO2] | 420 | 0.9 | (DMSO-d₆) δ 1.15 (d, J = 7.0 Hz, 3H), 1.40 (s, 9H), 2.44 (dt, J = 11.0, 5.3 Hz, 4H), 2.57 (s, 3H), 3.36 (q, J = 7.2 Hz, 1H), 3.46-3.47 (m, 4H), 6.13 (s, 2H), 7.61 (s, 1H), 8.34 (s, 1H), 12.75 (s, 1H). |
| 432 | 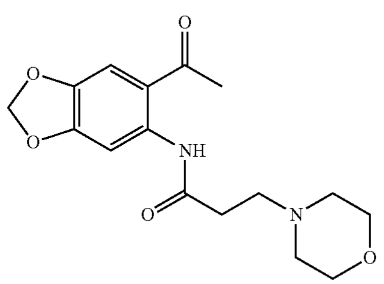 [SMILES: CC(=O)c1cc2c(cc1NC(=O)CCN1CCOCC1)OCO2] | 321 | 1.921 | (DMSO-d₆) δ 2.36-2.43 (m, 4H), 2.51-2.54 (m, 2H), 2.56 (s, 3H), 2.58-2.64 (m, 2H), 3.55 (t, J = 4.7 Hz, 4H), 6.13 (s, 2H), 7.56 (s, 1H), 8.07 (s, 1H), 11.77 (s, 1H). |
| 433 | 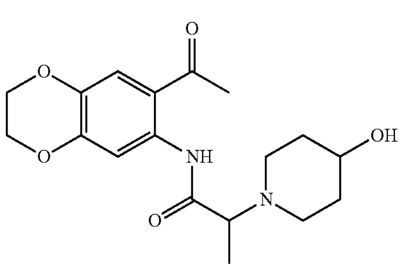 [SMILES: CC(=O)c1cc2c(cc1NC(=O)C(C)N1CCC(O)CC1)OCCO2] | 349 | 0.22 | (DMSO-d₆) δ 1.12 (d, J = 6.9 Hz, 3H), 1.59-1.67 (m, 2H), 1.77 (m, 2H), 2.16-2.22 (m, 1H), 2.29-2.34 (m, 1H), 2.56 (s, 3H), 2.59-2.60 (m, 1H), 2.66-2.69 (m, 1H), 3.26 (q, J = 6.9 Hz, 1H), 3.50 (m, 1H), 4.25-4.27 (m, 2H), 4.32-4.35 (m, 2H), 4.59 (d, J = 3.6 Hz, 1H), 7.55 (s, 1H), 8.28 (s, 1H), 12.40 (s, 1H). |

TABLE 4-continued

| SID | Structure | Obs Mol Ion MS; (M + H⁺) | hT2R54 IC50 (uM) | ¹H NMR (400 MHz) |
|---|---|---|---|---|
| 434 | 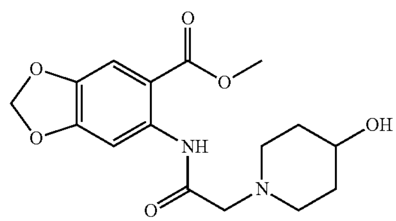 [SMILES: COC(=O)c1cc2c(cc1NC(=O)CN1CCC(O)CC1)OCO2] | 337 | 0.248 | (DMSO-d$_6$) δ 1.54-1.64 (m, 2H), 1.70-1.81 (m, 2H), 2.20-2.29 (m, 2H), 2.66-2.78 (m, 2H), 3.09 (s, 2H), 3.46-3.57 (m, 1H), 3.84 (s, 3H), 4.61 (d, J = 3.7 Hz, 1H), 6.12 (s, 2H), 7.40 (s, 1H), 8.29 (s, 1H), 11.93 (s, 1H). |
| 435 | 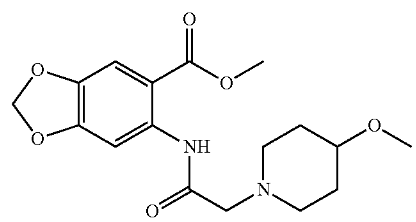 [SMILES: COC(=O)c1cc2c(cc1NC(=O)CN1CCC(OC)CC1)OCO2] | 351 | 0.419 | (DMSO-d$_6$) δ 1.55-1.68 (m, 2H), 1.82-1.91 (m, 2H), 2.22-2.32 (m, 2H), 2.64-2.74 (m, 2H), 3.09 (s, 2H), 3.22 (d, J = 1.1 Hz, 3H), 3.82 (d, J = 1.1 Hz, 3H), 6.10 (d, J = 1.1 Hz, 2H), 7.39 (d, J = 1.1 Hz, 1H), 8.28 (d, J = 1.1 Hz, 1H), 11.95 (s, 1H). |
| 436 | 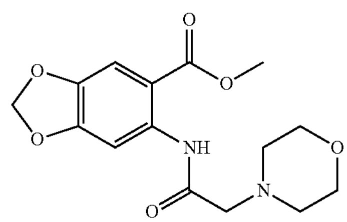 [SMILES: COC(=O)c1cc2c(cc1NC(=O)CN1CCOCC1)OCO2] | 323 | 0.287 | (DMSO-d$_6$) δ 2.50-2.54 (m, 4H), 3.14 (s, 2H), 3.68-3.74 (m, 4H), 3.85 (s, 3H), 6.12 (s, 2H), 7.41 (s, 1H), 8.29 (s, 1H), 12.02 (s, 1H). |
| 437 | 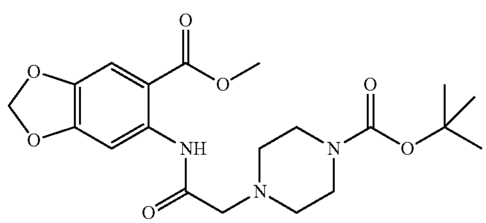 [SMILES: COC(=O)c1cc2c(cc1NC(=O)CN1CCN(C(=O)OC(C)(C)C)CC1)OCO2] | 422 | ~1 | (DMSO-d$_6$) δ 1.40 (s, 9H), 2.47 (t, J = 5.0 Hz, 4H), 3.00-3.05 (m, 4H), 3.16 (s, 2H), 3.44 (t, J = 5.0 Hz, 4H), 3.52 (t, J = 5.3 Hz, 4H), 3.84 (s, 3H), 6.12 (s, 2H), 7.41 (s, 1H), 8.29 (s, 1H), 12.01 (s, 1H). |
| 438 | 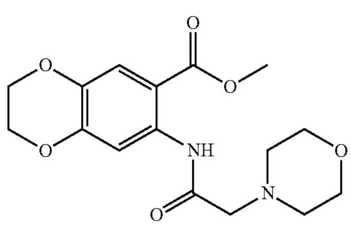 [SMILES: COC(=O)c1cc2c(cc1NC(=O)CN1CCOCC1)OCCO2] | 337 | 0.198 | (DMSO-d$_6$) δ 2.49-2.54 (m, 2H), 3.13 (s, 2H), 3.66-3.74 (m, 4H), 3.85 (s, 3H), 4.21-4.30 (m, 2H), 4.30-4.36 (m, 2H), 7.42 (s, 1H), 8.24 (s, 1H), 11.78 (s, 1H). |
| 439 | 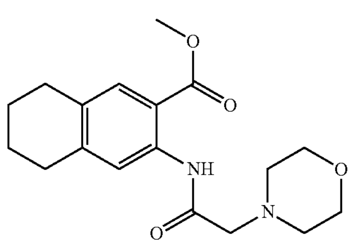 [SMILES: COC(=O)c1cc2c(cc1NC(=O)CN1CCOCC1)CCCC2] | 333 | ~2 | (DMSO-d$_6$) δ 1.70-1.74 (m, 4H), 2.50-2.54 (m, 4H), 2.66-2.76 (m, 4H), 3.13 (s, 2H), 3.67-3.75 (m, 4H), 3.87 (s, 3H), 7.69 (s, 1H), 8.39 (s, 1H), 11.72 (s, 1H). |

TABLE 4-continued

| SID | Structure | Obs Mol Ion MS; (M + H+) | hT2R54 IC50 (uM) | 1H NMR (400 MHz) |
|---|---|---|---|---|
| 440 | 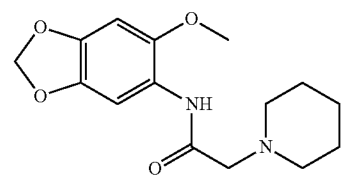 [SMILES: COc1cc2c(cc1NC(=O)CN1CCCCC1)OCO2] | 293 | 1.821 | (DMSO-d6) δ 1.36-1.47 (m, 2H), 1.57 (p, J = 5.6 Hz, 4H), 2.43-2.49 (m, 4H), 3.02 (s, 2H), 3.82 (s, 3H), 5.95 (s, 2H), 6.91 (s, 1H), 7.83 (s, 1H), 9.64 (s, 1H). |
| 441 | 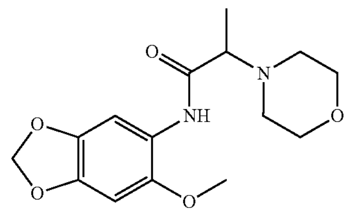 [SMILES: COc1cc2c(cc1NC(=O)C(C)N1CCOCC1)OCO2] | 309 | 1 | (DMSO-d6) δ 1.16 (d, J = 7.0 Hz, 3H), 2.46-2.54 (m, 4H), 3.27 (q, J = 7.1 Hz, 1H), 3.66 (q, J = 3.9 Hz, 4H) 3.83 (s, 3H), 5.94 (s, 2H), 6.91 (s, 1H), 7.78 (s, 1H), 9.74 (s, 1H). |
| 442 | 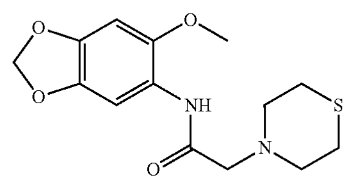 [SMILES: COc1cc2c(cc1NC(=O)CN1CCSCC1)OCO2] | 311 | 0.2 | 2.63-2.78 (m, 8H), 3.08 (s, 2H), 3.81 (s, 3H), 5.93 (s, 2H), 6.90 (s, 1H), 7.76 (s, 1H), 9.47 (s, 1H). |
| 443 | 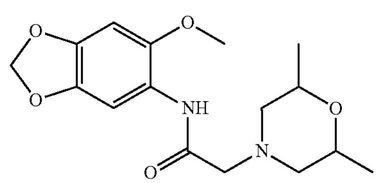 [SMILES: COc1cc2c(cc1NC(=O)CN1CC(C)OC(C)C1)OCO2] | 323 | 0.322 | (DMSO-d6) δ 1.07 (d, J = 6.3 Hz, 6H), 1.85-1.93 (m, 2H), 2.73-2.78 (m, 2H), 3.07 (s, 2H), 3.58-3.68 (m, 2H), 3.81 (s, 3H), 5.95 (s, 2H), 6.91 (s, 1H), 7.79 (s, 1H), 9.54 (s, 1H). |
| 444 | 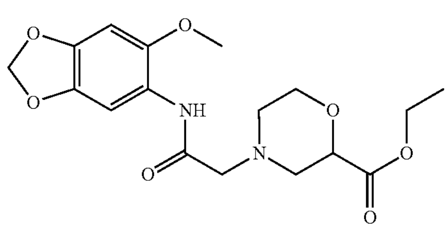 [SMILES: CCOC(=O)C1CN(CC(=O)Nc2cc3c(cc2OC)OCO3)CCO1] | 367 | 0.505 | (DMSO-d6) δ 1.16 (td, J = 7.1, 1.2 Hz, 3H), 2.41-2.48 (m, 1H), 2.54-2.68 (m, 2H), 2.88 (dd, J = 11.4, 3.2 Hz, 1H), 3.15 (s, 2H), 3.57-3.67 (m, 1H), 3.81 (d, J = 1.2 Hz, 3H), 3.89-3.99 (m, 1H), 4.08-4.17 (m, 2H), 4.26-4.33 (m, 1H), 5.95 (d, J = 1.2 Hz, 2H), 6.90 (d, J = 1.2 Hz, 1H), 7.75 (d, J = 1.2 Hz, 1H), 9.40 (s, 1H). |
| 445 | 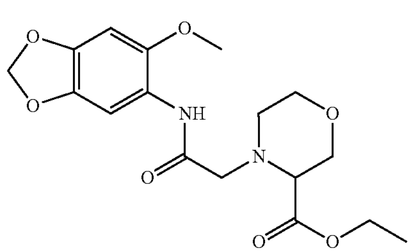 [SMILES: CCOC(=O)C1COCCN1CC(=O)Nc1cc2c(cc1OC)OCO2] | 367 | 0.526 | (DMSO-d6) δ 1.20 (td, J = 7.2, 1.2 Hz, 3H), 2.51-2.54 (m, 1H), 3.00-3.09 (m, 1H), 3.35 (d, J = 1.1 Hz, 2H), 3.56-3.68 (m, 2H), 3.72-3.79 (m, 2H), 3.84 (d, J = 1.2 Hz, 3H), 4.01 (dd, J = 11.2, 3.4 Hz, 1H), 4.09-4.18 (m, 2H), 5.95 (d, J = 1.2 Hz, 2H), 6.92 (d, J = 1.2 Hz, 1H), 7.83 (d, J = 1.2 Hz, 1H), 9.66 (s, 1H). |
| 446 | 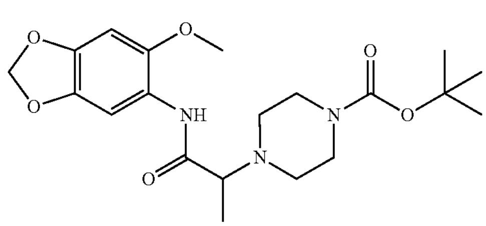 | 408 | 0.19 | (DMSO-d6) δ 1.15 (d, J = 7.2 Hz, 3H), 1.40 (s, 9H), 2.43-2.48 (m, 4H), 3.35-3.38 (m, 5H), 3.81 (s, 3H), 5.94 (s, 2H), 6.90 (s, 1H), 7.77 (s, 1H), 9.68 (s, 1H). |

TABLE 4-continued

| SID | Structure | Obs Mol Ion MS; (M + H⁺) | hT2R54 IC50 (uM) | ¹H NMR (400 MHz) |
|-----|-----------|--------------------------|------------------|-------------------|
| 447 | 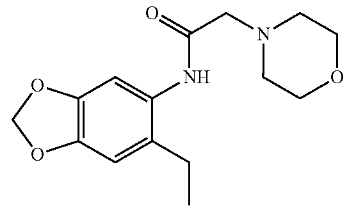 [SMILES: CCc1cc2c(cc1NC(=O)CN1CCOCC1)OCO2] | 293 | >>10 | (DMSO-d₆) δ 1.10 (t, J = 7.5 Hz, 3H), 2.46-2.48 (m, 2H), 2.53-2.55 (m, 4H), 3.10 (s, 2H), 3.63-3.66 (m, 4H), 5.97 (s, 2H), 6.82 (s, 1H), 7.23 (s, 1H), 9.29 (s, 1H). |
| 448 | 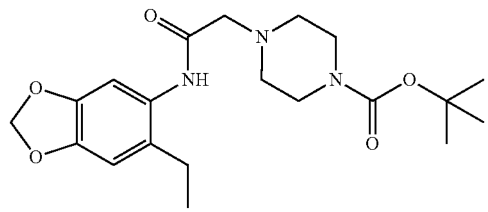 [SMILES: CCc1cc2c(cc1NC(=O)CN1CCN(C(=O)OC(C)(C)C)CC1)OCO2] | 392 | 0.7 | (DMSO-d₆) δ 1.10 (t, J = 7.5 Hz, 3H), 1.40 (s, 9H), 2.46 (m, 6H), 3.12 (s, 2H), 3.38 (t, J = 5.0 Hz, 4H), 5.97 (s, 2H), 6.82 (s, 1H), 7.20 (s, 1H), 9.26 (s, 1H). |
| 449 | 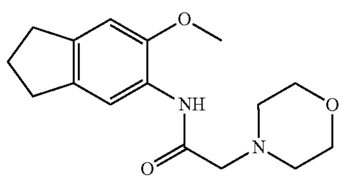 [SMILES: COc1cc2c(cc1NC(=O)CN1CCOCC1)CCC2] | 291 | 0.804 | ¹H NMR (400 MHz, DMSO-d₆) δ 1.99 (p, J = 7.4 Hz, 2H), 2.51-2.55 (m 4H), 2.80 (dt, J = 15.0, 7.4 Hz, 4H), 3.10 (d, J = 1.0 Hz, 2H), 3.65 (t, J = 4.6 Hz, 4H), 3.84 (s, 3H), 6.94 (s, 1H), 8.05 (s, 1H), 9.62 (s, 1H). |

Compounds with hT2R54 IC50 of 1p M or lower are considered especially potent.

Example 18—Synthesis of 1-(2-((6-Acetylbenzo[d][1,3]dioxol-5-yl)amino)-2-oxoethyl)-N-methylpiperidine-3-carboxamide (154)

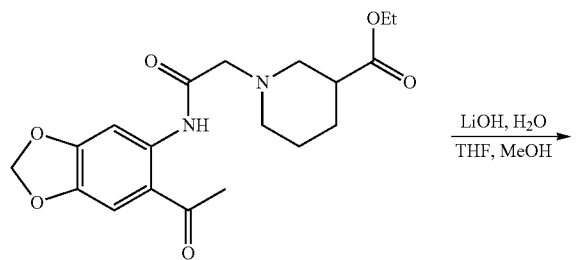

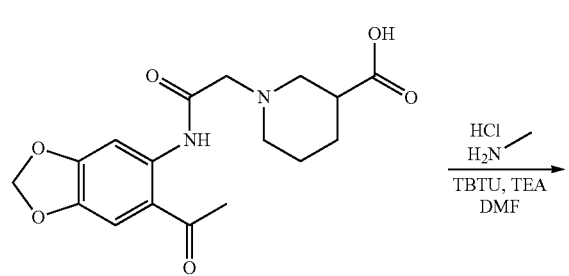

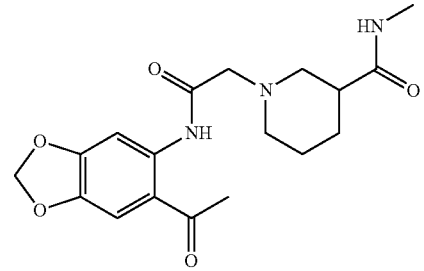

To a solution of 1-(2-(((6-acetylbenzo[d][1,3]dioxol-5-yl)amino)-2-oxoethyl)piperidine-3-carboxylic acid (Example 18a) (0.2 g, 0.6 mmol) in DMF (5 mL) was added O-(Benzotriazol-1-yl)-N,N,N',N'-tetramethyluronium tetrafluoroborate (TBTU) (0.2 g, 0.7 mmol), TEA (0.3 mL, 1.8 mmol), and methylamine HCl (0.1 g, 0.6 mmol). The mixture was stirred at room temperature overnight and purified by reverse phase HPLC using ACN/water gradient to give the title compound (96 mg, 44% yield) as a white solid. MS 362 (M+H⁺).

Example 18a. 1-(2-((6-Acetylbenzo[d][1,3]dioxol-5-yl)amino)-2-oxoethyl)piperidine-3-carboxylic Acid

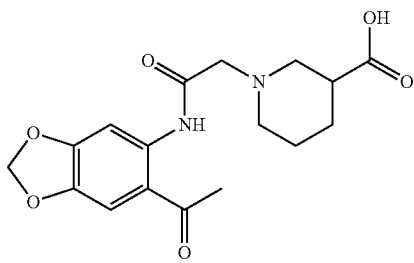 [SMILES: CC(=O)c1cc2c(cc1NC(=O)CN1CCCC(C(=O)O)C1)OCO2]

To a solution of ethyl 1-(2-((6-acetylbenzo[d][1,3]dioxol-5-yl)amino)-2-oxoethyl)piperidine-3-carboxylate (4.5 g, 12 mmol) in THF/MeOH (40/40 mL) was added LiOH (0.9 g, 42 mmol) in water (40 mL) and stirred at room temperature overnight. The solution was concentrated and used without further purification. MS 349 (M+H$^+$).

Compounds in Table 5 were prepared in a similar manner as in Example 18 from the corresponding ester starting material described herein and commercially available amine nucleophiles.

TABLE 5

| SID | Structure | Obs Mol Ion; MS (M + H$^+$) | hT2R54 IC50 (uM) | $^1$H NMR (400 MHz) |
|---|---|---|---|---|
| 154 | 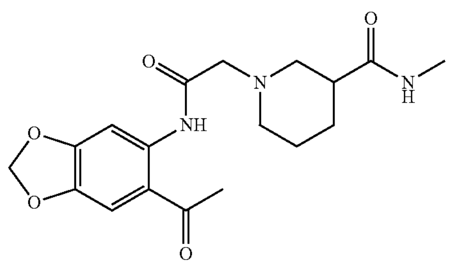 [SMILES: CNC(=O)C1CCCN(CC(=O)Nc2cc3c(cc2C(C)=O)OCO3)C1] | 362 | 0.024 | (DMSO-d$_6$) δ 1.31 (qd, J = 13.0, 4.5 Hz, 1H), 1.57-1.66 (m, 1H), 1.69-1.84 (m, 2H), 2.01-2.10 (m, 1H), 2.21 (t, J = 11.0 Hz, 1H), 2.53 (d, J = 4.6 Hz, 3H), 2.57 (s, 3H), 2.75 (br d, J = 10.8 Hz, 1H), 2.83 (br dd, J = 11.2, 4.0 Hz, 1H), 3.06 (d, J = 16.8 Hz, 1H), 3.15 (d, J = 16.8 Hz, 1H), 6.13 (s, 2H), 7.61 (s, 1H), 7.77 (d, J = 4.8 Hz, 1H), 8.34 (s, 1H), 12.57 (s, 1H). |
| 155 | 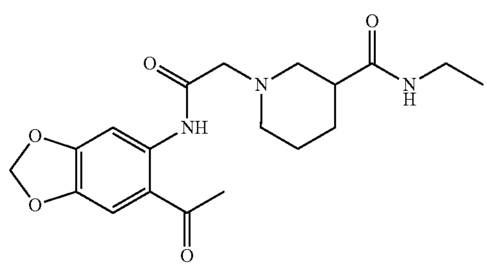 [SMILES: CCNC(=O)C1CCCN(CC(=O)Nc2cc3c(cc2C(C)=O)OCO3)C1] | 376 | 0.210 | (DMSO-d$_6$) δ 0.97 (t, J = 7.2 Hz, 3H), 1.24-1.39 (m, 1H), 1.54-1.65 (m, 1H), 1.70-1.86 (m, 2H), 1.99-2.11 (m, 1H), 2.22 (t, J = 11.0 Hz, 1H), 2.52-2.60 (m, 4H), 2.75 (br d, J = 10.8 Hz, 1H), 2.83 (br dd, J = 13.6, 3.6 Hz, 1H), 2.97-3.08 (m, 3H), 3.17 (d, J = 16.7 Hz, 1H), 6.13 (s, 2H), 7.61 (s, 1H), 7.83 (t, J = 5.5 Hz, 1H), 8.33 (s, 1H), 12.56 (s, 1H). |
| 156 | 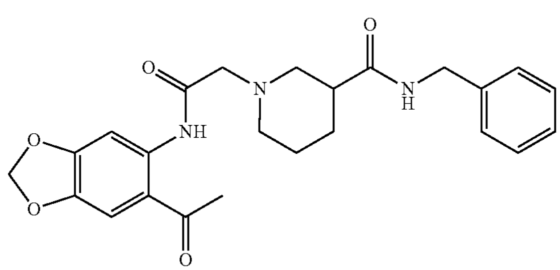 [SMILES: CC(=O)c1cc2c(cc1NC(=O)CN1CCCC(C(=O)NCc3ccccc3)C1)OCO2] | 438 | 0.114 | (DMSO-d$_6$) δ 1.36 (qd, J = 12.5, 3.9 Hz, 1H), 1.56-1.70 (m, 1H), 1.70-1.97 (m, 2H), 2.02-2.13 (m, 1H), 2.27 (t, J = 11.0 Hz, 1H), 2.56 (s, 3H), 2.68 (tt, J = 11.5, 3.7 Hz, 1H), 2.77 (br d, J = 11.2 Hz, 1H), 2.89 (br dd, J = 11.6, 3.6 Hz, 1H), 3.06 (d, J = 16.8 Hz, 1H), 3.19 (d, J = 16.8 Hz, 1H), 4.24 (d, J = 6.0 Hz, 2H), 6.13 (s, 2H), 7.16-7.26 (m, 3H), 7.25-7.35 (m, 2H), 7.61 (s, 1H), 8.33 (s, 1H), 8.41 (t, J = 6.0 Hz, 1H), 12.57 (s, 1H). |

TABLE 5-continued

| SID | Structure | Obs Mol Ion; MS (M + H⁺) | hT2R54 IC50 (uM) | ¹H NMR (400 MHz) |
|---|---|---|---|---|
| 157 | 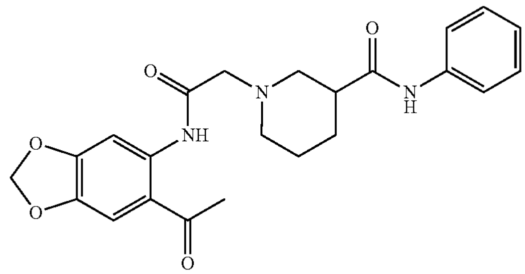 [SMILES: CC(=O)c1cc2c(cc1NC(=O)CN1CCCC(C(=O)Nc3ccccc3)C1)OCO2] | 424 | 0.565 | (DMSO-d$_6$) δ 1.41 (qd, J = 12.5, 3.9 Hz, 1H), 1.62-1.70 (m, 1H), 1.79-2.01 (m, 2H), 2.08 (dd, J = 11.9, 9.2 Hz, 1H), 2.35 (t, J = 11.0 Hz, 1H), 2.59 (s, 3H), 2.76-2.87 (m, 2H), 2.96 (br d, J = 11.0 Hz, 1H), 3.05 (d, J = 16.8 Hz, 1H), 3.26 (d, J = 16.8 Hz, 1H), 6.14 (d, J = 1.0 Hz, 2H), 6.95-7.08 (m, 1H), 7.23-7.29 (m, 2H), 7.55-7.65 (m, 3H), 8.34 (s, 1H), 9.99 (s, 1H), 12.58 (s, 1H). |
| 158 | 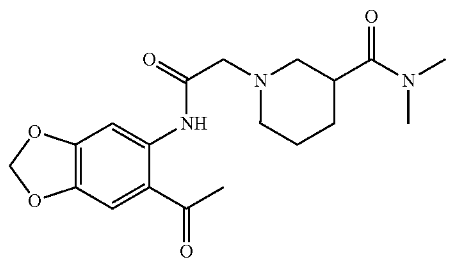 [SMILES: CC(=O)c1cc2c(cc1NC(=O)CN1CCCC(C(=O)N(C)C)C1)OCO2] | 376 | 0.107 | (DMSO-d$_6$) δ 1.25-1.40 (m, 1H), 1.61-1.70 (m, 1H), 1.71-1.85 (m, 2H), 2.15 (t, J = 11.1 Hz, 2H), 2.57 (s, 3H), 2.72-2.86 (m, 5H), 2.98 (s, 3H), 3.04 (d, J = 16.8 Hz, 1H), 3.09-3.19 (m, 1H), 3.20 (d, J = 16.8 Hz, 1H), 6.14 (s, 2H), 7.61 (s, 1H), 8.33 (s, 1H), 12.61 (s, 1H). |
| 159 | 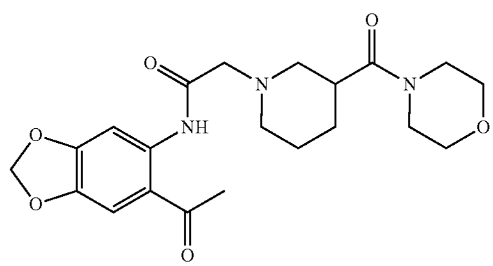 [SMILES: CC(=O)c1cc2c(cc1NC(=O)CN1CCCC(C(=O)N3CCOCC3)C1)OCO2] | 418 | 0.497 | (DMSO-d$_6$) δ 1.27-1.46 (m, 1H), 1.61-1.84 (m, 3H), 2.11-2.25 (m, 2H), 2.58 (s, 3H), 2.72-2.79 (m, 1H), 2.84 (d, 11.1 Hz, 1H), 3.05 (d, J = 16.8 Hz, 1H), 3.07-3.16 (m, 1H), 3.21 (d, J = 16.8 Hz, 1H), 3.36-3.56 (m, 8H), 6.14 (br s, 2H), 7.61 (s, 1H), 8.33 (s, 1H), 12.58 (s, 1H). |
| 160 | 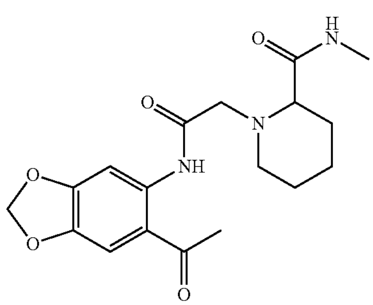 [SMILES: CNC(=O)C1CCCCN1CC(=O)Nc1cc2c(cc1C(C)=O)OCO2] | 362 | 1.27 | (DMSO-d$_6$, rotamers) δ 1.31-1.45 (m, 2H), 1.48-1.85 (m, 5H), 2.24-2.39 (m, 1H), 2.55-2.74 (m, 5H), 2.79-2.90 (m, 1H), 2.92-3.09 (m, 2H), 3.10-3.25 (m, 2H), 6.13-6.16 (m, 2H), 7.57-6.66 (three s, 1H), 7.71-7.80 (m, 1H), 8.13-8.65 (three s, 1H), 12.20-12.60 (three s, 1H). |
| 161 | 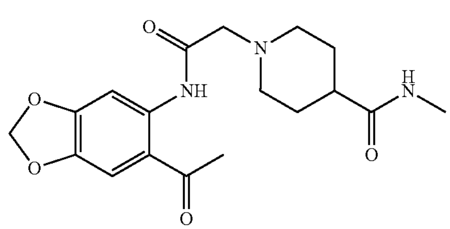 [SMILES: CNC(=O)C1CCN(CC(=O)Nc2cc3c(cc2C(C)=O)OCO3)CC1] | 362 | 1.35 | (DMSO-d$_6$) δ 1.66 (br d, J = 12.7 Hz, 2H), 1.83 (qd, J = 12.0, 3.7 Hz, 2H), 2.01-2.16 (m, 3H), 2.56 (s, 1.5H), 2.57 (s, 4.5H), 2.84 (br d, J = 11.4 Hz, 2H), 3.08 (s, 2H), 6.13 (s, 2H), 7.61 (s, 1H), 7.69 (m, 1H), 8.32 (s, 1H), 12.52 (s, 1H). |

TABLE 5-continued

| SID | Structure | Obs Mol Ion; MS (M + H+) | hT2R54 IC50 (uM) | ¹H NMR (400 MHz) |
|---|---|---|---|---|
| 162 | 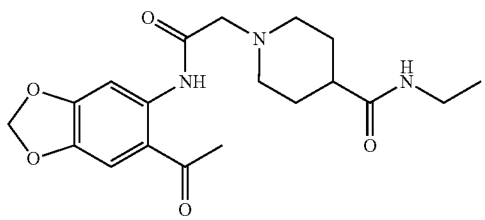 [SMILES: CCNC(=O)C1CCN(CC(=O)Nc2cc3c(cc2C(C)=O)OCO3)CC1] | 376 | 0.747 | (DMSO-d₆) δ 1.00 (t, J = 7.2 Hz, 3H), 1.65 (br d, J = 12.7 Hz, 2H), 1.83 (qd, J = 12.1, 3.6 Hz, 2H), 1.99-2.17 (m, 3H), 2.57 (s, 3H), 2.84 (dt, J = 11.2, 3.6 Hz, 2H), 3.00-3.12 (m, 4H), 6.13 (s, 2H), 7.61 (s, 1H), 7.74 (t, J = 5.6 Hz, 1H), 8.32 (s, 1H), 12.51 (s, 1H). |
| 163 | 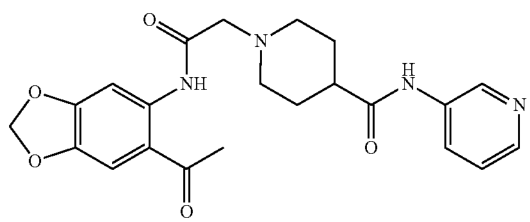 [SMILES: CC(=O)c1cc2c(cc1NC(=O)CN1CCC(C(=O)Nc3cccnc3)CC1)OCO2] | 425 | 0.459 | (DMSO-d₆) δ 1.76-2.03 (m, 3H), 2.14-2.26 (m, 2H), 2.30-2.42 (m, 2H), 2.44-2.57 (m, 2H), 2.58 (2, 3H), 2.65-2.68 (m, 05H), 2.87-2.95 (m, 2.5H), 3.13 (s, 2H), 6.14 (s, 2H), 7.29-7.37 (m, 1H), 7.62 (s, 1H), 8.04-8.08 (m, 1H), 8.24 (dd, J = 4.7, 1.5 Hz, 1H), 8.33 (s, 1H), 8.73-8.78 (m, 1H), 10.11 (s, 1H), 12.56 (s, 1H). |
| 164 | 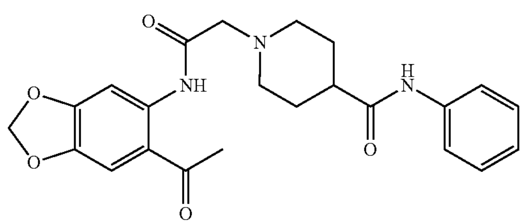 [SMILES: CC(=O)c1cc2c(cc1NC(=O)CN1CCC(C(=O)Nc3ccccc3)CC1)OCO2] | 424 | 2.09 | (DMSO-d₆) δ 1.78 (br d, J = 12.7 Hz, 2H), 1.94 (qd, J = 12.2, 3.6 Hz, 2H), 2.14-2.23 (m, 2H), 2.29-2.39 (m, 1H), 2.58 (s, 3H), 2.91 (br d, J = 11.4 Hz, 2H), 3.12 (s, 2H), 6.14 (s, 2H), 6.96-7.09 (m, 1H), 7.22-7.37 (m, 2H), 7.55-7.68 (m, 3H), 8.33 (s, 1H), 9.88 (s, 1H), 12.55 (s, 1H). |
| 165 | 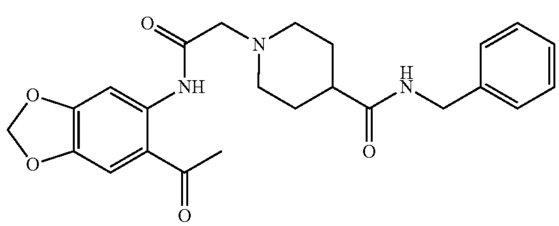 [SMILES: CC(=O)c1cc2c(cc1NC(=O)CN1CCC(C(=O)NCc3ccccc3)CC1)OCO2] | 438 | 1.40 | (DMSO-d₆) δ 1.71 (br d, J = 12.6 Hz, 2H), 1.88 (qd, J = 12.1, 11.6, 3.7 Hz, 2H), 2.07-2.26 (m, 3H), 2.57 (m, 3H), 2.86 (dt, J = 11.3, 3.2 Hz, 2H), 3.10 (s, 2H), 4.27 (d, J = 5.9 Hz, 2H), 6.13 (s, 2H), 7.18-7.26 (m, 3H), 7.28-7.35 (m, 2H), 7.61 (s, 1H), 8.23-8.38 (m, 2H), 12.54 (s, 1H). |
| 450 | 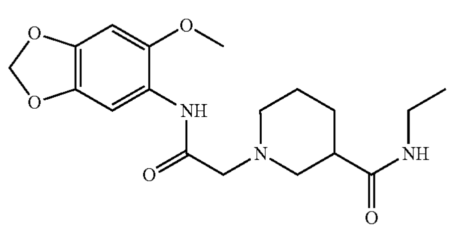 [SMILES: CCNC(=O)C1CCCN(CC(=O)Nc2cc3c(cc2OC)OCO3)C1] | 364 | 0.668 | (DMSO-d₆) δ 0.98 (t, J = 7.2 Hz, 3H), 1.30-1.43 (m, 1H), 1.43-1.58 (m, 1H), 1.64-1.79 (m, 2H), 2.07-2.17 (m, 1H), 2.25-2.35 (m, 1H), 2.34-2.42 (m, 1H), 2.73 (d, J = 11.3 Hz, 1H), 2.82 (d, J = 10.6 Hz, 1H), 2.97-3.08 (m, 3H), 3.13 (d, J = 16.5 Hz, 1H), 3.82 (s, 3H), 5.95 (s, 2H), 6.91 (s, 1H), 7.79 (s, 1H), 7.85 (t, J = 5.5 Hz, 1H), 9.53 (s, 1H). |
| 451 | 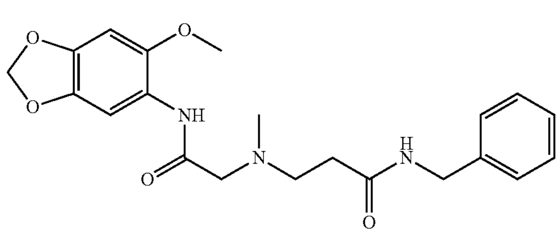 [SMILES: COc1cc2c(cc1NC(=O)CN(C)CCC(=O)NCc1ccccc1)OCO2] | 400 | 0.406 | (DMSO-d₆) δ 2.29 (s, 3H), 2.38 (t, J = 7.2 Hz, 2H), 2.73 (t, J = 7.1 Hz, 2H), 3.11 (s, 2H), 3.76 (s, 3H), 4.25 (d, J = 5.8 Hz, 2H), 5.95 (s, 2H), 6.89 (s, 1H), 7.22 (d, J = 7.4 Hz, 3H), 7.25-7.32 (m, 2H), 7.76 (s, 1H), 8.41 (t, J = 5.8 Hz, 1H), 9.35 (s, 1H). |

TABLE 5-continued

| SID | Structure | Obs Mol Ion; MS (M + H⁺) | hT2R54 IC50 (uM) | ¹H NMR (400 MHz) |
|---|---|---|---|---|
| 452 | 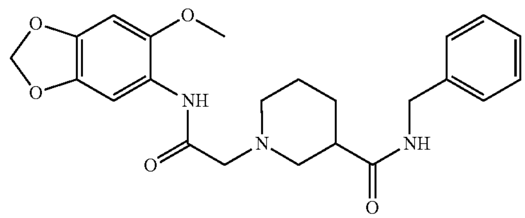 [SMILES: COc1cc2c(cc1NC(=O)CN1CCCC(C(=O)NCc3ccccc3)C1)OCO2] | 426 | 0.603 | (DMSO-d₆) δ 1.34-1.63 (m, 3H), 1.67-1.76 (m, 1H), 1.78-1.86 (m, 1H), 2.10-2.19 (m, 1H), 2.36 (t, J = 10.8 Hz, 1H), 2.70-2.78 (m, 1H), 2.84-2.92 (m, 1H), 3.03 (d, J = 16.6 Hz, 1H), 3.15 (d, J = 16.5 Hz, 1H), 3.81 (s, 3H), 4.20-4.30 (m, 2H), 5.95 (s, 2H), 6.90 (s, 1H), 7.16-7.25 (m, 3H), 7.27-7.32 (m, 2H), 7.79 (s, 1H), 8.42 (t, J = 6.0 Hz, 1H), 9.55 (s, 1H). |
| 453 | 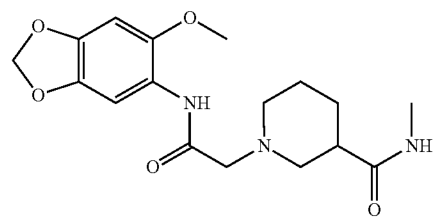 [SMILES: CNC(=O)C1CCCN(CC(=O)Nc2cc3c(cc2OC)OCO3)C1] | 350 | 0.969 | (DMSO-d₆) δ 1.30-1.43 (m, 1H), 1.44-1.59 (m, 1H), 1.64-1.80 (m, 2H), 2.06-2.18 (m, 1H), 2.23-2.44 (m, 2H), 2.54 (d, J = 4.5 Hz, 3H), 2.73 (d, J = 11.5 Hz, 1H), 2.82 (d, J = 10.7 Hz, 1H), 3.02 (d, J = 16.3 Hz, 1H), 3.12 (d, J = 16.5 Hz, 1H), 3.82 (s, 3H), 5.95 (s, 2H), 6.91 (s, 1H), 7.77-7.83 (m, 2H), 9.53 (s, 1H). |

Compounds with hT2R54 IC50 of 1 μM or lower are considered especially potent.

Example 19—Synthesis of 2-(4-Acetamidopiperidin-1-yl)-N-(6-acetylbenzo[d][1,3]dioxol-5-yl)acetamide (166)

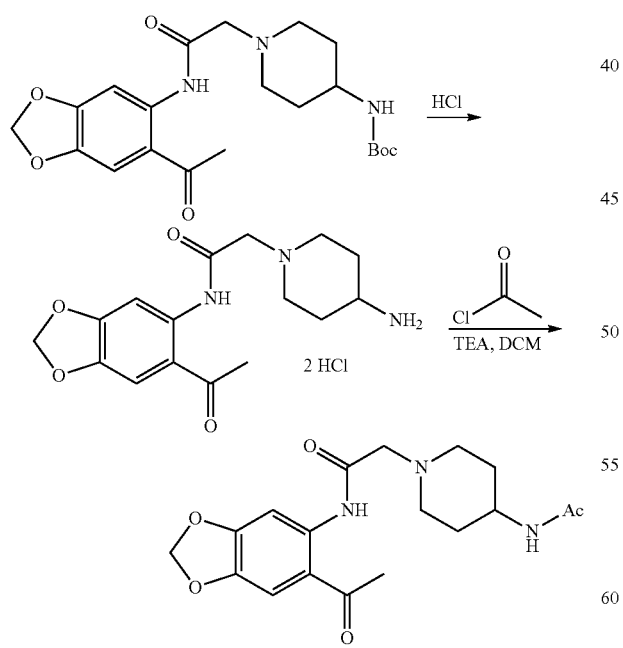

To a solution of N-(6-acetylbenzo[d][1,3]dioxol-5-yl)-2-(4-aminopiperidin-1-yl)acetamide dihydrochloride (Example 19a) (0.2 g, 0.5 mmol) in DCM (5 mL) was added acetyl chloride (0.04 g, 5 mmol) and TEA (0.3 mL, 2 mmol). The mixture was stirred overnight at room temperature and purified by reverse phase HPLC using ACN/water gradient to give the desired product (91 mg, 50% yield) as a white solid. MS 362 (M+H⁺).

Example 19a. N-(6-Acetylbenzo[d][1,3]dioxol-5-yl)-2-(4-aminopiperidin-1-yl)acetamide dihydrochloride To a solution of tert-butyl (1-(2-(((6-acetylbenzo[d][1,3]dioxol-5-yl)amino)-2-oxoethyl)piperidin-4-yl)carbamate (Example 19b) (3.3 g, 8 mmol) in anhydrous DCM (10 mL) was added 4M HCl in dioxane (10 mL). The reaction was allowed stir at room temperature overnight. The reaction was filtered, the solid washed successively with DCM and ether, and dried under vacuum to give the title compound (3.1 g, quantitative yield) as a light brown solid. ¹H NMR (400 MHz, DMSO-d₆) δ 1.85-2.21 (m, 5H), 2.58 (s, 3H), 3.19 (s, 3H), 4.25 (s, 2H), 6.17 (s, 2H), 7.61 (s, 1H), 7.81 (s, 1H), 8.45 (s, 3H), 10.43 (s, 1H), 11.77 (s, 1H).

Example 19b. tert-Butyl (1-(2-((6-Acetylbenzo[d][1,3]dioxol-5-yl)amino)-2-oxoethyl)piperidin-4-yl)carbamate

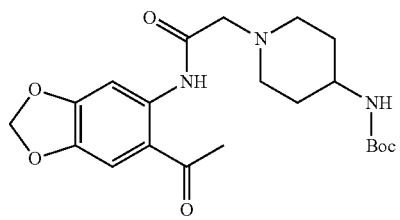 [SMILES: CC(=O)c1cc2c(cc1NC(=O)CN1CCC(NC(=O)OC(C)(C)C)CC1)OCO2]

Prepared in a similar manner as in Example 9 from N-(6-acetylbenzo[d][1,3]dioxol-5-yl)-2-chloroacetamide (Example 14a) (2.5 g, 10 mmol) and tert-butyl piperidin-4-ylcarbamate (2 g, 10 mmol) to give the desired product (3.3 g, 79 (yield) as a light brown solid.

Compounds in Table 6 were prepared in a similar manner as in Example 2, Example 18, and/or Example 19 from N-(6-acetylbenzo[d][1,3]dioxol-5-yl)-2-(4-aminopiperidin-1-yl)acetamide dihydrochloride (Example 19a) and the corresponding commercially available carboxylic acids and/or acyl chlorides.

TABLE 6

| SID | Structure | Obs Mol ion MS; (M + H⁺) | hT2R54 IC50 (uM) | ¹H NMR (400 MHz) |
|---|---|---|---|---|
| 166 | 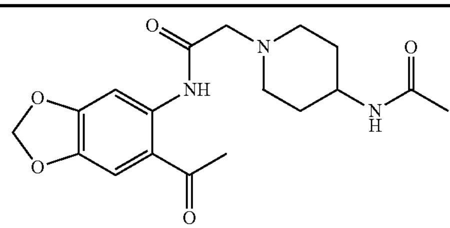 | 362 | 0.264 | (DMSO-d$_6$) δ 1.56-1.79 (m, 4H), 1.80 (s, 3H), 2.15-2.29 (m, 2H), 2.57 (s, 3H), 2.78 (d, J = 11.7 Hz, 2H), 3.10 (s, 2H), 3.53 (td, J = 11.3, 6.6 Hz, 1H), 6.13 (s, 2H), 7.61 (s, 1H), 7.89 (d, J = 7.4 Hz, 1H), 8.33 (s, 1H), 12.55 (s, 1H). |
| 167 | 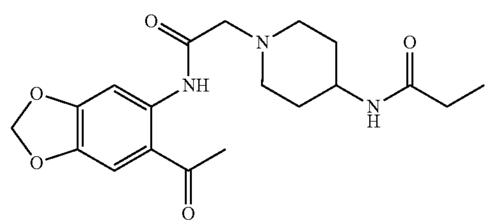 [SMILES: CCC(=O)NC1CCN(CC(=O)Nc2cc3c(cc2C(C)=O)OCO3)CC1] | 376 | 0.31 | (DMSO-d$_6$) δ 0.98 (t, J = 7.6 Hz, 3H), 1.56-1.80 (m, 4H), 2.07 (q, J = 7.6 Hz, 2H), 2.17-2.26 (m, 2H), 2.57 (s, 3H), 2.75-2.82 (m, 2H), 3.10 (s, 2H), 3.44-3.60 (m, 1H), 6.13 (s, 2H), 7.61 (s, 1H), 7.80 (d, J = 7.2 Hz, 1H), 8.33 (s, 1H), 12.54 (s, 1H). |
| 168 | 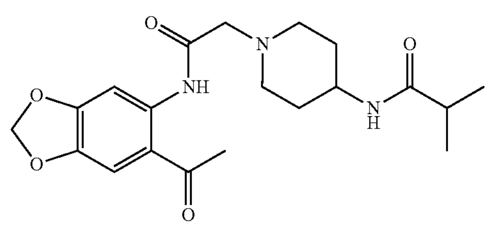 [SMILES: CC(=O)c1cc2c(cc1NC(=O)CN1CCC(NC(=O)C(C)C)CC1)OCO2] | 390 | 0.14 | (DMSO-d$_6$) δ 0.98 (d, J = 6.8 Hz, 6H), 1.58-1.80 (m, 4H), 2.14-2.27 (m, 2H), 2.33-2.43 (m, 1H), 2.58 (s, 3H), 2.79 (br dt, J = 11.1, 4.0 Hz, 2H), 3.10 (s, 2H), 3.45-3.59 (m, 1H), 6.13 (s, 2H), 7.61 (s, 1H), 7.75 (d, J = 7.4 Hz, 1H), 8.32 (s, 1H), 12.54 (s, 1H). |
| 169 | 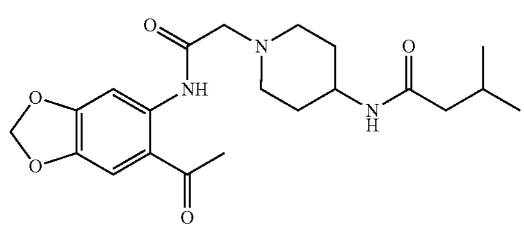 [SMILES: CC(=O)c1cc2c(cc1NC(=O)CN1CCC(NC(=O)CC(C)C)CC1)OCO2] | 404 | 0.14 | (DMSO-d$_6$) δ 0.82-0.90 (m, 6H), 1.56-1.81 (m, 4H), 1.91-2.01 (m, 3H), 2.17-2.26 (m, 2H), 2.57 (s, 3H), 2.79 (br d, J = 11.4 Hz, 2H), 3.10 (s, 2H), 3.50-3.61 (m, 1H), 6.13 (s, 2H), 7.61 (s, 1H), 7.82 (d, J = 7.5 Hz, 1H), 8.32 (s, 1H), 12.54 (s, 1H). |
| 170 | 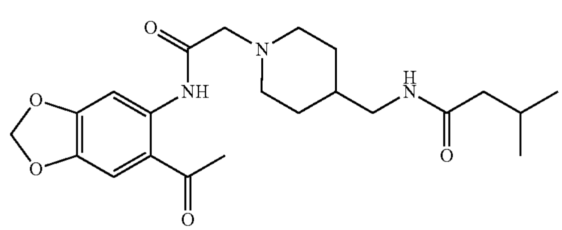 [SMILES: CC(=O)c1cc2c(cc1NC(=O)CN1CCC(CNC(=O)CC(C)C)CC1)OCO2] | 418 | 0.188 | (DMSO-d$_6$) δ 0.83-0.94 (d, J = 5.6 Hz, 6H), 1.11-1.44 (m, 3H), 1.55-1.66 ( (m, 2H), 1.90-2.02 (m, 2H), 2.04-2.15 (m, 2H), 2.36-2.54 (m, 1H), 2.57 (s, 3H), 2.81 (br d, J = 10.5 Hz, 2H), 2.96 (br t, J = 5.4 Hz, 2H), 3.08 (s, 2H), 6.13 (s, 2H), 7.61 (s, 1H), 7.81 (t, J = 5.6 Hz, 1H), 8.33 (s, 1H), 12.56 (s, 1H). |

TABLE 6-continued

| SID | Structure | Obs Mol ion MS; (M + H+) | hT2R54 IC50 (uM) | ¹H NMR (400 MHz) |
|---|---|---|---|---|
| 171 | 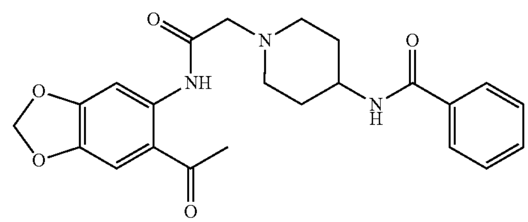 [SMILES: CC(=O)c1cc2c(cc1NC(=O)CN1CCC(NC(=O)c3ccccc3)CC1)OCO2] | 424 | 0.06 | (DMSO-d₆) δ 1.77-1.96 (m, 4H), 2.26 (td, J = 11.2, 10.8, 4.2 Hz, 2H), 2.58 (s, 3H), 2.87 (br d, J = 11.6 Hz, 2H), 3.14 (s, 2H), 3.74-3.84 (m, 1H), 6.14 (s, 2H), 7.40-7.48 (m, 2H), 7.48-7.55 (m, 1H), 7.62 (s, 1H), 7.84-7.91 (m, 2H), 8.33 (s, 1H), 8.42 (d, J = 7.4 Hz, 1H), 12.54 (s, 1H). |
| 172 | 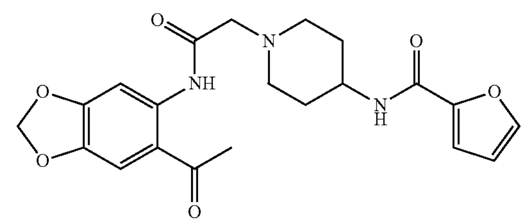 [SMILES: CC(=O)c1cc2c(cc1NC(=O)CN1CCC(NC(=O)c3ccco3)CC1)OCO2] | 414 | 0.69 | (DMSO-d₆) δ 1.74-1.91 (m, 4H), 2.24 (td, J = 11.5, 3.0 Hz, 2H), 2.58 (s, 3H), 2.85 (br d, J = 11.6 Hz, 2H), 3.13 (s, 2H), 3.66-3.81 (m, 1H), 6.14 (s, 2H), 6.60 (dd, J = 3.4, 1.7 Hz, 1H), 7.16 (dd, J = 3.5, 0.8 Hz, 1H), 7.62 (s, 1H), 7.81 (dd, J = 1.8, 0.8 Hz, 1H), 8.30 (d, J = 8.0 Hz, 1H), 8.32 (s, 1H), 12.52 (s, 1H). |
| 173 | 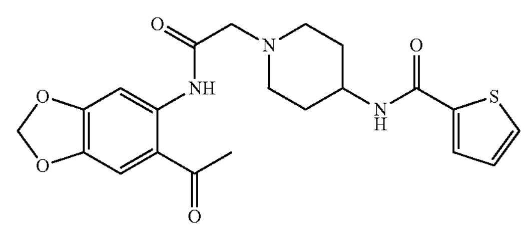 | 430 | 0.11 | (DMSO-d₆) δ 1.78-1.90 (m, 4H), 2.24 (td, J = 11.1, 4.9 Hz, 2H), 2.59 (s, 3H), 2.87 (br d, J = 11.3 Hz, 2H), 3.13 (s, 2H), 3.68-3.81 (m, 1H), 6.14 (s, 2H), 7.14 (dd, J = 5.0, 3.7 Hz, 1H), 7.62 (s, 1H), 7.73 (dd, J = 5.0, 1.1 Hz, 1H), 7.88 (dd, J = 3.8, 1.1 Hz, 1H), 8.33 (s, 1H), 8.43 (d, J = 7.4 Hz, 1H), 12.54 (s, 1H). |
| 174 | 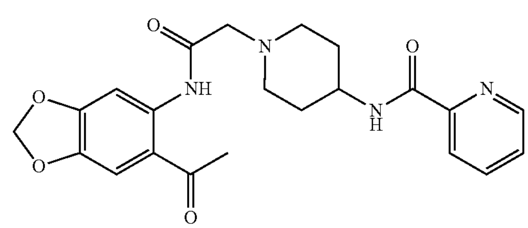 [SMILES: CC(=O)c1cc2c(cc1NC(=O)CN1CCC(NC(=O)c3ccccn3)CC1)OCO2] | 425 | 0.27 | (DMSO-d₆) δ 1.83-1.94 (m, 4H), 2.27-2.38 (m, 2H), 2.59 (s, 3H), 2.84 (br d, J = 11.5 Hz, 2H), 3.15 (s, 2H), 3.77-3.88 (m, 1H), 6.14 (s, 2H), 7.57-7.66 (m, 2H), 7.96-8.07 (m, 2H), 8.33 (s, 1H), 8.48 (d, J = 7.9 Hz, 1H), 8.66 (ddd, J = 4.8, 1.7, 1.0 Hz, 1H), 12.56 (s, 1H). |
| 175 | 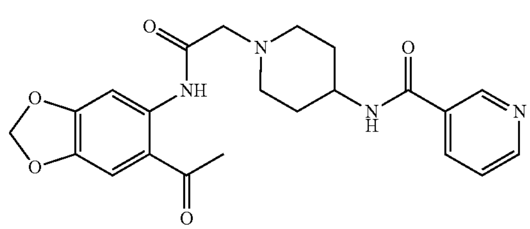 [SMILES: CC(=O)c1cc2c(cc1NC(=O)CN1CCC(NC(=O)c3cccnc3)CC1)OCO2] | 425 | 0.11 | (DMSO-d₆) δ 1.81-1.91 (m, 4H), 2.21-2.34 (m, 2H), 2.58 (s, 3H), 2.88 (br d, J = 11.5 Hz, 2H), 3.14 (s, 2H), 3.76-3.86 (m, 1H), 6.14 (s, 2H), 7.49 (ddd, J = 7.9, 4.8, 0.9 Hz, 1H), 7.62 (s, 1H), 8.21 (dt, J = 8.0, 2.0 Hz, 1H), 8.33 (s, 1H), 8.63 (d, J = 7.3 Hz, 1H), 8.69 (dd, J = 4.8, 1.6 Hz, 1H), 9.02 (dd, J = 2.3, 0.8 Hz, 1H), 12.55 (s, 1H). |
| 176 | 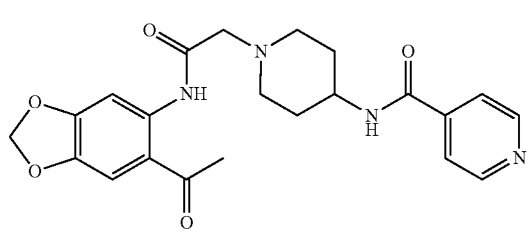 [SMILES: CC(=O)c1cc2c(cc1NC(=O)CN1CCC(NC(=O)c3ccncc3)CC1)OCO2] | 425 | 0.45 | (DMSO-d₆) δ 1.78-1.91 (m, 4H), 2.26 (td, J = 11.3, 10.9, 4.6 Hz, 3H), 2.58 (s, 3H), 2.88 (br d, J = 11.6 Hz, 2H), 3.14 (s, 2H), 3.71-3.87 (m, 1H), 6.14 (s, 2H), 7.62 (s, 1H), 7.73-7.82 (m, 2H), 8.33 (s, 1H), 8.66-8.75 (m, 3H), 12.54 (s, 1H). |

TABLE 6-continued

| SID | Structure | Obs Mol ion MS; (M + H⁺) | hT2R54 IC50 (uM) | ¹H NMR (400 MHz) |
|---|---|---|---|---|
| 177 | 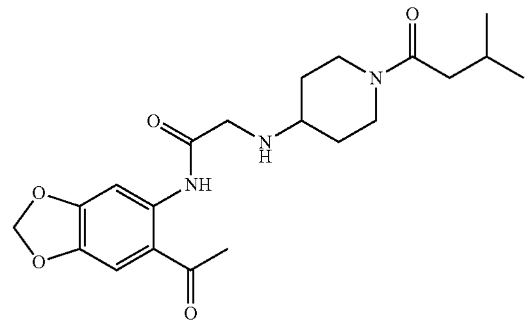 [SMILES: CC(=O)c1cc2c(cc1NC(=O)CNC1CCN(C(=O)CC(C)C)CC1)OCO2] | 404 | 0.20 | (DMSO-d$_6$) δ 0.88 (d, J = 6.6 Hz, 6H), 1.09-1.32 (m, 2H), 1.79-2.03 (m, 3H), 2.09-2.22 (m, 2H), 2.54 (s, 3H), 2.57-2.75 (m, 3H), 2.95-3.08 (m, 1H), 3.26-3.31 (m, 2H), 3.83 (br d, J = 13.7 Hz, 1H), 4.22 (br d, J = 13.2 Hz, 1H), 6.13 (s, 2H), 7.59 (s, 1H), 8.36 (s, 1H), 12.66 (s, 1H). |
| 178 | 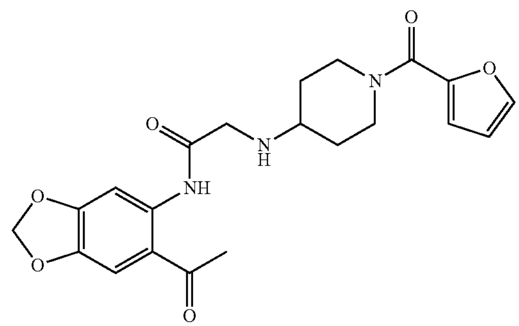 [SMILES: CC(=O)c1cc2c(cc1NC(=O)CNC1CCN(C(=O)c3ccco3)CC1)OCO2] | 414 | 0.06 | (DMSO-d$_6$) δ 1.18 (t, J = 7.3 Hz, 1H), 1.22-1.43 (m, 2H), 1.95 (br d, J = 12.8 Hz, 2H), 2.55 (s, 3H), 2.63-2.80 (m, 2H), 2.97-3.29 (m, 4H), 3.29-3.40 (m, 1H), 4.20 (br d, J = 13.2 Hz, 2H), 6.13 (s, 2H), 6.61 (dd, J = 3.4, 1.8 Hz, 1H), 6.94 (dd, J = 3.5, 0.8 Hz, 1H), 7.59 (s, 1H), 7.82 (dd, J = 1.8, 0.8 Hz, 1H), 8.34 (s, 1H), 12.63 (s, 1H). |
| 179 | 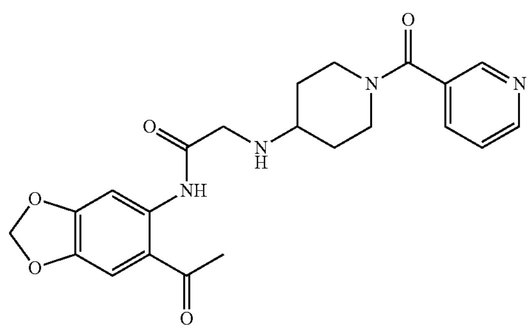 [SMILES: CC(=O)c1cc2c(cc1NC(=O)CNC1CCN(C(=O)c3cccnc3)CC1)OCO2] | 425 | 0.09 | (DMSO-d$_6$) δ 1.20-1.43 (m, 3H), 1.77-2.04 (m, 2H), 2.56 (s, 3H), 2.64-2.74 (m, 2H), 2.88-3.21 (m, 3H), 3.32 (s, 2H), 3.48-3.60 (m, 1H), 4.22-4.38 (m, 1H), 6.13 (s, 2H), 7.47 (ddd, J = 7.8, 4.9, 0.9 Hz, 1H), 7.59 (s, 1H), 7.79 (dt, J = 7.8, 1.9 Hz, 1H), 8.35 (s, 1H), 8.57 (dd, J = 2.3, 0.9 Hz, 1H), 8.64 (dd, J = 4.9, 1.7 Hz, 1H), 12.65 (s, 1H). |
| 180 | 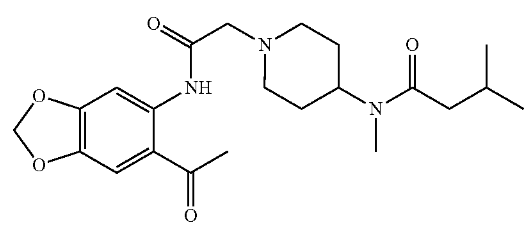 [SMILES: CC(=O)c1cc2c(cc1NC(=O)CN1CCC(N(C)C(=O)CC(C)C)CC1)OCO2] | 418 | 0.589 | (DMSO-d$_6$) δ 0.90 (d, J = 6.6 Hz, 6H), 1.36-1.45 (br d, 1.2H), 1.49-1.57 (br d, 0.8H), 1.89-2.45 (m, 8H), 2.58 (s, 3H), 2.74-2.94 (m, 6H), 3.13 (two s, 2H), 3.60-3.75 (m, 0.35H), 4.30-4.43 (m, 0.65H), 6.13 (s, 2H), 7.61 (s, 1H), 8.35 (s, 1H), 12.66-12.72 (two s, 1H). |
| 181 | 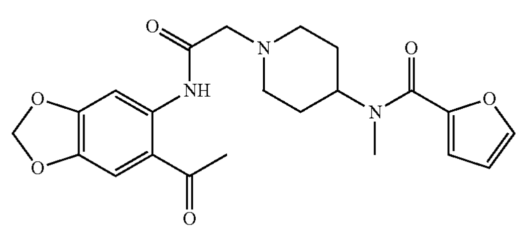 [SMILES: CC(=O)c1cc2c(cc1NC(=O)CN1CCC(N(C)C(=O)c3ccco3)CC1)OCO2] | 428 | 0.676 | (DMSO-d$_6$) δ 1.56-1.68 (m, 2H), 2.07-2.22 (m, 2H), 2.32 (br t, J = 12.2 Hz, 2H), 2.59 (s, 3H), 2.89 (br d, J = 10.8 Hz, 2H), 3.06 (br s, 2H), 3.14 (s, 3H), 3.84-4.55 (m, 2H), 6.14 (s, 2H), 6.62 dd, J = 3.2, 1.6 Hz, 1H), 6.99 (br-s, 1H), 7.62 (s, 1H), 7.84 (dd, J = 1.6, 0.8 Hz, 1H), 8.35 (s, 1H), 12.72 (s, 1H). |

TABLE 6-continued

| SID | Structure | Obs Mol ion MS; (M + H+) | hT2R54 IC50 (uM) | 1H NMR (400 MHz) |
|---|---|---|---|---|
| 182 | 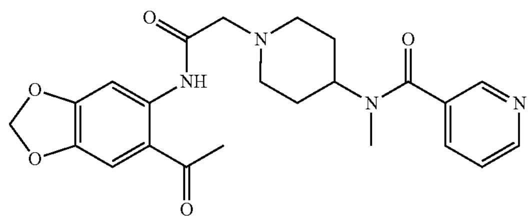 [SMILES: CC(=O)c1cc2c(cc1NC(=O)CN1CCC(N(C)C(=O)c3cccnc3)CC1)OCO2] | 439 | 0.455 | (DMSO-d$_6$) δ 1.63 (br s, 2H), 2.95-2.25 (m, 4H), 2.25-2.40 (m, 2H), 2.52-2.63 (m, 4H), 2.71-3.20 (m, 5H), 4.40 (br s, 1H), 6.13 (s, 2H), 7.44-7.53 (m, 1H), 7.61 (s, 1H), 7.84 (br s, 1H), 8.34 (br s, 1H), 8.55-8.71 (m, 2H), 12.69 (s, 1H). |

Compounds with hT2R54 IC50 of 1 μM or lower are considered especially potent.

Example 20—Synthesis of N-(6-Acetylbenzo[d][1,3]dioxol-5-yl)-2-((1-(furan-2-carbonyl)piperidin-4-yl)(methyl)amino)acetamide (183)

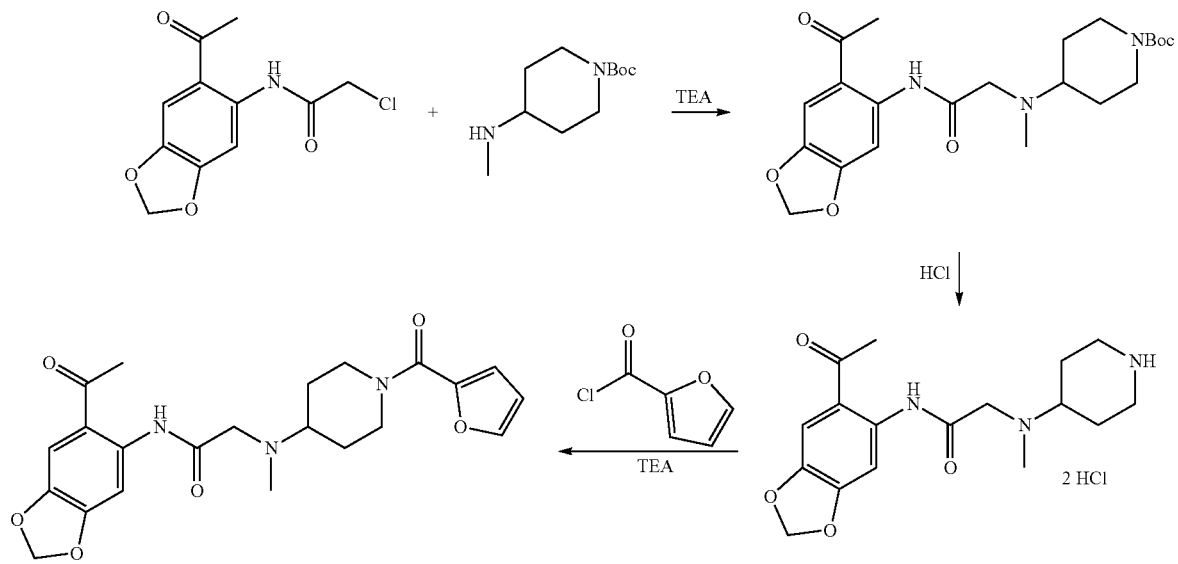

Prepared in a similar manner as in Example 19 from N-(6-acetylbenzo[d][1,3]dioxol-5-yl)-2-(methyl(piperidin-4-yl)amino)acetamide dihydrochloride (Example 20a) (0.2 g, 0.5 mmol), furan-2-carbonyl chloride (0.08 g, 0.6 mmol), and TEA (0.3 mL, 2 mmol) to give the title compound (119 mg, 56% yield) as a white solid. MS 428 (M+H+).

Example 20a. N-(6-Acetylbenzo[d][1,3]dioxol-5-yl)-2-(methyl(piperidin-4-yl)amino)acetamide Dihydrochloride

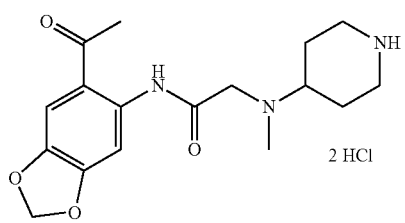 [SMILES: CC(=O)c1cc2c(cc1NC(=O)CN(C)C1CCNCC1)OCO2]

Prepared in a similar manner as in Example 19a from tert-butyl 4-((2-(((6-acetylbenzo[d][1,3]dioxol-5-yl)amino)-2-oxoethyl)(methyl)amino)piperidine-1-carboxylate (Example 20b) to give ~1.1 g (quantitative yield) of the desired product.

Example 20b. tert-Butyl 4-((2-((6-Acetylbenzo[d][1,3]dioxol-5-yl)amino)-2-oxoethyl)(methyl)amino)piperidine-1-carboxylate

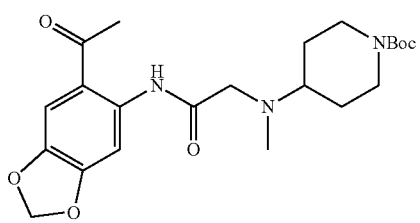 [SMILES: CC(=O)c1cc2c(cc1NC(=O)CN(C)C1CCN(C(=O)OC(C)(C)C)CC1)OCO2]

Prepared in a similar manner as in Example 9 from N-(6-acetylbenzo[d][1,3]-dioxol-5-yl)-2-chloroacetamide (Example 14a) (1.2 g, 4.7 mmol), tert-butyl 4-(methylamino)piperidine-1-carboxylate (1 g, 4.7 mmol), and TEA to give ~1.2 g (60% yield) of the title compound as white solid. $^1$H NMR (400 MHz, DMSO-$d_6$) δ 1.27-1.44 (m, 2H), 1.39 (s, 9H), 1.80 (d, J=12.4 Hz, 2H), 2.27 (s, 3H), 2.55 (s, 3H), 2.57-2.76 (m, 3H), 3.17 (s, 2H), 3.98 (d, J=13.2 Hz, 2H), 6.13 (s, 2H), 7.60 (s, 1H), 8.33 (s, 1H), 12.68 (s, 1H). MS 434 (M+H$^+$).

Example 21—Synthesis of N-(6-Acetylbenzo[d][1,3]dioxol-5-yl)-2-(methyl(1-(3-methylbutanoyl)piperidin-4-yl)amino)acetamide (184)

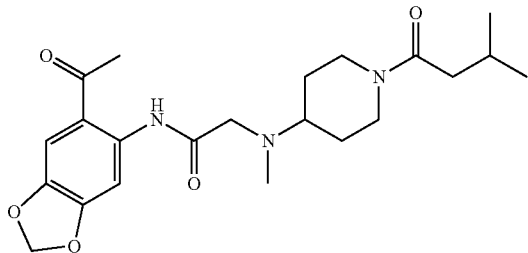 [SMILES: CC(=O)c1cc2c(cc1NC(=O)CN(C)C1CCN(C(=O)CC(C)C)CC1)OCO2]

Prepared in a similar manner as in Example 19 from N-(6-acetylbenzo[d][1,3]-dioxol-5-yl)-2-(methyl(piperidin-4-yl)amino)acetamide dihydrochloride (Example 20a) (0.2 g, 0.5 mmol) and 3-methylbutanoyl chloride (0.07 g, 0.6 mmol) to give the desired product (118 mg, 56% yield) as a white solid. MS 418 (M+H$^+$).

Compounds in Table 7 were prepared in a similar manner as in Example 19 from from N-(6-acetylbenzo[d][1,3]dioxol-5-yl)-2-(methyl(piperidin-4-yl)amino)acetamide dihydrochloride (Example 20a) and the corresponding commercially available carboxylic acids and/or acyl chlorides.

TABLE 7

| SID | Structure | Obs Mol Ion MS; (M + H$^+$) | hT2R54 IC50 (uM) | $^1$H NMR (400 MHz) |
|---|---|---|---|---|
| 183 | 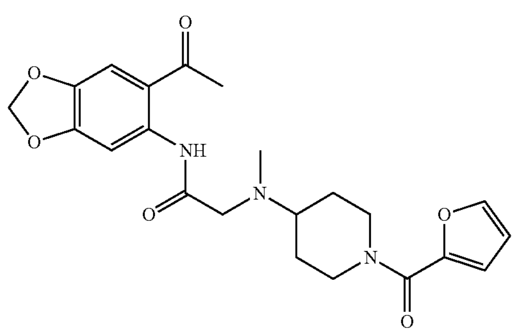 [SMILES: CC(=O)c1cc2c(cc1NC(=O)CN(C)C1CCN(C(=O)c3ccco3)CC1)OCO2] | 428 | 0.061 | (DMSO-$d_6$) δ 1.46 (d, J = 12.8 Hz, 2H), 1.91 (d, J = 12.3 Hz, 2H), 2.29 (s, 3H), 2.55 (s, 3H), 2.75-2.81 (m, 3H), 3.20 (s, 2H), 4.37 (bs, 2H), 6.13 (s, 2H), 6.61 (dd, J = 3.5, 1.8 Hz, 1H), 6.96 (dd, J = 3.4, 0.8 Hz, 1H), 7.60 (s, 1H), 7.82 (dd, J = 1.8, 0.8 Hz, 1H), 8.34 (s, 1H), 12.69 (s, 1H). |
| 184 | 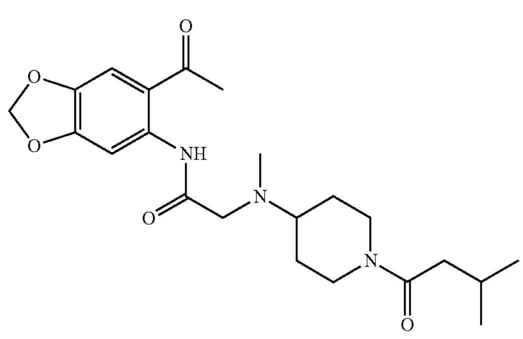 [SMILES: CC(=O)c1cc2c(cc1NC(=O)CN(C)C1CCN(C(=O)CC(C)C)CC1)OCO2] | 418 | 0.098 | (DMSO-$d_6$) δ 0.88 (m, J = 6.6, 1.4 Hz, 6H), 1.21-1.43 (m, 2H), 1.84 (br t, J = 15.4 Hz, 2H), 1.90-2.02 (m, 1H), 2.17 (dd, J = 7.0, 1.9 Hz, 2H), 2.28 (s, 3H), 2.55 (s, 3H), 2.61-2.73 (m, 1H), 2.97 (br t, J = 12.3 Hz, 1H), 3.17 (s, 2H), 3.93 (br d, J = 13.6 Hz, 1H), 4.45 (br d, J = 13.0 Hz, 1H), 6.13 (s, 2H), 7.60 (s, 1H), 8.33 (s, 1H), 12.68 (s, 1H). |

TABLE 7-continued

| SID | Structure | Obs Mol Ion MS; (M + H⁺) | hT2R54 IC50 (uM) | ¹H NMR (400 MHz) |
|---|---|---|---|---|
| 185 | 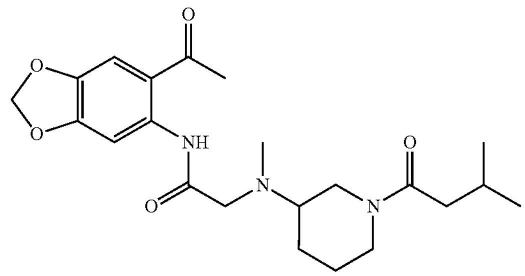 [SMILES: CC(=O)c1cc2c(cc1NC(=O)CN(C)C1CCCN(C(=O)CC(C)C)C1)OCO2] | 418 | 0.05 | (DMSO-d₆, rotamers) δ 0.81-0.89 (m, 6H), 1.13-1.40 (m, 1H), 1.41-1.58 (m, 1H), 1.65-1.83 (m, 1H), 1.89-2.01 (m, 2H), 2.15 (d, J = 6.9 Hz, 2H), 2.27-2.44 (m, 4H), 2.43-2.72 (m, 4H), 2.87-3.04 (m, 1H), 3.14-3.42 (m, 2H), 3.73 (br d, J = 13.5 Hz, 0.5H), 4.11 (br d, J = 13.0 Hz, 0.5H), 4.35 (br d, J = 12.9 Hz, 0.5H), 4.44 (br d, J = 12.1 Hz, 0.5H), 6.13 (s, 1H), 6.14 (s, 1H), 7.60 (s, 0.5H), 7.62 (s, 0.5H), 8.33 (s, 0.5H), 8.35 (s, 0.5H), 12.64 (s, 0.5H), 12.75 (s, 0.5H). |
| 186 | 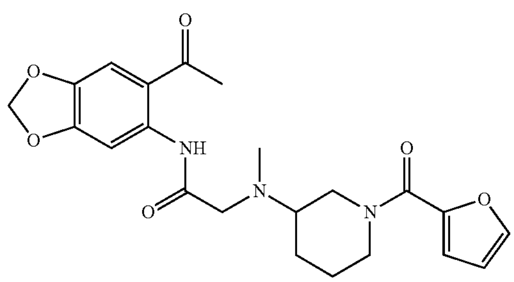 [SMILES: CC(=O)c1cc2c(cc1NC(=O)CN(C)C1CCCN(C(=O)c3ccco3)C1)OCO2] | 428 | 0.02 | (DMSO-d₆) δ 1.36-1.49 (m, 1H), 1.52-1.67 (m, 1H), 1.77-1.86 (m, 1H), 1.95-2.05 (m, 1H), 2.35 (s, 3H), 2.51-2.70 (m, 4H), 2.98 (br s, 2H), 3.18-3.29 (m, 2H), 4.21 (br-s, 1H), 4.43 (br d, J = 12.5 Hz, 1H), 6.13 (s, 2H), 6.58 (dd, J = 3.4, 1.8 Hz, 1H), 6.91 (dd, J = 3.5, 0.8 Hz, 1H), 7.60 (s, 1H), 7.77 (br s, 1H), 8.33 (s, 1H), 12.70 (s, 1H). |
| 187 | 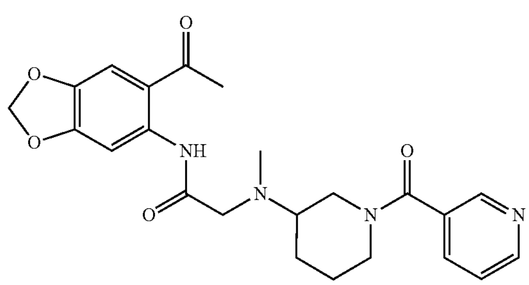 [SMILES: CC(=O)c1cc2c(cc1NC(=O)CN(C)C1CCCN(C(=O)c3cccnc3)C1)OCO2] | 439 | 0.10 | (DMSO-d₆, roramers) δ 1.37-1.85 (m, 3H), 1.97 (br d, J = 11.8 Hz, 1H), 2.16-2.79 (m, 8H), 2.86-3.48 (m, 4H), 3.74 (br d, J = 13.1 Hz, 0.5H), 4.37-4.58 (m, 1H), 6.12 (s, 2H), 7.34 (br s, 0.5H), 7.46 (br s, 0.5), 7.53-7.66 (m, 1H), 7.77 (d, J = 7.8 Hz, 1H), 8.27-7.39 (m, 1H), 8.53-8.69 (m, 2H), 12.61 (s, 0.5H), 12.70 (s, 0.5H). |
| 188 | 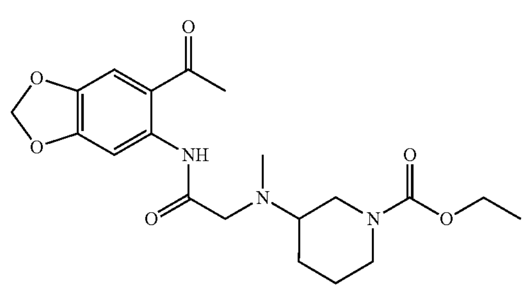 [SMILES: CCOC(=O)N1CCCC(N(C)CC(=O)Nc2cc3c(cc2C(C)=O)OCO3)C1] | 406 | 0.09 | (DMSO-d₆) δ 1.12 (t, J = 7.1 Hz, 3H), 1.24-1.53 (m, 2H), 1.67-1.77 (m, 1H), 1.86-1.94 (m, 1H), 2.32 (s, 3H), 2.56 (s, 3H), 2.62-2.90 (m, 3H), 3.19 (d, J = 16.8 Hz, 1H), 3.27 (d, J = 16.8 Hz, 1H), 3.79 (br d, J = 12.9 Hz, 1H), 3.94 (br q, J = 7.1 Hz, 2H), 4.06 (br d, J = 12.6 Hz, 1H), 6.11 (s, 2H), 7.59 (s, 1H), 8.32 (s, 1H), 12.65 (s, 1H). |

TABLE 7-continued

| SID | Structure | Obs Mol Ion MS; (M + H+) | hT2R54 IC50 (uM) | 1H NMR (400 MHz) |
|---|---|---|---|---|
| 189 | 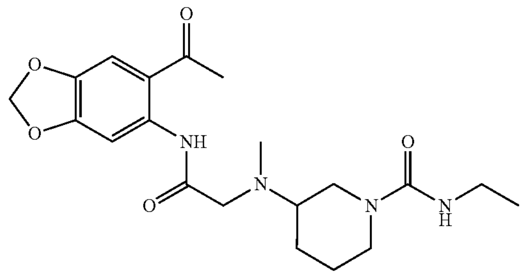 [SMILES: CCNC(=O)N1CCCC(N(C)CC(=O)Nc2cc3c(cc2C(C)=O)OCO3)C1] | 405 | 0.03 | (DMSO-$d_6$) δ 0.98 (t, J = 7.1 Hz, 3H), 1.23-1.46 (m, 2H), 1.61-1.71 (m, 1H), 1.96 (br d, J = 11.8 Hz, 1H), 2.33 (s, 3H), 2.35-2.45 (m, 1H), 2.46-2.59 (m, 5H), 2.96-3.06 (m, 2H), 3.18 (d, J = 17.2 Hz, 1H), 3.30 (d, J = 17.2 Hz, 1H), 3.82 (br d, J = 13.3 Hz, 1H), 4.10 (br d, J = 12.4 Hz, 1H), 6.13 (s, 2H), 6.39 (t, J = 5.4 Hz, 1H), 7.60 (s, 1H), 8.33 (s, 1H), 12.64 (s, 1H). |
| 190 | 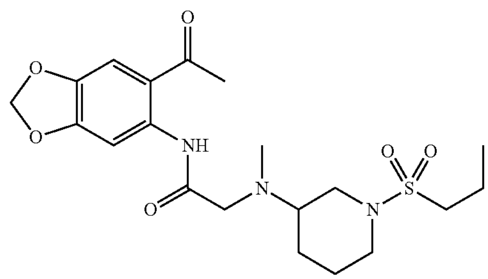 [SMILES: CCCS(=O)(=O)N1CCCC(N(C)CC(=O)Nc2cc3c(cc2C(C)=O)OCO3)C1] | 440 | 0.04 | (DMSO-$d_6$) δ 0.97 (t, J = 7.4 Hz, 3H), 1.30-1.52 (m, 2H), 1.62-1.74 (m, 2H), 1.75-1.83 (m, 1H), 1.95 (br d, J = 11.5 Hz, 1H), 2.34 (s, 3H), 2.56 (s, 3H), 2.59-2.69 (m, 2H), 2.74 (t, J = 11.0 Hz, 1H), 2.92-3.06 (m, 2H), 3.18-3.35 (m, 2H), 3.50 (br d, J = 11.9 Hz, 1H), 3.74 (br d, J = 11.0 Hz, 1H), 6.13 (s, 2H), 7.61 (s, 1H), 8.33 (s, 1H), 12.65 (s, 1H). |

Compounds with hT2R54 IC50 of 1 μM or lower are considered especially potent.

Example 22—Synthesis of Ethyl 1-(2-((6-Acetyl-benzo[d][1,3]dioxol-5-yl)amino)-2-oxoethyl)-4-(furan-2-carbonyl)piperazine-2-carboxylate (191, IC50=16 nM)

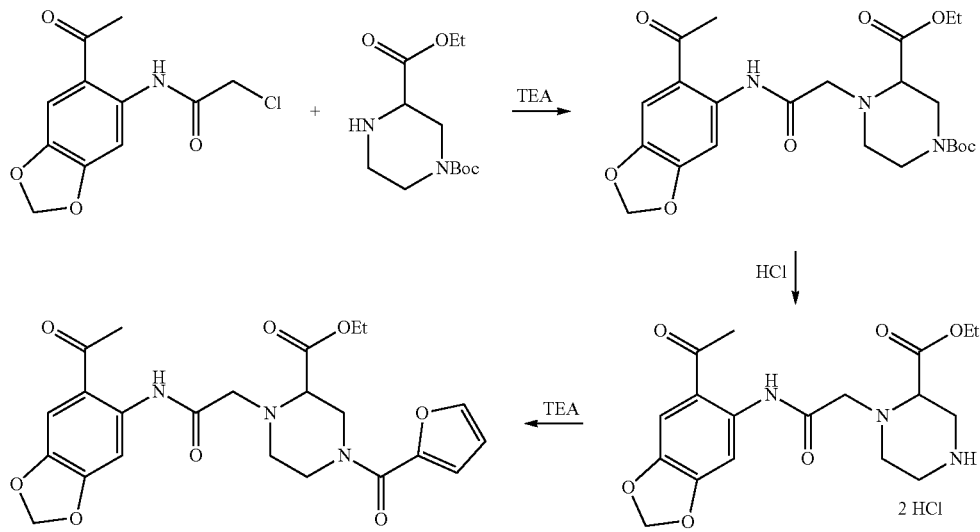

Prepared in a similar manner as in Example 19 from ethyl 1-(2-((6-acetylbenzo-[d][1,3]dioxol-5-yl)amino)-2-oxoethyl)piperazine-2-carboxylate dihydrochloride (Example 22a) (0.45 g, 1 mmol), furan-2-carbonyl chloride (0.13 g, 1 mmol), and TEA (0.6 mL, 4 mmol) to give the desired product (94 mg, 20% yield) as an off white solid. $^1$H NMR (400 MHz, DMSO-$d_6$) δ 1.05 (brs, 3H), 2.60 (s, 3H), 2.65 (d, J=12.2 Hz, 1H), 3.00-3.16 (m, 1H), 3.35-3.54 (m, 2H), 3.82 (t, J=3.1 Hz, 2H), 3.99 (d, J=7.6 Hz, 2H), 4.22 (d, J=13.0 Hz, 1H), 4.64 (brs, 1H), 6.15 (s, 2H), 6.63 (dd, J=3.5, 1.8 Hz, 1H), 7.04 (d, J=3.4 Hz, 1H), 7.64 (s, 1H), 7.85 (dd, J=1.8, 0.8 Hz, 1H), 8.37 (s, 1H), 12.77 (s, 1H). MS 472 (M+H$^+$).

Example 22a. Ethyl 1-(2-((6-Acetylbenzo[d][1,3]dioxol-5-yl)amino)-2-oxoethyl)-piperazine-2-carboxylate Dihydrochloride

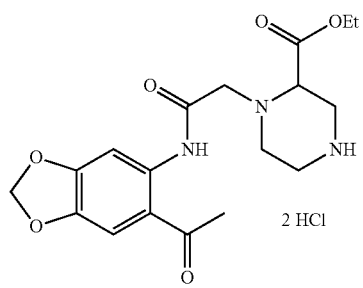 [SMILES: CCOC(=O)C1CNCCN1CC(=O)Nc1cc2c(cc1C(C)=O)OCO2]

Prepared in a similar manner as in Example 19a from 1-(tert-butyl) 3-ethyl 4-(2-((6-acetylbenzo[d][1,3]dioxol-5-yl)amino)-2-oxoethyl)piperazine-1,3-dicarboxylate (Example 22b) (1.4 g, 3 mmol) to give desired product (1.35 g, quantitative yield).

Example 22b. 1-(tert-Butyl) 3-ethyl 4-(2-((6-acetyl-benzo[d][1,3]dioxol-5-yl)amino)-2-oxoethyl)piperazine-1,3-dicarboxylate

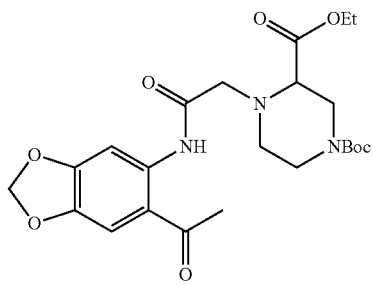 [SMILES: CCOC(=O)C1CN(C(=O)OC(C)(C)C)CCN1CC(=O)Nc1cc2c(cc1C(C)=O)OCO2]

Prepared in a similar manner as in Example 9 from N-(6-acetylbenzo[d][1,3]-dioxol-5-yl)-2-chloroacetamide (Example 14a) (1 g, 4 mmol), 1-(tert-butyl) 3-ethyl piperazine-1,3-dicarboxylate (1.0 g, 4 mmol) and TEA (1.7 mL, 12 mmol) to give ~1.4 g (75% yield) of the desired material as white solid. $^1$H NMR (400 MHz, DMSO-$d_6$) δ 1.20 (br s, 3H), 1.39 (s, 9H), 2.58 (s, 3H), 3.00-3.06 (m, 1H), 3.39-3.59 (m, 2H), 3.64-3.87 (m, 2H), 4.04-4.26 (m, 3H), 6.14 (s, 2H), 7.62 (s, 1H), 8.35 (s, 1H), 12.70 (s, 1H). MS 478 (M+H$^+$).

Example 23—Synthesis of Ethyl 1-(2-((6-Acetyl-benzo[d][1,3]dioxol-5-yl)amino)-2-oxoethyl)-4-(3-methylbutanoyl)piperazine-2-carboxylate (192, IC50=57 nM)

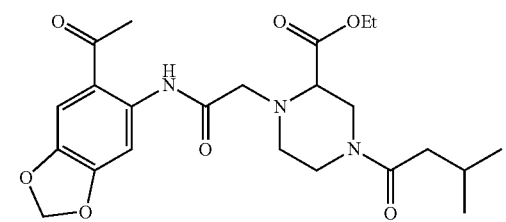 [SMILES: CCOC(=O)C1CN(C(=O)CC(C)C)CCN1CC(=O)Nc1cc2c(cc1C(C)=O)OCO2]

Prepared in a similar manner as in Example 20 from ethyl 1-(2-((6-acetylbenzo-[d][1,3]dioxol-5-yl)amino)-2-oxoethyl)piperazine-2-carboxylate dihydrochloride (Example 22a) (0.45 g, 1 mmol) and 3-methylbutanoyl chloride (0.12 g, 1 mmol) to give the desired product (82 mg, 18% yield) as a white solid. MS 462 (M+H$^+$).

Example 24—Synthesis of N-(6-acetylbenzo[d][1,3]dioxol-5-yl)-2-(1-(3-methylbutanoyl)piperidin-3-yl)acetamide (193)

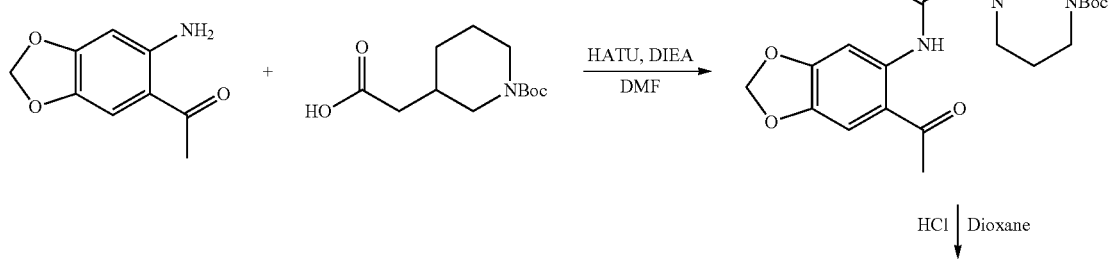

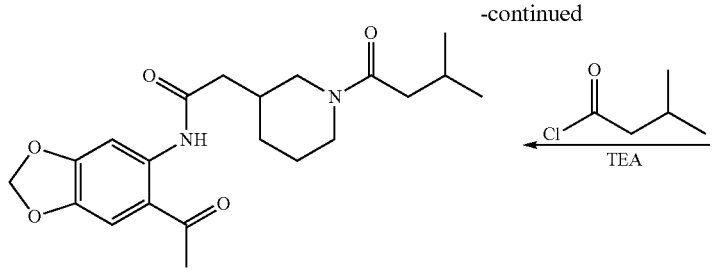 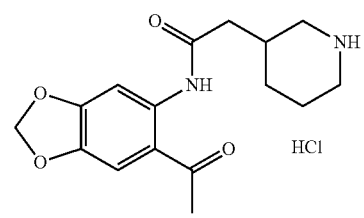

A solution of N-(6-acetylbenzo[d][1,3]dioxol-5-yl)-2-(piperidin-3-yl)acetamide HCl salt (53 mg, 0.156 mmol) and TEA (44 µL, 0.336 mmol) in dry DCM (4 mL) was treated with isovaleryl chloride (21 uL, 0.172 mmol) and the solution was stirred overnight at room temperature. The solvent was removed under vacuum and the residue purified by silica gel chromatography to afford the title compound as a colorless oil (64.4 mg, quantitative yield). MS 389 (M+H$^+$).

Example 24a. N-(6-Acetylbenzo[d][1,3]dioxol-5-yl)-2-(piperidin-3-yl)acetamide

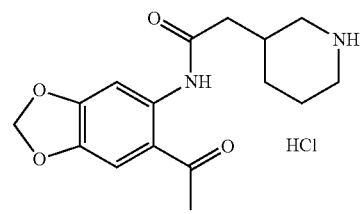 [SMILES: CC(=O)c1cc2c(cc1NC(=O)CC1CCCNC1)OCO2 ; Cl]

A solution of tert-butyl 3-(2-((6-acetylbenzo[d][1,3]dioxol-5-yl)amino)-2-oxoethyl)piperidine-1-carboxylate (Example 24b) (5.9 g) in 4M HCl in 1,4-dioxane (80 mL) was stirred overnight at room temperature. The precipitate was collected by filtration to give the title compound as a pale yellow solid in quantitative yield.

Example 24b. tert-Butyl 3-(2-((6-Acetylbenzo[d][1,3]dioxol-5-yl)amino)-2-oxoethyl)-piperidine-1-carboxylate

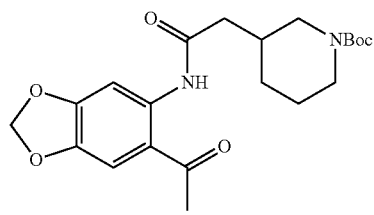 [SMILES: CC(=O)c1cc2c(cc1NC(=O)CC1CCCN(C(=O)OC(C)(C)C)C1)OCO2]

A mixture of 1-(6-aminobenzo[d][1,3]dioxol-5-yl)ethan-1-one (3.07 g, 17.13 mmol), 2-(1-(tert-butoxycarbonyl)piperidin-3-yl)acetic acid (5.0 g, 20.6 mmol), HATU (9.78 g, 25.70 mmol), and DIEA (8.95 mL, 51.40 mmol) in dry DMF was heated to 55° C., and stirred overnight at room temperature. The reaction mixture was concentrated and the residue was diluted with EtOAc and washed successively with water and brine. The organic phase was dried over MgSO$_4$, filtered, and concentrated on the rotavap. The residue was purified by silica gel chromatography using 20%-30% EtOAc in Hexanes as eluent. The fractions were collected and dried to give the title compound as a yellowish oil (5.9 g, 14.6 mmol, 85% yield). $^1$H NMR (400 MHz, DMSO-d$_6$) δ 1.23 (m, 2H), 1.35 (s, 9H), 1.56-1.62 (m, 1H), 1.73-1.79 (m, 1H), 1.88 (br. s, 1H), 2.28 (m, 2H), 2.57 (s, 3H), 2.84 (br. s, 2H), 3.71-3.83 (m, 2H), 6.14 (s, 2H), 7.59 (s, 1H), 8.12 (s, 1H), 11.83 (s, 1H).

Example 25—Synthesis of N-(6-Acetylbenzo[d][1,3]dioxol-5-yl)-2-(1-(furan-2-carbonyl)piperidin-3-yl)acetamide (194)

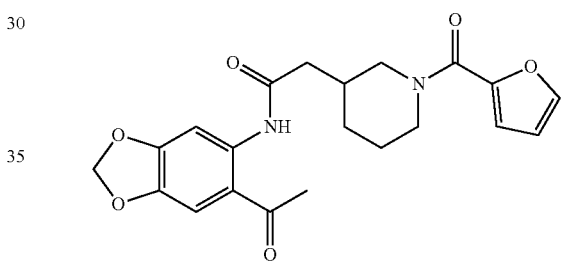

Prepared in a similar manner as in Example 24 from N-(6-acetylbenzo[d][1,3]-dioxol-5-yl)-2-(piperidin-3-yl)acetamide HCl salt (Example 24a) (42 mg, 0.123 mmol), and 2-furoyl chloride (13 uL, 0.135 mmol) to afford the title compound as a white solid (44.1 mg, 90% yield). MS 399 (M+H$^+$).

Example 26—Synthesis of N-(6-Acetylbenzo[d][1,3]dioxol-5-yl)-2-(1-(thiophene-2-carbonyl)piperidin-3-yl)acetamide (195)

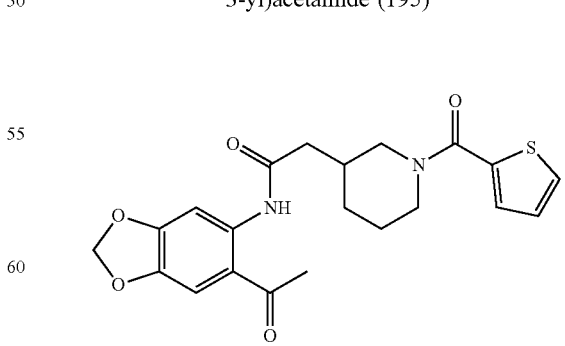

Prepared in a similar manner as in Example 24 from N-(6-acetylbenzo[d][1,3]-dioxol-5-yl)-2-(piperidin-3-yl)acetamide HCl salt (Example 24a) (41 mg, 0.120 mmol) and thiophene-2-carbonyl chloride (14 uL, 0.132 mmol) to afford the title compound as a white solid (47.6 mg, 96% yield). MS 415 (M+H$^+$).

Example 27—Synthesis of N-(6-Acetylbenzo[d][1,3]dioxol-5-yl)-2-(1-(furan-3-carbonyl)piperidin-3-yl)acetamide (196)

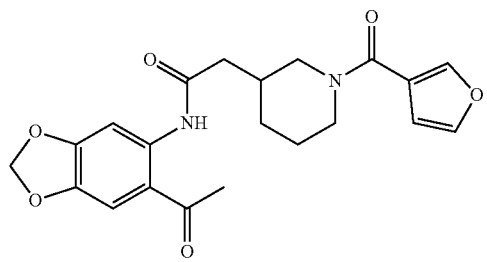 [SMILES: CC(=O)c1cc2c(cc1NC(=O)CC1CCCN(C(=O)c3ccoc3)C1)OCO2]

A solution of 3-furoic acid (18 mg, 0.161 mmol) and DIEA (51 μL, 0.294 mmol) in dry DCM (4 mL) was treated with TBTU (61 mg, 0.191 mmol) and the solution was stirred for 1 hour at room temperature. N-(6-Acetylbenzo[d][1,3]dioxol-5-yl)-2-(piperidin-3-yl)acetamide HCl salt (Example 24a) (50 mg, 0.147 mmol) was then added and the mixture stirred overnight at room temperature. The solvent was removed under vacuum and the residue purified by silica gel chromatography using 0-50% EtOAc in hexanes as eluent to afford the title compound as a white powder (66.5 mg, quantitative yield). MS 399 (M+H$^+$).

Example 28—Synthesis of N-(6-Acetylbenzo[d][1,3]dioxol-5-yl)-2-(1-(furan-2-carbonyl)piperidin-4-yl)acetamide (197)

Prepared in a similar manner as in Example 24 from N-(6-acetylbenzo[d][1,3]-dioxol-5-yl)-2-(piperidin-4-yl)acetamide HCl salt (Example 28a) (42 mg, 0.123 mmol), TEA (34 uL, 0.246 mmol), and 2-furoyl chloride (13 uL, 0.135 mmol) to afford the title compound as a white solid (44 mg, 90% yield). MS 399 (M+H$^+$).

Example 28a. N-(6-Acetylbenzo[d][1,3]dioxol-5-yl)-2-(piperidin-4-yl)acetamide Hydrochloride

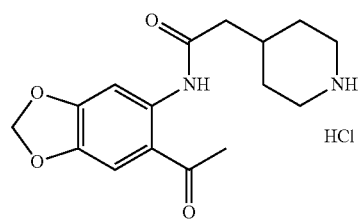 [SMILES: CC(=O)c1cc2c(cc1NC(=O)CC1CCNCC1)OCO2 ; Cl]

Prepared in a similar manner as in Example 24a from tert-butyl 4-(2-((6-acetylbenzo[d][1,3]dioxol-5-yl)amino)-2-oxoethyl)piperidine-1-carboxylate (Example 28b) (699 mg, 1.73 mmol) and 4N HCl in dioxane (4.5 mL) to afford the title compound as a yellow solid (556 mg, 94% yield). $^1$H NMR (400 MHz, DMSO-d$_6$) δ 1.48-1.28 (m, 2H), 1.82 (d, J=13.9 Hz, 2H), 1.97-2.14 (m, 1H), 2.35 (d, J=7.2 Hz, 2H), 2.57 (s, 3H), 2.88 (q, J=11.9 Hz, 2H), 3.26 (d, J=12.8 Hz, 2H), 6.14 (s, 2H), 7.59 (s, 1H), 8.08 (s, 1H), 8.24 (br. s, 1H), 8.54 (br. s, 1H), 11.78 (s, 1H).

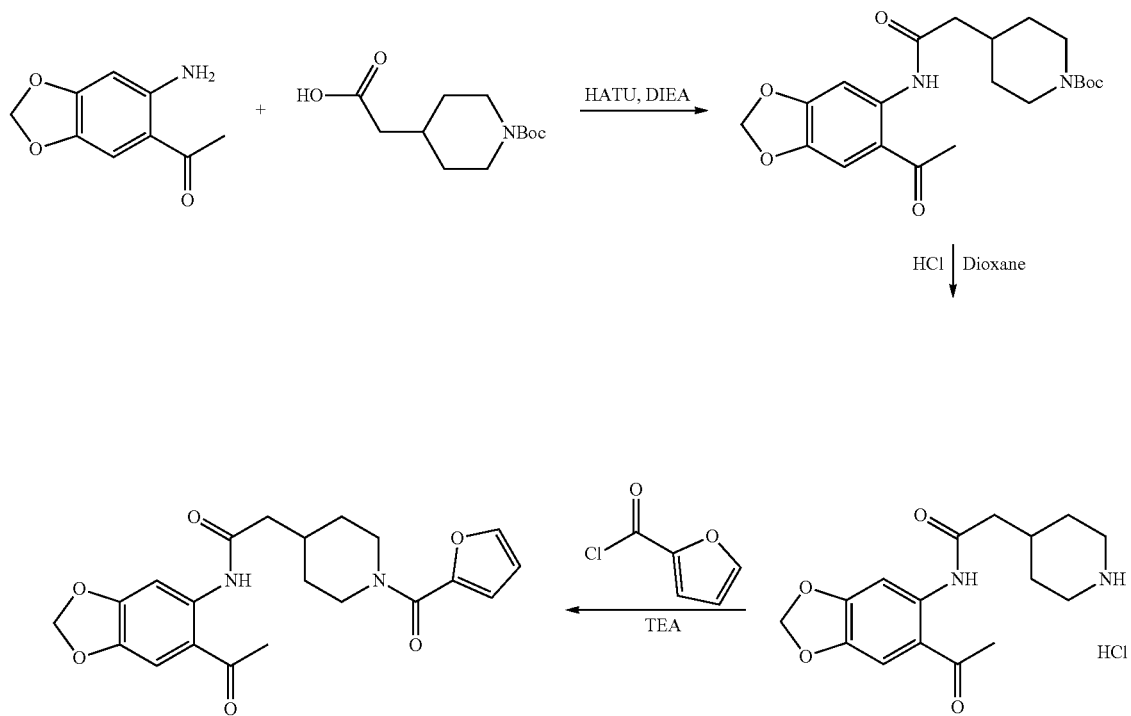

Example 28b. tert-Butyl 4-(2-((6-Acetylbenzo[d][1,3]dioxol-5-yl)amino)-2-oxoethyl)piperidine-1-carboxylate

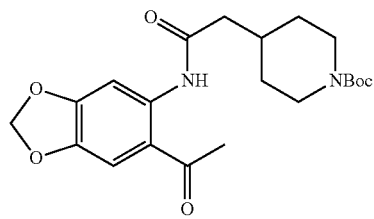 [SMILES: CC(=O)c1cc2c(cc1NC(=O)CC1CCN(C(=O)OC(C)(C)C)CC1)OCO2]

Prepared in a similar manner as in Example 24b from 1-(6-aminobenzo-[d][1,3]dioxol-5-yl)ethan-1-one (3.07 g, 17.13 mmol), 2-(1-(tert-butoxycarbonyl)-piperidin-4-yl)acetic acid (5.0 g, 20.6 mmol), HATU (9.78 g, 25.70 mmol), and DIEA (8.95 mL, 51.40 mmol) to give the title compound as a yellowish oil (6.5 g, 16.1 mmol, 94% yield). $^1$H NMR (400 MHz, DMSO-$d_6$) δ 1.07 (qd, J=12.3, 4.2 Hz, 2H), 1.38 (s, 9H), 1.65 (d, J=11.6 Hz, 2H), 1.87-1.99 (m, 1H), 2.30 (d, J=7.1 Hz, 2H), 2.57 (s, 3H), 2.60-2.84 (m, 2H), 3.89 (d, J=13.2 Hz, 2H), 6.13 (s, 2H), 7.58 (d, J=0.6 Hz, 1H), 8.11 (d, J=0.6 Hz, 1H), 11.80 (s, 1H). MS 305 (M+H$^+$).

Example 29—Synthesis of N-(6-acetylbenzo[d][1,3]dioxol-5-yl)-2-(1-(3-methylbutanoyl)piperidin-4-yl)acetamide (198)

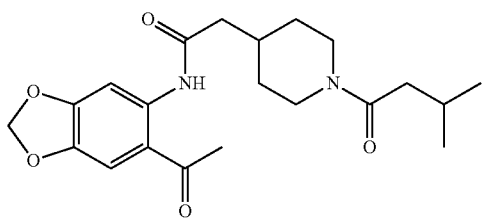

Prepared in a similar manner as in Example 24 from N-(6-acetylbenzo[d][1,3]-dioxol-5-yl)-2-(piperidin-4-yl)acetamide HCl salt (Example 28a) (40 mg, 0.117 mmol) and isovaleryl chloride (16 uL, 0.129 mmol) to afford the title compound as a colorless oil (43 mg, 96% yield). MS 389 (M+H$^+$).

Example 30—Synthesis of N-(6-Acetylbenzo[d][1,3]dioxol-5-yl)-2-(1-(thiophene-2-carbonyl)piperidin-4-yl)acetamide (199)

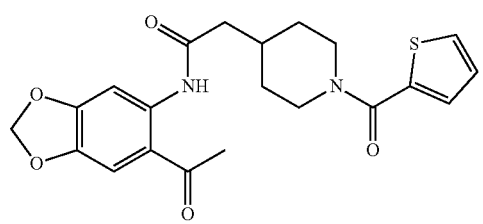 [SMILES: CC(=O)c1cc2c(cc1NC(=O)CC1CCN(C(=O)c3cccs3)CC1)OCO2]

Prepared in a similar manner as in Example 24 from N-(6-acetylbenzo[d][1,3]-dioxol-5-yl)-2-(piperidin-4-yl)acetamide HCl salt (Example 28a) (42 mg, 0.123 mmol) and thiophene-2-carbonyl chloride (15 uL, 0.135 mmol) to afford the title compound as a white solid (39 mg, 76% yield). MS 415 (M+H$^+$).

Example 31—Synthesis of N-(6-Acetylbenzo[d][1,3]dioxol-5-yl)-2-(1-(furan-3-carbonyl)piperidin-4-yl)acetamide (200)

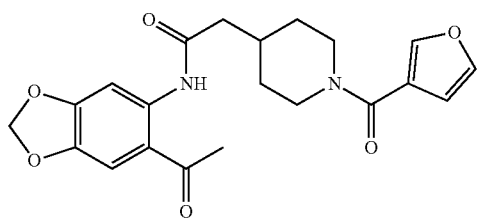 [SMILES: CC(=O)c1cc2c(cc1NC(=O)CC1CCN(C(=O)c3ccoc3)CC1)OCO2]

Prepared in a similar manner as in Example 18 from N-(6-acetylbenzo[d][1,3]-dioxol-5-yl)-2-(piperidin-4-yl)acetamide HCl salt (Example 28a) (50 mg, 0.147 mmol) and 3-furoic acid (18 mg, 0.161 mmol) to afford the title compound as a white powder (47.9 mg, 82% yield). MS 399 (M+H$^+$).

Example 32—Synthesis of N-(6-Acetylbenzo[d][1,3]dioxol-5-yl)-2-(1-(1-methyl-1H-pyrazole-4-carbonyl)piperidin-4-yl)acetamide (201)

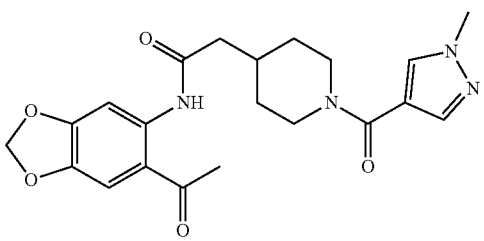 [SMILES: CC(=O)c1cc2c(cc1NC(=O)CC1CCN(C(=O)c3cnn(C)c3)CC1)OCO2]

Prepared in a similar manner as in Example 18 from N-(6-acetylbenzo[d][1,3]-dioxol-5-yl)-2-(piperidin-4-yl)acetamide HCl salt (Example 28a) (50 mg, 0.147 mmol) and 1-methyl-1H-pyrazole-4-carboxylic acid (19 mg, 0.147 mmol) to afford the title compound as a white solid (40.5 mg, 67% yield). MS 413 (M+H$^+$).

Compounds in Table 8 were prepared in a similar manner as in Example 2 and/or Example 27 from the corresponding amine hydrochlorides described herein (e.g. in Example 24a and 28a) and the corresponding commercially available carboxylic acids and/or acyl chlorides.

TABLE 8

| SID | Structure | Obs Mol Ion MS; (M + 1) | hT2R54 IC50 (uM) | ¹H NMR (400 MHz) |
|---|---|---|---|---|
| 193 | 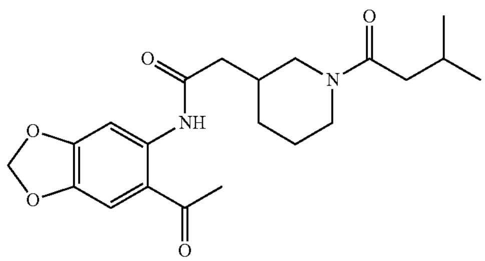 | 389 | 0.017 | (DMSO-$d_6$, 80° C.) δ 0.91 (d, J = 6.8 Hz, 6H), 1.25-1.39 (m, 2H), 1.64-1.67 (m, 1H), 1.82-1.85 (m, 1H), 1.91 (br. s, 1H), 1.96-2.03 (m, 1H), 2.16-2.18 (m, 2H), 2.25-2.40 (m, 2H), 2.56 (s, 3H), 2.80 (br. s, 2H), 3.88-4.10 (m, 2H), 6.11 (s, 2H), 7.51 (s, 1H), 8.06 (s, 1H) 11.61 (s, 1H). |
| 194 | 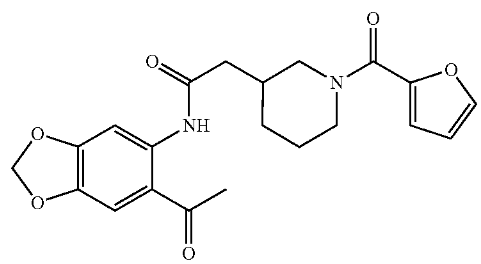 [SMILES: CC(=O)c1cc2c(cc1NC(=O)CC1CCCN(C(=O)c3ccco3)C1)OCO2] | 399 | 0.006 | (DMSO-$d_6$) δ 1.21-1.52 (m, 2H), 1.65-1.76 (m, 1H), 1.80-1.89 (m, 1H), 1.95-2.06 (m, 1H), 2.27-2.42 (m, 2H), 2.56 (s, 3H), 2.98 (br s, 2H), 4.06-4.28 (m, 2H), 6.14 (s, 2H), 6.57 (br. s, 1H), 6.97 (dd, J = 3.4, 0.7 Hz, 1H), 7.58 (s, 1H), 7.74 (br. s, 1H), 8.08 (s, 1H), 11.79 (s, 1H). |
| 195 | 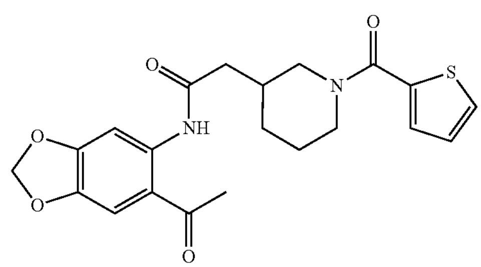 [SMILES: CC(=O)c1cc2c(cc1NC(=O)CC1CCCN(C(=O)c3cccs3)C1)OCO2] | 415 | 0.008 | (DMSO-$d6$) δ 1.15-1.49 (m, 2H), 1.69-1.72 (m, 1H), 1.84-1.87 (m, 1H), 2.02 (m, 1H), 2.35 (d, J = 6.8 Hz, 2H), 2.56 (s, 3H), 2.85-3.01 (m, 2H), 4.12-4.21 (m, 2H), 6.14 (s, 2H), 7.05 (t, J = 4.4 Hz, 1H), 7.36 (dt, J = 3.7, 0.8 Hz, 1H), 7.58 (s, 1H), 7.71 (d, J = 4.8 Hz, 1H), 8.06 (s, 1H), 11.78 (s, 1H). |
| 196 | 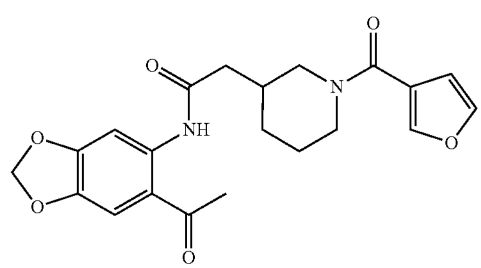 [SMILES: CC(=O)c1cc2c(cc1NC(=O)CC1CCCN(C(=O)c3ccoc3)C1)OCO2] | 399 | 0.184 | (DMSO-$d6$) δ 1.24-1.48 (m, 2H), 1.66-1.69 (m, 1H), 1.82-1.86 (m, 1H), 1.97 (m, 1H), 2.32 (m, 2H), 2.56 (s, 3H), 2.83-3.08 (m, 2H), 3.85-4.26 (m, 2H), 6.15 (s, 2H), 6.62 (s, 1H), 7.58 (s, 1H), 7.69 (br. s, 1H), 8.00 (s, 1H), 8.05 (br. s, 1H), 11.76 (br. s, 1H). |
| 197 | 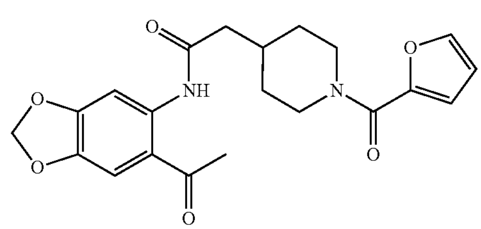 [SMILES: CC(=O)c1cc2c(cc1NC(=O)CC1CCN(C(=O)c3ccco3)CC1)OCO2] | 399 | 0.006 | (DMSO-$d_6$) δ 1.21-1.26 (m, 2H), 1.74-1.77 (m, 2H), 2.04-2.12 (m, 1H), 2.35 (d, J = 7.2 Hz, 2H), 2.57 (s, 3H), 2.98 (br. s, 2H), 4.29 (br. s, 2H), 6.14 (s, 2H), 6.60 (dd, J = 3.5, 1.8 Hz, 1H), 6.93 (dd, J = 3.5, 0.8 Hz, 1H), 7.58 (s, 1H), 7.81 (dd, J = 1.8, 0.8 Hz, 1H), 8.11 (s, 1H), 11.81 (s, 1H). |

TABLE 8-continued

| SID | Structure | Obs Mol Ion MS (M + 1) | hT2R54 IC50 (uM) | ¹H NMR (400 MHz) |
|---|---|---|---|---|
| 198 | 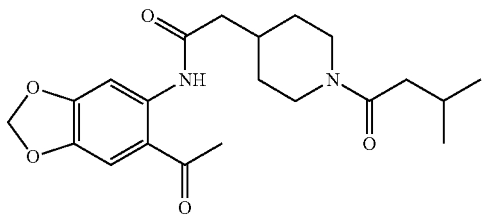 [SMILES: CC(=O)c1cc2c(cc1NC(=O)CC1CCN(C(=O)CC(C)C)CC1)OCO2] | 389 | 0.045 | (DMSO-d$_6$) δ 0.89 (d, J = 6.4 Hz, 6H), 0.98-1.23 (m, 3H), 1.68 (t, J = 15.2 Hz, 2H), 1.90-2.04 (m, 1H), 2.17 (d, J = 7.2 Hz, 2H), 2.31 (d, J = 13.6 Hz, 2H), 2.57 (s, 3H), 2.98 (t, J = 12.4 Hz, 2H), 3.88 (d, J = 15.2 Hz, 1H), 4.39 (d, J = 13.6 Hz, 1H), 6.14 (s, 2H), 7.58 (s, 1H), 8.11 (s, 1H), 11.80 (s, 1H). |
| 199 | 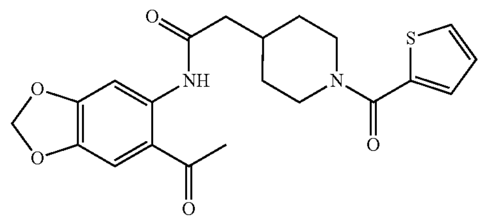 | 415 | 0.012 | (DMSO-d$_6$) δ 1.16-1.28 (m, 2H), 1.76 (d, J = 12.8 Hz, 2H), 2.08 (m, 1H), 2.36 (d, J = 7.2 Hz, 2H), 2.57 (s, 3H), 3.00 (br. s, 2H), 4.24 (br. s, 2H), 6.14 (s, 2H), 7.11 (dd, J = 5.0, 3.6 Hz, 1H), 7.36 (dd, J = 3.6, 1.0 Hz, 1H), 7.58 (s, 1H), 7.73 (dd, J = 5.0, 1.0 Hz, 1H), 8.12 (s, 1H), 11.82 (s, 1H). |
| 200 | 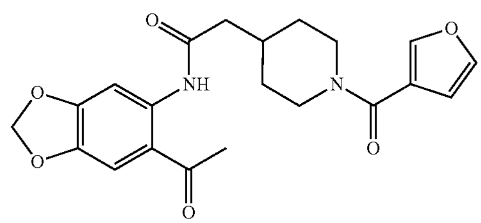 [SMILES: CC(=O)c1cc2c(cc1NC(=O)CC1CCN(C(=O)c3ccoc3)CC1)OCO2] | 399 | 0.149 | (DMSO-d$_6$) δ 1.16-1.23 (m, 2H), 1.73 (d, J = 11.6 Hz, 2H), 2.06 (m, 1H), 2.34 (d, J = 7.2 Hz, 2H), 2.57 (s, 3H), 3.10 (br. s, 2H), 4.39 (br. s, 2H), 6.14 (s, 2H), 6.63 (dd, J = 1.9, 0.8 Hz, 1H), 7.58 (s, 1H), 7.73 (t, J = 1.6 Hz, 1H), 7.99 (dd, J = 1.6, 0.9 Hz, 1H), 8.12 (s, 1H), 11.82 (s, 1H). |
| 201 | 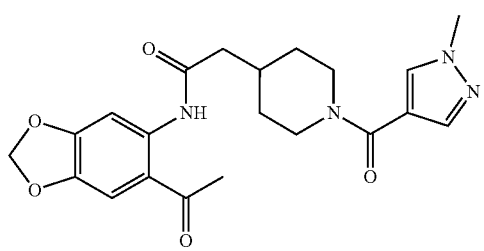 [SMILES: CC(=O)c1cc2c(cc1NC(=O)CC1CCN(C(=O)c3cnn(C)c3)CC1)OCO2] | 413 | 0.339 | (400 MHz, DMSO-d$_6$) δ 1.15-1.27 (m, 2H), 1.74 (d, J = 12.8 Hz, 2H), 2.06 (m, 1H), 2.34 (d, J = 7.2 Hz, 2H), 2.57 (s, 3H), 3.14 (m, 1H), 3.62 (m, 1H), 3.84 (s, 3H), 4.21 (br. s, 2H), 6.14 (s, 2H), 7.58 (s, 1H), 7.61 (d, J = 0.8 Hz, 1H), 8.01 (s, 1H), 8.12 (s, 1H), 11.82 (s, 1H). |
| 202 | 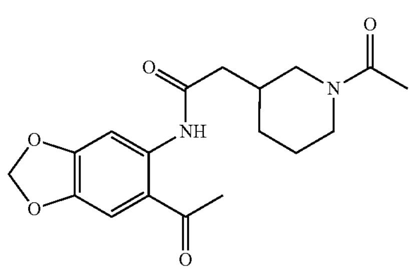 [SMILES: CC(=O)c1cc2c(cc1NC(=O)CC1CCCN(C(C)=O)C1)OCO2] | 347 | 0.035 | (DMSO-d$_6$, rotamers) δ 1.21-1.42 (m, 2H), 1.57-1.83 (m, 2H), 1.96 (s, 1.5H), 1.98 (s, 1.5H), 2.22-2.41 (m, 2H), 2.57 (s, 3H), 2.67-2.72 (m, 1H), 2.87 (dd, J = 13.4, 9.9 Hz, 1H), 3.00 (ddd, J = 13.6, 11.4, 3.0 Hz, 1H), 3.65-3.76 (m, 1H), 4.09-4.23 (m, 1H), 6.14 (s, 2H), 7.58 (s, 1H), 8.07 (s, 0.5H), 8.11 (s, 0.5H), 11.76 (s, 0.5H), 11.81 (s, 0.5H). |

TABLE 8-continued

| SID | Structure | Obs Mol Ion MS; (M + 1) | hT2R54 IC50 (uM) | ¹H NMR (400 MHz) |
|---|---|---|---|---|
| 203 | 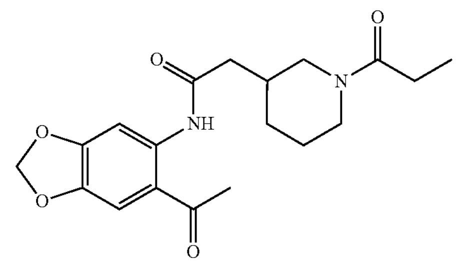 [SMILES: CCC(=O)N1CCCC(CC(=O)Nc2cc3c(cc2C(C)=O)OCO3)C1] | 361 | 0.017 | (DMSO-d$_6$, rotamers) δ 0.97 (t, J = 7.6 Hz, 3H), 1.10-1.43 (m, 2H), 1.58-1.80 (m, 2H), 2.25-2.43 (m, 5H), 2.56 (s, 3H), 2.83 (dd, J = 13.4, 10.4 Hz, 1H), 2.95-3.02 (m, 1H), 3.68-3.80 (m, 1H), 4.10-4.23 (m, 1H), 6.14 (s, 2H), 7.58 (s, 1H), 8.06 (s, 0.5H), 8.11 (s, 0.5H), 11.74 (s, 0.5H), 11.80 (s, 0.5H). |
| 204 | 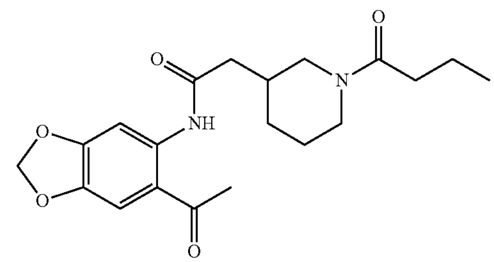 [SMILES: CCCC(=O)N1CCCC(CC(=O)Nc2cc3c(cc2C(C)=O)OCO3)C1] | 375 | 0.016 | (DMSO-d$_6$, rotamers) δ 0.86 (two t, J = 7.4 Hz, 3H), 1.23-1.30 (m, 2H), 1.49 (q, J = 7.4 Hz, 2H), 1.59-1.91 (m, 2H), 2.22-2.40 (m, 5H), 2.57 (s, 3H), 2.84 (dd, J = 13.3, 10.3 Hz, 1H), 2.99 (ddd, J = 13.9, 11.2, 2.8 Hz, 1H), 3.70-3.80 (m, 1H), 4.11-4.23 (m, 1H), 6.14 (s, 2H), 7.58 (s, 1H), 8.06 (s, 0.5H), 8.11 (s, 0.5H), 11.76 (s, 0.5H), 11.81 (s, 0.5H). |
| 205 | 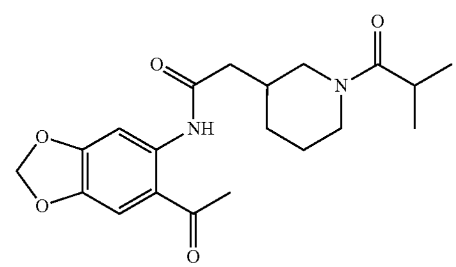 [SMILES: CC(=O)c1cc2c(cc1NC(=O)CC1CCCN(C(=O)C(C)C)C1)OCO2] | 375 | 0.012 | (DMSO-d$_6$, rotamers) δ 0.95-0.99 (m, 6H), 1.24-1.29 (m, 2H), 1.61-1.80 (m, 2H), 2.21-2.38 (m, 3H), 2.56 (s, 3H), 2.80-2.87 (m, 2H), 3.02-3.07 (m, 1H), 3.76-3.91 (m, 1H), 4.21 (d, J = 9.2 Hz, 1H), 6.14 (s, 2H), 7.58 (s, 1H), 8.05 (s, 0.5H), 8.11 (s, 0.5H), 11.75 (s, 0.5H), 11.80 (s, 0.5H). |
| 206 | 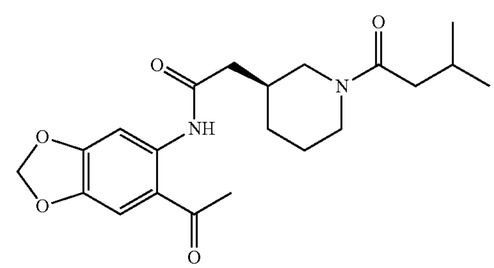 [SMILES: CC(=O)c1cc2c(cc1NC(=O)C[C@@H]1CCCN(C(=O)CC(C)C)C1)OCO2] | 389 | 0.025 | (DMSO-d$_6$, rotamers) δ 0.87 (two d, J = 15.9 Hz, 6H), 1.06-1.41 (m, 2H), 1.54-1.70 (m, 1H), 1.74-1.85 (m, 2H), 1.88-2.06 (m, 1H), 2.05-2.50 (m, 4.5H), 2.56 (s, 3H), 2.59-2.70 (m, 0.5H), 2.78-2.89 (m, 0.5H), 2.94-3.05 (m, 0.5H), 3.68-3.84 (m, 1H), 4.11-4.26 (m, 1H), 6.14 (s, 2H), 7.58 (s, 1H), 8.07 (s, 0.5H), 8.11 (s, 0.5H), 11.77 (s, 0.5H), 11.81 (s, 0.5H). |

TABLE 8-continued

| SID | Structure | Obs Mol Ion MS (M + 1) | hT2R54 IC50 (uM) | ¹H NMR (400 MHz) |
|---|---|---|---|---|
| 207 | 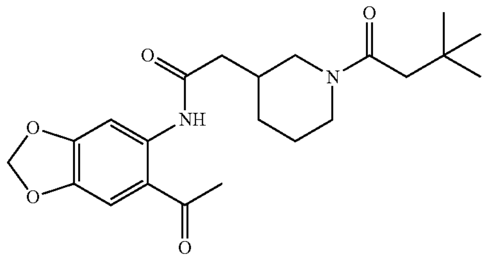 [SMILES: CC(=O)c1cc2c(cc1NC(=O)CC1CCCN(C(=O)CC(C)(C)C)C1)OCO2] | 403 | 0.36 | (DMSO-d$_6$, rotamers) δ 0.94 (s, 4.5H), 0.97 (s, 4.5H), 1.09-1.31 (m, 2H), 1.60-1.91 (m, 3H), 2.17-2.46 (m, 4H), 2.57 (s, 3H), 2.84 (dd, J = 13.4, 10.2 Hz, 1H), 3.01 (ddd, J = 13.7, 11.5, 2.6 Hz, 1H), 3.84 (dd, J = 29.6, 13.5 Hz, 1H), 4.24 (t, J = 15.2 Hz, 1H), 6.14 (s, 2H), 7.58 (s, 1H), 8.07 (s, 0.5H), 8.12 (s, 0.5H), 11.76 (s, 0.5H), 11.82 (s, 0.5H). |
| 208 | 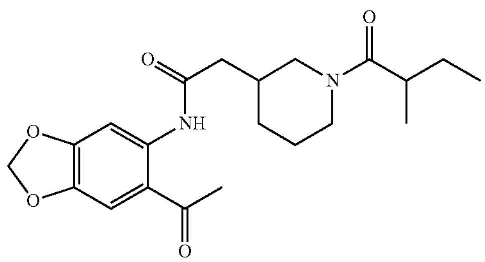 [SMILES: CCC(C)C(=O)N1CCCC(CC(=O)Nc2cc3c(cc2C(C)=O)OCO3)C1] | 389 | 0.17 | (DMSO-d$_6$, rotamers) δ 0.75-0.82 (m, 3H), 0.93-0.97 (m, 3H), 1.23-1.31 (m, 2H), 1.50-1.57 (m, 3H), 2.24-2.39 (m, 3H), 2.56 (s, 3H), 2.80-2.87 (m, 1H), 3.04-3.07 (m, 1H), 3.80-3.94 (m, 1H), 4.17-4.26 (m, 1H), 6.14 (s, 2H), 7.58 (s, 1H), 8.06 (s, 0.5H), 8.12 (s, 0.5H), 11.72 (s, 0.5H), 11.81 (s, 0.5H). |
| 209 | 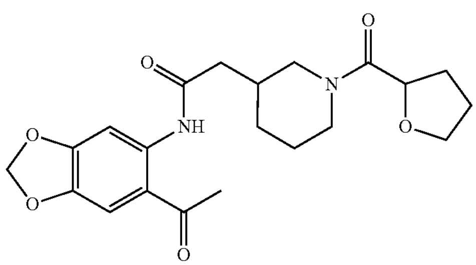 [SMILES: CC(=O)c1cc2c(cc1NC(=O)CC1CCCN(C(=O)C3CCCO3)C1)OCO2] | 403 | 0.056 | (DMSO-d$_6$, rotamers) δ 1.24-1.43 (m, 2H), 1.60-1.67 (m, 2H), 1.77-1.86 (m, 4H), 1.98 (m, 1H), 2.22-2.39 (m, 2H), 2.56 (s, 3H), 2.84-2.89 (m, 1H), 2.97-3.09 (m, 1H), 3.65-3.92 (m, 3H), 4.08-4.18 (m, 1H), 4.58-4.66 (m, 1H), 6.14 (s, 2H), 7.58 (s, 1H), 8.07 (s, 0.5H), 8.11 (s, 0.5H), 11.77 (s, 0.5H), 11.80 (s, 0.5H). |
| 210 | 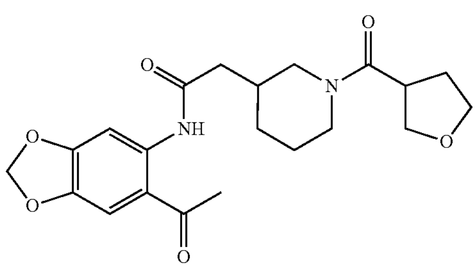 [SMILES: CC(=O)c1cc2c(cc1NC(=O)CC1CCCN(C(=O)C3CCOC3)C1)OCO2] | 403 | 1.34 | (DMSO-d$_6$, rotamers) δ 1.24-1.29 (m, 2H), 1.64-2.07 (m, 5H), 2.26-2.45 (m, 3H), 2.57 (s, 3H), 2.84 (dd, J = 13.4, 10.3 Hz, 1H), 3.00-3.08 (m, 1H), 3.59-3.72 (m, 4H), 3.78-3.94 (m, 1H), 4.18-4.21 (m, 1H), 6.14 (s, 2H), 7.58 (s, 1H), 8.05 (s, 0.5H), 8.11 (s, 0.5H), 11.74 (s, 0.5H), 11.80 (s, 0.5H). |
| 211 | 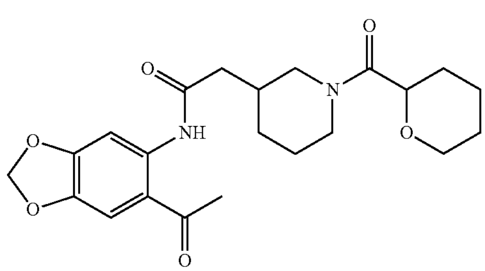 [SMILES: CC(=O)c1cc2c(cc1NC(=O)CC1CCCN(C(=O)C3CCCCO3)C1)OCO2] | 417 | 0.018 | (DMSO-d$_6$, rotamers) δ 1.23-1.29 (m, 2H), 1.40-1.66 (m, 6H), 1.77-1.81 (m, 2H), 1.94 (m, 1H), 2.22-2.36 (m, 2H), 2.57 (s, 1.5H), 2.57 (s, 1.5H), 2.81-2.89 (m, 1H), 2.95-3.07 (m, 1H), 3.72-4.21 (m, 3H), 6.14 (s, 2H), 7.58 (s, 0.5H), 7.59 (s, 0.5H), 8.09-8.15 (three s, 1H), 11.77-11.88 (three s, 1H). |

TABLE 8-continued

| SID | Structure | Obs Mol Ion MS; (M + 1) | hT2R54 IC50 (uM) | $^1$H NMR (400 MHz) |
|---|---|---|---|---|
| 212 | 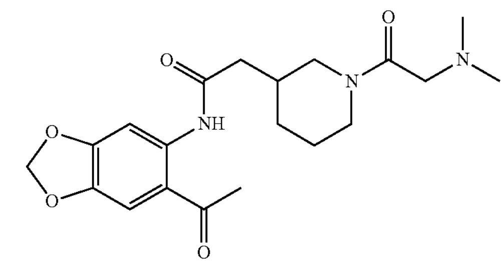 [SMILES: CC(=O)c1cc2c(cc1NC(=O)CC1CCCN(C(=O)CN(C)C)C1)OCO2] | 390 | >1 | (DMSO-d$_6$, rotamers) δ 1.23-1.45 (m, 2H), 1.60-1.65 (m, 1H), 1.76-1.84 (m, 1H), 1.96 (m, 1H), 2.07 (s, 3H), 2.16 (s, 3H), 2.26-2.33 (m, 2H), 2.56 (s, 1.5H), 2.57 (s, 1.5H), 2.67-2.75 (m, 1H), 2.86 (dd, J = 13.1, 9.9 Hz, 0.5H), 2.96-3.00 (m, 2H), 3.07-3.10 (m, 0.5H), 3.84-3.94 (m, 1H), 4.02-4.05 (m, 0.5H), 4.14-4.18 (m, 0.5H), 6.14 (s, 2H), 7.58 (s, 0.5H), 7.59 (s, 0.5H), 8.11 (s, 0.5H), 8.13 (s, 0.5H), 11.81 (s, 0.5H), 11.83 (s, 0.5H). |
| 213 | 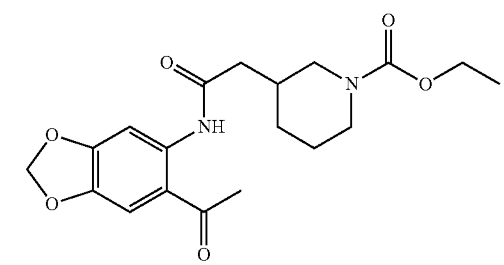 [SMILES: CCOC(=O)N1CCCC(CC(=O)Nc2cc3c(cc2C(C)=O)OCO3)C1] | 377 | 0.05 | $^1$H NMR (400 MHz, DMSO-d$_6$) δ 1.09-1.39 (m, 7H), 1.58-1.63 (m, 1H), 2.23-2.37 (m, 2H), 2.57 (s, 3H), 2.85 (ddd, J = 13.4, 11.0, 3.2 Hz, 1H), 3.75-3.86 (m, 2H), 4.00 (q, J = 7.0 Hz, 2H), 6.14 (s, 2H), 7.58 (s, 1H), 8.10 (s, 1H), 11.79 (s, 1H). |
| 214 | 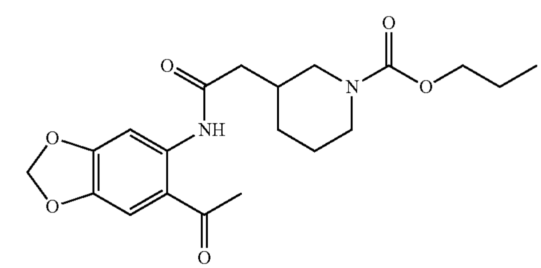 [SMILES: CCCOC(=O)N1CCCC(CC(=O)Nc2cc3c(cc2C(C)=O)OCO3)C1] | 391 | 0.32 | (DMSO-d$_6$) δ 0.80-0.89 (m, 3H), 1.11-1.38 (m, 4H), 1.52-1.64 (m, 2H), 1.89 (m, 1H), 2.24-2.36 (m, 3H), 2.57 (s, 3H), 2.85 (ddd, J = 13.6, 10.9, 3.1 Hz, 1H), 3.78-3.92 (m, 4H), 6.14 (s, 2H), 7.58 (s, 1H), 8.10 (s, 1H), 11.80 (s, 1H). |
| 215 | 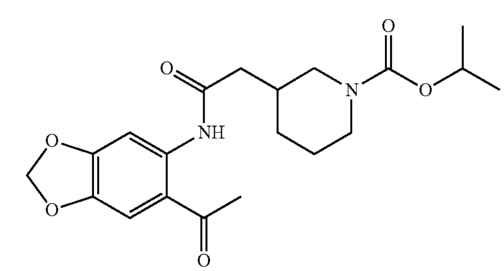 [SMILES: CC(=O)c1cc2c(cc1NC(=O)CC1CCCN(C(=O)OC(C)C)C1)OCO2] | 391 | 0.16 | (DMSO-d$_6$) δ 1.14 (m, 6H), 1.26-1.36 (m, 1H), 1.57-1.62 (m, 1H), 1.74-1.79 (m, 1H), 1.89 (m, 1H), 2.23-2.36 (m, 3H), 2.57 (s, 3H), 2.67-2.87 (m, 2H), 3.76 (m, 2H), 4.70-4.75 (m, 1H), 6.14 (s, 2H), 7.58 (s, 1H), 8.10 (s, 1H), 11.80 (s, 1H). |
| 216 | 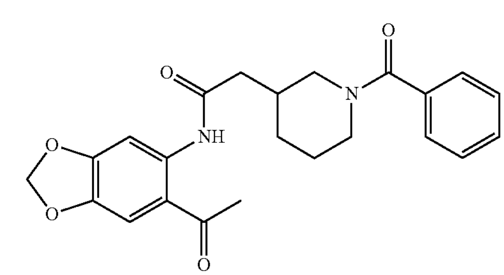 [SMILES: CC(=O)c1cc2c(cc1NC(=O)CC1CCCN(C(=O)c3ccccc3)C1)OCO2] | 409 | 0.08 | (DMSO-d$_6$, rotamers) δ 1.29-1.35 (m, 1H), 1.46 (br.s, 1H), 1.58 (br.s, 0.5H), 1.72 (br.s, 0.5H), 1.83-1.86 (m, 1H), 2.00 (br.s, 1H), 2.19-2.40 (m, 2H), 2.56 (s, 3H), 2.72-3.01 (m, 2H), 3.46 (br.s, 0.5H), 3.57 (br.s, 0.5H), 4.30 (br.s, 1H), 6.14 (s, 2H), 7.33-7.43 (m, 5H), 7.57 (s, 1H), 7.89 (br.s, 0.5H), 8.13 (br.s, 0.5H), 11.67 (br.s, 0.5H), 11.83 (br.s, 0.5H). |

TABLE 8-continued

| SID | Structure | Obs Mol Ion MS (M + 1) | hT2R54 IC50 (uM) | ¹H NMR (400 MHz) |
|---|---|---|---|---|
| 217 | 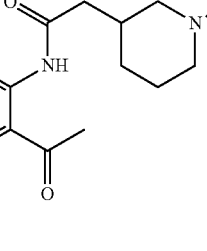 | 425 | 0.48 | (DMSO-d₆, rotamers) δ 1.23-1.32 (m, 1H), 1.36-1.44 (m, 1H), 1.61 (m, 1H), 1.79-1.81 (m, 1H), 1.97 (m, 1H), 2.28 (m, 2H), 2.56 (s, 3H), 2.72-2.78 (m, 1H), 2.91 (m, 1H), 3.42 (m, 1H), 4.27 (m, 1H), 6.14 (s, 2H), 6.80 (m, 2H), 7.05 (br.s, 1H), 7.15 (br.s, 1H), 7.57 (s, 1H), 7.89 (br.s, 0.5H), 7.12 (br.s, 0.5H), 9.71 (br.s, 1H), 11.69 (br.s, 0.5H), 11.82 (br.s, 0.5H). |
| 218 | 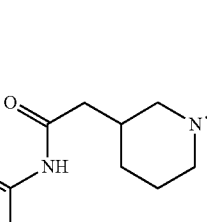 | 425 | >1 | (DMSO-d₆, rotamers) δ 1.23-1.33 (m, 1H), 1.40 (m, 1H), 1.59-1.69 (m, 1H), 1.82-1.84 (m, 1H), 1.97 (m, 1H), 2.29 (m, 2H), 2.56 (s, 3H), 2.84-2.97 (m, 2H), 3.49 (br.s, 0.5H), 3.59 (br.s, 0.5H), 4.28 (m, 1H), 6.14 (s, 2H), 6.69-6.81 (m, 3H), 7.05-7.24 (m, 1H), 7.57 (s, 1H), 7.93 (br.s, 0.5H), 8.13 (br.s, 0.5H), 9.58 (br.s, 0.5H), 9.64 (br.s, 0.5H), 11.69 (br.s, 0.5H), 11.83 (br.s, 0.5H). |
| 219 | 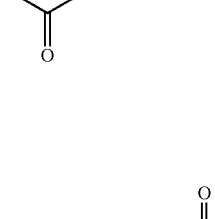 | 425 | 1.46 | (DMSO-d₆) δ 1.23-1.33 (m, 1H), 1.38-1.47 (m, 1H), 1.64 (m, 1H), 1.82-1.85 (m, 1H), 1.97 (m, 1H), 2.29 (m, 2H), 2.56 (s, 3H), 2.74 (br.s, 1H), 2.91 (br.s, 1H), 3.96 (br.s, 2H), 6.14 (s, 2H), 6.73 (m, 2H), 7.19 (d, J = 8.4 Hz, 2H), 7.58 (s, 1H), 8.05 (br.s, 1H), 9.77 (s, 1H), 11.78 (s, 1H). |
| 220 | 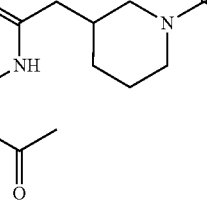 | 399 | ~0.01 | (DMSO-d₆) δ 1.21-1.52 (m, 2H), 1.65-1.76 (m, 1H), 1.80-1.89 (m, 1H), 1.95-2.06 (m, 1H), 2.27-2.42 (m, 2H), 2.56 (s, 3H), 2.98 (br s, 2H), 4.06-4.28 (m, 2H), 6.14 (s, 2H), 6.57 (br. s, 1H), 6.97 (dd, J = 3.4, 0.7 Hz, 1H), 7.58 (s, 1H), 7.74 (br. s, 1H), 8.08 (s, 1H), 11.79 (s, 1H). |
| 221 | 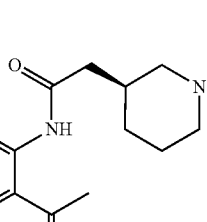 | 413 | 0.060 | (DMSO-d₆) δ 1.29-1.45 (m, 2H), 1.62-1.67 (m, 1H), 1.80-1.83 (m, 1H), 2.30-2.33 (m, 3H), 2.54 (s, 3H), 3.09-3.15 (m, 2H), 3.56-3.63 (m, 2H), 3.79 (s, 3H), 6.12 (s, 2H), 7.60 (s, 1H), 7.98 (s, 1H), 8.06 (s, 1H), 8.14 (br.s, 1H), 11.76 (br.s, 1H). |

TABLE 8-continued

| SID | Structure | Obs Mol Ion MS; (M + 1) | hT2R54 IC50 (uM) | ¹H NMR (400 MHz) |
|---|---|---|---|---|
| 222 | 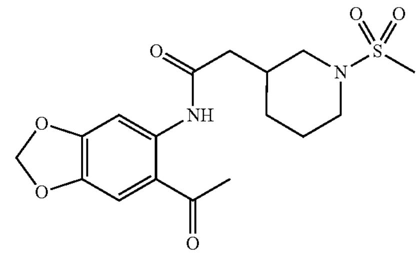 [SMILES: CC(=O)c1cc2c(cc1NC(=O)CC1CCCN(S(C)(=O)=O)C1)OCO2] | 383 | 0.06 | (DMSO-d₆) δ 1.12-1.29 (m, 2H), 1.49-1.52 (m, 1H), 1.71-1.77 (m, 1H), 2.05 (m, 1H), 2.30-2.42 (m, 2H), 2.57 (s, 3H), 2.67-2.73 (m, 2H), 2.83 (s, 3H), 3.40-3.43 (m, 1H), 3.51 (dd, J = 11.6, 3.2 Hz, 1H), 6.14 (s, 2H), 7.58 (s, 1H), 8.09 (s, 1H), 11.79 (s, 1H). |
| 223 | 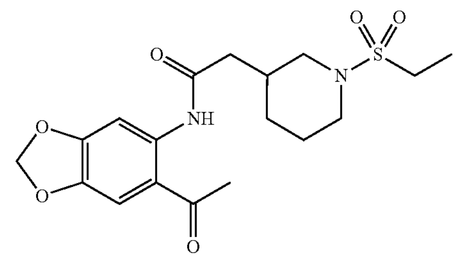 [SMILES: CCS(=O)(=O)N1CCCC(CC(=O)Nc2cc3c(cc2C(C)=O)OCO3)C1] | 397 | 0.04 | (DMSO-d₆) δ 1.19 (t, J = 7.2 Hz, 3H), 1.42-1.49 (m, 2H), 1.67-1.78 (m, 2H), 2.28-2.41 (m, 3H), 2.57 (s, 3H), 2.62 (dd, J = 11.8, 9.9 Hz, 1H), 2.80 (td, J = 11.5, 2.6 Hz, 1H), 3.01 (q, J = 7.4, 2H), 3.44-3.47 (m, 1H), 3.55 (dd, J = 12.2, 3.6 Hz, 1H), 6.14 (s, 2H), 7.58 (s, 1H), 8.09 (s, 1H), 11.86 (s, 1H). |
| 224 | 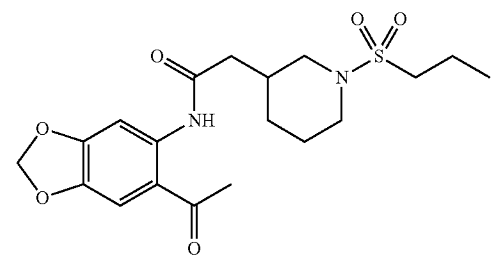 [SMILES: CCCS(=O)(=O)N1CCCC(CC(=O)Nc2cc3c(cc2C(C)=O)OCO3)C1] | 411 | 0.04 | (DMSO-d₆) δ 0.97 (t, J = 7.4 Hz, 3H), 1.11-1.28 (m, 2H), 1.43-1.51 (m, 2H), 1.62-1.77 (m, 2H), 2.28-2.41 (m, 3H), 2.57 (s, 3H), 2.60-2.63 (m, 1H), 2.77 (dd, J = 11.4, 2.0 Hz, 1H), 2.91-3.02 (m, 2H), 3.43-3.46 (m, 1H), 3.54 (dd, J = 11.2, 1.8 Hz, 1H), 6.14 (s, 2H), 7.58 (s, 1H), 8.09 (s, 1H), 11.79 (s, 1H). |
| 225 | 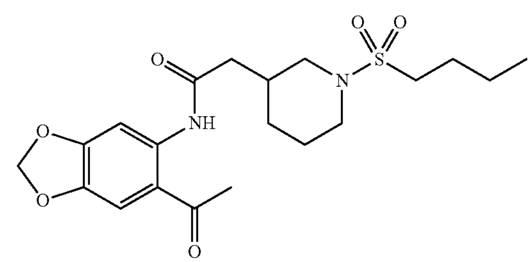 [SMILES: CCCCS(=O)(=O)N1CCCC(CC(=O)Nc2cc3c(cc2C(C)=O)OCO3)C1] | 425 | 0.07 | (DMSO-d₆) δ 0.89 (t, J = 7.6 Hz, 3H), 1.11-1.29 (m, 2H), 1.38 (dq, J = 14.6, 7.3 Hz, 2H), 1.46-1.48 (m, 1H), 1.58-1.73 (m, 3H), 2.28-2.41 (m, 3H), 2.58 (s, 3H), 2.61 (dd, J = 11.5, 10.1 Hz, 1H), 2.79 (td, J = 11.4, 10.8, 2.3 Hz, 1H), 2.97-3.01 (m, 2H), 3.44-3.47 (m, 1H), 3.54 (dd, J = 11.6, 3.5 Hz, 1H), 6.14 (s, 2H), 7.58 (s, 1H), 8.09 (s, 1H), 11.80 (s, 1H). |
| 226 | 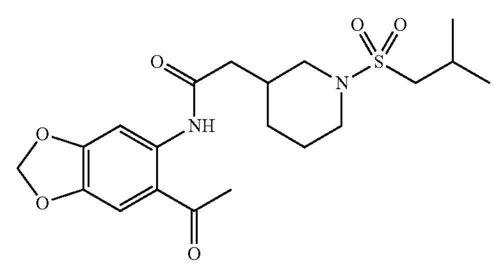 [SMILES: CC(=O)c1cc2c(cc1NC(=O)CC1CCCN(S(=O)(=O)CC(C)C)C1)OCO2] | 425 | 0.16 | (DMSO-d₆) δ 1.01 (d, J = 6.8 Hz, 6H), 1.13-1.19 (m, 1H), 1.23-1.30 (m, 1H), 1.68-1.77 (m, 2H), 1.99-2.13 (m, 2H), 2.29-2.41 (m, 2H), 2.54-2.59 (m, 4H), 2.75 (td, J = 11.2, 10.8, 2.2 Hz, 1H), 2.86 (d, J = 6.4 Hz, 2H), 6.14 (s, 2H), 7.58 (s, 1H), 8.09 (s, 1H), 11.79 (s, 1H). |

TABLE 8-continued

| SID | Structure | Obs Mol Ion MS (M + 1) | hT2R54 IC50 (uM) | ¹H NMR (400 MHz) |
|---|---|---|---|---|
| 227 | 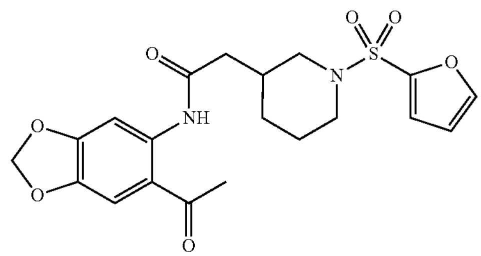 [SMILES: CC(=O)c1cc2c(cc1NC(=O)CC1CCCN(S(=O)(=O)c3ccco3)C1)OCO2] | 435 | 0.13 | (DMSO-d₆) δ 1.08-1.10 (m, 1H), 1.42-1.48 (m, 1H), 1.67-1.70 (m, 2H), 1.99 (m, 1H), 2.26-2.43 (m, 3H), 2.55 (s, 3H), 2.59-2.62 (m, 1H), 3.46-3.49 (m, 1H), 3.56-3.59 (m, 1H), 6.14 (s, 2H), 6.73 (dd, J = 3.5, 1.8 Hz, 1H), 7.17 (dd, J = 3.5, 0.9 Hz, 1H), 7.58 (s, 1H), 8.02 (dd, J = 1.8, 0.9 Hz, 1H), 8.08 (s, 1H), 11.76 (s, 1H). |
| 228 | 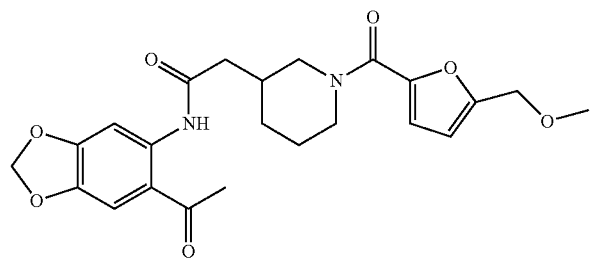 [SMILES: COCc1ccc(C(=O)N2CCCC(CC(=O)Nc3cc4c(cc3C(C)=O)OCO4)C2)o1] | 443 | 0.02 | (DMSO-d₆) δ 1.23-1.47 (m, 2H), 1.68-1.72 (m, 1H), 1.82-1.86 (m, 1H), 2.04 (m, 1H), 2.35 (d, J = 7.2 Hz, 2H), 2.56 (s, 3H), 2.94 (br.s, 2H), 3.23 (s, 3H), 4.11-4.14 (m, 1H), 4.19-4.23 (m, 1H), 4.34 (br.s, 2H), 6.14 (s, 2H), 6.15 (br.s, 1H), 6.90 (d, J = 3.2 Hz, 1H), 7.58 (s, 1H), 8.08 (s, 1H), 11.79 (s, 1H). |
| 229 | 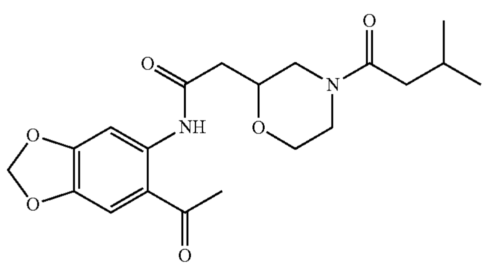 | 391 | 0.22 | (DMSO-d₆, rotamers) δ 0.85-0.92 (two d, J = 6.4 Hz, 6H), 1.94-2.02 (m, 1H), 2.12-2.27 (m, 2H), 2.57 (s, 3H), 2.63-2.71 (m, 2H), 2.90-2.96 (m, 1H), 3.08-3.15 (m, 1H), 3.70-3.92 (m, 3H), 4.17-4.21 (m, 1H), 4.31-4.35 (m, 1H), 6.14 (s, 2H), 7.58 (s, 1H), 8.10 (s, 0.5H), 8.12 (s, 0.5H), 11.83 (s, 0.5H), 11.86 (s, 0.5H). |
| 230 | 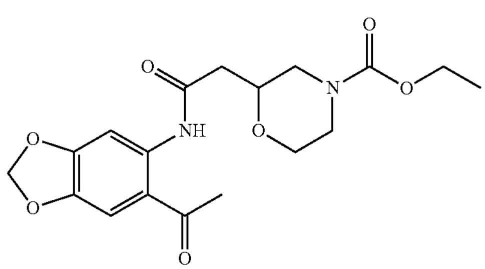 | 379 | 0.16 | (DMSO-d₆) δ 1.18 (t, J = 7.2 Hz, 3H), 2.57 (s, 3H), 2.63-2.68 (m, 2H), 3.43 (td, J = 11.6, 2.8 Hz, 2H), 3.73-3.92 (m, 5H), 4.02-4.07 (m, 2H), 6.14 (s, 2H), 7.58 (s, 1H), 8.11 (s, 1H), 11.85 (s, 1H). |
| 231 | 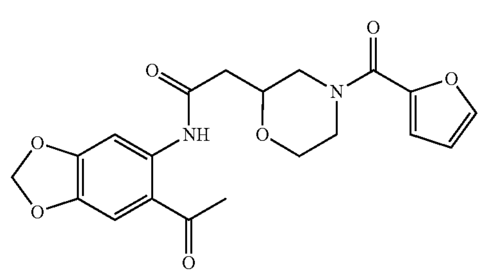 [SMILES: CC(=O)c1cc2c(cc1NC(=O)CC1CN(C(=O)c3ccco3)CCO1)OCO2] | 401 | 0.24 | (DMSO-d₆) δ 2.57 (s, 3H), 2.71 (dd, J = 15.2, 4.3 Hz, 2H), 3.48-3.55 (m, 2H), 3.85-3.91 (m, 3H), 4.13-4.20 (m, 1H), 4.33 (d, J = 13.6 Hz, 1H), 6.14 (s, 2H), 6.63 (dd, J = 3.5, 1.8 Hz, 1H), 6.98-7.09 (m, 1H), 7.58 (s, 1H), 7.84 (dd, J = 1.7, 0.7 Hz, 1H), 8.11 (s, 1H), 11.86 (s, 1H). |

TABLE 8-continued

| SID | Structure | Obs Mol Ion MS; (M + 1) | hT2R54 IC50 (uM) | ¹H NMR (400 MHz) |
|---|---|---|---|---|
| 232 | 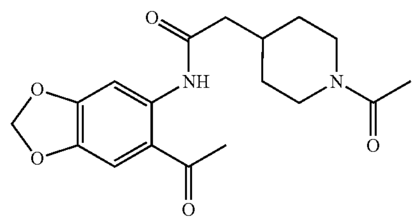 [SMILES: CC(=O)c1cc2c(cc1NC(=O)CC1CCN(C(C)=O)CC1)OCO2] | 347 | >1 | (DMSO-d$_6$) δ 0.95-1.24 (m, 2H), 1.60-1.74 (m, 2H), 1.9-2.06 (m, 4H), 2.30 (d, J = 7.1 Hz, 2H), 2.57 (s, 3H), 3.00 (ddd, J = 13.5, 12.2, 2.7 Hz, 1H), 3.27-3.43 (m, 1H), 3.72-3.83 (m, 1H), 4.33 (dm, J = 13.1 Hz, 1H), 6.13 (s, 2H), 7.58 (s, 1H), 8.11 (s, 1H), 11.81 (s, 1H). |
| 233 | 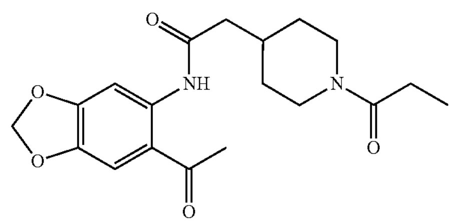 [SMILES: CCC(=O)N1CCC(CC(=O)Nc2cc3c(cc2C(C)=O)OCO3)CC1] | 361 | 0.086 | (DMSO-d$_6$) δ 0.97 (t, J = 7.4 Hz, 3H), 1.00-1.21 (m, 2H), 1.68 (t, J = 14.8 Hz, 2H), 1.93-2.06 (m, 1H), 2.25-2.34 (m, 4H), 2.50-2.56 (m, 1H), 2.57 (s, 3H), 2.91-3.04 (m, 1H), 3.82 (d, J = 13.7 Hz, 1H), 4.35 (d, J = 13.0 Hz, 1H), 6.13 (s, 2H), 7.58 (s, 1H), 8.11 (s, 1H), 11.81 (s, 1H). |
| 234 | 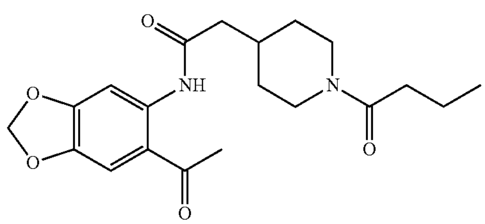 | 375 | >1 | (DMSO-d$_6$) δ 0.87 (t, J = 7.4 Hz, 3H), 0.92-1.23 (m, 2H), 1.49 (h, J = 7.4 Hz, 2H), 1.68 (t, J = 15.3 Hz, 2H), 1.94-2.06 (m, 1H), 2.22-2.28 (m, 2H), 2.30 (d, J = 7.0 Hz, 2H), 2.52-2.56 (m, 1H), 2.57 (s, 3H), 2.98 (t, J = 13.0 Hz, 1H), 3.84 (d, J = 13.8 Hz, 1H), 4.36 (d, J = 13.2 Hz, 1H), 6.13 (s, 2H), 7.58 (s, 1H), 8.11 (s, 1H), 11.80 (s, 1H). |
| 235 | 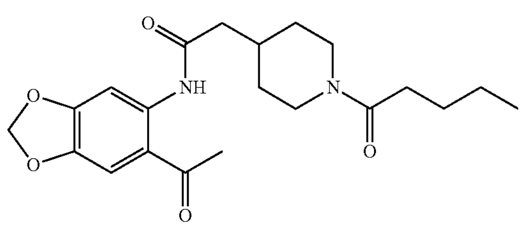 [SMILES: CCCCC(=O)N1CCC(CC(=O)Nc2cc3c(cc2C(C)=O)OCO3)CC1] | 389 | 0.077 | (DMSO-d$_6$) δ 0.87 (t, J = 7.3 Hz, 3H), 0.95-1.21 (m, 2H), 1.23-1.33 (m, 2H), 1.39-1.51 (m, 2H), 1.62-1.74 (m, 2H), 1.93-2.06 (m, 1H), 2.23-2.34 (m, 4H), 2.47-2.55 (m, 1H), 2.57 (s, 3H), 2.92-3.03 (m, 1H), 3.84 (d, J = 13.6 Hz, 1H), 4.35 (d, J = 13.2 Hz, 1H), 6.13 (s, 2H), 7.58 (s, 1H), 8.11 (s, 1H), 11.80 (s, 1H). |
| 236 | 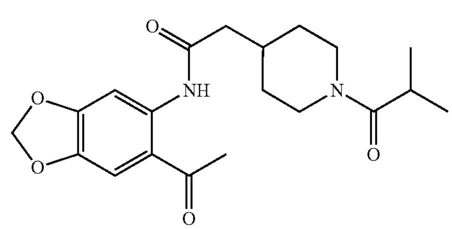 [SMILES: CC(=O)c1cc2c(cc1NC(=O)CC1CCN(C(=O)C(C)C)CC1)OCO2] | 375 | >1 | (DMSO-d$_6$) δ 0.93-1.21 (m, 8H), 1.61-1.78 (m, 2H), 1.94-2.07 (m, 1H), 2.31 (d, J = 7.1 Hz, 2H), 2.50-2.56 (m, 1H), 2.57 (s, 3H), 2.79-2.90 (m, 1H), 3.00 (t, J = 12.3 Hz, 1H), 3.92 (d, J = 13.6 Hz, 1H), 4.37 (d, J = 13.0 Hz, 1H), 6.13 (s, 2H), 7.58 (s, 1H), 8.11 (s, 1H), 11.80 (s, 1H). |

TABLE 8-continued

| SID | Structure | Obs Mol Ion MS; (M + 1) | hT2R54 IC50 (uM) | $^1$H NMR (400 MHz) |
|---|---|---|---|---|
| 237 | 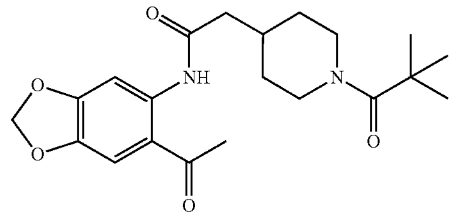 [SMILES: CC(=O)c1cc2c(cc1NC(=O)CC1CCN(C(=O)C(C)(C)C)CC1)OCO2] | 389 | 0.19 | (DMSO-d$_6$) δ 0.99-1.15 (m, 2H), 1.17 (s, 9H), 1.69 (d, J = 12.9 Hz, 2H), 1.96-2.08 (m, 1H), 2.31 (d, J = 7.1 Hz, 2H), 2.57 (s, 3H), 2.77 (t, J = 12.7 Hz, 2H), 4.25 (d, J = 13.4 Hz, 2H), 6.13 (s, 2H), 7.58 (s, 1H), 8.11 (s, 1H), 11.80 (s, 1H). |
| 238 | 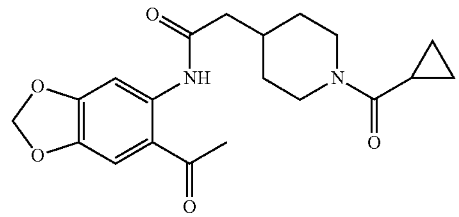 [SMILES: CC(=O)c1cc2c(cc1NC(=O)CC1CCN(C(=O)C3CC3)CC1)OCO2] | 373 | 0.47 | $^1$H NMR (400 MHz, DMSO-d$_6$) δ 0.60-0.74 (m, 4H), 0.96-1.24 (m, 2H), 1.60-1.80 (m, 2H), 1.89-2.10 (m, 2H), 2.32 (d, J = 7.1 Hz, 2H), 2.52-2.62 (m, 4H), 3.07 (t, J = 13.2 Hz, 1H), 4.17-4.38 (m, 2H), 6.14 (s, 2H), 7.58 (s, 1H), 8.12 (s, 1H), 11.81 (s, 1H). |
| 239 | 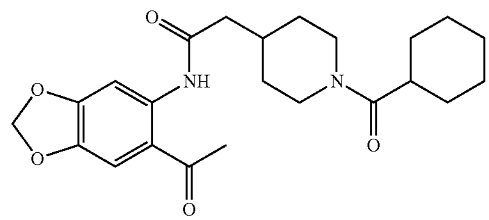 [SMILES: CC(=O)c1cc2c(cc1NC(=O)CC1CCN(C(=O)C3CCCCC3)CC1)OCO2] | 415 | >1 | (DMSO-d$_6$) δ 0.92-1.38 (m, 7.5H), 1.54-1.77 (m, 7.5H), 1.94-2.06 (m, 1H), 2.30 (d, J = 7.1 Hz, 2H), 2.50-2.56 (m, 1H), 2.57 (s, 3H), 2.99 (t, J = 12.8 Hz, 1H), 3.91 (d, J = 13.7 Hz, 1H), 4.36 (d, J = 13.1 Hz, 1H), 6.13 (s, 2H), 7.58 (s, 1H), 8.11 (s, 1H), 11.80 (s, 1H). |
| 240 | 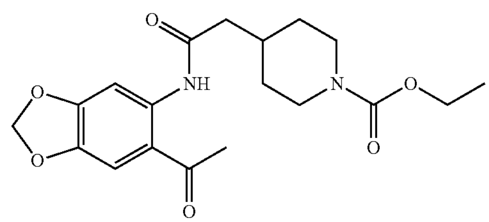 [SMILES: CCOC(=O)N1CCC(CC(=O)Nc2cc3c(cc2C(C)=O)OCO3)CC1] | 377 | 0.034 | (DMSO-d$_6$) δ 1.04-1.14 (m, 2H), 1.17 (t, J = 7.1 Hz, 3H), 1.66 (br d, J = 13.2 Hz, 2H), 1.89-1.99 (m, 1H), 2.31 (d, J = 7.1 Hz, 2H), 2.57 (s, 3H), 2.69-2.87 (m, 2H), 3.95 (br d, J = 13.2 Hz, 2H), 4.04 (q, J = 7.2 Hz, 2H), 6.13 (s, 2H), 7.58 (s, 1H), 8.11 (s, 1H), 11.81 (s, 1H). |
| 241 | 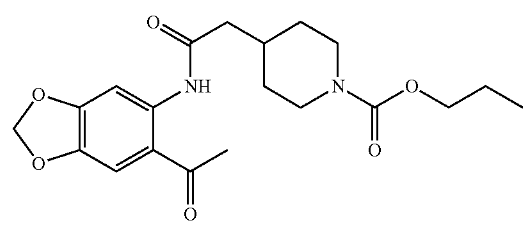 [SMILES: CCCOC(=O)N1CCC(CC(=O)Nc2cc3c(cc2C(C)=O)OCO3)CC1] | 391 | 0.072 | (DMSO-d$_6$) δ 0.88 (t, J = 7.4 Hz, 3H), 1.04-1.16 (m, 2H), 1.51-1.61 (m, 2H), 1.62-1.70 (m, 2H), 1.89-2.00 (m, 1H), 2.31 (d, J = 7.1 Hz, 2H), 2.56 (s, 3H), 2.68-2.86 (m, 2H), 3.87-4.00 (m, 4H), 6.13 (s, 2H), 7.58 (s, 1H), 8.11 (s, 1H), 11.80 (s, 1H). |
| 242 | 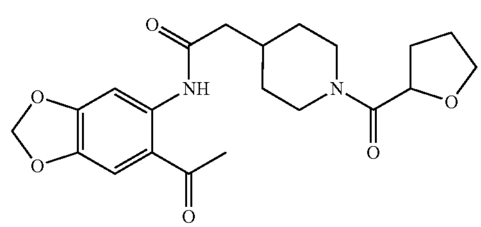 [SMILES: CC(=O)c1cc2c(cc1NC(=O)CC1CCN(C(=O)C3CCCO3)CC1)OCO2] | 403 | 0.068 | (DMSO-d$_6$) δ 0.96-1.25 (m, 2H), 1.63-1.74 (m, 2H), 1.74-1.89 (m, 2H), 1.89-2.07 (m, 3H), 2.31 (d, J = 7.1 Hz, 2H), 2.51-2.61 (m, 1H), 2.57 (s, 3H), 2.92-306 (m, 1H), 3.65-3.81 (m, 2H), 3.96 (br d, J = 13.6 Hz, 1H), 4.30 (br d, J = 12.8 Hz, 1H), 4.59-4.66 (m, 1H), 6.13 (s, 2H), 7.58 (s, 1H), 8.11 (two s, 1H), 11.79 (s, 0.5H), 11.81 (s, 0.5H). |

TABLE 8-continued

| SID | Structure | Obs Mol Ion MS; (M + 1) | hT2R54 IC50 (uM) | ¹H NMR (400 MHz) |
|---|---|---|---|---|
| 243 | 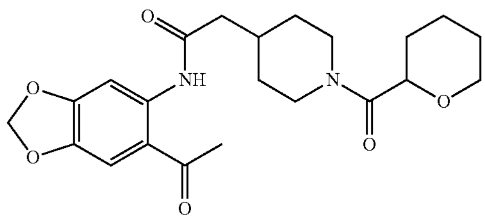 [SMILES: CC(=O)c1cc2c(cc1NC(=O)CC1CCN(C(=O)C3CCCCO3)CC1)OCO2] | 417 | 0.096 | (DMSO-d₆), rotamers) δ 0.93-1.08 (m, 1H), 1.12-1.23 (m, 1H), 1.37-1.60 (m, 4H), 1.69 (br s, 2H), 1.74-1.82 (m, 1H), 1.91-2.05 (m, 1H), 2.30 (d, J = 7.1 Hz, 2H), 2.57 (s, 3H), 2.97 (q, J = 12.8, 12.3 Hz, 1H), 3.42-3.50 (m, 1H), 3.84 (br d, J = 11.5 Hz, 1H), 3.94 (br d, J = 13.2 Hz, 1H), 4.09 (br d, J = 9.6 Hz, 1H), 4.30 (br s, 1H), 6.13 (s, 2H), 7.58 (s, 1H), 8.10-8.12 (two s, 1H), 11.77-11.83 (two s, 1H). |
| 244 | 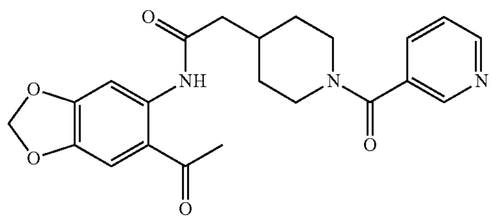 [SMILES: CC(=O)c1cc2c(cc1NC(=O)CC1CCN(C(=O)c3cccnc3)CC1)OCO2] | 410 | 0.051 | (DMSO-d6) δ 1.20-1.28 (m, 2H), 1.62-1.65 (m, 1H), 1.77-1.80 (m, 1H), 2.06 (m, 1H), 2.34 (d, J = 6.5 Hz, 2H), 2.57 (s, 3H), 2.71-2.84 (m, 1H), 3.07-3.13 (m, 1H), 3.49-3.52 (m, 1H), 4.45 (m, 1H), 6.13 (s, 2H), 7.47 (ddd, J = 7.8, 4.9, 0.9 Hz, 1H), 7.58 (s, 1H), 7.81 (dt, J = 7.8, 1.8 Hz, 1H), 8.11 (s, 1H), 8.59 (dd, J = 2.2, 0.9 Hz, 1H), 8.63 (dd, J = 4.9, 1.7 Hz, 1H), 11.82 (s, 1H). |
| 245 | 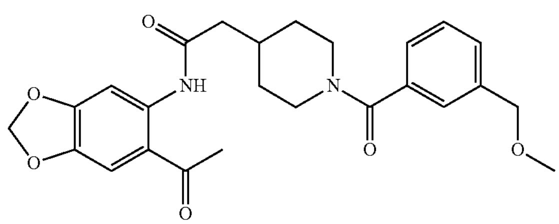 [SMILES: COCc1cccc(C(=O)N2CCC(CC(=O)Nc3cc4c(cc3C(C)=O)OCO4)CC2)c1] | 453 | 0.044 | (DMSO-d₆) δ 1.22 (br s, 2H), 1.63 (br s, 1H), 1.75 (br s, 1H), 1.97-2.12 (m, 1H), 2.34 (d, J = 7.2 Hz, 2H), 2.52-2.54 (m, 1H), 2.57 (s, 3H), 2.78 (br s, 1H), 3.04 (br s, 1H), 3.28-3.30 (m, 3H), 3.53 (br s, 1H), 4.37 (s, 2H), 6.13 (s, 2H), 7.24-7.34 (m, 2H), 7.31-7.46 (m, 2H), 7.57 (s, 1H), 8.11 (s, 1H), 11.81 (s, 1H). |
| 246 | 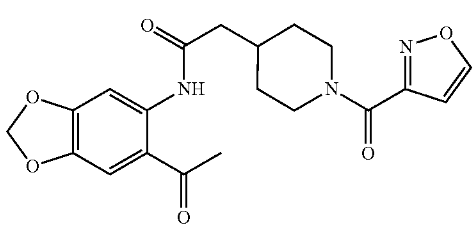 [SMILES: CC(=O)c1cc2c(cc1NC(=O)CC1CCN(C(=O)c3ccon3)CC1)OCO2] | 400 | 2.31 | (DMSO-d₆) δ 1.22-1.27 (m, 2H), 1.69-1.81 (m, 2H), 2.09 (m, 1H), 2.34 (d, J = 6.4 Hz, 2H), 2.57 (s, 3H), 2.85 (td, J = 12.7, 2.9 Hz, 1H), 3.10-3.17 (m, 1H), 3.82 (d, J = 13.5 Hz, 1H), 4.45 (d, J = 13.1 Hz, 1H), 6.13 (d, J = 0.7 Hz, 2H), 6.80 (dd, J = 1.7, 0.6 Hz, 1H), 7.58 (s, 1H), 8.11 (s, 1H), 9.07 (dd, J = 1.7, 0.7 Hz, 1H), 11.81 (s, 1H). |

TABLE 8-continued

| SID | Structure | Obs Mol Ion MS; (M + 1) | hT2R54 IC50 (uM) | ¹H NMR (400 MHz) |
|---|---|---|---|---|
| 247 | 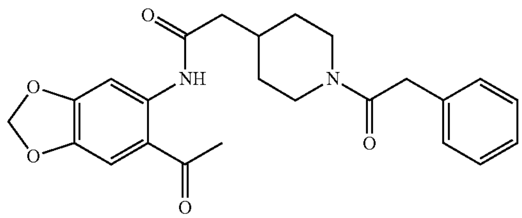 [SMILES: CC(=O)c1cc2c(cc1NC(=O)CC1CCN(C(=O)Cc3ccccc3)CC1)OCO2] | 423 | 0.49 | (DMSO-d$_6$) δ 0.9-1.08 (m, 2H), 1.64 (t, J = 16.3 Hz, 2H), 1.91-2.05 (m, 1H), 2.26 (d, J = 7.1 Hz, 2H), 2.51-2.60 (m, 4H), 2.98 (t, J = 12.7 Hz, 1H), 3.69 (s, 2H), 3.93 (d, J = 13.5 Hz, 1H), 4.36 (d, J = 13.1 Hz, 1H), 6.13 (s, 2H), 7.18-7.33 (m, 5H), 7.57 (s, 1H), 8.09 (s, 1H), 11.77 (s, 1H). |
| 248 | 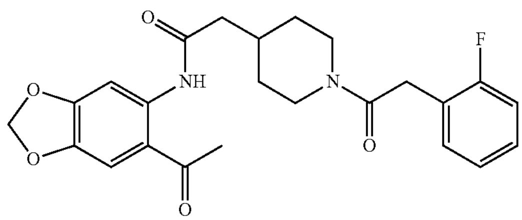 [SMILES: CC(=O)c1cc2c(cc1NC(=O)CC1CCN(C(=O)Cc3ccccc3F)CC1)OCO2] | 441 | 0.42 | (DMSO-d$_6$) δ 0.98-1.21 (m, 2H), 1.69 (t, J = 11.4 Hz, 2H), 1.95-2.08 (m, 1H), 2.31 (d, J = 7.1 Hz, 2H), 2.52-2.64 (m, 4H), 2.99-3.11 (m, 1H), 3.68-3.78 (m, 2H), 3.95 (d, J = 13.6 Hz, 1H), 4.35 (d, J = 13.0 Hz, 1H), 6.13 (s, 2H), 7.10-7.16 (m, 2H), 7.18-7.35 (m, 2H), 7.57 (s, 1H), 8.11 (s, 1H), 11.82 (s, 1H). |
| 249 | 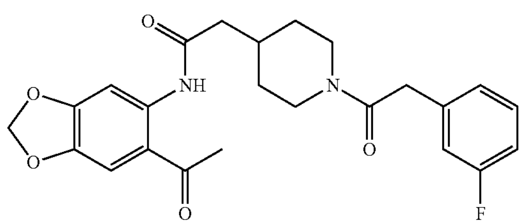 [SMILES: CC(=O)c1cc2c(cc1NC(=O)CC1CCN(C(=O)Cc3cccc(F)c3)CC1)OCO2] | 441 | 2.54 | (DMSO-d$_6$) δ 0.95-1.29 (m, 2H), 1.57-1.74 (m, 2H), 1.91-2.07 (m, 1H), 2.27 (d, J = 7.0 Hz, 2H), 2.52-2.64 (m, 4H), 3.00 (br t, J = 13.7 Hz, 1H), 3.72 (s, 2H), 3.93 (br d, J = 17.6 Hz, 1H), 4.36 (br d, J = 13.6 Hz, 1H), 6.13 (s, 2H), 6.98-7.09 (m, 3H), 7.26-7.38 (m, 1H), 7.56 (s, 1H), 8.10 (s, 1H), 11.80 (s, 1H). |
| 250 | 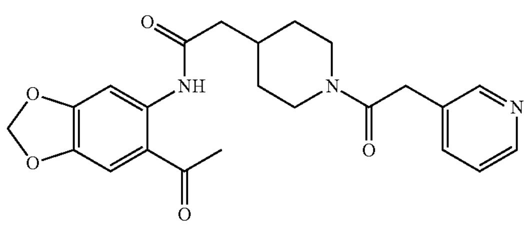 [SMILES: CC(=O)c1cc2c(cc1NC(=O)CC1CCN(C(=O)Cc3cccnc3)CC1)OCO2] | 424 | 0.76 | (DMSO-d$_6$) δ 0.96-1.17 (m, 2H), 1.64-1.74 (m, 2H), 1.92-2.06 (m, 1H), 2.30 (d, J = 7.0 Hz, 2H), 2.52-2.64 (m, 4H), 2.97-3.10 (m, 1H), 3.74 (s, 2H), 3.98 (br d, J = 12.8 Hz, 1H), 4.35 (br d, J = 13.3 Hz, 1H), 6.13 (s, 2H), 7.32 (ddd, J = 7.9, 4.8, 0.9 Hz, 1H), 7.58 (s, 1H), 7.60 (dt, J = 8.0, 2.0 Hz, 1H), 8.11 (s, 1H), 8.38-8.45 (m, 2H), 11.80 (s, 1H). |
| 251 | 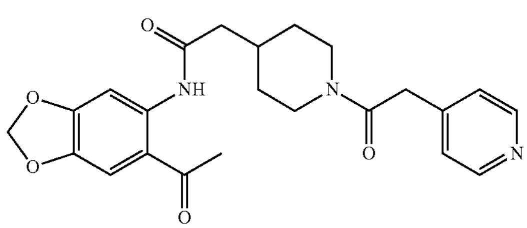 [SMILES: CC(=O)c1cc2c(cc1NC(=O)CC1CCN(C(=O)Cc3ccncc3)CC1)OCO2] | 424 | 0.58 | (DMSO-d$_6$) δ 0.99-1.12 (m, 2H), 1.67 (d, J = 12.8 Hz, 2H), 1.94-2.06 (m, 1H), 2.29 (d, J = 7.1 Hz, 2H), 2.54-2.63 (m, 1H), 2.57 (s, 3H), 2.96-3.07 (m, 1H), 3.75 (s, 2H), 3.91 (d, J = 13.5 Hz, 1H), 4.35 (d, J = 13.1 Hz, 1H), 6.13 (s, 2H), 7.19-7.26 (m, 2H), 7.58 (s, 1H), 8.10 (s, 1H), 8.43-8.51 (m, 2H), 11.79 (s, 1H). |

TABLE 8-continued

| SID | Structure | Obs Mol Ion MS (M + 1) | hT2R54 IC50 (uM) | ¹H NMR (400 MHz) |
|---|---|---|---|---|
| 252 | 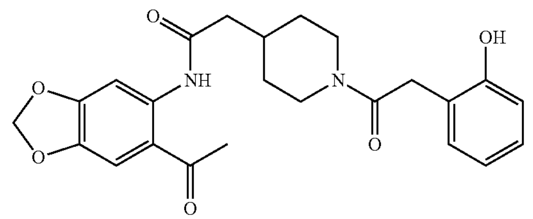 [SMILES: CC(=O)c1cc2c(cc1NC(=O)CC1CCN(C(=O)Cc3ccccc3O)CC1)OCO2] | 439 | 1.09 | (DMSO-d₆) δ 0.92-1.09 (m, 2H), 1.65 (t, J = 14.4 Hz, 2H), 1.92-2.06 (m, 1H), 2.27 (d, J = 7.0 Hz, 2H), 2.52-2.56 (m, 4H), 2.94-3.05 (m, 1H), 3.46-3.64 (m, 2H), 3.92 (br d, J = 13.7 Hz, 1H), 4.36 (br d, J = 13.1 Hz, 1H), 6.13 (s, 2H), 6.68-6.82 (m, 2H), 6.99-7.08 (m, 2H), 7.57 (s, 1H), 8.10 (s, 1H), 9.54 (s, 1H), 11.78 (s, 1H). |
| 253 | 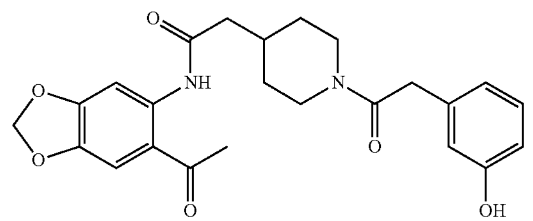 [SMILES: CC(=O)c1cc2c(cc1NC(=O)CC1CCN(C(=O)Cc3cccc(O)c3)CC1)OCO2] | 439 | 0.75 | ¹H NMR (400 MHz, DMSO-d₆) δ 0.89-1.10 (m, 2H), 1.63 (dd, J = 23.3, 13.2 Hz, 2H), 1.91-2.03 (m, 1H), 2.26 (d, J = 7.1 Hz, 2H), 2.53-2.60 (m, 4H), 2.90-3.01 (m, 1H), 3.53-2.65 (m, 2H), 3.88 (br d, J = 13.6 Hz, 1H), 4.36 (br d, J = 13.3 Hz, 1H), 6.13 (s, 2H), 6.56-6.66 (m, 3H), 7.03-7.12 (m, 1H), 7.57 (s, 1H), 8.09 (s, 1H), 9.31 (s, 1H), 11.77 (s, 1H). |
| 254 | 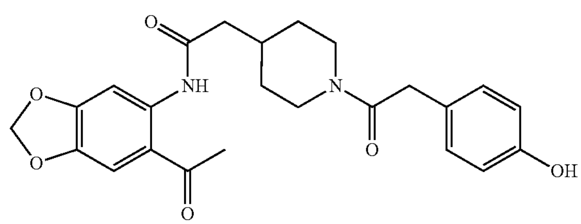 [SMILES: CC(=O)c1cc2c(cc1NC(=O)CC1CCN(C(=O)Cc3ccc(O)cc3)CC1)OCO2] | 439 | 0.32 | (DMSO-d₆) δ 0.88-1.08 (m, 2H), 1.63 (br t, J = 15.2 Hz, 2H), 1.89-2.03 (m, 1H), 2.25 (d, J = 7.1 Hz, 2H), 2.51-2.60 (m, 4H), 2.95 (br t, J = 13.6 Hz, 1H), 3.54 (s, 2H), 3.90 (br d, J = 14.0 Hz, 1H), 4.35 (br d, J = 13.4 Hz, 1H), 6.12 (s, 1H), 6.57-6.72 (m, 2H), 6.96-7.04 (m, 2H), 7.55 (s, 1H), 8.09 (s, 1H), 9.25 (s, 1H), 11.78 (s, 1H). |
| 255 | 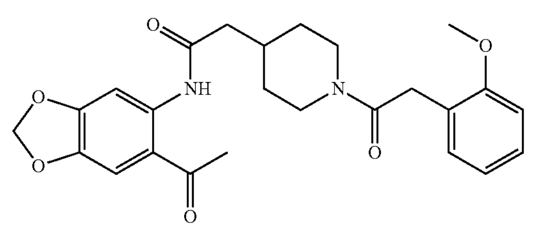 [SMILES: COc1ccccc1CC(=O)N1CCC(CC(=O)Nc2cc3c(cc2C(C)=O)OCO3)CC1] | 453 | 1.30 | (DMSO-d₆) δ 0.96-1.12 (m, 2H), 1.56-1.73 (m, 2H), 1.90-2.06 (m, 1H), 2.28 (d, J = 7.0 Hz, 2H), 2.51-2.63 (m, 4H), 2.94-3.06 (m, 1H), 3.49-3.65 (m, 2H), 3.75 (s, 3H), 3.88 (br d, J = 13.7 Hz, 1H), 4.36 (br d, J = 13.2 Hz, 1H), 6.13 (s, 2H), 6.82-7.03 (m, 2H), 7.05-7.26 (m, 2H), 7.56 (s, 1H), 8.11 (s, 1H), 11.81 (s, 1H). |
| 256 | 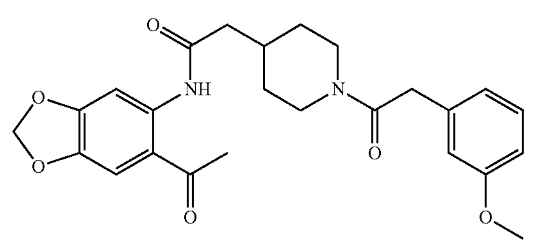 [SMILES: COc1cccc(CC(=O)N2CCC(CC(=O)Nc3cc4c(cc3C(C)=O)OCO4)CC2)c1] | 453 | 0.38 | (DMSO-d₆) δ 0.89-1.10 (m, 2H), 1.63 (br t, J = 15.6 Hz, 2H), 1.90-2.06 (m, 1H), 2.26 (d, J = 7.0 Hz, 2H), 2.51-2.60 (m, 4H), 2.97 (td, J = 13.4, 2.9 Hz, 1H), 3.66 (s, 2H), 3.72 (s, 3H), 3.92 (br d, J = 14.0 Hz, 1H), 4.36 (br d, J = 10.3 Hz, 1H), 6.13 (s, 2H), 6.74-6.82 (m, 3H), 7.15-7.25 (m, 1H), 7.56 (s, 1H), 8.10 (s, 1H), 11.79 (s, 1H). |

TABLE 8-continued

| SID | Structure | Obs Mol Ion MS (M + 1) | hT2R54 IC50 (uM) | $^1$H NMR (400 MHz) |
|---|---|---|---|---|
| 257 | 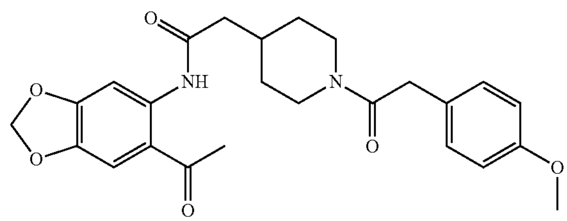 [SMILES: COc1ccc(CC(=O)N2CCC(CC(=O)Nc3cc4c(cc3C(C)=O)OCO4)CC2)cc1] | 453 | 1.57 | (DMSO-d$_6$) δ 0.90-1.09 (m, 2H), 1.64 (br t, J = 14.9 Hz, 2H), 1.90-2.06 (m, 1H), 2.26 (d, J = 7.1 Hz, 2H), 2.51-2.60 (m, 4H), 2.90-3.02 (m, 1H), 3.61 (s, 2H), 3.72 (s, 3H), 3.92 (br d, J = 14.4 Hz, 1H), 4.35 (br d, J = 13.0 Hz, 1H), 6.13 (s, 2H), 6.81-6.90 (m, 2H), 7.08-7.17 (m, 2H), 7.57 (s, 1H), 8.10 (s, 1H), 11.78 (s, 1H). |
| 258 | 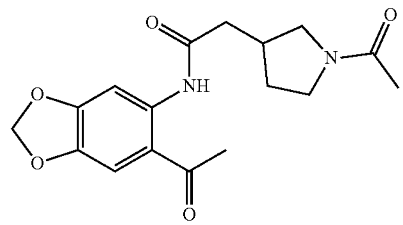 [SMILES: CC(=O)c1cc2c(cc1NC(=O)CC1CCN(C(C)=O)C1)OCO2] | 333 | 0.928 | (DMSO-d$_6$, rotamers) δ 1.48-1.72 (m, 1H), 1.91 (two s, 3H), 1.93-2.12 (m, 1H), 2.43-2.68 (m, 6H), 2.87-2.95 (m, 0.5H), 3.05-3.24 (m, 1H), 3.33-3.69 (m, 2.5H), 6.14 (s, 2H), 7.58 (s, 1H), 8.08 (s, 0.5H), 8.09 (s, 0.5H) 11.78 (s, 0.5H), 11.79 (s, 0.5H). |
| 259 | 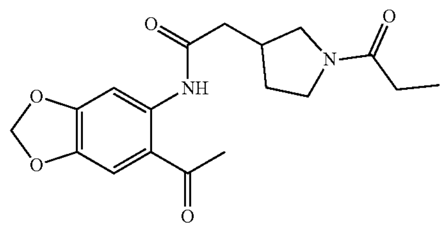 [SMILES: CCC(=O)N1CCC(CC(=O)Nc2cc3c(cc2C(C)=O)OCO3)C1] | 347 | 2.596 | (DMSO-d$_6$, rotamers) δ 0.96 (two t, J = 7.4 Hz, 3H), 1.45-1.71 (m, 1H), 1.92-2.12 (m, 1H), 2.14-2.26 (m, 2H), 2.42-2.65 (m, 6H), 2.93 (dd, J = 11.6, 6.9 Hz, 0.5H), 3.09 (dd, J = 10.0, 7.7 Hz, 0.5H), 3.13-3.25 (m, 0.5H), 3.31-3.67 (m, 2.5H), 6.14 (s, 2H), 7.58 (s, 1H), 8.08 (s, 0.5H), 8.09 (s, 0.5H) 11.77 (s, 0.5H), 11.79 (s, 0.5H). |
| 260 | 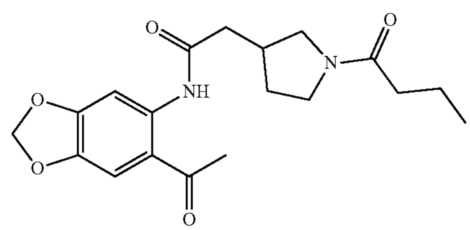 | 361 | 0.844 | (DMSO-d$_6$, rotamers) δ 0.87 (two s, J = 7.4, 3H), 1.43-1.70 (m, 3H), 1.92-2.12 (m, 1H), 2.14-2.26 (m, 2H), 2.36-2.65 (m, 6H), 2.93 (dd, J = 11.6, 6.9 Hz, 0.5H), 3.09 (dd, J = 10.0, 7.7 Hz, 0.5H), 3.13-3.25 (m, 0.5H), 3.27-3.67 (m, 2.5H), 6.14 (s, 2H), 7.58 (s, 1H), 8.08 (s, 0.5H), 8.09 (s, 0.5H) 11.77 (s, 0.5H), 11.79 (s, 0.5H). |
| 261 | 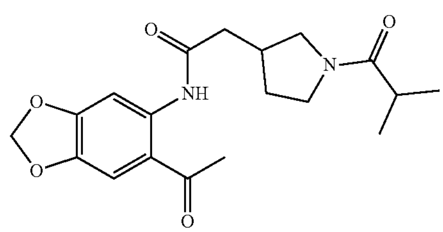 [SMILES: CC(=O)c1cc2c(cc1NC(=O)CC1CCN(C(=O)C(C)C)C1)OCO2] | 361 | 0.958 | (DMSO-d$_6$, rotamers) δ 0.95-1.02 (m, 6H), 1.48-1.70 (m, 1H), 1.93-2.15 (m, 1H), 2.43-2.68 (m, 6H), 2.87-2.97 (m, 0.5H), 3.11-3.26 (m, 1H), 3.38-3.49 (m, 1H), 3.51-3.63 (m, 1H), 3.71 (dd, J = 10.1, 6.9 Hz, 0.5H), 6.14 (s, 2H), 7.58 (s, 1H), 8.08 (s, 0.5H), 8.09 (s, 0.5H) 11.77 (s, 0.5H), 11.79 (s, 0.5H). |

TABLE 8-continued

| SID | Structure | Obs Mol Ion MS; (M + 1) | hT2R54 IC50 (uM) | ¹H NMR (400 MHz) |
|---|---|---|---|---|
| 262 | 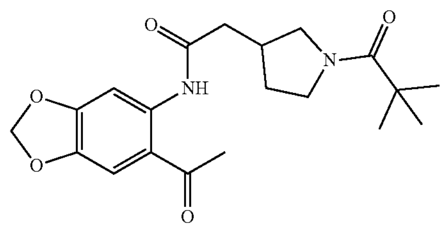 [SMILES: CC(=O)c1cc2c(cc1NC(=O)CC1CCN(C(=O)C(C)(C)C)C1)OCO2] | 375 | 0.29 | (400 MHz, DMSO-d₆) δ 1.15 (s, 9H), 1.54 (br s, 2H), 1.99 (br s, 2H), 2.56 (s, 3H), 2.80-3.96 (m, 5H), 6.14 (s, 2H), 7.58 (s, 1H), 8.08 (s, 1H), 11.77 (s, 1H). |
| 263 | 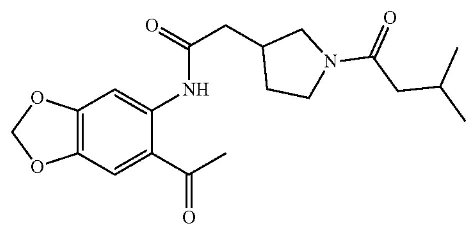 [SMILES: CC(=O)c1cc2c(cc1NC(=O)CC1CCN(C(=O)CC(C)C)C1)OCO2] | 375 | 0.374 | (DMSO-d₆, rotamers) δ 0.84-0.95 (m, 6H), 1.45-1.70 (m, 1H), 1.92-2.15 (m, 4H), 2.44-2.62 (m, 6H), 2.88-2.98 (m, 0.5H), 3.05-3.25 (m, 1H), 3.34-3.69 (m, 2.5H), 6.14 (s, 2H), 7.58 (s, 1H), 8.08 (s, 0.5H), 8.09 (s, 0.5H) 11.77 (s, 0.5H), 11.79 (s, 0.5H). |
| 264 | 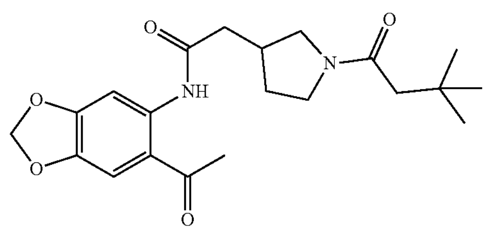 [SMILES: CC(=O)c1cc2c(cc1NC(=O)CC1CCN(C(=O)CC(C)(C)C)C1)OCO2] | 389 | 0.381 | (DMSO-d₆, rotamers) δ 0.94-1.05 (two s, 9H), 1.45-1.70 (m, 1H), 1.92-2.14 (m, 3H), 2.39-2.63 (m, 5H), 2.93 (dd, J = 12.1, 6.6 Hz, 0.5H), 3.06-3.26 (m, 1H), 3.34-3.71 (m, 3.5H), 6.13 (s, 2H), 7.57 (s, 1H), 8.08 (s, 0.5H), 8.09 (s, 0.5H) 11.77 (s, 0.5H), 11.80 (s, 0.5H). |
| 265 | 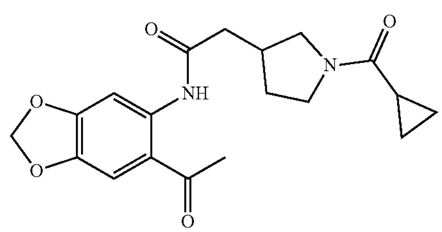 [SMILES: CC(=O)c1cc2c(cc1NC(=O)CC1CCN(C(=O)C3CC3)C1)OCO2] | 359 | 0.682 | (DMSO-d₆, rotamers) δ 0.63-0.76 (m, 4H), 1.48-1.78 (m, 2H), 1.94-2.06 (m, 1H), 2.06-2.16 (m, 1H), 2.51-2.67 (m, 5H), 2.89-2.98 (m, 0.5H), 3.15-3.32 (m, 1H), 3.40-3.62 (m, 1.5H), 3.73 (ddd, J = 9.9, 8.1, 3.7 Hz, 0.5H), 3.86 (dd, J = 10.0, 7.1 Hz, 0.5H), 6.14 (s, 2H), 7.58 (s, 1H), 8.07 (s, 0.5H), 8.09 (s, 0.5H), 11.79 (s, 1H). |
| 266 | 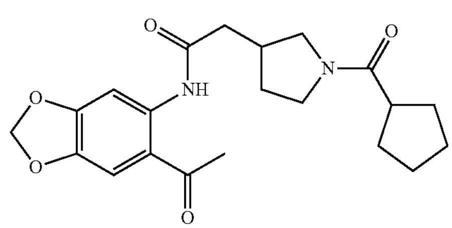 [SMILES: CC(=O)c1cc2c(cc1NC(=O)CC1CCN(C(=O)C3CCCC3)C1)OCO2] | 387 | 0.506 | (DMSO-d₆, rotamers) δ 1.45-1.80 (m, 10H), 1.92-2.05 (m, 0.5H), 2.03 2.13 (m, 0.5H), 2.42-2.64 (m, 5H), 2.72-2.86 (m, 1H), 2.93 (dd, J = 11.7, 7.1 Hz, 0.5H), 3.11-3.26 (m, 1H), 3.37-3.49 (m, 1H), 3.51-3.64 (m, 1H), 3.71 (dd, J = 10.1, 6.9 Hz, 0.5H), 6.14 (s, 2H), 7.58 (s, 1H), 8.08 (s, 0.5H), 8.09 (s, 0.5H) 11.77 (s, 0.5H), 11.79 (s, 0.5H). |

TABLE 8-continued

| SID | Structure | Obs Mol Ion MS (M + 1) | hT2R54 IC50 (uM) | $^1$H NMR (400 MHz) |
|---|---|---|---|---|
| 267 | 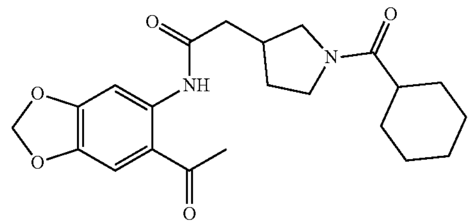 [SMILES: CC(=O)c1cc2c(cc1NC(=O)CC1CCN(C(=O)C3CCCCC3)C1)OCO2] | 401 | 2.249 | (DMSO-d$_6$, rotamers) δ 1.07-1.36 (m, 5H), 1.45-1.57 (m, 0.5H), 1.58-1.74 (m, 6H), 1.91-2.04 (m, 0.5H), 2.03-2.11 (m, 0.5H), 2.27-2.41 (m, 1H), 2.41-2.65 (m, 5H), 2.91 (dd, J = 11.7, 7.3 Hz, 0.5H), 3.11-3.24 (m, 1H), 3.37-3.48 (m, 1H), 3.49-3.64 (m, 1H), 3.71 (dd, J = 10.1. 6.9 Hz, 0.5H), 6.13-2.15 (two s, 2H), 7.58 (s, 1H), 8.07 (s, 0.5H), 8.09 (s, 0.5H) 11.77 (s, 0.5H), 11.79 (s, 0.5H). |
| 268 | 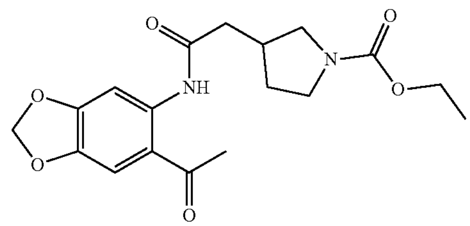 [SMILES: CCOC(=O)N1CCC(CC(=O)Nc2cc3c(cc2C(C)=O)OCO3)C1] | 363 | 0.117 | (DMSO-d$_6$) δ 1.12-1.21 (m, 3H), 1.48-1.66 (m, 2H), 1.93-2.07 (m, 2H), 2.38-2.54 (m, 1H), 2.57 (s, 3H), 2.88-3.07 (m, 1H), 3.15-3.43 (m, 2H), 3.48-3.57 (m, 1H), 4.01 (q, J = 7.2 Hz, 2H), 6.14 (s, 1H), 7.58 (s, 1H), 8.08 (s, 1H), 11.78 (s, 1H). |
| 269 | 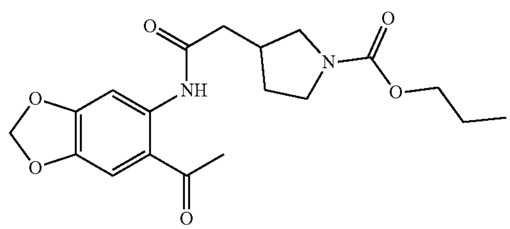 [SMILES: CCCOC(=O)N1CCC(CC(=O)Nc2cc3c(cc2C(C)=O)OCO3)C1] | 377 | 0.103 | (DMSO-d$_6$) δ 0.88 (two t, J = 7.4 Hz, 3H), 1.48-1.64 (m, 3H), 1.96-2.05 (m, 1H), 2.56 (s, 3H), 2.89-3.01 (m, 1H), 3.15-3.33 (m, 1H), 3.34-3.42 (m, 1H), 3.46-3.57 (m, 1H), 3.92 (t, J = 6.4 Hz, 2H), 6.14 (s, 2H), 7.58 (s, 1H), 8.08 (s, 1H), 11.78 (s, 1H). |
| 454 | 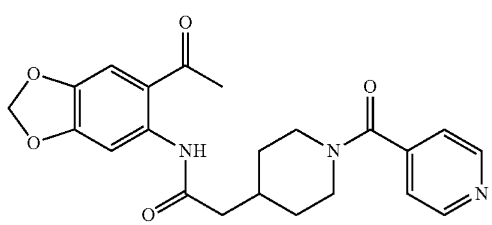 | 410 | 0.3 | (DMSO-d$_6$) δ 1.11-1.33 (m, 2H), 1.62 (d, J = 12.8 Hz, 1H), 1.78 (d, J = 12.8 Hz, 1H), 2.07 (m, 1H), 2.34 (dd, J = 7.1, 2.8 Hz, 2H), 2.57 (s, 3H), 2.72-2.88 (m, 1H), 3.06 (t, J = 12.5 Hz, 1H), 3.36-3.50 (m, 1H), 4.45 (d, J = 13.1 Hz, 1H), 6.13 (s, 2H), 7.27-7.43 (m, 2H), 7.58 (s, 1H), 8.11 (s, 1H), 8.59-8.69 (m, 2H), 11.82 (s, 1H). |
| 455 | 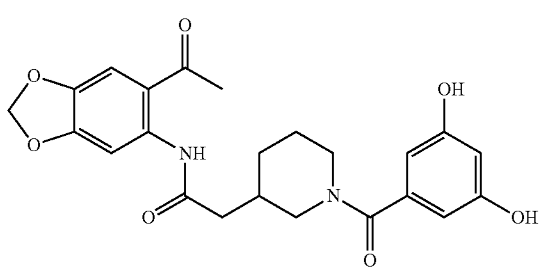 [SMILES: CC(=O)c1cc2c(cc1NC(=O)CC1CCCN(C(=O)c3cc(O)cc(O)c3)C1)OCO2] | 441 | 6.0 | |

TABLE 8-continued

| SID | Structure | Obs Mol Ion MS; (M + 1) | hT2R54 IC50 (uM) | ¹H NMR (400 MHz) |
|---|---|---|---|---|
| 456 | 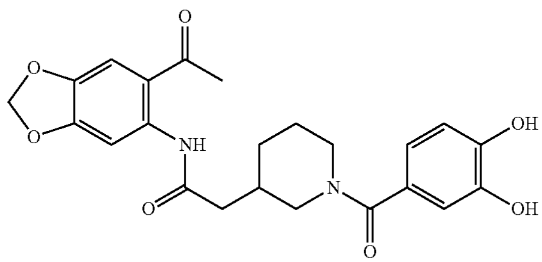 [SMILES: CC(=O)c1cc2c(cc1NC(=O)CC1CCCN(C(=O)c3ccc(O)c(O)c3)C1)OCO2] | 441 | 1.3 | (DMSO-d₆) δ 1.23-1.45 (m, 2H), 1.63 (m, 1H), 1.83 (m, 1H), 1.95 (m, 1H), 2.29 (d, J = 7.4 Hz, 2H), 2.56 (s, 3H), 2.72-2.89 (m, 2H), 3.97 (br.s, 2H), 6.14 (s, 2H), 6.63-6.76 (m, 3H), 7.57 (s, 1H), 8.06 (s, 1H), 9.13 (s, 1H), 9.23 (s, 1H), 11.78 (s, 1H). |
| 457 | 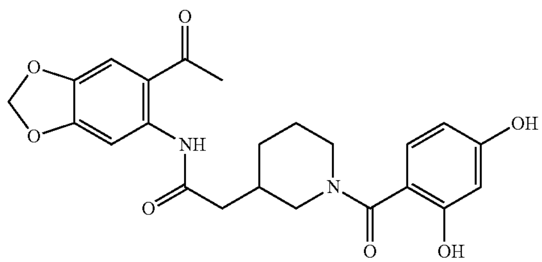 [SMILES: CC(=O)c1cc2c(cc1NC(=O)CC1CCCN(C(=O)c3ccc(O)cc3O)C1)OCO2] | 441 | 0.14 | (DMSO-d₆) δ 1.19-1.41 (m, 2H), 1.61 (m, 1H), 1.80 (m, 1H), 1.95 (m, 1H), 2.30 (m, 2H), 2.56 (s, 3H), 2.66-2.93 (m, 2H), 3.74-4.00 (m, 2H), 6.14 (s, 2H), 6.17-6.20 (m, 1H), 6.25 (d, 2.3 Hz, 1H), 6.89 (d, J = 8.3 Hz, 1H), 7.57 (s, 1H), 8.07 (s, 1H), 9.51 (s, 1H), 9.67 (s, 1H), 11.79 (s, 1H). |
| 458 | 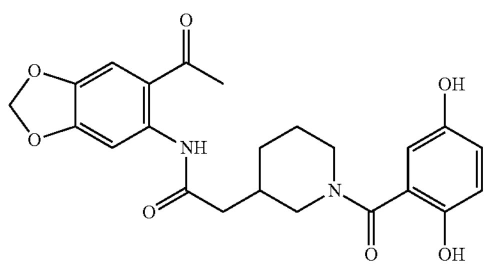 [SMILES: CC(=O)c1cc2c(cc1NC(=O)CC1CCCN(C(=O)c3cc(O)ccc3O)C1)OCO2] | 441 | 0.16 | (Methanol-d₄) δ 1.18-1.41 (m, 2H), 1.54-1.60 (m, 1H), 1.74 (m, 1H), 2.15 (m, 1H), 2.33 (m, 2H), 2.57 (s, 3H), 2.89-2.94 (m, 2H), 4.37 (m, 2H), 6.06 (s, 2H), 6.54-6.67 (m, 3H), 7.46 (s, 1H), 8.11 (br.s, 1H). |
| 459 | 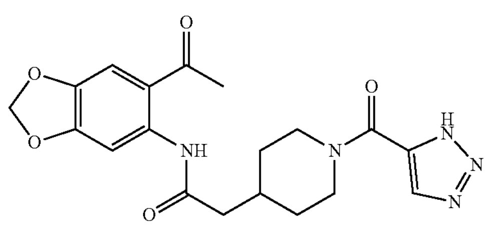 [SMILES: CC(=O)c1cc2c(cc1NC(=O)CC1CCN(C(=O)c3cnn[nH]3)CC1)OCO2] | 400 | 0.095 | (DMSO-d₆) δ 1.19 (m, 2H), 1.74 (t, J = 17.1 Hz, 2H), 2.06 (m, 1H), 2.32 (d, J = 7.0 Hz, 2H), 2.55 (s, 3H), 2.77 (t, J = 12.6 Hz, 1H), 3.13 (t, J = 12.7 Hz, 1H), 4.45 (m, 2H), 6.12 (s, 2H), 7.56 (s, 1H), 8.02 (br, 0.5H), 8.10 (s, 1H), 8.46 (br, 0.5H), 11.80 (s, 1H). |
| 460 | 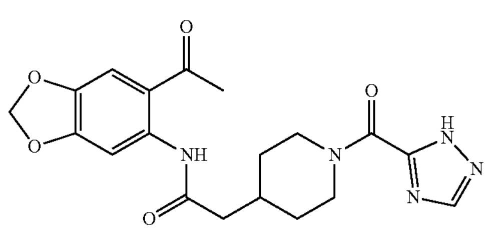 [SMILES: CC(=O)c1cc2c(cc1NC(=O)CC1CCN(C(=O)c3ncn[nH]3)CC1)OCO2] | 400 | 0.3 | (DMSO-d₆) δ 1.20 (m, 2H), 1.75 (dd, J = 35.5, 13.2 Hz, 2H), 2.09 (m, 2H), 2.34 (d, J = 7.1 Hz, 2H), 2.57 (s, 3H), 2.75-2.91 (m, 2H), 3.11 (t, J = 12.7 Hz, 1H), 4.46 (d, J = 13.2 Hz, 1H), 6.13 (s, 2H), 7.58 (s, 1H), 8.11 (s, 1H), 8.43 (s, 1H), 11.80 (s, 1H). |

TABLE 8-continued

| SID | Structure | Obs Mol Ion MS; (M + 1) | hT2R54 IC50 (uM) | $^1$H NMR (400 MHz) |
|---|---|---|---|---|
| 461 | 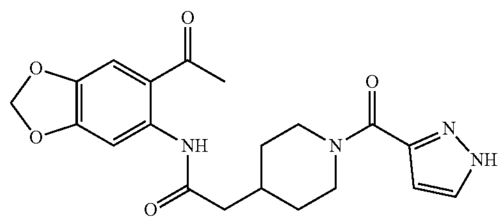 [SMILES: CC(=O)c1cc2c(cc1NC(=O)CC1CCN(C(=O)c3cc[nH]n3)CC1)OCO2] | 399 | 0.15 | (DMSO-d$_6$) δ 1.06-1.28 (m, 2H), 1.72 (m, 2H), 1.99-2.17 (m, 1H), 2.33 (d, J = 6.9 Hz, 2H), 2.57 (s, 3H), 2.73 (m, 1H), 3.08 (t, J = 12.5 Hz, 1H), 4.54 (dd, J = 56.7, 13.3 Hz, 2H), 6.13 (s, 2H), 6.52 (s, 1H), 7.58 (s, 1H), 7.79 (s, 1H), 8.11 (s, 1H), 11.81 (s, 1H), 13.12 (s, 1H). |
| 462 | 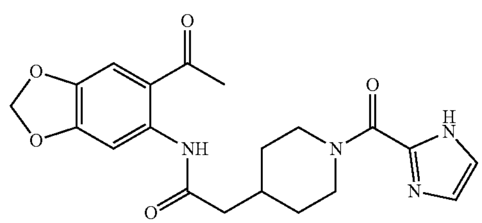 [SMILES: CC(=O)c1cc2c(cc1NC(=O)CC1CCN(C(=O)c3ncc[nH]3)CC1)OCO2] | 399 | 0.03 | (DMSO-d$_6$) δ 1.22 (m, 2H), 1.75 (m, 2H), 2.09 (m, 1H), 2.33 (d, J = 7.0 Hz, 2H), 2.57 (s, 3H), 2.78 (t, J = 12.6 Hz, 1H), 3.16 (t, J = 12.6 Hz, 1H), 4.48 (d, J = 13.0 Hz, 1H), 5.64 (d, J = 13.4 Hz, 1H), 6.14 (s, 2H), 7.05 (t, J = 1.3 Hz, 1H), 7.22 (dd, J = 2.4, 1.1 Hz, 1H), 7.58 (s, 1H), 8.12 (s, 1H), 11.81 (s, 1H), 12.84 (s, 1H). |
| 463 | 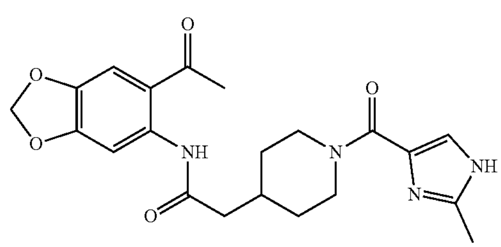 [SMILES: CC(=O)c1cc2c(cc1NC(=O)CC1CCN(C(=O)c3c[nH]c(C)n3)CC1)OCO2] | 413 | 0.4 | (DMSO-d$_6$) δ 1.19 (m, 2H), 1.75 (d, J = 12.7 Hz, 2H), 2.1 (m, 1H), 2.34 (m, 2H), 2.41 (s, 3H), 2.57 (d, J = 1.2 Hz, 3H), 2.84-2.89 (m, 1H), 4.28 (m, 1H), 4.47 (m, 2H), 6.14 (d, J = 1.1 Hz, 2H), 7.59 (s, 1H), 7.70 (s, 1H), 8.12 (d, J = 3.7 Hz, 1H), 11.82 (s, 1H). |
| 464 | 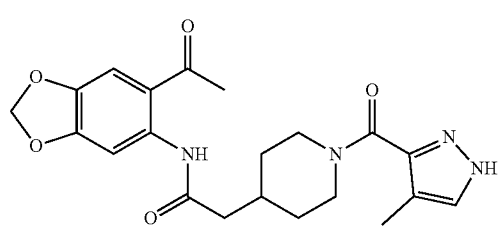 [SMILES: CC(=O)c1cc2c(cc1NC(=O)CC1CCN(C(=O)c3n[nH]cc3C)CC1)OCO2] | 413 | 0.2 | (DMSO-d$_6$) δ 1.16 (m, 2H), 1.71 (dd, J = 41.1, 13.1 Hz, 2H), 2.03 (m, 4H), 2.29-2.36 (m, 2H), 2.57 (s, 3H), 2.73 (t, J = 12.4 Hz, 1H), 3.02 (t, J = 12.8 Hz, 1H), 4.17 (m, 1H), 4.47 (d, J = 13.0 Hz, 1H), 6.13 (s, 2H), 7.56 (s, 1H), 7.58 (s, 1H), 8.11 (s, 1H), 11.80 (s, 1H), 12.77 (s, 1H). |

TABLE 8-continued

| SID | Structure | Obs Mol Ion MS (M + 1) | hT2R54 IC50 (uM) | ¹H NMR (400 MHz) |
|---|---|---|---|---|
| 465 | 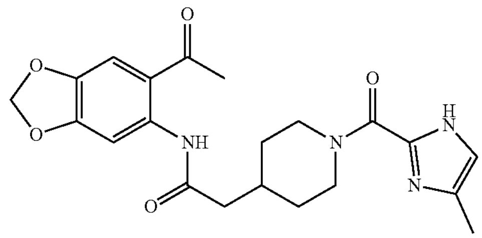 [SMILES: CC(=O)c1cc2c(cc1NC(=O)CC1CCN(C(=O)c3nc(C)c[nH]3)CC1)OCO2] | 413 | 0.046 | (DMSO-d₆) δ 1.08-1.28 (m, 2H), 1.69-1.81 (m, 2H), 2.01-2.13 (m, 1H), 2.13 (s, 1.5H), 2.17 (s, 1.5H), 2.32 (d, J = 6.9 Hz, 2H), 2.57 (s, 3H), 2.75 (t, J = 12.4 Hz, 1H), 3.07-3.19 (m, 1H), 4.46 (d, J = 13.0 Hz, 1H), 5.68 (d, J = 13.3 Hz, 1H), 6.14 (s, 2H), 6.74 (s, 0.5H), 6.92 (s, 0.5H), 7.58 (s, 1H), 8.12 (s, 1H), 11.81 (s, 1H), 12.52 (s, 0.5H), 12.60 (s, 0.5H). |
| 466 | 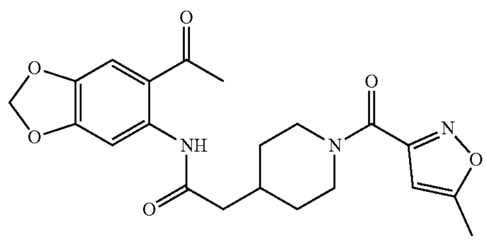 [SMILES: CC(=O)c1cc2c(cc1NC(=O)CC1CCN(C(=O)c3cc(C)on3)CC1)OCO2] | 414 | 0.7 | (DMSO-d₆) δ 1.10-1.30 (m, 2H), 1.74 (dd, J = 34.4, 13.0 Hz, 2H), 2.11 (m, H), 2.27-2.37 (m, 2H), 2.44 (s, 3H), 2.57 (s, 3H), 2.82 (m, 1H), 3.03-3.20 (m, 1H), 3.86 (d, J = 13.6 Hz, 1H), 4.43 (d, J = 13.1 Hz, 1H), 6.13 (s, 2H), 6.41 (s, 1H), 7.58 (s, 1H), 7.73 (s, 1H), 11.8 (br, 1H) |
| 467 | 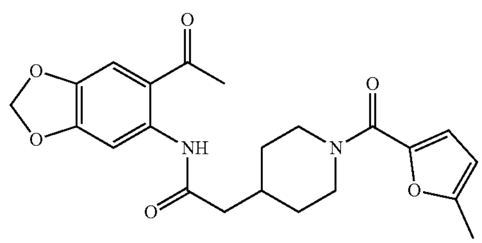 [SMILES: CC(=O)c1cc2c(cc1NC(=O)CC1CCN(C(=O)c3ccc(C)o3)CC1)OCO2] | 413 | 0.058 | (DMSO-d₆) δ 1.11-1.25 (m, 2H), 1.69-1.79 (m, 2H), 2.01-2.14 (m, 1H), 2.31 (s, 3H), 2.34 (d, J = 7.0 Hz, 2H), 2.57 (d, J = 1.2 Hz, 3H), 2.95 (br s, 2H), 4.31 (d, J = 13.3 Hz, 2H), 6.14 (d, J = 1.2 Hz, 2H), 6.19-6.21 (m, 1H), 6.82 (dd, J = 3.2, 0.9 Hz, 1H), 7.58 (d, J = 1.2 Hz, 1H), 8.12 (d, J = 1.2 Hz, 1H), 11.81 (s, 1H). |
| 468 | 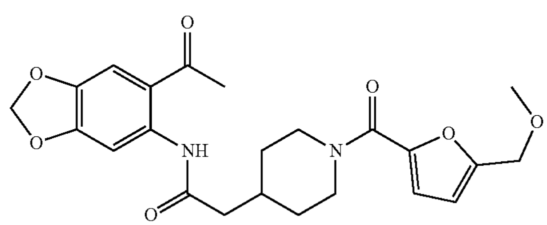 [SMILES: COCc1ccc(C(=O)N2CCC(CC(=O)Nc3cc4c(cc3C(C)=O)OCO4)CC2)o1] | 443 | 0.070 | (DMSO-d₆) δ 1.13-1.29 (m, 2H), 1.75 (d, J = 13.0 Hz, 2H), 2.01-2.14 (m, 1H), 2.34 (d, J = 7.1 Hz, 2H), 2.56 (d, J = 0.9 Hz, 3H), 2.98 (br s, 2H), 3.26 (d, J = 1.0 Hz, 3H), 4.20-4.34 (m, 2H), 4.38 (s, 2H), 6.13 (d, J = 0.9 Hz, 2H), 6.55 (dd, J = 3.4, 0.9 Hz, 1H), 6.88 (dd, J = 3.4, 0.9 Hz, 1H), 7.57 (d, J = 0.9 Hz, 1H), 8.11 (d, J = 0.9 Hz, 1H), 11.81 (s, 1H). |
| 469 | 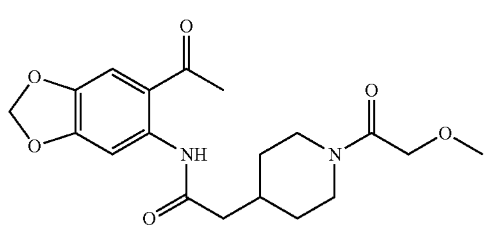 [SMILES: COCC(=O)N1CCC(CC(=O)Nc2cc3c(cc2C(C)=O)OCO3)CC1] | 377 | 0.5 | |

TABLE 8-continued

| SID | Structure | Obs Mol Ion MS; (M + 1) | hT2R54 IC50 (uM) | ¹H NMR (400 MHz) |
|---|---|---|---|---|
| 470 | 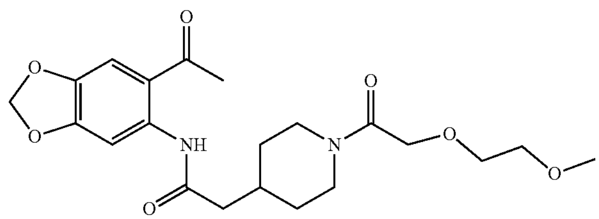 [SMILES: COCCOCC(=O)N1CCC(CC(=O)Nc2cc3c(cc2C(C)=O)OCO3)CC1] | 421 | 0.7 | |
| 471 | 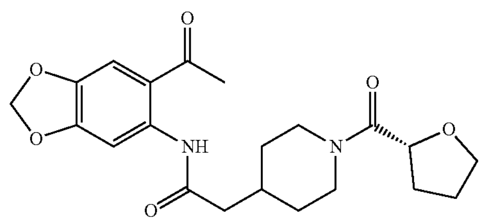 [SMILES: CC(=O)c1cc2c(cc1NC(=O)CC1CCN(C(=O)[C@H]3CCCO3)CC1)OCO2] | 403 | 0.3 | (DMSO-d₆, rotamers) δ 1.03-1.26 (m, 3H), 1.69 (m, 2H), 1.76-1.85 (m, 2H), 1.94-2.04 (m, 2H), 2.31 (d, J = 7.1 Hz, 2H), 2.57 (s, 3H), 2.99 (q, J = 13.7 Hz, 1H), 3.28-3.33 (m, 1H), 3.69-3.80 (m, 2H), 3.97 (d, J = 13.8 Hz, 1H), 4.30 (d, J = 13.1 Hz, 1H), 4.63 (dd, J = 7.5, 5.8 Hz, 1H), 6.13 (s, 2H), 7.58 (s, 1H), 8.10 (s, 0.5H), 8.11 (s, 0.5H), 11.79 (s, 0.5H), 11.80 (s, 0.5H). |
| 472 | 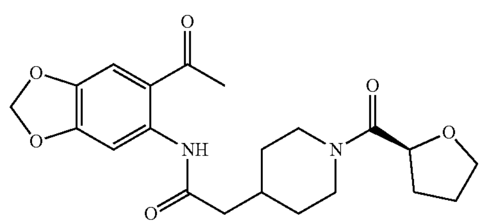 [SMILES: CC(=O)c1cc2c(cc1NC(=O)CC1CCN(C(=O)[C@@H]3CCCO3)CC1)OCO2] | 403 | 0.3 | (DMSO-d₆, rotamers) δ 1.16-1.20 (m, 3H), 1.68 (m, 2H), 1.78-1.84 (m, 2H), 1.95-2.04 (m, 2H), 2.31 (d, J = 7.1 Hz, 2H), 2.57 (s, 3H), 2.94-3.04 (m, 1H), 3.33 (m, 1H), 3.70-3.78 (m, 2H), 3.97 (d, J = 13.9 Hz, 1H), 4.30 (d, J = 13.1 Hz, 1H), 4.63 (dd, J = 7.5, 5.8 Hz, 1H), 6.13 (s, 2H), 7.58 (s, 1H), 8.10 (s, 0.5H), 8.11 (s, 0.5H), 11.79 (s, 0.5H), 11.80 (s, 0.5H). |
| 473 | 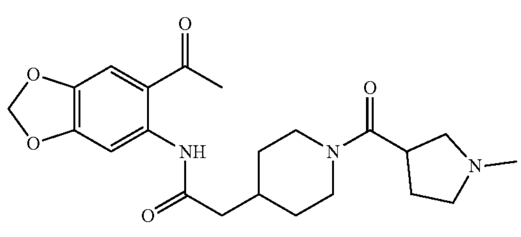 [SMILES: CC(=O)c1cc2c(cc1NC(=O)CC1CCN(C(=O)C3CCN(C)C3)CC1)OCO2] | 416 | >50 | |
| 474 | 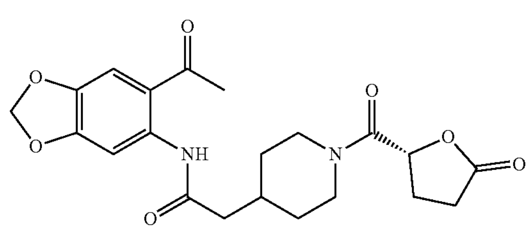 [SMILES: CC(=O)c1cc2c(cc1NC(=O)CC1CCN(C(=O)[C@H]3CCC(=O)O3)CC1)OCO2] | 417 | 0.13 | (DMSO-d₆) δ 2.12-2.22 (m, 1H), 2.30-2.48 (m, 3H), 2.52-2.62 (m, 7H), 3.19 (d, J = 1.6 Hz, 2H), 3.63 (m, 4H), 5.52 (m, 1H), 6.14 (s, 2H), 7.63 (s, 1H), 8.33 (s, 1H), 12.68 (s, 1H). |

TABLE 8-continued

| SID | Structure | Obs Mol Ion MS; (M + 1) | hT2R54 IC50 (uM) | ¹H NMR (400 MHz) |
|---|---|---|---|---|
| 475 | 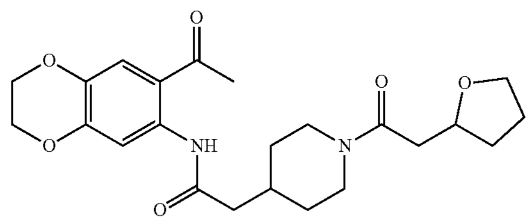 [SMILES: CC(=O)c1cc2c(cc1NC(=O)CC1CCN(C(=O)CC3CCCO3)CC1)OCCO2] | 431 | 0.3 | (DMSO-d₆) δ 0.89-1.24 (m, 2H), 1.35-1.53 (m, 1H), 1.67 (t, J = 12.8 Hz, 2H), 1.80 (m, 2H), 1.90-2.05 (m, 2H), 2.28 (d, J = 7.1 Hz, 2H), 2.37 (m, 1H), 2.50, (m, 2H), 2.56 (s, 3H), 2.62 (m, 1H), 2.90-3.03 (m, 1H), 3.56 (m, 1H), 3.72 (m, 1H), 3.87 (d, J = 13.6 Hz, 1H), 4.07 (m, 1H), 4.21-4.41 (m, 4H), 7.54 (s, 1H), 8.04 (s, 1H), 11.43 (s, 1H). |
| 476 | 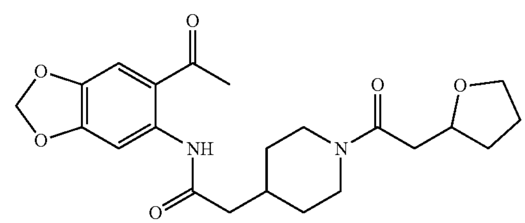 [SMILES: CC(=O)c1cc2c(cc1NC(=O)CC1CCN(C(=O)CC3CCCO3)CC1)OCO2] | 417 | 0.3 | (DMSO-d₆) δ 0.93-1.24 (m, 2H), 1.36-1.54 (m, 1H), 1.69 (m, 2H), 1.73-1.90 (m, 2H), 1.90-2.05 (m, 2H), 2.30 (d, J = 7.0 Hz, 2H), 2.32-2.44 (m, 1H), 2.57 (s, 3H), 2.62 (m, 2H), 2.97 (t, J = 13.1 Hz, 1H), 3.56 (m, 1H), 3.72 (m, 1H), 3.87 (d, J = 13.8 Hz, 1H), 4.07 (m, 1H), 4.35 (d, J = 13.1 Hz, 1H), 6.13 (s, 2H), 6.57 (s, 1H), 7.58 (s, 1H), 11.80 (s, 1H). |
| 477 | 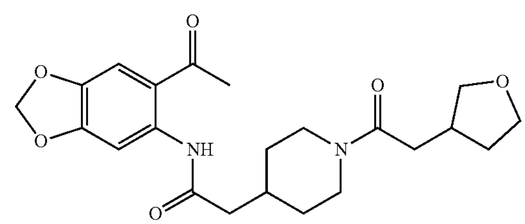 [SMILES: CC(=O)c1cc2c(cc1NC(=O)CC1CCN(C(=O)CC3CCOC3)CC1)OCO2] | 417 | 0.4 | (DMSO-d₆) δ 0.93-1.24 (m, 3H), 1.47 (m, 1H), 1.68 (t, J = 14.1 Hz, 2H), 1.92-2.07 (m, 2H), 2.31 (d, J = 7.1 Hz, 2H), 2.33-2.48 (m, 3H), 2.57 (s, 3H), 2.98 (dd, J = 13.6, 11.2 Hz, 1H), 3.15-3.26 (m, 1H), 3.60 (m, 1H), 3.69 (m, 1H), 3.77-3.88 (m, 2H), 4.35 (d, J = 13.1 Hz, 1H), 6.14 (s, 2H), 7.58 (s, 1H), 8.11 (s, 1H), 11.81 (s, 1H). |
| 478 | 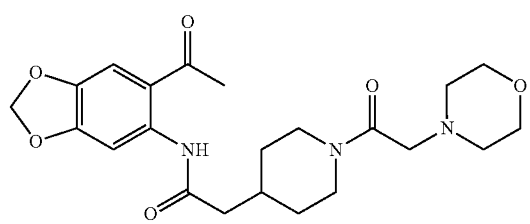 [SMILES: CC(=O)c1cc2c(cc1NC(=O)CC1CCN(C(=O)CN3CCOCC3)CC1)OCO2] | 431 | >10 | |
| 479 | 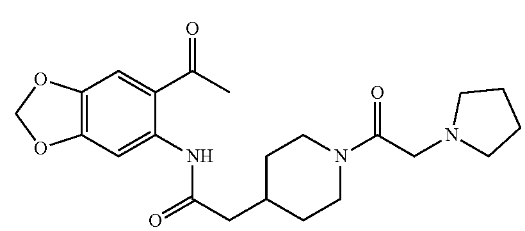 [SMILES: CC(=O)c1cc2c(cc1NC(=O)CC1CCN(C(=O)CN3CCCC3)CC1)OCO2] | 416 | >10 | |

TABLE 8-continued

| SID | Structure | Obs Mol Ion MS; (M + 1) | hT2R54 IC50 (uM) | ¹H NMR (400 MHz) |
|---|---|---|---|---|
| 480 | 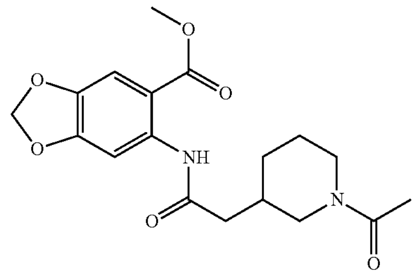 [SMILES: COC(=O)c1cc2c(cc1NC(=O)CC1CCCN(C(C)=O)C1)OCO2] | 363 | 1.4 | (DMSO-d₆) δ 1.17-1.48 (m, 2H), 1.54-1.69 (m, 1H), 1.75-1.96 (m, 2H), 1.97 (s, 1.5H), 1.98 (s, 1.5H), 2.18-2.48 (m, 2.5H), 2.65-2.76 (m, 0.5H), 2.83-2.92 (m, 0.5H), 2.96-3.05 (m, 0.5H), 3.62-3.77 (m, 1H), 3.82 (s, 3H), 4.02-4.09 (m, 0.5H), 4.18-4.25 (m, 0.5H), 6.12 (s, 2H), 7.37 (s, 0.5H), 7.38 (s, 0.5H), 7.93 (s, 0.5H), 7.98 (s, 0.5H), 10.79 (s, 0.5H), 10.82 (s, 0.5H). |
| 481 | 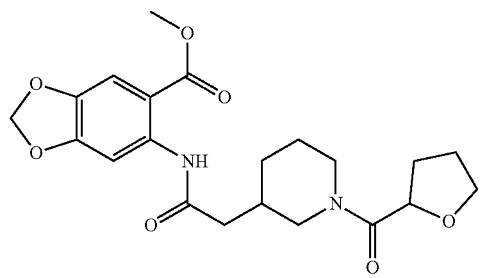 [SMILES: COC(=O)c1cc2c(cc1NC(=O)CC1CCCN(C(=O)C3CCCO3)C1)OCO2] | 419 | 2.2 | (DMSO-d₆) δ 1.20-1.47 (m, 2H), 1.56-1.71 (m, 1H), 1.71-2.06 (m, 6.5H), 2.21-2.44 (m, 2H), 2.51-2.58 (m, 0.5H), 2.65-2.73 (m, 0.5H), 2.83-2.91 (m, 0.5H), 2.95-3.10 (m, 0.5H), 3.59-3.79 (m, 2H), 3.82 (s, 3H), 3.85-3.95 (m, 0.5H), 4.04-4.12 (m, 0.5H), 4.13-4.20 (m, 0.5H), 4.56-4.69 (m, 1H), 6.12 (s, 2H), 7.38 (s, 1H), 7.95 (s, 0.5H), 7.98 (s, 0.5H), 10.76-10.85 (m, 1H). |
| 482 | 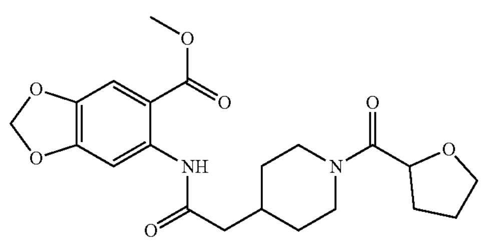 [SMILES: COC(=O)c1cc2c(cc1NC(=O)CC1CCN(C(=O)C3CCCO3)CC1)OCO2] | 419 | 1.4 | (DMSO-d₆) δ 0.99-1.23 (m, 2H), 1.65-1.74 (m, 2H), 1.74-1.90 (m, 2H), 1.90-2.08 (m, 3H), 2.32 (d, J = 7.1 Hz, 2H), 2.52-2.61 (m, 1H), 2.92-3.05 (m, 1H), 3.68-3.78 (m, 2H), 3.82 (s, 3H), 3.97 (d, J = 13.7 Hz, 1H), 4.31 (d, J = 13.1 Hz, 1H), 4.59-4.69 (m, 1H), 6.12 (s, 2H), 7.38 (s, 1H), 7.99 (d, J = 3.6 Hz, 1H), 10.81 (d, J = 5.6 Hz, 1H). |
| 483 | 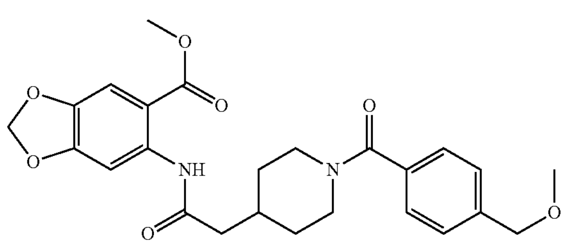 [SMILES: COCc1ccc(C(=O)N2CCC(CC(=O)Nc3cc4c(cc3C(=O)OC)OCO4)CC2)cc1] | 469 | 0.64 | (DMSO-d₆) δ 1.11-1.27 (m, 2H), 1.55-1.83 (m, 2H), 1.97-2.10 (m, 1H), 2.33 (d, J = 7.0 Hz, 2H), 2.76 (br s, 1H), 3.02 (br s, 1H), 3.29 (s, 3H), 3.54 (br s, 1H), 3.81 (s, 3H), 4.42 (s, 2H), 4.43 (br s, 1H), 6.10 (s, 2H), 7.31-7.39 (m, 5H), 7.97 (s, 1H), 10.82 (s, 1H). |

TABLE 8-continued

| SID | Structure | Obs Mol Ion MS (M + 1) | hT2R54 IC50 (uM) | ¹H NMR (400 MHz) |
|---|---|---|---|---|
| 484 | 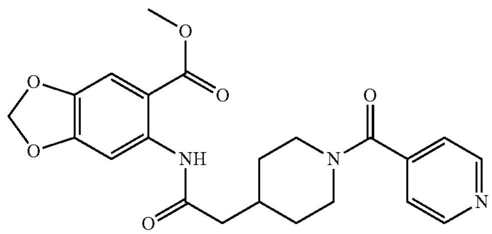 [SMILES: COC(=O)c1cc2c(cc1NC(=O)CC1CCN(C(=O)c3ccncc3)CC1)OCO2] | 426 | 0.46 | (DMSO-d₆) δ 1.13-1.30 (m, 2H), 1.63 (d, J = 13.1 Hz, 1H), 1.80 (d, J = 13.1 Hz, 1H), 2.01-2.15 (m, 1H), 2.35 (dd, J = 7.1, 2.5 Hz, 2H), 2.77-2.88 (m, 1H), 3.01-3.11 (m, 1H), 3.41 (d, J = 13.5 Hz, 1H), 3.82 (s, 3H), 4.45 (d, J = 13.1 Hz, 1H), 6.12 (s, 2H), 7.32-7.41 (m, 3H), 7.99 (s, 1H), 8.62-8.70 (m, 2H), 10.84 (s, 1H). |
| 485 | 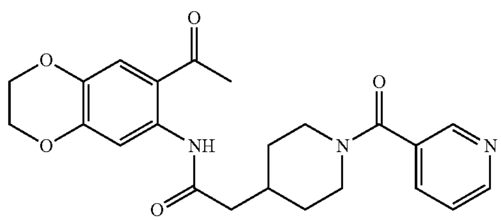 [SMILES: CC(=O)c1cc2c(cc1NC(=O)CC1CCN(C(=O)c3cccnc3)CC1)OCCO2] | 424 | 0.24 | (DMSO-d₆) δ 0.92-1.35 (m, 2H), 1.68 (m, 2H), 1.94-2.14 (m, 1H), 2.31 (m, 2H), 2.56 (s, 3H), 2.58-3.22 (m, 3H), 3.50 (d, J = 13.6 Hz, 1H), 4.22-4.37 (m, 4H), 7.40-7.49 (m, 1H), 7.54 (s, 1H), 7.81 (m, 1H), 8.04 (s, 1H), 8.54-8.69 (m, 2H), 11.45 (d, J = 8.2 Hz, 1H). |
| 486 | 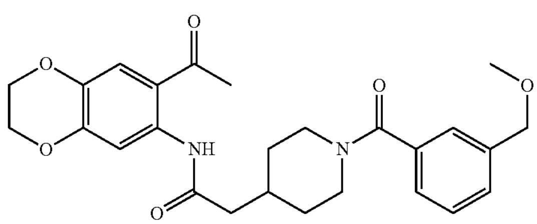 [SMILES: COCc1cccc(C(=O)N2CCC(CC(=O)Nc3cc4c(cc3C(C)=O)OCCO4)CC2)c1] | 467 | 0.188 | (DMSO-d₆) δ 1.20 (br s, 2H), 1.61 (br s, 1H), 1.75 (br s, 1H), 1.97-2.10 (m, 1H), 2.32 (d, J = 7.0 Hz, 2H), 2.56 (s, 3H), 2.77 (br s, 1H), 3.03 (br s, 1H), 3.30 (s, 3H), 3.53 (br s, 1H), 4.23-4.29 (m, 2H), 4.31-4.36 (m, 2H), 4.45 (br s, 1H), 4.44 (s, 2H), 7.25-7.31 (m, 2H), 7.35-7.43 (m, 2H), 7.53 (s, 1H), 8.04 (s, 1H), 11.45 (s, 1H). |
| 487 | 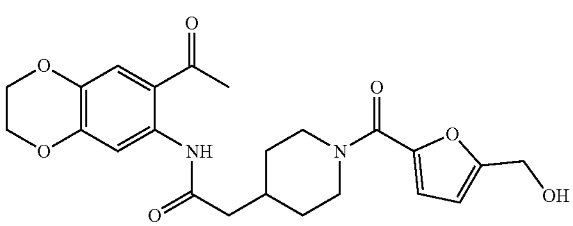 [SMILES: CC(=O)c1cc2c(cc1NC(=O)CC1CCN(C(=O)c3ccc(CO)o3)CC1)OCCO2] | 443 | 0.25 | (DMSO-d₆) δ 0.89-1.27 (m, 2H), 1.73 (m, 2H), 1.97-2.18 (m, 1H), 2.31 (m, 2H), 2.56 (s, 3H), 2.58-2.76 (m, 2H), 2.98 (m, 1H), 4.23-4.39 (m, H), 4.42 (d, J = 5.8 Hz, 2H), 5.36 (t, J = 5.9 Hz, 1H), 6.41 (dd, J = 3.4, 0.7 Hz, 1H), 6.86 (d, J = 3.3 Hz, 1H), 7.54 (s, 1H), 8.04 (s, 1H), 11.44 (s, 1H). |
| 488 | 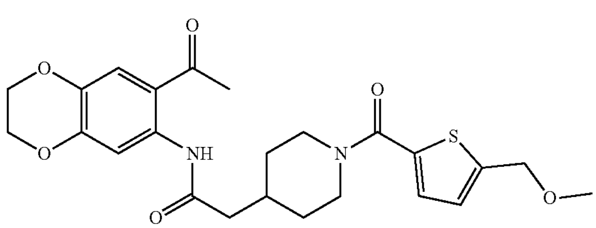 | 473 | 0.015 | (DMSO-d₆) δ 1.21 (m, 2H), 1.73 (d, J = 12.1 Hz, 2H), 2.07 (m, 1H), 2.32 (d, J = 7.0 Hz, 2H), 2.56 (s, 3H), 2.98 (br, 2H). 3.23-3.31 (m, 3H), 4.14-4.38 (m, 6H), 4.58 (d, J = 0.9 Hz, 2H), 7.02 (dt, J = 3.6, 0.7 Hz, 1H), 7.23 (d, J = 3.6 Hz, 1H), 7.54 (s, 1H), 8.05 (s, 1H), 11.45 (s, 1H). |

TABLE 8-continued

| SID | Structure | Obs Mol Ion MS (M + 1) | hT2R54 IC50 (uM) | ¹H NMR (400 MHz) |
|---|---|---|---|---|
| 489 | 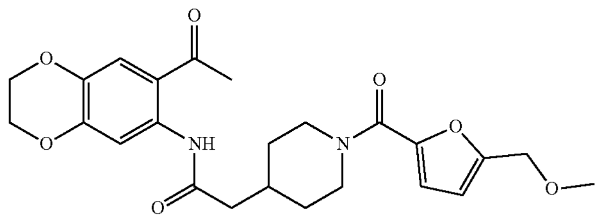 [SMILES: COCc1ccc(C(=O)N2CCC(CC(=O)Nc3cc4c(cc3C(C)=O)OCCO4)CC2)s1] | 457 | 0.15 | (DMSO-d₆) δ 1.20 (m, 2H), 1.75 (m, 2H), 2.07 (m, 1H), 2.32 (d, J = 7.1 Hz, 2H), 2.56 (s, 3H), 2.99 (br, 2H). 3.26 (s, 2H), 4.17-4.37 (m, 6H), 4.38 (s, 3H), 6.55 (d, J = 3.4 Hz, 1H), 6.88 (d, J = 3.4 Hz, 1H), 7.54 (s, 1H), 8.05 (s, 1H), 11.44 (s, 1H). |
| 490 | 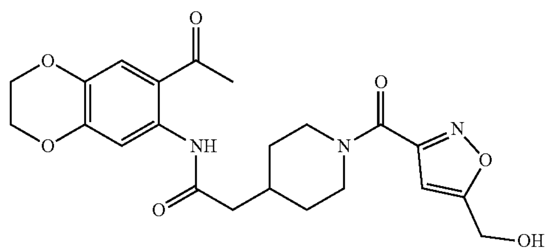 [SMILES: CC(=O)c1cc2c(cc1NC(=O)CC1CCN(C(=O)c3cc(CO)on3)CC1)OCCO2] | 444 | 0.16 | (DMSO-d₆) δ 1.18 (m, 2H), 1.66-1.87 (m, 2H), 2.06 (m, 1H), 2.26-2.35 (m, 2H), 2.56 (s, 3H), 2.83 (m, 1H), 3.09 (m, 1H), 3.84 (d, J = 13.5 Hz, 1H), 4.22-4.38 (m, 4H), 4.43 (d, J = 13.2 Hz, 1H), 4.60 (d, J = 5.2 Hz, 2H), 5.73 (t, J = 6.0 Hz, 1H), 6.55 (s, 1H), 7.54 (d, J = 0.7 Hz, 1H), 7.96 (s, 1H). 8.04 (d, J = 1.0 Hz, 1H), 11.44 (s, 1H). |
| 491 | 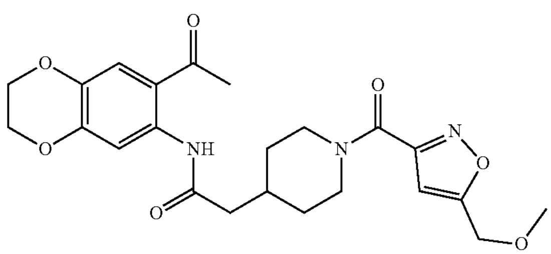 [SMILES: COCc1cc(C(=O)N2CCC(CC(=O)Nc3cc4c(cc3C(C)=O)OCCO4)CC2)no1] | 458 | 0.16 | (DMSO-d₆) δ 1.20 (m, 2H), 1.74 (dd, J = 34.5, 12.9 Hz, 2H), 2.10 (m, 1H), 2.32 (dd, J = 7.1, 1.8 Hz, 2H), 2.56 (s, 3H), 2.77-2.90 (m, 1H), 3.13 (t, J = 12.4 Hz, 1H), 3.32 (s, 3H), 3.83 (d, J = 13.6 Hz, 1H), 4.23-4.37 (m, 4H), 4.44 (d, J = 13.3 Hz, 1H), 4.59 (s, 2H), 6.71 (s, 1H), 7.54 (s, 1H), 8.04 (s, 1H), 11.44 (s, 1H). |
| 492 | 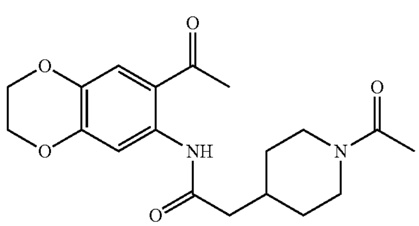 | 361 | 0.17 | (DMSO-d₆) δ 1.09-1.24 (m, 2H), 1.67 (t, J = 15.0 Hz, 2H), 1.97 (m, 4H), 2.28 (d, J = 7.1 Hz, 2H), 2.5 (m, 2H), 2.56 (s, 3H), 3.00 (m, 1H), 3.77 (d, J = 13.7 Hz, 1H), 4.22-4.37 (m, 4H), 7.54 (s, 1H), 8.05 (s, 1H), 11.44 (s, 1H). |
| 493 | 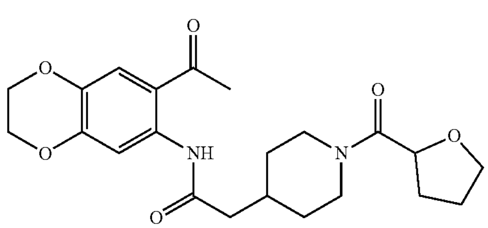 | 417 | 0.45 | (DMSO-d₆, rotamers) δ 0.89-1.26 (m, 3H), 1.68 (m, 2H), 1.81 (q, J = 7.4 Hz, 2H), 1.97 (m, 2H), 2.29 (d, J = 7.1 Hz, 2H), 2.56 (s, 3H), 2.99 (q, J = 13.7 Hz, 1H), 3.30 (m, 2H), 3.74 (dq, J = 13.1, 6.9, 6.3 Hz, 2H), 3.99 (d, J = 16.4 Hz, 1H), 4.21-4.40 (m, 4H), 4.63 (dd, J = 7.3, 5.9 Hz, 1H), 7.54 (s, 1H), 8.04 (s, 0.5H), 8.05 (s, 0.5H), 11.43 (s, 0.5H), 11.44 (s, 0.5H). |

TABLE 8-continued

| SID | Structure | Obs Mol Ion MS (M + 1) | hT2R54 IC50 (uM) | ¹H NMR (400 MHz) |
|---|---|---|---|---|
| 494 | 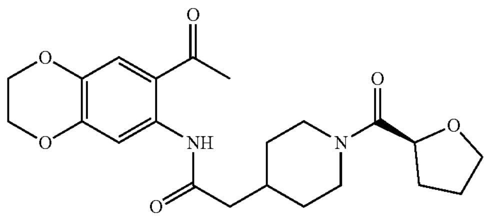 [SMILES: CC(=O)c1cc2c(cc1NC(=O)CC1CCN(C(=O)[C@@H]3CCCO3)CC1)OCCO2] | 417 | 0.3 | (DMSO-d$_6$, rotamers) δ 1.02-1.26 (m, 3H), 1.68 (m, 2H), 1.81 (q, J = 7.4 Hz, 2H), 1.97 (m, 2H), 2.29 (d, J = 7.1 Hz, 2H), 2.56 (s, 3H), 2.99 (q, J = 13.7 Hz, 1H), 3.30 (m, 2H), 3.74 (dq, J = 13.1, 6.9, 6.3 Hz, 2H), 3.99 (d, J = 16.4 Hz, 1H), 4.21-4.40 (m, 4H), 4.63 (dd, J = 7.3, 5.9 Hz, 1H), 7.54 (s, 1H), 8.04 (s, 0.5H), 8.05 (s, 0.5H), 11.43 (s, 0.5H), 11.44 (s, 0.5H). |
| 495 | 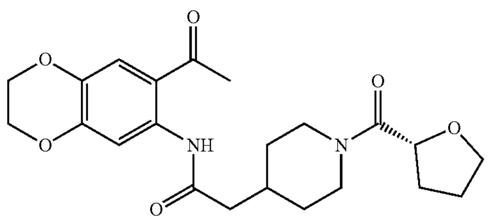 | 417 | 0.2 | (DMSO-d$_6$, rotamers) δ 1.04-1.23 (m, 3H), 1.68 (m, 2H), 1.81 (m, 2H), 1.99 (m, 2H), 2.28 (d, J = 7.1 Hz, 2H), 2.56 (s, 3H), 2.99 (q, J = 13.8, 13.4 Hz, 1H), 3.33 (m, 2H), 3.74 (dt, J = 13.7, 7.2 Hz, 2H), 3.96 (d, J = 13.9 Hz, 1H), 4.19-4.39 (m, 4H), 4.63 (dd, J = 7.2, 6.0 Hz, 1H), 7.54 (s, 1H), 8.03 (s, 0.5H), 8.04 (s, 0.5H), 11.42 (s, 0.5H), 11.43 (s, 0.5H). |
| 496 | 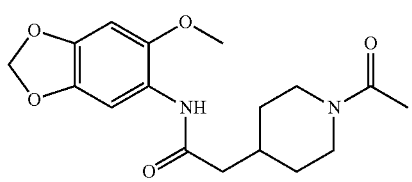 [SMILES: COc1cc2c(cc1NC(=O)CC1CCN(C(C)=O)CC1)OCO2] | 335 | >10 | |
| 497 | 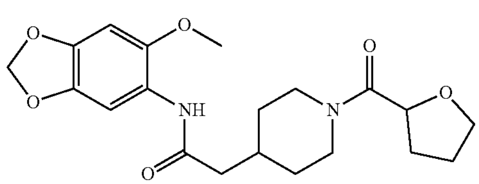 [SMILES: COc1cc2c(cc1NC(=O)CC1CCN(C(=O)C3CCCO3)CC1)OCO2] | 391 | >10 | |
| 498 | 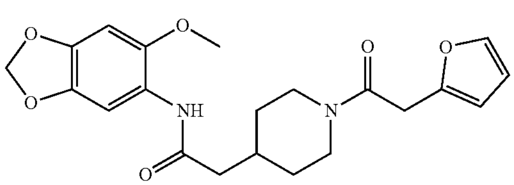 [SMILES: COc1cc2c(cc1NC(=O)CC1CCN(C(=O)Cc3ccco3)CC1)OCO2] | 401 | >10 | |
| 499 | 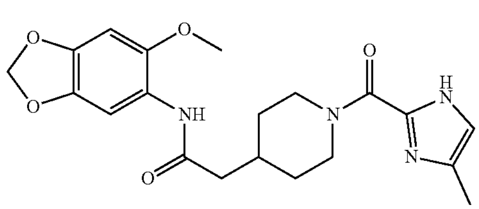 [SMILES: COc1cc2c(cc1NC(=O)CC1CCN(C(=O)c3nc(C)c[nH]3)CC1)OCO2] | 401 | >10 | |

TABLE 8-continued

| SID | Structure | Obs Mol Ion MS; (M + 1) | hT2R54 IC50 (uM) | ¹H NMR (400 MHz) |
|---|---|---|---|---|
| 500 | 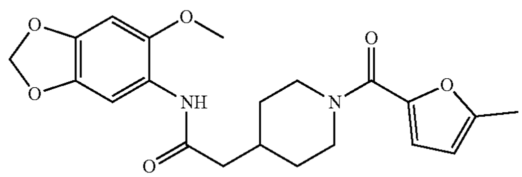 [SMILES: COc1cc2c(cc1NC(=O)CC1CCN(C(=O)c3ccc(C)o3)CC1)OCO2] | 401 | 4 | |
| 501 | 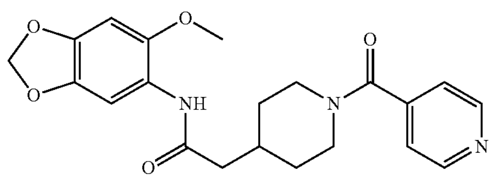 [SMILES: COc1cc2c(cc1NC(=O)CC1CCN(C(=O)c3ccncc3)CC1)OCO2] | 398 | >50 | |
| 502 | 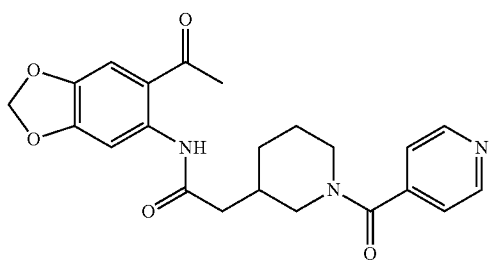 [SMILES: CC(=O)c1cc2c(cc1NC(=O)CC1CCCN(C(=O)c3ccncc3)C1)OCO2] | 410 | 0.170 | |
| 503 | 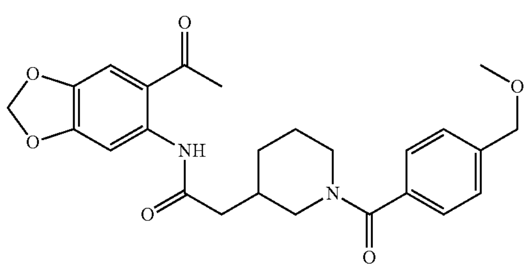 [SMILES: COCc1ccc(C(=O)N2CCCC(CC(=O)Nc3cc4c(cc3C(C)=O)OCO4)C2)cc1] | 453 | 0.099 | |
| 504 | 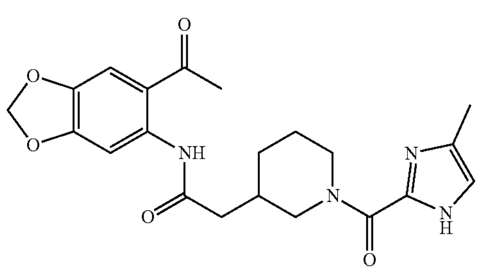 [SMILES: CC(=O)c1cc2c(cc1NC(=O)CC1CCCN(C(=O)c3nc(C)c[nH]3)C1)OCO2] | 413 | 0.159 | |
| 505 | 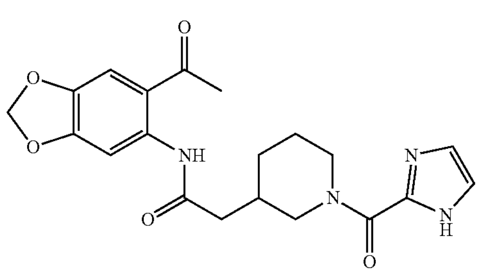 [SMILES: CC(=O)c1cc2c(cc1NC(=O)CC1CCCN(C(=O)c3ncc[nH]3)C1)OCO2] | 399 | 0.130 | |

TABLE 8-continued

| SID | Structure | Obs Mol Ion MS (M + 1) | hT2R54 IC50 (uM) | ¹H NMR (400 MHz) |
|---|---|---|---|---|
| 506 | 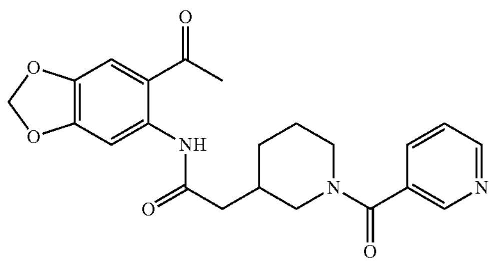 [SMILES: CC(=O)c1cc2c(cc1NC(=O)CC1CCCN(C(=O)c3cccnc3)C1)OCO2] | 410 | 0.113 | |
| 507 | 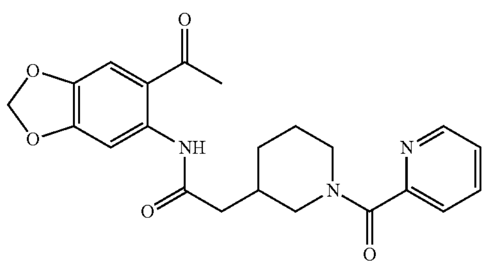 [SMILES: CC(=O)c1cc2c(cc1NC(=O)CC1CCCN(C(=O)c3ccccn3)C1)OCO2] | 410 | 0.275 | |
| 508 | 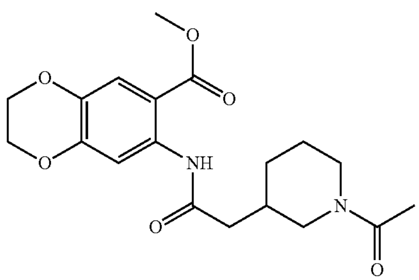 [SMILES: COC(=O)c1cc2c(cc1NC(=O)CC1CCCN(C(C)=O)C1)OCCO2] | 377 | 1.2 | (DMSO-d₆) δ 1.15-1.44 (m, 2H), 1.54-1.68 (m, 1H), 1.72-1.93 (m, 2H), 1.95 (s, 1.5H), 1.96 (s, 1.5H), 2.16-2.46 (m, 2.5H), 2.63-2.76 (m, 0.5H), 2.82-2.89 (m, 0.5H), 2.94-3.02 (m, 0.5H), 3.60-3.76 (m, 1H), 3.80 (s, 3H), 3.98-4.07 (m, 0.5H), 4.16-4.22 (m, 0.5H), 4.21-4.26 (m, 2H), 4.27-4.34 (m, 2H), 7.36 (s, 0.5H), 7.36 (s, 0.5H), 7.85 (s, 0.5H), 7.90 (s, 0.5H), 10.51 (s, 0.5H), 10.53 (s, 0.5H). |
| 509 | 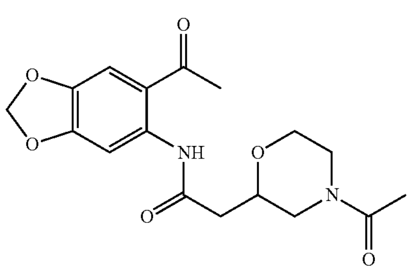 [SMILES: CC(=O)c1cc2c(cc1NC(=O)CC1CN(C(C)=O)CCO1)OCO2] | 349 | 0.18 | (DMSO-d₆, rotamers) δ 2.01 (s, 3H), 2.57 (s, 3H), 2.93-2.99 (m, 1H), 3.11-3.17 (m, 1H), 3.43-3.50 (m, 1H), 3.65-3.84 (m, 4H), 4.14 (d, J = 13.2 Hz, 1H), 4.29 (d, J = 12.8 Hz, 1H), 6.13 (s, 1H), 6.14 (s, 1H), 7.58 (s, 0.5H), 7.59 (s, 0.5H), 8.11 (s, 0.5H), 8.12 (s, 0.5H), 11.85 (s, 0.5H), 11.87 (s, 0.5H). |

TABLE 8-continued

| SID | Structure | Obs Mol Ion MS; (M + 1) | hT2R54 IC50 (uM) | ¹H NMR (400 MHz) |
|---|---|---|---|---|
| 510 | 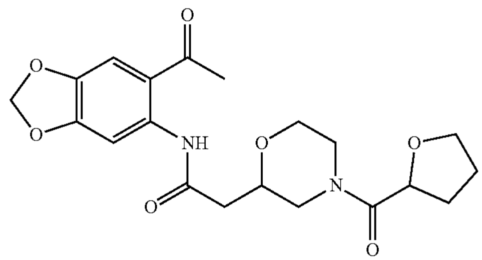 [SMILES: CC(=O)c1cc2c(cc1NC(=O)CC1CN(C(=O)C3CCCO3)CCO1)OCO2] | 405 | 0.15 | (DMSO-d₆, rotamers) δ 1.12 (d, J = 6.6 Hz, 1H), 1.27 (d, J = 7.1 Hz, 1H), 1.80-1.83 (m, 1H), 2.03-2.08 (m, 1H), 2.57 (s, 3H), 2.64-2.69 (m, 1H), 2.95-2.99 (m, 1H), 3.12-3.15 (m, 1H), 3.42-3.48 (m, 1H), 3.72-3.85 (m, 5H), 4.12 (d, J = 13.2 Hz, 1H), 4.26 (d, J = 13.1 Hz, 1H), 4.67 (m, 1H), 6.13 (s, 1H), 6.14 (s, 1H), 7.58 (s, 1H), 8.10 (s, 0.5H), 8.12 (s, 0.5H), 11.83 (s, 0.5H), 11.86 (s, 0.5H). |
| 511 | 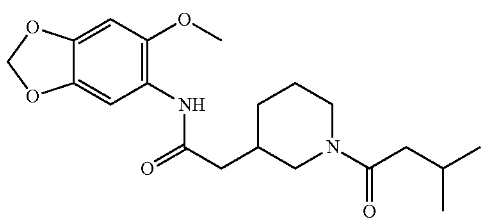 [SMILES: COc1cc2c(cc1NC(=O)CC1CCCN(C(=O)CC(C)C)C1)OCO2] | 377 | >>10 | |
| 512 | 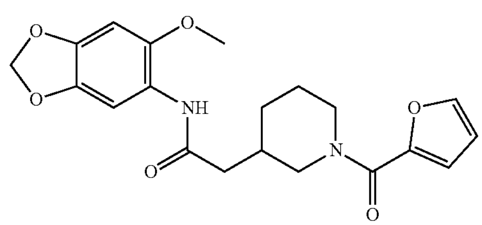 [SMILES: COc1cc2c(cc1NC(=O)CC1CCCN(C(=O)c3ccco3)C1)OCO2] | 387 | 7.7 | |
| 513 | 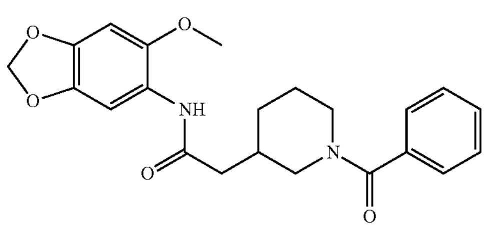 [SMILES: COc1cc2c(cc1NC(=O)CC1CCCN(C(=O)c3ccccc3)C1)OCO2] | 397 | 2.7 | (DMSO-d₆) δ 1.23-1.28 (m, 1H), 1.44 (m, 1H), 1.59 (m, 1H), 1.71 (m, 1H), 1.95 (m, 1H), 2.13-2.25 (m, 2H), 2.79-2.99 (m, 2H), 3.71-3.75 (br.s, 3H), 4.22 (m, 1H), 4.33 (m, 1H), 5.95 (s, 2H), 6.83 (br.s, 1H), 7.13 (br.s, 1H), 7.35-7.42 (m, 5H), 9.09 (br.s, 1H). |
| 514 | 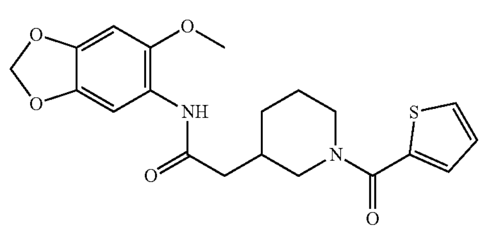 [SMILES: COc1cc2c(cc1NC(=O)CC1CCCN(C(=O)c3cccs3)C1)OCO2] | 403 | 1.0 | (DMSO-d₆) δ 1.23-1.30 (m, 1H), 1.44-1.48 (m, 1H), 1.70-1.73 (m, 1H), 1.83-1.86 (m, 1H), 1.96 (m, 1H), 2.30 (m, 2H), 2.81-2.99 (m, 2H), 3.73 (s, 3H), 4.20-4.23 (m, 2H), 5.95 (s, 2H), 6.84 (s, 1H), 7.06 (t, J = 4.0 Hz, 1H), 7.35 (s, 1H), 7.38 (dd, J = 3.6, 1.1 Hz, 1H), 7.72 (dd, J = 5.0, 1.1 Hz, 1H), 9.08 (s, 1H). |

TABLE 8-continued

| SID | Structure | Obs Mol Ion MS; (M + 1) | hT2R54 IC50 (uM) | ¹H NMR (400 MHz) |
|---|---|---|---|---|
| 515 | 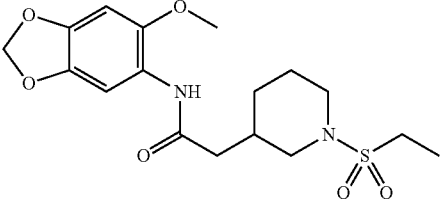 [SMILES: CCS(=O)(=O)N1CCCC(CC(=O)Nc2cc3c(cc2OC)OCO3)C1] | 385 | 0.5 | (DMSO-d₆) δ 1.08-1.13 (m, 1H), 1.20 (t, J = 7.4 Hz, 3H), 1.46 (m, 1H), 1.73 (t, J = 16.6 Hz, 2H), 1.94 (m, 1H), 2.29 (d, J = 7.0 Hz, 2H), 2.56 (m, 1H), 2.78 (td, J = 11.4, 2.5 Hz, 1H), 3.01 (q, J = 7.3 Hz, 2H), 3.46 (m, 1H), 3.57 (dd, J = 11.7, 3.8 Hz, 1H), 3.75 (s, 3H), 5.94 (s, 2H), 6.84 (s, 1H), 7.39 (s, 1H), 9.06 (s, 1H). |

Example 33—Synthesis of N-(6-Acetylbenzo[d][1,3]dioxol-5-yl)-2-(tetrahydro-2H-pyran-4-yl)acetamide (270)

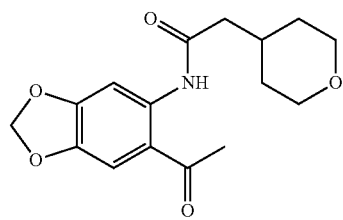

Prepared in a similar manner as in Example 24b from 2-(tetrahydro-2H-pyran-4-yl)acetic acid (70 mg, 0.5 mmol), 1-(6-aminobenzo[d][1,3]dioxol-5-yl)ethan-1-one (90 mg, 0.5 mmol), and TEA (150 mg, 1.5 mmol) to give 87 mg (58% yield) of the title compound as a light yellow solid. Alternatively, prepared as in Example 1c from 1-(6-aminobenzo[d][1,3]dioxol-5-yl)ethan-1-one and 2-(tetrahydro-2H-pyran-4-yl)acetyl chloride. MS 306 (M+H⁺).

Compounds in Table 9 were prepared in similar manner as in Example 1c and/or 24b from 1-(6-aminobenzo[d][1,3]dioxol-5-yl)ethan-1-one and the corresponding commercially available carboxylic acids and/or acyl chlorides.

TABLE 9

| SID | Structure | Obs Mol Ion; MS (M + 1) | hT2R54 IC50 (uM) | ¹H NMR (400 MHz) |
|---|---|---|---|---|
| 270 | 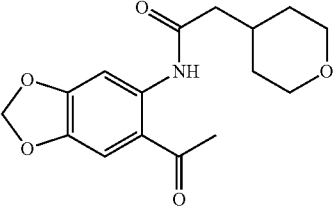 [SMILES: CC(=O)c1cc2c(cc1NC(=O)CC1CCOCC1)OCO2] | 306 | 0.561 | (CD3OD) δ 1.71-1.84 (m, 2H), 2.07-2.15 (m, 2H), 2.51-2.61 (m, 1H), 2.78 (d, J = 7.2 Hz, 2H), 3.07 (s, 3H), 3.27 (d, J = 0.5 Hz, 1H), 3.80 (td, J = 11.9, 2.2 Hz, 2H), 4.27-4.36 (m, 2H), 6.53-6.60 (m, 2H), 7.96 (s, 1H), 8.83 (s, 1H), 12.58 (s, 1H). |
| 271 | 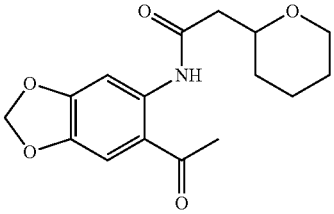 [SMILES: CC(=O)c1cc2c(cc1NC(=O)CC1CCCCO1)OCO2] | 306 | 0.152 | (DMSO-d₆) δ 1.19-1.31 (m, 1H), 1.37-1.56 (m, 3H), 1.61 (br d, J = 13.1 Hz, 1H), 1.70-1.82 (m, 1H), 2.38 (dd, J = 14.8, 8.8 Hz, 1H), 2.47-2.53 (m, 1H), 2.56 (s, 3H), 3.33-3.41 (m, 1H), 3.66-3.73 (m, 1H), 3.79-3.97 (m, 1H), 6.13 (br d, J = 1.0 Hz, 2H), 7.58 (s, 1H), 8.15 (s, 1H), 11.85 (s, 1H). |

TABLE 9-continued

| SID | Structure | Obs Mol Ion; MS (M + 1) | hT2R54 IC50 (uM) | $^1$H NMR (400 MHz) |
|---|---|---|---|---|
| 272 | 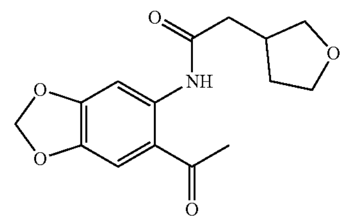 [SMILES: CC(=O)c1cc2c(cc1NC(=O)CC1CCOC1)OCO2] | 292 | 1.39 | (DMSO-d$_6$) δ 1.49-1.59 (m, 1H), 1.98-2.08 (m, 1H), 2.45-2.50 (m, 3H), 2.53-2.60 (m, 4H), 3.27-3.32 (m, 1H), 3.58-3.65 (m, 1H), 3.68-3.75 (m, 1H), 3.82 (dd, J = 8.4, 6.8 Hz, 1H), 6.13 (s, 2H), 7.58 (s, 1H), 8.08 (s, 1H), 11.80 (s, 1H). |
| 273 | 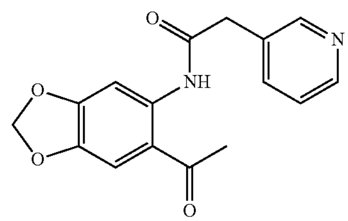 [SMILES: CC(=O)c1cc2c(cc1NC(=O)Cc1cccnc1)OCO2] | 299 | 0.454 | (DMSO-d$_6$) δ 2.53 (d, J = 0.8 Hz, 3H), 3.81 (s, 2H), 6.13 (d, J = 0.8 Hz, 2H), 7.29-7.43 (m, 1H), 7.57 (d, J = 0.7 Hz, 1H), 7.73-7.77 (m, 1H), 8.07 (d, J = 0.8 Hz, 1H), 8.47-8.51 (m, 1H), 8.54 (d, J = 2.3 Hz, 1H), 11.83 (s, 1H). |
| 274 | 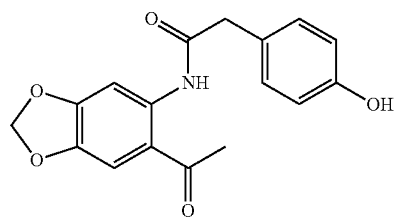 [SMILES: CC(=O)c1cc2c(cc1NC(=O)Cc1ccc(O)cc1)OCO2] | 314 | 0.554 | (DMSO-d$_6$) δ 2.51 (s, 3H), 3.57 (s, 2H), 6.12 (s, 2H), 6.72 (d, J = 8.5 Hz, 2H), 7.12 (d, J = 8.5 Hz, 2H), 7.55 (s, 1H), 8.14 (s, 1H), 9.34 (s, 1H), 11.80 (s, 1H). |
| 275 | 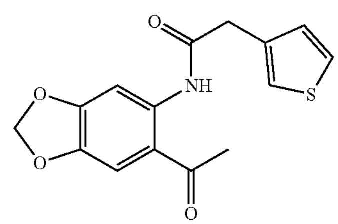 [SMILES: CC(=O)c1cc2c(cc1NC(=O)Cc1ccsc1)OCO2] | 304 | 0.704 | (DMSO-d$_6$) δ 2.52 (s, 3H), 3.75 (s, 2H), 6.13 (s, 2H), 7.08 (dd, J = 4.9, 1.3 Hz, 1H), 7.34-7.44 (m, 1H), 7.52 (dd, J = 4.9, 2.9 Hz, 1H), 7.56 (s, 1H), 8.13 (s, 1H), 11.81 (s, 1H). |
| 276 | 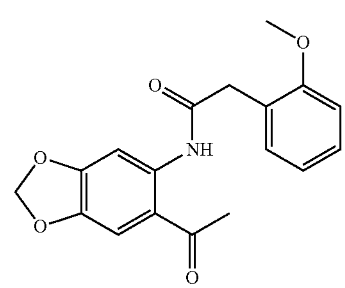 [SMILES: COc1ccccc1CC(=O)Nc1cc2c(cc1C(C)=O)OCO2] | 328 | 0.804 | (DMSO-d$_6$) δ 2.50 (s, 3H), 3.64 (s, 2H), 3.76 (s, 3H), 6.12 (s, 2H), 6.94 (td, J = 7.4, 1.1 Hz, 1H), 7.01 (dd, J = 8.2, 1.0 Hz, 1H), 7.24-7.34 (m, 2H), 7.55 (s, 1H), 8.16 (s, 1H), 11.76 (s, 1H). |
| 277 | 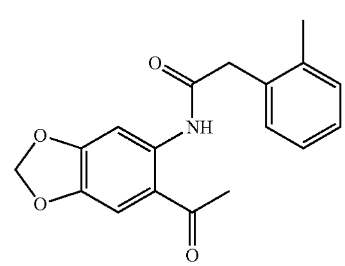 [SMILES: CC(=O)c1cc2c(cc1NC(=O)Cc1ccccc1C)OCO2] | 312 | 0.74 | (DMSO-d$_6$) δ 2.26 (s, 3H), 2.50 (s, 3H), 3.75 (s, 2H), 6.12 (d, J = 0.6 Hz, 2H), 7.16-7.22 (m, 3H), 7.26-7.30 (m, 1H), 7.55 (d, J = 0.6 Hz, 1H), 8.15 (d, J = 0.6 Hz, 1H), 11.79 (s, 1H). |

TABLE 9-continued

| SID | Structure | Obs Mol Ion; MS (M + 1) | hT2R54 IC50 (uM) | ¹H NMR (400 MHz) |
|---|---|---|---|---|
| 278 | 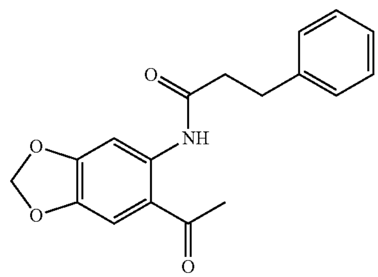 [SMILES: CC(=O)c1cc2c(cc1NC(=O)CCc1ccccc1)OCO2] | 312 | 1.224 | (DMSO-d$_6$) δ 2.54 (s, 3H), 2.69 (t, J = 7.6 Hz, 2H), 2.92 (t, J = 1.6 Hz, 2H), 6.13 (s, 2H), 7.14-7.31 (m, 4H), 7.56 (s, 1H), 8.09 (s, 1H), 11.81 (s, 1H). |
| 279 | 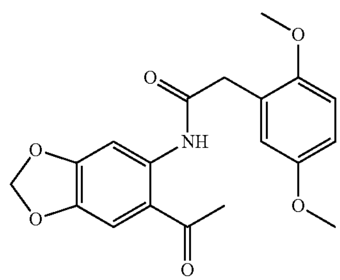 [SMILES: COc1ccc(OC)c(CC(=O)Nc2cc3c(cc2C(C)=O)OCO3)c1] | 358 | 1.472 | (DMSO-d$_6$) δ 2.51 (s, 3H), 3.62 (s, 2H), 3.71 (d, J = 4.5 Hz, 6H), 6.12 (s, 2H), 6.77-7.03 (m, 3H), 7.55 (s, 1H), 8.16 (s, 1H), 11.75 (s, 1H). |
| 280 | 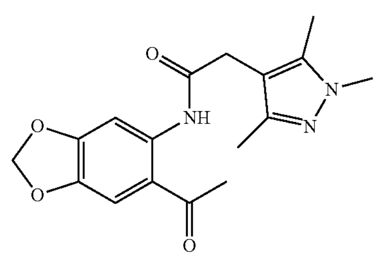 [SMILES: CC(=O)c1cc2c(cc1NC(=O)Cc1c(C)nn(C)c1C)OCO2] | 330 | 1.72 | (DMSO-d$_6$) δ 2.04 (s, 3H), 2.17 (d, J = 0.6 Hz, 3H), 2.50 (d, J = 0.6 Hz, 2H), 3.41 (s, 2H), 3.64 (s, 3H), 6.12 (d, J = 0.6 Hz, 2H), 7.55 (d, J = 0.5 Hz, 1H), 8.19 (d, J = 0.6 Hz, 1H), 11.71 (s, 1H). |
| 281 | 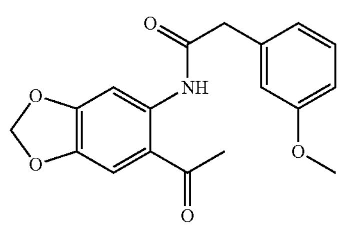 [SMILES: COc1cccc(CC(=O)Nc2cc3c(cc2C(C)=O)OCO3)c1] | 328 | 1.805 | (DMSO-d$_6$) δ 2.52 (s, 3H), 3.69 (s, 2H), 3.75 (s, 3H), 6.13 (s, 2H), 6.82-6.95 (m, 3H), 7.22-7.29 (m, 1H), 7.56 (s, 1H), 8.11 (s, 1H), 11.83 (s, 1H). |
| 516 | 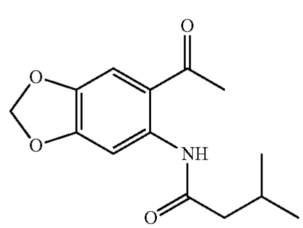 [SMILES: CC(=O)c1cc2c(cc1NC(=O)CC(C)C)OCO2] | 264 | 3 | |
| 517 | 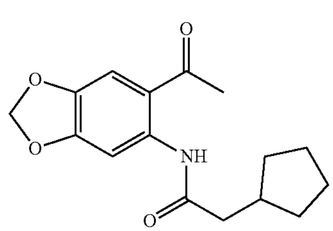 [SMILES: CC(=O)c1cc2c(cc1NC(=O)CC1CCCC1)OCO2] | 290 | 0.414 | (DMSO-d$_6$) δ 1.11-1.24 (m, 2H), 1.45-1.67 (m, 4H), 1.71-1.82 (m, 2H), 2.15-2.27 (m, 1H), 2.35 (d, J = 7.4 Hz, 2H), 2.57 (s, 3H), 6.13 (s, 2H), 7.58 (s, 1H), 8.14 (s, 1H), 11.85 (s, 1H). |

TABLE 9-continued

| SID | Structure | Obs Mol Ion; MS (M + 1) | hT2R54 IC50 (uM) | ¹H NMR (400 MHz) |
|---|---|---|---|---|
| 518 | 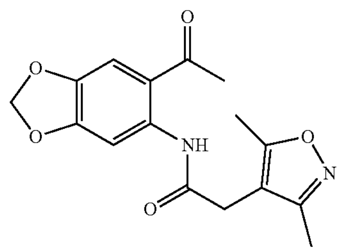 [SMILES: CC(=O)c1cc2c(cc1NC(=O)Cc1c(C)noc1C)OCO2] | 317 | 3.8 | |
| 519 | 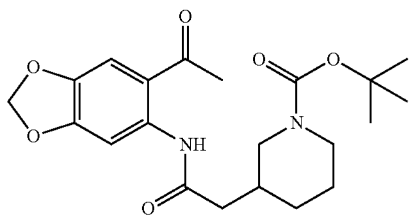 [SMILES: CC(=O)c1cc2c(cc1NC(=O)CC1CCCN(C(=O)OC(C)(C)C)C1)OCO2] | 405 | 0.9 | (DMSO-d$_6$) δ 1.23 (m, 2H), 1.35 (s, 9H), 1.56-1.62 (m, 1H), 1.73-1.79 (m, 1H), 1.88 (br.s, 1H), 2.29 (d, J = 7.5 Hz, 2H), 2.57 (s, 3H), 2.84 (br.s, 2H), 3.77 (br.s, 2H), 6.14 (s, 2H), 7.59 (s, 1H), 8.12 (s, 1H), 11.83 (s, 1H). |
| 520 | 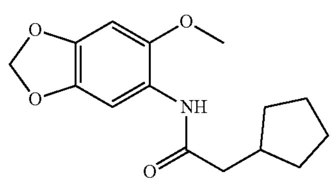 [SMILES: COc1cc2c(cc1NC(=O)CC1CCCC1)OCO2] | 278 | 0.308 | (DMSO-d$_6$) δ 1.11-1.23 (m, 2H), 1.43-1.64 (m, 4H), 1.67-1.78 (m, 2H), 2.11-2.24 (m, 1H), 2.32 (d, J = 7.4 Hz, 2H), 3.74 (d, J = 1.2Hz, 3H), 5.94 (d, J = 1.2 Hz, 2H), 6.84 (d, J = 1.1 Hz, 1H), 7.42 (d, J = 1.1 Hz, 1H), 8.92 (s, 1H). |
| 521 | 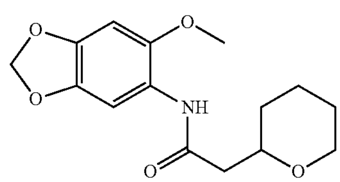 [SMILES: COc1cc2c(cc1NC(=O)CC1CCCCO1)OCO2] | 294 | 2.256 | (DMSO-d$_6$) δ 1.17-1.30 (m, 1H), 1.39-1.53 (m, 3H), 1.56-1.64 (m, 1H), 1.72-1.81 (m, 1H), 2.32-2.40 (m, 1H), 2.51-2.57 (m, 1H), 3.34-3.42 (m, 1H), 3.61-3.69 (m, 1H), 3.76 (d, J = 1.2 Hz, 3H), 3.86-3.93 (m, 1H), 5.92-5.96 (m, 2H), 6.86 (d, J = 1.1 Hz, 1H), 7.60 (d, J = 1.1 Hz, 1H), 9.16 (s, 1H). |
| 522 | 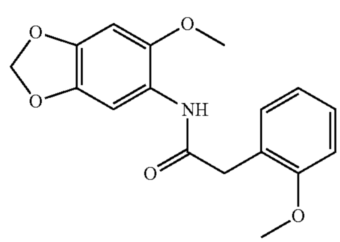 [SMILES: COc1ccccc1CC(=O)Nc1cc2c(cc1OC)OCO2] | 316 | 0.886 | (DMSO-d$_6$) δ 3.63 (s, 2H), 3.76 (d, J = 1.1 Hz, 3H), 3.82 (d, J = 1.1 Hz, 3H), 5.93 (d, J = 1.1 Hz, 2H), 6.86 (d, J = 1.1 Hz, 1H), 6.88-6.95 (m, 1H), 7.02 (d, J = 8.1 Hz, 1H), 7.19-7.29 (m, 2H), 7.58 (d, J = 1.1 Hz, 1H), 8.88 (s, 1H). |
| 523 | 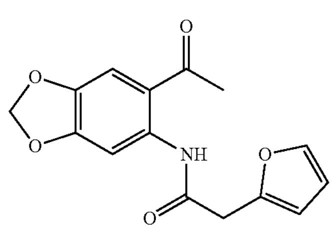 [SMILES: CC(=O)c1cc2c(cc1NC(=O)Cc1ccco1)OCO2] | 288 | 2.307 | (DMSO-d$_6$) δ 2.53 (s, 3H), 3.82 (s, 2H), 6.14 (s, 2H), 6.37-6.39 (m, 1H), 6.45 (dd, J = 3.2, 1.9 Hz, 1H), 7.57 (s, 1H), 7.61 (dd, J = 1.9, 0.9 Hz, 1H), 8.12 (s, 1H), 11.86 (s, 1H). |
| 524 | 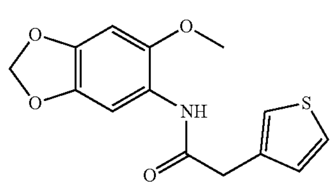 [SMILES: COc1cc2c(cc1NC(=O)Cc1ccsc1)OCO2] | 292 | 0.868 | (DMSO-d$_6$) δ 3.70 (s, 2H), 3.75 (d, J = 1.1 Hz, 3H), 5.94 (d, J = 1.1 Hz, 2H), 6.86 (d, J = 1.1 Hz, 1H), 7.08 (dt, J = 4.9, 1.3 Hz, 1H), 7.28-7.36 (m, 1H), 7.42-7.53 (m, 2H), 9.13 (s, 1H). |

TABLE 9-continued

| SID | Structure | Obs Mol Ion; MS (M + 1) | hT2R54 IC50 (uM) | ¹H NMR (400 MHz) |
|---|---|---|---|---|
| 525 | 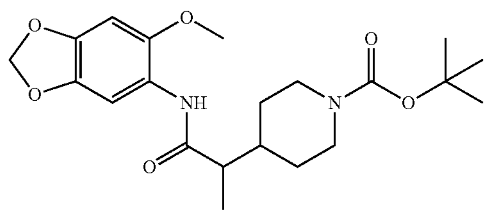 | 407 | 3.0 | (DMSO-d₆) δ 1.03 (d, J = 6.7 Hz, 3H), 1.38 (s, 9H), 1.53-1.72 (m, 5H), 2.37-2.42 (m, 1H), 3.74 (s, 3H), 3.93 (m, 4H), 5.94 (s, 2H), 6.84 (s, 1H), 7.39 (s, 1H), 8.93 (s, 1H). |
| 526 | 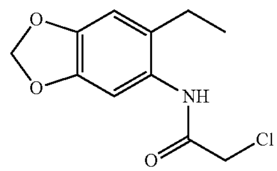 [SMILES: CCc1cc2c(cc1NC(=O)CCl)OCO2] | 242 | | (DMSO-d₆) δ 1.07 (t, J = 7.5 Hz, 3H), 2.45 (q, J = 7.5 Hz, 2H), 4.25 (s, 2H), 5.99 (s, 2H), 6.82 (s, 1H), 6.83 (s, 1H), 9.55 (s, 1H), MS 242 (MH⁺). |
| 527 | 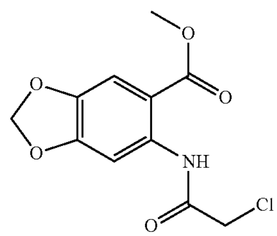 [SMILES: COC(=O)c1cc2c(cc1NC(=O)CCl)OCO2] | 272 | | (DMSO-d₆) δ 3.85 (s, 3H), 4.44 (s, 2H), 6.15 (s, 2H), 7.42 (s, 1H), 8.05 (s, 1H), 11.57 (s, 1H). |
| 528 | 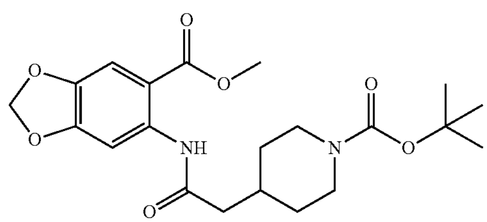 [SMILES: COC(=O)c1cc2c(cc1NC(=O)CC1CCN(C(=O)OC(C)(C)C)CC1)OCO2] | 421 | ~1 | (DMSO-d₆) δ 1.10-1.35 (m, 3H), 1.33 (s, 9H), 1.56 (m, 1H), 1.75 (m, 1H), 1.86 (m, 1H), 2.29 (m, 2H), 2.82 (m, 1H), 3.62-3.79 (m, 2H), 3.82 (s, 3H), 6.11 (s, 2H), 7.36 (s, 1H), 7.98 (s, 1H), 10.83 (s, 1H). |
| 529 | 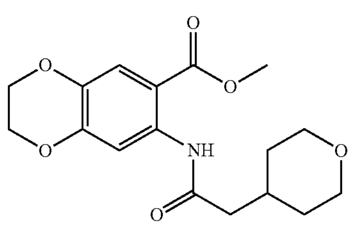 [SMILES: COC(=O)c1cc2c(cc1NC(=O)CC1CCOCC1)OCCO2] | 336 | 12 | |
| 530 | 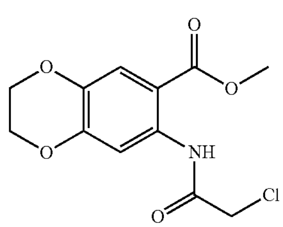 [SMILES: COC(=O)c1cc2c(cc1NC(=O)CCl)OCCO2] | 286 | | (DMSO-d₆) δ 3.84 (s, 3H), 4.24-4.29 (m, 2H), 4.31-4.37 (m, 2H), 4.42 (s, 2H), 7.44 (s, 1H), 8.01 (s, 1H), 11.33 (s, 1H). |
| 531 | 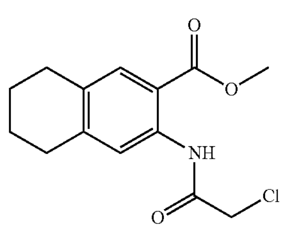 [SMILES: COC(=O)c1cc2c(cc1NC(=O)CCl)CCCC2] | 282 | | (DMSO-d₆) δ 1.68-1.79 (m, 4H), 2.66-2.79 (m, 4H), 3.86 (s, 3H), 4.42 (s, 2H), 7.70 (s, 1H), 8.14 (s, 1H), 11.23 (s, 1H). |

Example 34—Synthesis of 1-(6-Methyl-2-phenylpyrimidin-4-yl)piperidine-4-carboxamide (A)

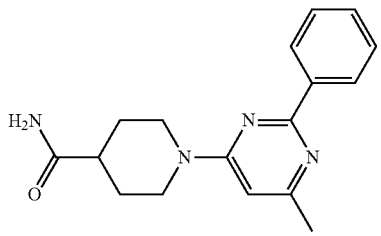 [SMILES: Cc1cc(N2CCC(C(N)=O)CC2)nc(-c2ccccc2)n1]

A mixture of 4-chloro-6-methyl-2-phenylpyrimidine (1 g, 4.89 mmol) and piperidine-4-carboxamide (0.627 g, 4.89 mmol) and trimethylamine (1.02 mL, 7.34 mmol) in anhydrous DMF (25 mL) was heated to reflux for 4 hours, upon completion, the reaction mixture was cooled to room temperature, and then was concentrated to dry, the residue was stirred in a mixed solution of EtOAc (10 mL) and water (20 mL) for about 30 min. and then the solid product was collected by filtration to obtain 1.4 g compound, then it was re-crystallized from EtOH/$H_2O$, after dry obtained 900 mg of the title compound as a white solid in 62% yield. MS ($MH^+$) 297.

Other T2R54 bitter blockers provided by the present disclosure or suitable to be used for methods of the present disclosure include the following compounds.

TABLE 10

|  | ΔF/F | Compound 1 |
|---|---|---|
| R1 | 0.29 | 91 |
| R3 | 0.20 | 83 |
| R4 | 0.08 | 112 |
| R5 | 0.31 | 104 |
| R7 | 0.30 | 97 |
| R8 | 0.48 | 108 |
| R9 | 0.27 | 80 |
| R10 | 0.51 | 82 |
| R13 | 0.25 | 90 |
| R14 | 0.44 | 91 |
| R16 | 1.13 | 100 |
| R44 | 0.15 | 89 |
| R51 | 0.49 | 103 |
| R54 | 0.20 | 15 |
| R55 | 0.15 | 100 |
| R61 | 0.48 | 61 |
| R63 | 0.22 | 83 |
| R63Rs | 0.48 | 107 |
| R64 | 0.14 | 42 |
| R65 | 0.34 | 87 |
| R67 | 0.78 | 90 |
| R71 | 0.17 | 97 |
| R75 | 0.27 | 5 |

The results shown in Table 10 demonstrate that in this assay, in the presence of Compound 1 and a bitter compound only 61% of activity of T2R61 was retained, only 42% of the activity of T2R64 was retained, only 15% of the activity of T2R54 was retained, and only 5% of the activity of T2R75

| Cmpd No. | Compound | Obs Mol Ion; MS (M + 1) | hT2R54 $IC_{50}$ (μM) | $^1$H NMR (400 MHz) |
|---|---|---|---|---|
| A | (structure: 1-(6-methyl-2-phenylpyrimidin-4-yl)piperidine-4-carboxamide) | 297 | 2.9 | (400 MHz) δ: 1.48 (m, 2H), 1.78 (m, 2H), 2.32 (s, 3H), 2.40 (m, 1H), 2.94 (m, 2H), 4.49 (m, 2H), 6.7 (s, 1H), 6.79 (s, 1H), 7.29 (s, 1H), 7.44 (m, 3H), 8.31 (m, 1H); |
| B | (structure: benzodioxole-methylamine-quinazoline-dimethoxy) | 340 | 1.8 |  |

Compounds described in this application show potent bitter antagonist effect on T2R54 in receptor based assays. In some cases they also exhibit bitter antagonist effect on other T2Rs. For example, in addition to T2R54, Cmpd 1 (Table 2) exhibits significant bitter blocking effect on T2R61, T2R64, and T2R75, respectively. Antagonist activity of 1-(6-methyl-2-phenylpyrimidin-4-yl)piperidine-4-carboxamide against a panel of bitter taste receptors is shown in Table 10, with the identity of each T2R as indicated in the left column, and the percentage activity remaining is indicated in the far right column.

was retained, as compared to the activity of the receptor in the presence of the bitter compound alone.

Example 35—Sensory Experiments

To determine the effectiveness of an individual antagonist in blocking the bitterness, taste tests were performed comparing epigallocatechin gallate (EGCg) alone, which is known to activate T2R54 with EGCg and a bitter blocker described herein, namely compound 22 (Table 2). The results shown in Table 11 below indicate clearly that compound 22 has the ability to reduce EGCg bitterness.

TABLE 11

| Samples | Total |
| --- | --- |
| 600 uM EGCG | 36 |
| 600 uM EGCG + 15 uM of compound 22 | 20 |
| Total | 56 |
| 600 uM EGCG alone selected as more bitter (p-value) | 0.044 |

Example 36—Method of Preparing the Composition

In order to manipulate or block bitter taste associated with any of the applications discussed herein, the compounds and compositions discussed herein may be used in combination with any of the products necessary for any of said applications. For example, the compounds and compositions of the present disclosure may be combined with any element associated with a product and/or application discussed herein using a method recognized in the art for preparing such a composition.

In order to manipulate or block bitter taste associated with any of the applications discussed herein, the compounds and compositions discussed herein may be used in combination with any of the products necessary for any of said applications, and may further be combined with one or more of the excipients and other additive compounds discussed in detail herein. For example, the compounds and compositions of the present disclosure may be combined with one or more of such compounds using an art recognized method, and then this mixture may further be combined with any element associated with a product and/or application discussed herein using a method recognized in the art for preparing such a composition.

The composition may be prepared e.g., by combining the ingredients with any of the compounds as shown in the table below:

TABLE 12

| | 1 | 2 | 3 | 4 | 5 | 6 | 7 | 8 | 9 | 10 | 11 | 12 | 13 | 14 | 15 | 16 | 17 | 18 |
| --- | --- | --- | --- | --- | --- | --- | --- | --- | --- | --- | --- | --- | --- | --- | --- | --- | --- | --- |
| Compound(s) | ● | ● | ● | ● | ● | ● | ● | ● | ● | ● | ● | ● | ● | ● | ● | ● | ● | ● |
| Cooling agent(s) | ◊ | ● | ● | ● | ● | ● | ● | ● | ● | ● | ● | ● | ● | ● | ● | ● | ● | ● |
| Pharmaceutical ingredient(s) | ◊ | ◊ | ● | ◊ | ◊ | ◊ | ◊ | ◊ | ◊ | ◊ | ◊ | ◊ | ◊ | ◊ | ◊ | ◊ | ◊ | ◊ |
| Food additive(s) | ◊ | ◊ | ◊ | ● | ◊ | ◊ | ◊ | ◊ | ◊ | ◊ | ◊ | ◊ | ◊ | ◊ | ◊ | ◊ | ◊ | ◊ |
| Flavorant(s) | ◊ | ◊ | ◊ | ◊ | ● | ◊ | ◊ | ◊ | ◊ | ◊ | ◊ | ◊ | ◊ | ◊ | ◊ | ◊ | ◊ | ◊ |
| Bitter compounds | ◊ | ◊ | ◊ | ◊ | ◊ | ● | ◊ | ◊ | ◊ | ◊ | ◊ | ◊ | ◊ | ◊ | ◊ | ◊ | ◊ | ◊ |
| Foodstuffs | ◊ | ◊ | | | | | ● | | | | | ◊ | ◊ | ◊ | ◊ | | | |
| Compounds known to be used in oral care products, and/or consumer products, and/or animal products, and/or pet care products | ◊ | ◊ | | | | | | ● | | | | ● | ● | ● | ● | ● | | |
| Plant products, cannabis-derived, or cannabis-related products | ◊ | ◊ | | | | | | | ● | | | ◊ | ◊ | ◊ | ◊ | | ● | ● |
| Preparations | ◊ | ◊ | | | | | | | | ● | | ◊ | ◊ | ◊ | ◊ | | | |
| Beverages, and/or scents, and/or perfumes, and/or odorants | ◊ | ◊ | | | | | | | | | ● | ◊ | ◊ | ◊ | ◊ | | | |
| Silicone compound(s) | ◊ | ◊ | ◊ | ◊ | ◊ | ◊ | ◊ | ◊ | ◊ | ◊ | ◊ | ● | ◊ | ◊ | ◊ | ◊ | ● | ◊ |
| Abrasive(s) | ◊ | ◊ | ◊ | ◊ | ◊ | ◊ | ◊ | ◊ | ◊ | ◊ | ◊ | ◊ | ● | ◊ | ◊ | ◊ | ◊ | ● |
| Surfactant(s) | ◊ | ◊ | ◊ | ◊ | ◊ | ◊ | ◊ | ◊ | ◊ | ◊ | ◊ | ◊ | ◊ | ● | ◊ | ◊ | ◊ | ◊ |
| Warming agent(s) | ◊ | ◊ | ◊ | ◊ | ◊ | ◊ | ◊ | ◊ | ◊ | ◊ | ◊ | ◊ | ◊ | ◊ | ● | ◊ | ◊ | ◊ |
| Probiotic bacteria or supplement(s) | ◊ | ◊ | ◊ | ◊ | ◊ | ◊ | ◊ | ◊ | ◊ | ◊ | ◊ | ◊ | ◊ | ◊ | ◊ | ● | ◊ | ◊ |

| | 19 | 20 | 21 | 22 | 23 | 24 | 25 | 26 | 27 | 28 | 29 | 30 | 31 | 32 | 33 | 34 | 35 | 36 |
| --- | --- | --- | --- | --- | --- | --- | --- | --- | --- | --- | --- | --- | --- | --- | --- | --- | --- | --- |
| Compound(s) | ● | ● | ● | ● | ● | ● | ● | ● | ● | ● | ● | ● | ● | ● | ● | ● | ● | ● |
| Cooling agent(s) | ● | ● | ● | ● | ● | ● | ● | ● | ● | ● | ● | ● | ● | ● | ● | ● | ● | ● |
| Pharmaceutical ingredient(s) | ◊ | ◊ | ◊ | ◊ | ◊ | ◊ | ◊ | ◊ | ◊ | ◊ | ◊ | ◊ | ◊ | ◊ | ◊ | ◊ | ◊ | ◊ |
| Food additive(s) | ◊ | ◊ | ◊ | ◊ | ◊ | ◊ | ◊ | ◊ | ◊ | ◊ | ◊ | ◊ | ◊ | ◊ | ◊ | ◊ | ◊ | ◊ |
| Flavorant(s) | ◊ | ◊ | ◊ | ◊ | ◊ | ◊ | ◊ | ◊ | ◊ | ◊ | ◊ | ◊ | ◊ | ◊ | ◊ | ◊ | ◊ | ◊ |
| Bitter compounds | ◊ | ◊ | ◊ | ◊ | ◊ | ◊ | ◊ | ◊ | ◊ | ◊ | ◊ | ◊ | ◊ | ◊ | ◊ | ◊ | ◊ | ◊ |
| Foodstuffs | | | | | | | | | | | | | | ● | ● | ● | ● | ● |
| Compounds known to be used in oral care products, and/or consumer products, and/or animal products, and/or pet care products | | | | | | | | | | | | | | | | | | |
| Plant products, cannabis-derived, or cannabis-related products | ● | ● | ● | | | | | | | | | | | | | | | |
| Preparations | | | | ● | ● | ● | ● | ● | | | | | | | | | | |
| Beverages, and/or scents, and/or perfumes, and/or odorants | | | | | | | | | ● | ● | ● | ● | ● | | | | | |
| Silicone compound(s) | ◊ | ◊ | ◊ | ● | ◊ | ◊ | ◊ | ◊ | ● | ◊ | ◊ | ◊ | ◊ | ● | ◊ | ◊ | ◊ | ◊ |
| Abrasive(s) | ◊ | ◊ | ◊ | ◊ | ● | ◊ | ◊ | ◊ | ◊ | ● | ◊ | ◊ | ◊ | ● | ◊ | ◊ | ◊ | ● |
| Surfactant(s) | ● | ◊ | ◊ | ◊ | ◊ | ● | ◊ | ◊ | ◊ | ● | ◊ | ◊ | ◊ | ● | ◊ | ◊ | ● | ◊ |
| Warming agent(s) | ◊ | ● | ◊ | ◊ | ◊ | ◊ | ● | ◊ | ◊ | ◊ | ◊ | ◊ | ◊ | ◊ | ◊ | ◊ | ● | ◊ |
| Probiotic bacteria or supplement(s) | ◊ | ◊ | ● | ◊ | ◊ | ◊ | ◊ | ● | ◊ | ◊ | ◊ | ◊ | ◊ | ◊ | ◊ | ◊ | ◊ | ● |

● refers to an ingredient that is typically be present in a composition
◊ refers to an ingredient that could be present in a composition Preparations refer to any combination of pharmaceutical preparations and topical preparations. Pharmaceutical ingredient(s) refer to any combination of inactive drug ingredients and active pharmaceutical ingredients. Flavorant(s) refer to any combination of sweetener(s), sour flavorant(s), umami flavorant(s), salty flavorant(s), bitterant(s), and flavor enhancer(s). Compound(s) refers to one or a combination of two or more compounds of the present invention, as described above.

Example 37—Cell-Based Assay for Measuring hT2R54 Inhibition

Cells stably expressing hT2R54 and a promiscuous G protein were seeded in 384 well plates 24 hours prior to the experiment. Cells were loaded with the calcium indicator Fluo4AM, washed and loaded in a FLIPR instrument with a compound plate containing increasing doses of acetaminophen in quadruplicates and prepared at 2× of final concentration. Baseline was recorded for 10 seconds, then 25 µl of Cmpd 109 (Table 4) was added onto 25 µl of cells and resulting changes in fluorescence were monitored over an additional 3 minutes. The host cell line overexpressing the G protein but not hT2R54 was treated as described above. Results of this experiment are shown in FIG. 1. The results show that cells expressing hT2R54, but not control cells, exhibited a measurable change in intracellular calcium in response to the bitter tastant acetaminophen.

Figure 2:
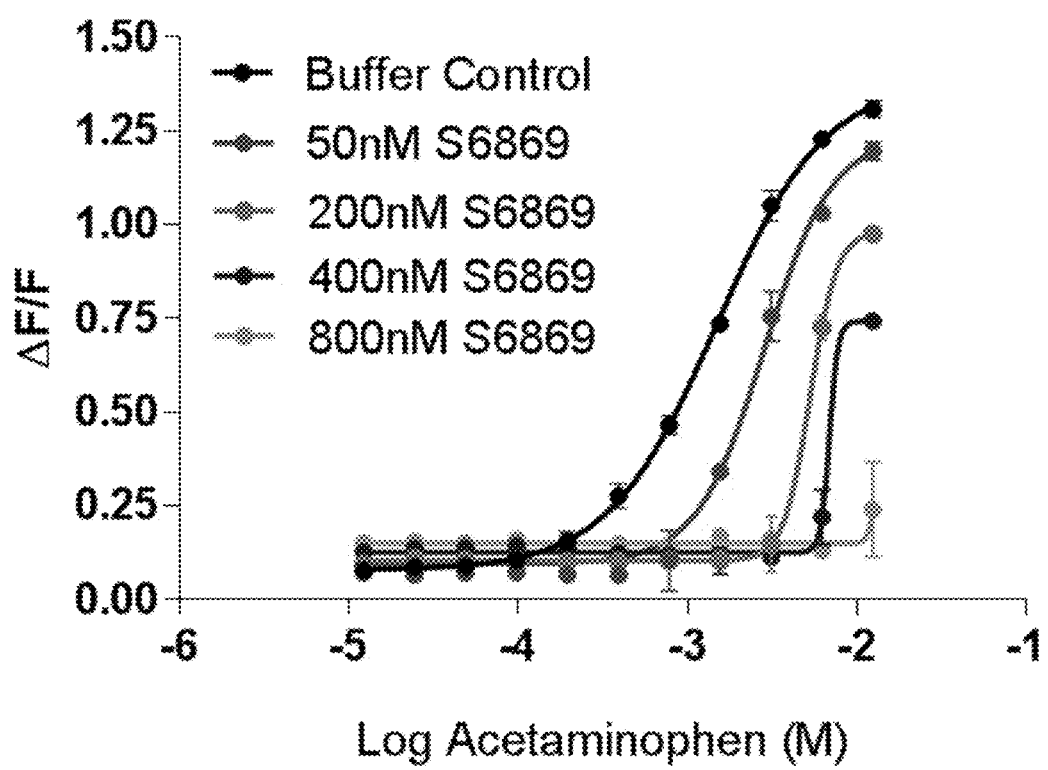
FIG. 2 shows a graph of the effect of an increase in a test compound concentration on acetaminophen dose-response (DR) on hT2R54-expressing cells. The test compound dose dependency shifts the DR curve to the right, but also causes a decrease in efficacy of acetaminophen, suggesting the test compound behaves as a non-competitive antagonist of hT2R54. Each increase in dosage shifted the curve rightward and downward; in order from left to right, the DR curves respectively correspond to 0, 50 μM, 200 μM, 400 μM, and 800 μM of test compound.

The ability of a test compound that blocks bitter taste elicited through hT2R54 was measured in this assay, as follows. Cells stably expressing hT2R54 and a promiscuous G protein were seeded in 384 well plates 24 hours prior to the experiment. Cells were loaded with the calcium indicator Fluo4AM, washed and loaded in a FLIPR instrument with a compound plate containing increasing doses of acetaminophen in buffer and increasing doses of acetaminophen with depicted fixed concentrations of Cmpd 109 (Table 4). Base line was recorded for 10 seconds, then 25 µl of compound and compound mixtures were added onto 25 µl of cells and resulting changes in fluorescence were monitored over an additional 3 minutes. Results of this experiment are shown in FIG. 2. The concentration of test compound that blocks half of the response when the bitter compound alone is present is presented as the EC50 or IC50 value.

In the examples above, the EC50 of compounds for blocking bitter taste elicited through T2R54 was measured in the same manner.

What is claimed is:

1. A compound having a formula

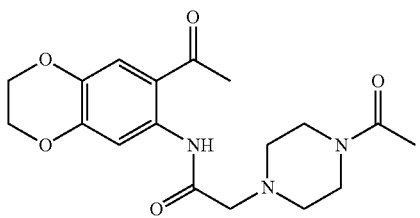 [SMILES: CC(=O)c1cc2c(cc1NC(=O)CN1CCN(C(C)=O)CC1)OCCO2]

or a salt thereof.

2. A method of reducing a bitter taste of a composition, comprising introducing to the composition a compound of claim 1.

3. The method of claim 2, wherein the composition comprises a bitter tastant.

4. A comestible or pharmaceutical composition, wherein the composition comprises a compound of claim 1.

5. The comestible or pharmaceutical composition of claim 4, further comprising a bitter tastant.

* * * * *